(12) United States Patent
Yan et al.

(10) Patent No.: US 11,702,672 B2
(45) Date of Patent: Jul. 18, 2023

(54) METHODS TO PRODUCE CHIMERIC ADENO-ASSOCIATED VIRUS/BOCAVIRUS PARVOVIRUS

(71) Applicants: University of Iowa Research Foundation, Iowa City, IA (US); University of Kansas, Lawrence, KS (US)

(72) Inventors: Ziying Yan, Iowa City, IA (US); John F. Engelhardt, Iowa City, IA (US); Jianming Qiu, Overland Park, KS (US)

(73) Assignees: University of Iowa Research Foundation, Iowa City, IA (US); University of Kansas, Lawrence, KS (US)

( * ) Notice: Subject to any disclaimer, the term of this patent is extended or adjusted under 35 U.S.C. 154(b) by 0 days.

(21) Appl. No.: 16/076,219

(22) PCT Filed: Feb. 8, 2017

(86) PCT No.: PCT/US2017/017021
§ 371 (c)(1),
(2) Date: Aug. 7, 2018

(87) PCT Pub. No.: WO2017/139381
PCT Pub. Date: Aug. 17, 2017

(65) Prior Publication Data
US 2021/0079421 A1    Mar. 18, 2021

Related U.S. Application Data

(60) Provisional application No. 62/292,613, filed on Feb. 8, 2016, provisional application No. 62/453,745, filed on Feb. 2, 2017.

(51) Int. Cl.
| | | |
|---|---|---|
| *C12N 15/63* | (2006.01) | |
| *C12N 15/85* | (2006.01) | |
| *C07H 21/04* | (2006.01) | |
| *C12N 15/86* | (2006.01) | |
| *C07K 14/015* | (2006.01) | |

(52) U.S. Cl.
CPC ............ *C12N 15/86* (2013.01); *C07K 14/015* (2013.01); *C12N 2750/14143* (2013.01); *C12N 2800/22* (2013.01); *C12N 2810/6027* (2013.01)

(58) Field of Classification Search
CPC .................... C12N 15/63; C12N 15/86; C12N 2750/14143; C12N 2800/22; C12N 2810/6027; C07H 21/04
See application file for complete search history.

(56) References Cited

U.S. PATENT DOCUMENTS

| | | |
|---|---|---|
| 4,501,729 A | 2/1985 | Boucher et al. |
| 5,292,498 A | 3/1994 | Boucher, Jr. |
| 5,478,745 A | 12/1995 | Samulski et al. |
| 5,512,269 A | 4/1996 | Molina y Vedia et al. |
| 5,604,090 A | 2/1997 | Alexander et al. |
| 5,628,984 A | 5/1997 | Boucher, Jr. |
| 5,635,160 A | 6/1997 | Stutts, III et al. |
| 5,651,957 A | 7/1997 | Molina y Vedia et al. |
| 5,656,256 A | 8/1997 | Boucher et al. |
| 5,658,772 A | 8/1997 | Odell et al. |
| 5,683,675 A | 11/1997 | Molina y Vedia et al. |
| 5,691,176 A | 11/1997 | Lebkowski et al. |
| 5,716,931 A | 2/1998 | Molina y Vedia et al. |
| 5,725,842 A | 3/1998 | Boucher, Jr. et al. |
| 5,801,030 A | 9/1998 | McVey et al. |
| 5,831,068 A | 11/1998 | Nair et al. |
| 5,834,182 A | 11/1998 | Alexander et al. |
| 5,843,742 A | 12/1998 | Natsoulis et al. |
| 5,849,706 A | 12/1998 | Molina y Vedia et al. |
| 5,853,716 A | 12/1998 | Tattersall et al. |
| 5,855,918 A | 1/1999 | Mrsny et al. |
| 5,869,305 A | 2/1999 | Samulski et al. |
| 5,876,700 A | 3/1999 | Boucher, Jr. et al. |
| 5,902,567 A | 5/1999 | Boucher, Jr. |
| 5,916,803 A | 6/1999 | Sedlacek et al. |
| 5,935,555 A | 8/1999 | Stutts, III et al. |
| 5,990,137 A | 11/1999 | Ternansky et al. |
| 6,022,527 A | 2/2000 | Boucher, Jr. et al. |
| 6,033,688 A | 3/2000 | Mrsny et al. |
| 6,037,177 A | 3/2000 | Snyder |
| 6,083,702 A | 7/2000 | Mitchell et al. |
| 6,083,713 A | 7/2000 | Manly et al. |
| 6,110,744 A | 8/2000 | Fang et al. |
| 6,133,247 A | 10/2000 | Boucher, Jr. |
| 6,143,279 A | 11/2000 | Boucher, Jr. et al. |

(Continued)

FOREIGN PATENT DOCUMENTS

| | | |
|---|---|---|
| AU | 4091299 | 12/1999 |
| AU | 0759093 | 4/2003 |

(Continued)

OTHER PUBLICATIONS

Kaspar, Brian, 2018, US 20180282684 A1, effective filing date, Nov. 5, 2014.*
"U.S. Appl. No. 14/782,876, Non Final Office Action dated Feb. 16, 2017", 10 pgs.
"U.S. Appl. No. 14/782,876, Notice of Allowance dated Jul. 25, 2017", 8 pgs.
"U.S. Appl. No. 14/782,876, Preliminary Amendment filed Oct. 7, 2015", 9 pgs.
"U.S. Appl. No. 14/782,876, Response filed Jan. 11, 2017 to Restriction Requirement dated Oct. 14, 2016", 8 pgs.
"U.S. Appl. No. 14/782,876, Response filed Jun. 16, 2017 to Non Final Office Action dated Feb. 16, 2017", 8 pgs.

(Continued)

*Primary Examiner* — Shin Lin Chen
(74) *Attorney, Agent, or Firm* — Schwegman Lundberg & Woessner, P.A.

(57) ABSTRACT

A method of preparing a chimeric virus comprising bocavirus capsid protein (VP) and a recombinant adeno-associated (AAV) viral genome, and isolated mutant bocavirus genomes, are provided.

12 Claims, 33 Drawing Sheets

Figure 1A:
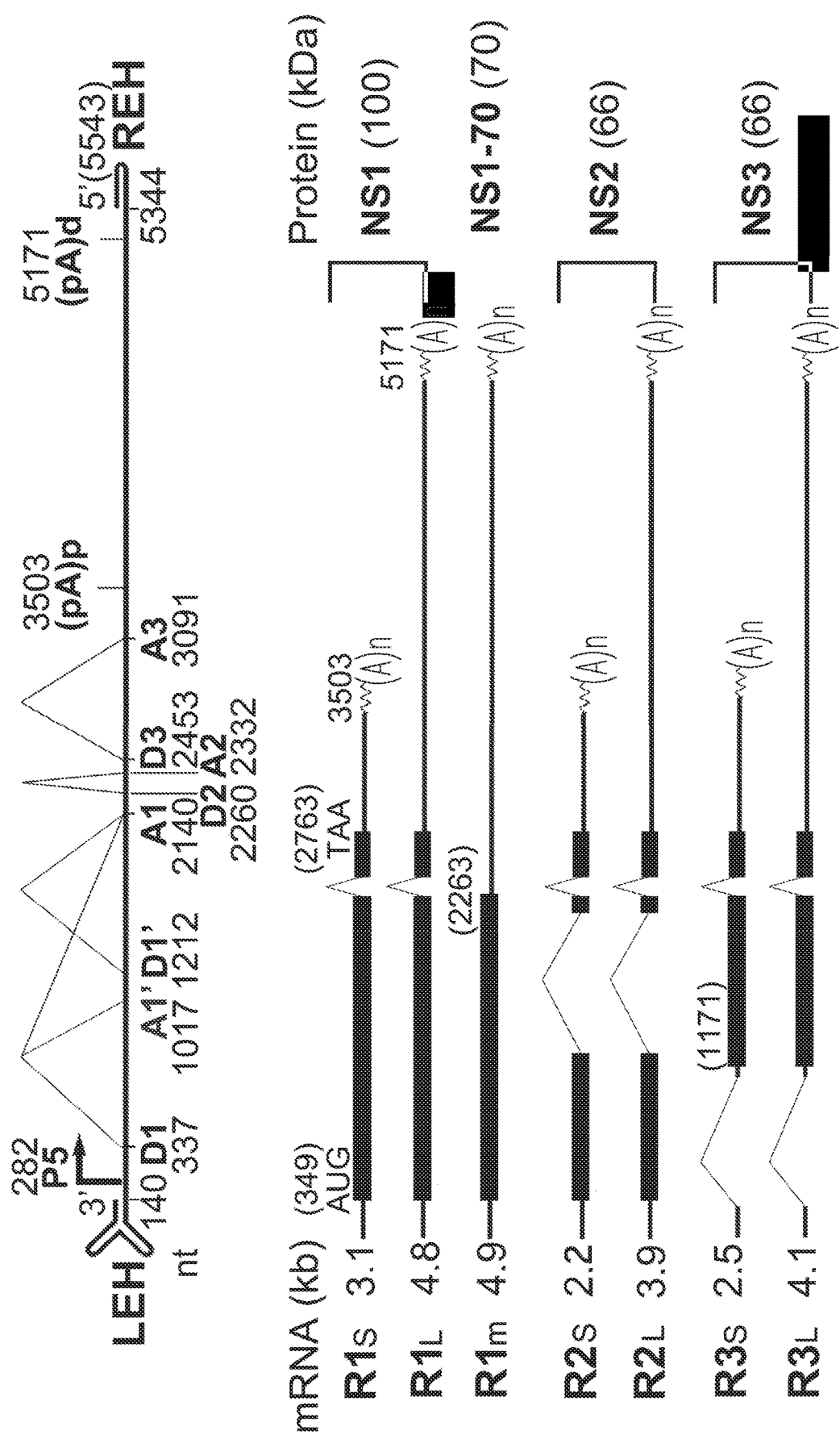

Specification includes a Sequence Listing.

(56) References Cited

U.S. PATENT DOCUMENTS

| | | |
|---|---|---|
| 6,153,436 A | 11/2000 | Hermonat et al. |
| 6,156,303 A | 12/2000 | Russell et al. |
| 6,200,560 B1 | 3/2001 | Couto et al. |
| 6,214,536 B1 | 4/2001 | Boucher, Jr. |
| 6,221,349 B1 | 4/2001 | Couto et al. |
| 6,235,266 B1 | 5/2001 | Stutts, III et al. |
| 6,264,975 B1 | 7/2001 | Boucher, Jr. |
| 6,270,996 B1 | 8/2001 | Wilson et al. |
| 6,287,569 B1 | 9/2001 | Kipps et al. |
| 6,290,951 B1 | 9/2001 | Mikulski et al. |
| 6,323,187 B1 | 11/2001 | Yerxa et al. |
| 6,329,181 B1 | 12/2001 | Xiao et al. |
| 6,358,524 B1 | 3/2002 | Sedlacek et al. |
| 6,416,759 B1 | 7/2002 | Firestone et al. |
| 6,420,347 B1 | 7/2002 | Jacobus et al. |
| 6,436,392 B1 | 8/2002 | Engelhardt et al. |
| 6,451,288 B1 | 9/2002 | Boucher, Jr. et al. |
| 6,468,771 B1 | 10/2002 | Einerhand et al. |
| 6,475,509 B1 | 11/2002 | Boucher, Jr. |
| 6,475,537 B1 | 11/2002 | King et al. |
| 6,485,950 B1 | 11/2002 | Kumar et al. |
| 6,491,907 B1 | 12/2002 | Rabinowitz et al. |
| 6,492,429 B1 | 12/2002 | Graus et al. |
| 6,521,225 B1 | 2/2003 | Srivastava et al. |
| 6,544,786 B1 | 4/2003 | Xiao et al. |
| 6,586,416 B2 | 7/2003 | Bubien |
| 6,596,535 B1 | 7/2003 | Carter |
| 6,602,667 B1 | 8/2003 | Walker et al. |
| 6,607,741 B2 | 8/2003 | Boucher, Jr. |
| 6,613,345 B2 | 9/2003 | Boucher, Jr. |
| 6,630,344 B1 | 10/2003 | Fang et al. |
| 6,642,051 B1 | 11/2003 | Lynch et al. |
| 6,670,365 B1 | 12/2003 | Gallemi et al. |
| 6,855,549 B1 | 2/2005 | McCray, Jr. et al. |
| 6,897,045 B2 | 5/2005 | Engelhardt et al. |
| 7,060,497 B2 | 6/2006 | Nakai et al. |
| 7,067,659 B2 | 6/2006 | Stamler et al. |
| 7,122,335 B1 | 10/2006 | Engelhardt et al. |
| 7,125,717 B2 | 10/2006 | Carter |
| 7,129,374 B2 | 10/2006 | Weissbach et al. |
| 7,241,447 B1 | 7/2007 | Engelhardt et al. |
| 7,749,491 B2 | 7/2010 | Engelhardt et al. |
| 7,803,622 B2 | 9/2010 | Engelhardt et al. |
| 8,110,350 B2 | 2/2012 | Allander et al. |
| 8,241,622 B2 | 8/2012 | Engelhardt et al. |
| 8,846,030 B2 | 9/2014 | Engelhardt et al. |
| 9,828,587 B2 | 11/2017 | Yan et al. |
| 10,793,835 B2 | 10/2020 | Yan et al. |
| 11,142,775 B2 | 10/2021 | Yan et al. |
| 2001/0034349 A1 | 10/2001 | Boucher, Jr. |
| 2001/0041682 A1 | 11/2001 | Stutts, III et al. |
| 2001/0051611 A1 | 12/2001 | Srivastava et al. |
| 2002/0045264 A1 | 4/2002 | During et al. |
| 2002/0076754 A1 | 6/2002 | Sun et al. |
| 2002/0095135 A1 | 7/2002 | Meeker et al. |
| 2002/0099023 A1 | 7/2002 | Boucher, Jr. |
| 2002/0115619 A1 | 8/2002 | Rubenstein et al. |
| 2002/0128203 A1 | 9/2002 | Schild |
| 2002/0131956 A1 | 9/2002 | Walsh et al. |
| 2002/0132770 A1 | 9/2002 | Caplan et al. |
| 2002/0137017 A1 | 9/2002 | Aronheim |
| 2002/0156057 A1 | 10/2002 | Bubien |
| 2002/0158255 A1 | 10/2002 | Boucher, Jr. |
| 2002/0165239 A1 | 11/2002 | Boucher, Jr. |
| 2002/0197237 A1 | 12/2002 | Engelhardt et al. |
| 2003/0003583 A1 | 1/2003 | Hirsch et al. |
| 2003/0053990 A1 | 3/2003 | Rabinowitz et al. |
| 2003/0087818 A1 | 5/2003 | Jiang et al. |
| 2003/0103939 A1 | 6/2003 | Engelhardt et al. |
| 2003/0108920 A1 | 6/2003 | Zhang et al. |
| 2003/0148506 A1 | 8/2003 | Kotin |
| 2003/0166284 A1 | 9/2003 | Srivastava et al. |
| 2004/0029106 A1 | 2/2004 | Samulski et al. |
| 2004/0235947 A1 | 11/2004 | Paquin et al. |
| 2004/0248301 A1 | 12/2004 | Engelhardt et al. |
| 2005/0037497 A1 | 2/2005 | Engelhardt et al. |
| 2005/0095225 A1 | 5/2005 | Engelhardt et al. |
| 2005/0158281 A1 | 7/2005 | Chamberlain et al. |
| 2005/0181423 A1 | 8/2005 | Barak et al. |
| 2005/0239807 A1 | 10/2005 | Stamler et al. |
| 2005/0255087 A1 | 11/2005 | Engelhardt et al. |
| 2006/0093585 A1 | 5/2006 | Engelhardt et al. |
| 2007/0110724 A1 | 5/2007 | Samulski et al. |
| 2007/0265350 A1 | 11/2007 | Engelhardt et al. |
| 2008/0166758 A1 | 7/2008 | Engelhardt et al. |
| 2008/0206198 A1 | 8/2008 | Engelhardt et al. |
| 2008/0206792 A1 | 8/2008 | Engelhardt et al. |
| 2008/0213221 A1 | 9/2008 | Engelhardt et al. |
| 2008/0226600 A1 | 9/2008 | Engelhardt et al. |
| 2008/0249050 A1 | 10/2008 | Engelhardt et al. |
| 2008/0261201 A1 | 10/2008 | Engelhardt et al. |
| 2008/0292654 A1 | 11/2008 | Allander et al. |
| 2009/0017062 A1 | 1/2009 | Engelhardt et al. |
| 2009/0239243 A1 | 9/2009 | Engelhardt et al. |
| 2009/0241206 A1 | 9/2009 | Sun et al. |
| 2009/0265796 A1 | 10/2009 | Engelhardt et al. |
| 2009/0297557 A1 | 12/2009 | Delwart et al. |
| 2011/0014723 A1 | 1/2011 | Erdman et al. |
| 2011/0054247 A1 | 3/2011 | Sun et al. |
| 2013/0012574 A1 | 1/2013 | Monahan et al. |
| 2016/0068821 A1 | 3/2016 | Yan et al. |
| 2018/0282702 A1 | 10/2018 | Yan et al. |
| 2019/0083657 A1 | 3/2019 | Engelhardt et al. |
| 2019/0203229 A1 | 7/2019 | Engelhardt et al. |
| 2019/0338312 A1 | 11/2019 | Yan et al. |
| 2021/0255170 A1 | 8/2021 | Engelhardt et al. |
| 2022/0154213 A1 | 5/2022 | Yan et al. |
| 2022/0195461 A1 | 6/2022 | Engelhardt et al. |
| 2022/0241436 A1 | 8/2022 | Engelhardt et al. |

FOREIGN PATENT DOCUMENTS

| | | |
|---|---|---|
| AU | 0784420 | 3/2006 |
| AU | 2017229347 A1 | 11/2018 |
| AU | 2014251099 B2 | 1/2019 |
| CA | 2302627 | 9/2001 |
| CA | 2328447 | 4/2007 |
| CN | 105431170 A | 3/2016 |
| CN | 105431170 B | 10/2019 |
| CN | 114340683 A | 4/2022 |
| CN | 114641318 A | 6/2022 |
| EA | 201892006 A1 | 4/2019 |
| EA | 202192819 A1 | 2/2022 |
| EA | 202192818 A1 | 3/2022 |
| EP | 0041682 A1 | 12/1981 |
| EP | 0132770 A1 | 2/1985 |
| EP | 0158255 A2 | 10/1985 |
| EP | 1153612 A1 | 11/2001 |
| EP | 1486567 A1 | 12/2004 |
| EP | 3426787 A1 | 1/2019 |
| EP | 2983707 B1 | 6/2019 |
| HK | 1217916 B | 9/2020 |
| IN | 10078DELNP2015 A | 4/2016 |
| JP | 2002538770 A | 11/2002 |
| JP | 2003501068 | 1/2003 |
| JP | 2003201255 | 7/2003 |
| JP | 2006521825 A | 9/2006 |
| JP | 4969002 | 4/2012 |
| JP | 2013518899 A | 5/2013 |
| JP | 2016518121 A | 6/2016 |
| JP | 6516725 B2 | 4/2019 |
| JP | 2022529457 A | 6/2022 |
| JP | 2022529470 A | 6/2022 |
| WO | WO-9413788 A1 | 6/1994 |
| WO | WO-9507351 A1 | 3/1995 |
| WO | WO-9513365 A1 | 5/1995 |
| WO | WO-9515384 A1 | 6/1995 |
| WO | WO-9522323 A1 | 8/1995 |
| WO | WO-9610402 A1 | 4/1996 |
| WO | WO-9722250 A1 | 6/1997 |
| WO | WO-9809657 A2 | 3/1998 |
| WO | WO-9824479 A1 | 6/1998 |
| WO | WO-9853839 A2 | 12/1998 |
| WO | WO-9918227 A1 | 4/1999 |

(56) References Cited

FOREIGN PATENT DOCUMENTS

| WO | WO-9920773 A2 | 4/1999 |
|---|---|---|
| WO | WO-9932647 A1 | 7/1999 |
| WO | WO-9960146 A1 | 11/1999 |
| WO | WO-9961601 A2 | 12/1999 |
| WO | WO-0047220 A1 | 2/2000 |
| WO | WO-0028004 A1 | 5/2000 |
| WO | WO-0038709 A1 | 7/2000 |
| WO | WO-0065038 A2 | 11/2000 |
| WO | WO-0075365 A2 | 12/2000 |
| WO | WO-0075365 A3 | 12/2000 |
| WO | WO-0125465 A1 | 4/2001 |
| WO | WO-01025465 A1 | 4/2001 |
| WO | WO-0168888 A2 | 9/2001 |
| WO | WO-0183692 A2 | 11/2001 |
| WO | WO-0192551 A2 | 12/2001 |
| WO | WO-0212525 A2 | 2/2002 |
| WO | WO-0214526 A2 | 2/2002 |
| WO | WO-0224172 A1 | 3/2002 |
| WO | WO-0224177 A2 | 3/2002 |
| WO | WO-02087306 A2 | 11/2002 |
| WO | WO-03006616 A2 | 1/2003 |
| WO | WO-03006990 A1 | 1/2003 |
| WO | WO-03042361 A2 | 5/2003 |
| WO | WO-03057847 A2 | 7/2003 |
| WO | WO-03087399 A1 | 10/2003 |
| WO | WO-03095667 A2 | 11/2003 |
| WO | WO-03104392 A2 | 12/2003 |
| WO | WO-2004010045 A1 | 1/2004 |
| WO | WO-04064844 A1 | 8/2004 |
| WO | WO-2004064844 A1 | 8/2004 |
| WO | WO-04089423 A2 | 10/2004 |
| WO | WO-04089423 A3 | 10/2004 |
| WO | WO-4090145 A2 | 10/2004 |
| WO | WO-04090145 A3 | 10/2004 |
| WO | WO-2004090145 A2 | 10/2004 |
| WO | WO-2004112727 A2 | 12/2004 |
| WO | WO-2005056762 A2 | 6/2005 |
| WO | WO-05111220 A2 | 11/2005 |
| WO | WO-2005105806 A1 | 11/2005 |
| WO | WO-2005111220 A3 | 11/2005 |
| WO | WO-05119251 A2 | 12/2005 |
| WO | WO-2005116224 A2 | 12/2005 |
| WO | WO-2005119251 A2 | 12/2005 |
| WO | WO-2006009975 A2 | 1/2006 |
| WO | WO-20060099755 A1 | 1/2006 |
| WO | WO-2006116503 A2 | 11/2006 |
| WO | WO-2007079141 A2 | 7/2007 |
| WO | WO-2007079141 C2 | 7/2007 |
| WO | WO-2007127464 A2 | 11/2007 |
| WO | WO-2007127464 A3 | 11/2007 |
| WO | WO-2008034637 A1 | 3/2008 |
| WO | WO-2008133904 A1 | 11/2008 |
| WO | WO-2009028387 A1 | 3/2009 |
| WO | WO-2011097456 A2 | 8/2011 |
| WO | WO-2014168953 A1 | 10/2014 |
| WO | WO-2015164758 A1 | 10/2015 |
| WO | WO-2017139381 A1 | 8/2017 |
| WO | WO-2017155973 A1 | 9/2017 |
| WO | 2017205739 | 11/2017 |
| WO | WO-W02018132747 | 7/2018 |
| WO | WO-2019178267 A2 | 9/2019 |
| WO | WO-2019178267 A3 | 9/2019 |
| WO | WO-2020214668 A1 | 10/2020 |
| WO | WO-2020214672 A1 | 10/2020 |
| WO | WO-2022006253 A2 | 1/2022 |
| WO | WO-2022006253 A3 | 1/2022 |

OTHER PUBLICATIONS

"U.S. Appl. No. 14/782,876, Restriction Requirement dated Oct. 14, 2016", 10 pgs.
"U.S. Appl. No. 15/822,956, Preliminary Amendment filed Nov. 27, 2017", 3 pgs.
"U.S. Appl. No. 15/822,956, Supplemental Preliminary Amendment filed Apr. 23, 2018", 9 pgs.
"Australian Application Serial No. 2014251099, First Examination Report dated May 30, 2018", 4 pgs.
"Chinese Application Serial No. 201480032420.6, Office Action dated May 3, 2017", w/English Translation of Claims, 20 pgs.
"Chinese Application Serial No. 201480032420.6, Office Action dated Jul. 13, 2018", w/English translation, 8 pgs.
"Chinese Application Serial No. 201480032420.6, Office Action dated Dec. 14, 2017", (English Translation), 8 pgs.
"Chinese Application Serial No. 201480032420.6, Response filed Feb. 27, 2018 to Office Action dated Dec. 14, 2017", w/ Amended Claims, 73 pgs.
"Chinese Application Serial No. 201480032420.6, Response filed Sep. 18, 2017 to Office Action dated May 3, 2017", w/English Claims, 25 pgs.
"European Application Serial No. 14783418.8, Communication Pursuant to Article 94(3) EPC dated Mar. 27, 2018", 4 pgs.
"European Application Serial No. 14783418.8, Extended European Search Report dated Feb. 27, 2017", 15 pgs.
"European Application Serial No. 14783418.8, Response filed May 26, 2016", 13 pgs.
"European Application Serial No. 14783418.8, Response filed May 30, 2018 to Communication Pursuant to Article 94(3) EPC dated Mar. 27, 2018", 271 pgs.
"European Application Serial No. 14783418.8, Response filed Sep. 22, 2017", 11 pgs.
"International Application Serial No. PCT/US2014/033343, International Preliminary Report on Patentability dated Oct. 13, 2015", 12 pgs.
"International Application Serial No. PCT/US2014/033343, International Search Report dated Sep. 2, 2014", 4 pgs.
"International Application Serial No. PCT/US2014/033343, Written Opinion dated Sep. 2, 2014", 10 pgs.
"International Application Serial No. PCT/US2017/017021, International Preliminary Report on Patentability dated Aug. 23, 2018", 12 pgs.
"Japanese Application Serial No. 2016-507610, Office Action dated Feb. 21, 2018", with English translation of claims, 16 pgs.
"Japanese Application Serial No. 2016-507610, Response filed Aug. 21, 2018 to Office Action dated Feb. 21, 2018", with English translation of claims, 27 pgs.
Brown, Kevin E., "The expanding range of parvoviruses which infect humans", Reviews in Medical Virology, GB, (2010), vol. 20, No. 4, (2010), 231-244.
Cheung, Andrew K., et al., "identification and molecular cloning of a novel porcine parvovirus", Archives of Virology; Official Journal of the Virology Division of the International Union of Microbiological Societies, Springer-Verlag, VI, vol. 155, No. 5, (2010), 801-806.
Deng, Xuefeng, et al., "In vitro modeling of human bocavirus 1 infection of polarized primary human airway epithelia", J Virol. vol. 87, No. 7, 4097-4102, (Jan. 23, 2013), 7 pgs.
Gurda, Brittney L., et al., "Human Bocavirus Capsid Structure: Insights into the Structural Repertoire of the Parvoviridae", Journal of Virology, 84(12), (Jun. 2010), 5880-5889.
Haung, Qinfeng, et al., "Establishment of a Reverse Genetics System for Studying Human Bocavirus in Human Airway Epithelia", Journal PLOS Pathogens vol. 8(8), (2012), 1-14.
Ishiawata, Akira, et al., "Phenotype correction of hemophilia A mice with adeno-associated virus vectors carrying the B domain-deleted canine factor VIII gene", Thrombosis Research, Tarrytown, NY, US, vol. 118, No. 5, (2006), (2006), 627-635.
Kapoor, Amit, et al., "Bocavirus Episome in infected Human Tissue Contains Non-Identical Termini", PLOS ONE, (2011), vol. 6, No. 6, e21362, (2011), 8 pgs.
Kapoor, Amit, et al., "Identification and Characterization of a New Bocavirus Species in Gorillas", PLOS ONE, (2010), vol. 5, No. 7, p. e11948 (Jul. 2010), 6 pgs.
Li, Wuping, et al., "Generation of Novel AAV Variants by Directed Evolution for Improved CFTR Delivery to Human Ciliated Airway Epithelium", Journal of Molecular Therapy vol. 17(12), (Dec. 2009), 2067-2077.

(56) References Cited

OTHER PUBLICATIONS

Mihaylov, Ivailo, et al., "Complementation for an essential ancillary non-structural protein function across parvovirus genera", Virology, vols. 468-470, (2014), 226-237.

Qiu, Jianming, et al., "Characterization of the transcription profile of adeno-associated virus type 5 reveals a number of unique features compared to previously characterized adeno-associated viruses", Journal of Virol., 76, No. 24, (2002), 12435-12447.

Qiu, Jianming, et al., "The Transcription Pro?le of the Bocavirus Bovine Parvovirus is Unlike Those of Previously Characterized Parvoviruses", Journal of Virology, vol. 81, No. 21, [Online], Retrieved from the Internet: «URL https://jvi.asm.org/>, (2007), 12080-12085.

Ros, C, et al., "The ubiquitin-proteasome machinery is essential for nuclear translocation of incoming minute virus of mice", Virology 324, (2004), 350-360.

Sun, et al., "Molecular Characterization of Infectious Clones of the Minute Virus of Canines Reveals Unique Features of Bocaviruses", Journal of Virology, 83(8), (Apr. 2009), 3956-3967.

Yan, Z, et al., "A Novel Chimeric Adenoassociated Virus 2/ Human Bocavirus 1 Parvovirus Vector Ef?ciently Transduces Human Airway Epithelia", Molecular Therapy, vol. 21 No. 12, (Dec. 2013), 2181-2194.

Yang, Wan-Zhu, et al., "Genome characterization of a novel porcine bocavirus", Archives of Virology ; Official Journal of the Virology Divisionof the International Union of Microbiological Societies, Springer-Verlag, VI, (2012), vol. 157, No. 11 ,, (Jul. 21, 2012), 2125-2132.

"International Application Serial No. PCT/US2017/017021, International Search Report dated May 23, 2017", 8 pgs.

"International Application Serial No. PCT/US2017/017021, Written Opinion dated May 23, 2017", 10 pgs.

Julia, Fakhiri, et al., "254. New Chimeric Gene Therapy Vectors Based on Four Different Mammalian Bocaviruses", Molecular Therapy, vol. 24, No. S1, (May 1, 2016), S100.

Olufemi, Fasina O, et al., "NP1 protein of the Bocaparvovirus Minute Virus of Canines controls acess to the viral capsid genes via its role in RNA processing", Journal of Virology., vol. 90, No. 4, (Dec. 4, 2015), 1718-1728.

Qinfeng, Huang, et al., "Internal polyadenylation of parvoviral precursor mRNA limits progeny virus production", Virology, Elsevier, Amsterdam, NL, vol. 426, No. 2, (Jan. 26, 2012), 167-177.

Sukhu, L, et al., "Characterization of the Nonstructural Proteins of the Bocavirus Minute Virus of Canines", Journal of Virology., vol. 87, No. 2, (Nov. 7, 2012), 1098-1104.

Wei, Ran Shen, et al., "Identification and functional analysis of novel nonstructural proteins of human bocavirus 1", Journal of Virology., vol. 89, No. 19, (Oct. 1, 2015), 10097-10109.

Wei, Zou, et al., "Nonstructural Protein NP1 of Human Bocavirus 1 Plays a Critical Role in the Expression of Viral Capsid Proteins", Journal of Virology., vol. 90, No. 9, (May 1, 2016), 4658-4669.

Yan, Z., et al., "A novel chimeric adenoassociated virus 2/human bocavirus 1 parvovirus vector efficiently transduces human airway epithelia", Mol Ther. vol. 21, No. 12, (Jul. 30, 2013), 2181-2194.

"Chinese Application Serial No. 201480032420.6, Response filed Nov. 26, 2018 to Office Action dated Jul. 13, 2018", w English Claims, 73 pgs.

"International Application Serial No. PCT US2017 034678, International Preliminary Report on Patentability dated Dec. 6, 2018", 9 pgs.

"Israel Application Serial No. 241954, Office Action dated Oct. 9, 2018", W English Translation, 10 pgs.

"International Application Serial No. PCT US2017 034678, Written Opinion dated Oct. 16, 2017", 6 pgs.

"International Application Serial No. PCT US2017 034678, International Search Report dated Oct. 16, 2017", 7 pgs.

Gao, Feng, "DNA-guided genome editing using the Nalronobacterium gregoryi Argonaute", In Journal of Nature Biotechnology Advance Online Publication, (May 2, 2016), 1-7.

Shen, Weiran, "Analysis of cis and trans Requirements for DNA Replication at the Right-End Hairpin of the Human Bocavirus 1 Genome", Journal of Virology 90.17, (2016), 7761-7777.

Y, Sun, "Molecular Characterization of Infectious Clones of the Minute Virus of Canines Reveals Unique Features of Bocaviruse", Journal of Virology vol. 83 No. 8, (Feb. 11, 2009), 3956-3967.

Zou, Wei, "Nonstructural Protein NP1 of Human Bocavirus 1 Plays Critical Role in the Expression of Viral Capsid Protein", Journal of Virology May 2016 vol. 90 No. 9, (Feb. 18, 2016), 4658-4669.

"U.S. Appl. No. 16/304,064, Restriction Requirement dated Aug. 6, 2021", 7 pgs.

"U.S. Appl. No. 09/276,625, 312 Amendment filed Jan. 10, 2002", 2 pgs.

"U.S. Appl. No. 09/276,625, Non Final Office Action dated Feb. 13, 2001", 9 pgs.

"U.S. Appl. No. 09/276,625, Notice of Allowance dated Oct. 10, 2001", 8 pgs.

"U.S. Appl. No. 09/276,625, Preliminary Amendment filed Jul. 20, 2000", 2 pgs.

"U.S. Appl. No. 09/276,625, PTO Response to 312 Amendment dated May 15, 2002", 2 pgs.

"U.S. Appl. No. 09/276,625, Response filed Aug. 13, 2001 to Non Final Office Action dated Feb. 13, 2001", 10 pgs.

"U.S. Appl. No. 09/276,625, Response filed Nov. 20, 2000 to Restriction Requirement dated Sep. 14, 2000", 5 pgs.

"U.S. Appl. No. 09/276,625, Restriction Requirement dated Sep. 14, 2000", 5 pgs.

"U.S. Appl. No. 09/684,554, Examiner Interview Summary dated May 17, 2005", 3 pgs.

"U.S. Appl. No. 09/684,554, Examiner Interview Summary dated Jun. 27, 2003", 2 pgs.

"U.S. Appl. No. 09/684,554, Examiner Interview Summary dated Sep. 7, 2004", 3 pgs.

"U.S. Appl. No. 09/684,554, Final Office Action dated Apr. 19, 2004", 10 pgs.

"U.S. Appl. No. 09/684,554, Final Office Action dated Apr. 19, 2004", 14 pgs.

"U.S. Appl. No. 09/684,554, Final Office Action dated Nov. 15, 2005", 11 pgs.

"U.S. Appl. No. 09/684,554, Final Office Action dated Nov. 15, 2005", 10 pgs.

"U.S. Appl. No. 09/684,554, Non-Final Office Action dated Feb. 25, 2005", 9 pgs.

"U.S. Appl. No. 09/684,554, Non-Final Office Action dated Mar. 11, 2003", 10 pgs.

"U.S. Appl. No. 09/684,554, Non-Final Office Action dated Mar. 11, 2003", 14 pgs.

"U.S. Appl. No. 09/684,554, Non-Final Office Action dated Jul. 20, 2006", 10 pgs.

"U.S. Appl. No. 09/684,554, Non-Final Office Action dated Jul. 20, 2006", 9 pgs.

"U.S. Appl. No. 09/684,554, Notice of Allowance dated Mar. 2, 2007", 9 pgs.

"U.S. Appl. No. 09/684,554, Notice of Allowance dated Mar. 2, 2007", 7 pgs.

"U.S. Appl. No. 09/684,554, Response filed Apr. 10, 2006 to Final Office Action dated Nov. 15, 2005", 14 pgs.

"U.S. Appl. No. 09/684,554, Response filed Jun. 4, 2002 to Restriction Requirement dated Dec. 4, 2001", 6 pgs.

"U.S. Appl. No. 09/684,554, Response filed Aug. 11, 2003 to Non Final Office Action dated Mar. 11, 2003", 13 pgs.

"U.S. Appl. No. 09/684,554, Response filed Aug. 17, 2005 to Non Final Office Action dated Feb. 25, 2005", 15 pgs.

"U.S. Appl. No. 09/684,554, Response filed Oct. 19, 2004 to Final Office Action dated Apr. 19, 2004", 14 pgs.

"U.S. Appl. No. 09/684,554, Response filed Nov. 20, 2006 to Non Final Office Action dated Jul. 20, 2006", 15 pgs.

"U.S. Appl. No. 09/684,554, Response filed Nov. 26, 2002 to Restriction Requirement dated Aug. 26, 2002", 13 pgs.

"U.S. Appl. No. 09/684,554, Restriction Requirement dated Aug. 26, 2002", 10 pgs.

"U.S. Appl. No. 09/684,554, Restriction Requirement dated Dec. 4, 2001", 6 pgs.

(56) References Cited

OTHER PUBLICATIONS

"U.S. Appl. No. 09/689,136, Advisory Action dated Nov. 3, 2004", 3 pgs.

"U.S. Appl. No. 09/689,136, Examiner Interview Summary dated Apr. 18, 2005", 3 pgs.

"U.S. Appl. No. 09/689,136, Examiner Interview Summary dated May 16, 2005", 3 pgs.

"U.S. Appl. No. 09/689,136, Examiner Interview Summary dated Sep. 28, 2004", 3 pgs.

"U.S. Appl. No. 09/689,136, Final Office Action dated Feb. 24, 2003", 11 pgs.

"U.S. Appl. No. 09/689,136, Final Office Action dated Jun. 18, 2004", 8 pgs.

"U.S. Appl. No. 09/689,136, Non Final Office Action dated Jan. 7, 2005", 10 pgs.

"U.S. Appl. No. 09/689,136, Non Final Office Action dated Jun. 26, 2002", 13 pgs.

"U.S. Appl. No. 09/689,136, Non Final Office Action dated Aug. 12, 2003", 8 pgs.

"U.S. Appl. No. 09/689,136, Notice of Allowance dated Sep. 12, 2005", 10 pgs.

"U.S. Appl. No. 09/689,136, Preliminary Amendment filed Oct. 12, 2000", 2 pgs.

"U.S. Appl. No. 09/689,136, Response filed Jan. 12, 2004 to Non Final Office Action dated Aug. 12, 2003", 12 pgs.

"U.S. Appl. No. 09/689,136, Response filed Apr. 11, 2002 to Restriction Requirement dated Oct. 11, 2001", 12 pgs.

"U.S. Appl. No. 09/689,136, Response filed May 18, 2005 to Non Final Office Action dated Jan. 7, 2005", 14 pgs.

"U.S. Appl. No. 09/689,136, Response filed May 30, 2003 to Final Office Action dated Feb. 24, 2003", 13 pgs.

"U.S. Appl. No. 09/689,136, Response filed Oct. 18, 2004 to Final Office Action dated Jun. 18, 2004", 13 pgs.

"U.S. Appl. No. 09/689,136, Response filed Nov. 26, 2002 to Non Final Office Action dated Jun. 26, 2002", 14 pgs.

"U.S. Appl. No. 09/689,136, Restriction Requirement dated Oct. 11, 2001", 9 pgs.

"U.S. Appl. No. 09/689,136, Supplemental Amendment filed Aug. 3, 2005", 13 pgs.

"U.S. Appl. No. 09/689,136, Supplemental Amendment filed Nov. 18, 2004", 11 pgs.

"U.S. Appl. No. 10/054,665, Non-Final Office Action dated Jun. 16, 2004", 7 pgs.

"U.S. Appl. No. 10/054,665, Notice of Allowance dated Nov. 8, 2004", 10 pgs.

"U.S. Appl. No. 10/054,665, Preliminary Amendment filed Jun. 25, 2002", 10 pgs.

"U.S. Appl. No. 10/054,665, Response filed Mar. 24, 2004 to Restriction Requirement dated Feb. 24, 2004", 1 pg.

"U.S. Appl. No. 10/054,665, Response filed Sep. 16, 2004 to Non-Final Office Action dated Jun. 16, 2004", 13 pgs.

"U.S. Appl. No. 10/054,665, Restriction Requirement dated Feb. 24, 2004", 5 pgs.

"U.S. Appl. No. 10/194,421, Preliminary Amendment filed Jan. 14, 2003", 2 pgs.

"U.S. Appl. No. 10/194,421, Restriction Requirement dated Mar. 21, 2005", 5 pgs.

"U.S. Appl. No. 10/815,262, Advisory Action dated Aug. 14, 2008", 3 pgs.

"U.S. Appl. No. 10/815,262, Examiner Interview Summary dated Feb. 6, 2007", 4 pgs.

"U.S. Appl. No. 10/815,262, Examiner Interview Summary dated Mar. 30, 2009", 4 pgs.

"U.S. Appl. No. 10/815,262, Examiner Interview Summary dated Nov. 18, 2009", 4 pgs.

"U.S. Appl. No. 10/815,262, Final Office Action dated Apr. 23, 2008", 24 pgs.

"U.S. Appl. No. 10/815,262, Final Office Action dated Aug. 6, 2009", 24 pgs.

"U.S. Appl. No. 10/815,262, Non Final Office Action dated May 15, 2007", 25 pgs.

"U.S. Appl. No. 10/815,262, Non-Final Office Action dated Oct. 30, 2007", 24 pgs.

"U.S. Appl. No. 10/815,262, Non-Final Office Action dated Dec. 4, 2008", 28 pgs.

"U.S. Appl. No. 10/815,262, Notice of Allowance dated Feb. 23, 2010", 9 pgs.

"U.S. Appl. No. 10/815,262, Response filed Jan. 31, 2008 to Non-Final Office Action dated Oct. 30, 2007", 26 pgs.

"U.S. Appl. No. 10/815,262, Response filed Mar. 19, 2007 to Restriction Requirement dated Sep. 18, 2006", 15 pgs.

"U.S. Appl. No. 10/815,262, Response filed May 4, 2009 to Non Final Office Action dated Dec. 4, 2008", 22 pgs.

"U.S. Appl. No. 10/815,262, Response filed Jul. 23, 2008 to Final Office Action dated Apr. 23, 2008", 22 pgs.

"U.S. Appl. No. 10/815,262, Response filed Aug. 14, 2007 to Non Final Office Action dated May 15, 2007", 24 pgs.

"U.S. Appl. No. 10/815,262, Response filed Dec. 7, 2009 to Final Office Action dated Aug. 6, 2009", 11 pgs.

"U.S. Appl. No. 10/815,262, Restriction Requirement dated Sep. 18, 2006", 15 pgs.

"U.S. Appl. No. 10/815,262, Supplemental Amendment dated Aug. 22, 2007", 1 pg.

"U.S. Appl. No. 10/815,557, Examiner Interview Summary dated Feb. 6, 2007", 4 pgs.

"U.S. Appl. No. 10/815,557, Final Office Action dated Nov. 14, 2007", 29 pgs.

"U.S. Appl. No. 10/815,557, Non Final Office Action dated May 21, 2007", 24 pgs.

"U.S. Appl. No. 10/815,557, Non-Final Office Action dated Feb. 3, 2009", 23 pgs.

"U.S. Appl. No. 10/815,557, Non-Final Office Action dated Aug. 13, 2008", 25 pgs.

"U.S. Appl. No. 10/815,557, Preliminary Amendment filed Dec. 28, 2004", 4 pgs.

"U.S. Appl. No. 10/815,557, Response filed Mar. 27, 2007 to Restriction Requirement dated Oct. 5, 2006", 13 pgs.

"U.S. Appl. No. 10/815,557, Response filed May 14, 2008 to Final Office Action dated Nov. 14, 2007", 18 pgs.

"U.S. Appl. No. 10/815,557, Response filed Aug. 21, 2007 to Non Final Office Action dated May 21, 2007", 22 pgs.

"U.S. Appl. No. 10/815,557, Response filed Nov. 13, 2008 to Non-Final Office Action dated Aug. 13, 2008", 19 pgs.

"U.S. Appl. No. 10/815,557, Restriction Requirement dated Oct. 5, 2006", 19 pgs.

"U.S. Appl. No. 10/837,029, Examiner Interview Summary dated Nov. 15, 2007", 3 pgs.

"U.S. Appl. No. 10/837,029, Eximaner Interwiew Summary dated Jan. 9, 2012", 3 pgs.

"U.S. Appl. No. 10/837,029, Final Office Action dated Jan. 8, 2009", 9 pgs.

"U.S. Appl. No. 10/837,029, Final Office Action dated Mar. 9, 2012", 10 pgs.

"U.S. Appl. No. 10/837,029, Final Office Action dated Sep. 13, 2010", 13 pgs.

"U.S. Appl. No. 10/837,029, Non Final Office Action dated Apr. 11, 2007", 9 pgs.

"U.S. Appl. No. 10/837,029, Non Final Office Action dated Oct. 7, 2011", 17 pgs.

"U.S. Appl. No. 10/837,029, Non-Final Office Action dated Mar. 24, 2010", 11 pgs.

"U.S. Appl. No. 10/837,029, Non-Final Office Action dated Jun. 2, 2008", 8 pgs.

"U.S. Appl. No. 10/837,029, Non-Final Office Action dated Jun. 23, 2009", 11 pgs.

"U.S. Appl. No. 10/837,029, Non-Final Office Action dated Jul. 15, 2008", 7 pgs.

"U.S. Appl. No. 10/837,029, Notice of Allowance dated Apr. 11, 2012", 10 pgs.

"U.S. Appl. No. 10/837,029, Notice of Allowance dated Nov. 15, 2007", 8 pgs.

(56) References Cited

OTHER PUBLICATIONS

"U.S. Appl. No. 10/837,029, Preliminary Amendment dated Feb. 15, 2008", 12 pgs.
"U.S. Appl. No. 10/837,029, Response filed Jan. 6, 2012 to Non Final Office Action dated Oct. 7, 2011", 18 pgs.
"U.S. Appl. No. 10/837,029, Response filed Feb. 15, 2007 to Restriction Requirement mailed Nov. 15, 2006", 17 pgs.
"U.S. Appl. No. 10/837,029, Response filed Mar. 22, 2012 to Final Office Action dated Mar. 9, 2012", 15 pgs.
"U.S. Appl. No. 10/837,029, Response filed Apr. 6, 2009 to Final Office Action dated Jan. 8, 2009", 13 pgs.
"U.S. Appl. No. 10/837,029, Response filed Jun. 21, 2010 to Non-Final Office Action dated Mar. 24, 2010", 14 pgs.
"U.S. Appl. No. 10/837,029, Response filed Aug. 17, 2007 to Non-Final Office Action dated Apr. 11, 2007", 20 pgs.
"U.S. Appl. No. 10/837,029, Response filed Oct. 15, 2008 to Non-Final Office Action dated Jul. 15, 2008", 13 pgs.
"U.S. Appl. No. 10/837,029, Response filed Nov. 19, 2009 to Non Final Office Action dated Jun. 23, 2009", 14 pgs.
"U.S. Appl. No. 10/837,029, Response filed Dec. 8, 2010 to Final Office Action dated Sep. 13, 2010", 18 pgs.
"U.S. Appl. No. 10/837,029, Restriction Requirement dated Nov. 15, 2006", 6 pgs.
"U.S. Appl. No. 10/837,029, Supplemental Amendment filed Oct. 16, 2007 to Non-Final Office Action dated Apr. 11, 2007", 14 pgs.
"U.S. Appl. No. 11/058,751, Advisory Action dated Dec. 8, 2008", 3 pgs.
"U.S. Appl. No. 11/058,751, Final Office Action dated Jan. 4, 2010", 6 pgs.
"U.S. Appl. No. 11/058,751, Final Office Action dated Mar. 3, 2009", 7 pgs.
"U.S. Appl. No. 11/058,751, Final Office Action dated Apr. 19, 2007", 7 pgs.
"U.S. Appl. No. 11/058,751, Non Final Office Action dated Aug. 25, 2006", 12 pgs.
"U.S. Appl. No. 11/058,751, Non-Final Office Action dated Jan. 28, 2008", 5 pgs.
"U.S. Appl. No. 11/058,751, Non-Final Office Action dated Jun. 12, 2009", 6 pgs.
"U.S. Appl. No. 11/058,751, Non-Final Office Action dated Jul. 22, 2008", 6 pgs.
"U.S. Appl. No. 11/058,751, Notice of Allowance dated May 3, 2010", 4 pgs.
"U.S. Appl. No. 11/058,751, Response filed Jan. 25, 2007 to Non Final Office Action dated Aug. 25, 2006", 10 pgs.
"U.S. Appl. No. 11/058,751, Response filed Apr. 5, 2010 to Final Office Action dated Jan. 4, 2010", 6 pgs.
"U.S. Appl. No. 11/058,751, Response filed Apr. 22, 2008 to Non-Final Office Action dated Jan. 28, 2008", 7 pgs.
"U.S. Appl. No. 11/058,751, Response filed Jun. 3, 2009 to Final Office Action dated Mar. 3, 2009", 7 pgs.
"U.S. Appl. No. 11/058,751, Response filed Jun. 14, 2006 to Restriction Requirement dated Dec. 14, 2005", 9 pgs.
"U.S. Appl. No. 11/058,751, Response filed Aug. 17, 2007 to Final Office Action dated Apr. 19, 2007", 9 pgs.
"U.S. Appl. No. 11/058,751, Response filed Sep. 14, 2009 to Non Final Office Action dated Jun. 12, 2009", 8 pgs.
"U.S. Appl. No. 11/058,751, Response filed Oct. 22, 2008 to Non Final Office Action dated Jul. 22, 2008", 6 pgs.
"U.S. Appl. No. 11/058,751, Restriction Requirement dated Dec. 14, 2005", 6 pgs.
"U.S. Appl. No. 11/058,751, Supplemental Amendment filed Oct. 19, 2007", 8 pgs.
"U.S. Appl. No. 11/301,601 , Response filed Feb. 21, 2014 to Non Final Office Action dated Nov. 22, 2013", 11 pgs.
"U.S. Appl. No. 11/301,601, Advisory Action dated Mar. 24, 2008", 6 pgs.
"U.S. Appl. No. 11/301,601, Examiner Interview Summary dated Jan. 31, 2013", 3 pgs.
"U.S. Appl. No. 11/301,601, Examiner Interview Summary dated Apr. 25, 2007", 4 pgs.
"U.S. Appl. No. 11/301,601, Examiner Interview Summary dated May 28, 2010", 3 pgs.
"U.S. Appl. No. 11/301,601, Final Office Action dated Mar. 30, 2010", 16 pgs.
"U.S. Appl. No. 11/301,601, Final Office Action dated Apr. 3, 2009", 16 pgs.
"U.S. Appl. No. 11/301,601, Final Office Action dated Dec. 6, 2011", 12 pgs.
"U.S. Appl. No. 11/301,601, Final Office Action dated Dec. 13, 2007", 15 pgs.
"U.S. Appl. No. 11/301,601, Non Final Office Action dated Mar. 28, 2013", 12 pgs.
"U.S. Appl. No. 11/301,601, Non Final Office Action dated Jun. 27, 2011", 10 pgs.
"U.S. Appl. No. 11/301,601, Non Final Office Action dated Nov. 22, 2013", 13 pgs.
"U.S. Appl. No. 11/301,601, Non-Final Office Action dated Jul. 12, 2007", 29 pgs.
"U.S. Appl. No. 11/301,601, Non-Final Office Action dated Sep. 28, 2009", 13 pgs.
"U.S. Appl. No. 11/301,601, Non-Final Office Action dated Oct. 2, 2008", 15 pgs.
"U.S. Appl. No. 11/301,601, Notice of Allowance dated May 22, 2014", 7 pgs.
"U.S. Appl. No. 11/301,601, Preliminary Amendment filed Dec. 13, 2005", 9 pgs.
"U.S. Appl. No. 11/301,601, Response filed Jan. 4, 2010 to Non Final Office Action dated Sep. 28, 2009", 12 pgs.
"U.S. Appl. No. 11/301,601, Response filed Mar. 13, 2008 to Final Office Action dated Dec. 13, 2007", 10 pgs.
"U.S. Appl. No. 11/301,601, Response filed Mar. 22, 2012 to Final Office Action dated Dec. 6, 2011", 11 pgs.
"U.S. Appl. No. 11/301,601, Response filed May 2, 2007 to Restriction Requirement dated Jan. 3, 2007", 11 pgs.
"U.S. Appl. No. 11/301,601, Response filed Jun. 27, 2013 to Non Final Office Action dated Mar. 28, 2013", 11 pgs.
"U.S. Appl. No. 11/301,601, Response filed Jun. 30, 2010 to Final Office Action dated Mar. 30, 2010", 11 pgs.
"U.S. Appl. No. 11/301,601, Response filed Jul. 1, 2009 to Final Office Action dated Apr. 3, 2009", 12 pgs.
"U.S. Appl. No. 11/301,601, Response filed Sep. 27, 2011 to Non-Final Office Action dated Jun. 27, 2011", 10 pgs.
"U.S. Appl. No. 11/301,601, Response filed Oct. 11, 2007 to Non-Final Office Action dated Jul. 12, 2007", 14 pgs.
"U.S. Appl. No. 11/301,601, Response filed Dec. 31, 2008 to Non Final Office Action dated Oct. 2, 2008", 12 pgs.
"U.S. Appl. No. 11/301,601, Restriction Requirement dated Jan. 3, 2007", 5 pgs.
"U.S. Appl. No. 11/301,601, Second Preliminary Amendment filed Jan. 25, 2006", 3 pgs.
"U.S. Appl. No. 11/617,491 , Response filed Oct. 3, 2013 to Non Final Office Action dated Jul. 3, 2013", 10 pgs.
"U.S. Appl. No. 11/617,491, Decision on Appeal Brief dated Apr. 3, 2014", 2 pgs.
"U.S. Appl. No. 11/617,491, Examiner Interview Summary dated Jul. 30, 2010", 3 pgs.
"U.S. Appl. No. 11/617,491, Final Office Action dated Mar. 2, 2009", 11 pgs.
"U.S. Appl. No. 11/617,491, Final Office Action dated Nov. 8, 2013", 11 pgs.
"U.S. Appl. No. 11/617,491, Final Office Action dated Nov. 26, 2010", 12 pgs.
"U.S. Appl. No. 11/617,491, Non Final Office Action dated Jul. 3, 2013", 9 pgs.
"U.S. Appl. No. 11/617,491, Non-Final Office Action dated May 27, 2010", 19 pgs.
"U.S. Appl. No. 11/617,491, Non-Final Office Action dated Jun. 26, 2008", 11 pgs.
"U.S. Appl. No. 11/617,491, Non-Final Office Action dated Oct. 2, 2009", 7 pgs.

(56) References Cited

OTHER PUBLICATIONS

"U.S. Appl. No. 11/617,491, Pre Appeal Brief Request for Review filed Jan. 9, 2014", 5 pgs.
"U.S. Appl. No. 11/617,491, Preliminary Amendment filed Apr. 11, 2007", 5 pgs.
"U.S. Appl. No. 11/617,491, Response filed Jan. 21, 2011 to Final Office Action dated Nov. 26, 2010", 15 pgs.
"U.S. Appl. No. 11/617,491, Response filed Jan. 28, 2010 to Non-Final Office Action dated Oct. 2, 2009", 9 pgs.
"U.S. Appl. No. 11/617,491, Response filed Feb. 8, 2008 to Restriction Requirement dated Dec. 28, 2007", 10 pgs.
"U.S. Appl. No. 11/617,491, Response filed Jun. 30, 2009 to Final Office Action dated Mar. 2, 2009", 14 pgs.
"U.S. Appl. No. 11/617,491, Response filed Aug. 26, 2010 to Non Final Office Action dated May 27, 2010", 14 pgs.
"U.S. Appl. No. 11/617,491, Response filed Nov. 26, 2008 to Non Final Office Action dated Jun. 26, 2008", 12 pgs.
"U.S. Appl. No. 11/617,491, Restriction Requirement dated Dec. 28, 2007", 8 pgs.
"U.S. Appl. No. 11/796,605, Preliminary Amendment filed Sep. 11, 2007", 6 pgs.
"U.S. Appl. No. 11/796,605, Restriction Requirement dated Jul. 7, 2009", 7 pgs.
"U.S. Appl. No. 11/821,116, Restriction Requirement dated Jun. 26, 2009", 8 pgs.
"U.S. Appl. No. 11/890,761, Final Office Action dated Dec. 22, 2009", 40 pgs.
"U.S. Appl. No. 11/890,761, Non Final Office Action dated Jul. 12, 2011", 15 pgs.
"U.S. Appl. No. 11/890,761, Non-Final Office Action dated Jul. 16, 2009", 16 pgs.
"U.S. Appl. No. 11/890,761, Preliminary Amendment filed May 19, 2008", 8 pgs.
"U.S. Appl. No. 11/890,761, Response filed Mar. 16, 2010 to Final Office Action dated Dec. 22, 2009", 11 pgs.
"U.S. Appl. No. 11/890,761, Response filed Apr. 14, 2009 to Restriction Requirement dated Oct. 14, 2008", 7 pgs.
"U.S. Appl. No. 11/890,761, Response filed Oct. 29, 2009 to Non Final Office Action dated Jul. 16, 2009", 19 pgs.
"U.S. Appl. No. 11/890,761, Restriction Requirement dated Oct. 14, 2008", 5 pgs.
"U.S. Appl. No. 11/890,762, Restriction Requirement dated Jun. 23, 2009", 8 pgs.
"U.S. Appl. No. 11/890,767, Restriction Requirement dated Sep. 30, 2009", 8 pgs.
"U.S. Appl. No. 11/890,775, Response filed Dec. 2, 2009 to Restriction Requirement dated Oct. 2, 2009", 6 pgs.
"U.S. Appl. No. 11/890,775, Restriction Requirement dated Feb. 23, 2010", 6 pgs.
"U.S. Appl. No. 11/890,775, Restriction Requirement dated Oct. 2, 2009", 6 pgs.
"U.S. Appl. No. 11/890,776, Preliminary Amendment dated May 9, 2008", 6 pgs.
"U.S. Appl. No. 11/890,776, Restriction Requirement dated Dec. 17, 2008", 8 pgs.
"U.S. Appl. No. 11/890,777, Preliminary Amendment dated Aug. 7, 2007", 9 pgs.
"U.S. Appl. No. 11/890,777, Restriction Requirement dated Mar. 18, 2010", 5 pgs.
"U.S. Appl. No. 11/890,778, Preliminary Amendment filed Jan. 28, 2009", 4 pgs.
"U.S. Appl. No. 11/890,779, Preliminary Amendment filed May 9, 2008", 5 pgs.
"U.S. Appl. No. 11/890,779, Restriction Requirement dated Feb. 18, 2010", 5 pgs.
"U.S. Appl. No. 11/890,787, Preliminary Amendment filed May 12, 2008", 6 pgs.
"U.S. Appl. No. 11/890,787, Restriction Requirement dated Apr. 17, 2009", 5 pgs.
"U.S. Appl. No. 12/397,583, Non-Final Office Action dated Sep. 23, 2010", 16 pgs.
"U.S. Appl. No. 12/397,583, Response filed Aug. 9, 2010 to Restriction Requirement dated Jul. 20, 2010", 7 pgs.
"U.S. Appl. No. 12/397,583, Restriction Requirement dated Jul. 20, 2010", 12 pgs.
"U.S. Appl. No. 12/835,102, Preliminary Amendment filed Sep. 29, 2010", 10 pgs.
"U.S. Appl. No. 12/835,102, Restriction Requirement dated Jun. 7, 2011", 8 pgs.
"U.S. Appl. No. 15/822,956, Final Office Action dated Sep. 23, 2019", 9 pgs.
"U.S. Appl. No. 15/822,956, Non Final Office Action dated May 8, 2019", 16 pgs.
"U.S. Appl. No. 15/822,956, Notice of Allowance dated Jun. 1, 2020", 5 pgs.
"U.S. Appl. No. 15/822,956, Notice of Allowance dated Dec. 18, 2019", 8 pgs.
"U.S. Appl. No. 15/822,956, Response filed Apr. 8, 2019 to Restriction Requirement dated Feb. 7, 2019", 6 pgs.
"U.S. Appl. No. 15/822,956, Response Filed Nov. 22, 2019 to Final Office Action dated Sep. 23, 2019", 8 pgs.
"U.S. Appl. No. 15/822,956, Response filed Aug. 8, 2019 to Non-Final Office Action dated May 8, 2019", 9 pgs.
"U.S. Appl. No. 15/822,956, Restriction Requirement dated Feb. 7, 2019", 9 pgs.
"U.S. Appl. No. 16/082,767, Final Office Action dated Jan. 12, 2022", 13 pgs.
"U.S. Appl. No. 16/082,767, Non Final Office Action dated Apr. 28, 2021", 17 pgs.
"U.S. Appl. No. 16/082,767, Response filed Jan. 6, 2021 to Restriction Requirement dated Oct. 6, 2020", 5 pgs.
"U.S. Appl. No. 16/082,767, Response filed Apr. 12, 2022 to Final Office Action dated Jan. 12, 2022", 6 pgs.
"U.S. Appl. No. 16/082,767, Response filed Sep. 28, 2021 to Non Final Office Action dated Apr. 28, 2021", 9 pgs.
"U.S. Appl. No. 16/082,767, Restriction Requirement dated Oct. 6, 2020", 8 pgs.
"U.S. Appl. No. 16/304,064, Non Final Office Action dated Jan. 6, 2022", 23 pgs.
"U.S. Appl. No. 16/304,064, Response filed Oct. 6, 2021 to Restriction Requirement dated Aug. 6, 2021", 9 pgs.
"U.S. Appl. No. 16/477,762, Non Final Office Action dated Jan. 27, 2021", 13 pgs.
"U.S. Appl. No. 16/477,762, Notice of Allowability dated Jun. 28, 2021", 3 pgs.
"U.S. Appl. No. 16/477,762, Notice of Allowance dated Jun. 10, 2021", 8 pgs.
"U.S. Appl. No. 16/477,762, Preliminary Amendment filed Jul. 12, 2019", 8 pgs.
"U.S. Appl. No. 16/477,762, Response filed Apr. 27, 2021 to Non Final Office Action dated Jan. 27, 2021", 8 pgs.
"U.S. Appl. No. 16/477,762, Response filed Oct. 7, 2020 to Restriction Requirement dated Aug. 25, 2020", 8 pgs.
"U.S. Appl. No. 16/477,762, Restriction Requirement dated Aug. 25, 2020", 12 pgs.
"U.S. Appl. No. 16/980,268, Preliminary Amendment filed Sep. 11, 2020", 7 pgs.
"U.S. Appl. No. 17/470,560, Preliminary Amendment filed Feb. 2, 2022", 6 pgs.
"U.S. Appl. No. 17/603,831, Preliminary Amendment filed Oct. 14, 2021", 7 pgs.
"U.S. Appl. No. 17/603,840, Preliminary Amendment filed Oct. 14, 2021", 7 pgs.
"U.S. Appl. No. 60/305,204. Application filed Jul. 13, 2001", 115 pgs.
"Australia Application No. 2006332728, Examiner's Report dated Jun. 6, 2011", 2 pgs.
"Australia Application Serial No. 2005243221 Examiner Report dated Dec. 10, 2009", 3 pgs.
"Australian Application No. 58694/00, Response filed Oct. 28, 2004 to Examiner's Report dated Nov. 26, 2003", 20 pgs.

(56) References Cited

OTHER PUBLICATIONS

"Australian Application Serial No. 2004/227358, Office Action dated Sep. 23, 2008", 4 pgs.
"Australian Application Serial No. 2004227358, Examiner Report No. 2 dated Aug. 27, 2009", 2 pgs.
"Australian Application Serial No. 2004227358, Response filed Jul. 10, 2009 to Examiner's First Report dated Sep. 23, 2008", 10 pgs.
"Australian Application Serial No. 2004227358, Response filed Oct. 22, 2009 to Examiner's Second Report dated Aug. 27, 2009", 16 pgs.
"Australian Application Serial No. 2004227915,, Examiner Report dated Dec. 5, 2008", 2 pgs.
"Australian Application Serial No. 2006202785, Examiner's First Report dated Sep. 21, 2007", 3 pgs.
"Australian Application Serial No. 2006202785, Response filed Sep. 19, 2008 to Examiner's First Report dated Sep. 21, 2007", 29 pgs.
"Australian Application Serial No. 2006332728, Response filed Nov. 14, 2011 to Examiner Report dated Jun. 6, 2011", 12 pgs.
"Australian Application Serial No. 2006332728, Subsequent Examiner Report dated Nov. 24, 2011", 2 pgs.
"Australian Application Serial No. 2014251099, Response filed Dec. 19, 2018 to Examiner's Report dated May 30, 2018", 39 pgs.
"Australian Application Serial No. 2017229347, First Examination Report dated Dec. 20, 2019", 3 pgs.
"Australian Application Serial No. 2017229347, Response filed Oct. 2, 2020 to First Examination Report dated Dec. 20, 2019", 19 pgs.
"Australian Application Serial No. 2017229347, Response filed Dec. 10, 2020 to Subsequent Examiners Report dated Oct. 8, 2020", 16 pgs.
"Australian Application Serial No. 2017229347, Subsequent Examiners Report dated Oct. 8, 2020", 6 pgs.
"Australian Application Serial No. 2017229347, Third Examiners Report dated Dec. 16, 2020", 4 pgs.
"Australian Application Serial No. 40192/99, Response filed Dec. 10, 2002 to Examiner's First Report dated May 24, 2002", 15 pgs.
"Australian Application Serial No. 58694/00, Examiner Report No. 2 dated Nov. 18, 2004", 3 pgs.
"Australian Application Serial No. 58694/00, Examiner's Report dated Jul. 18, 2005", 2 pgs.
"Australian Application Serial No. 58694/00, Response filed Jul. 7, 2005 to Examiner's Report dated Nov. 18, 2004", 15 pgs.
"Australian Application Serial No. 80032/00, First Examiner's Report dated May 19, 2004", 2 pgs.
"Australian Application Serial No. 80032/00, Response filed Feb. 2, 2006 to Second Examiner's Report dated Jan. 3, 2006", 56 pgs.
"Australian Application Serial No. 80032/00, Response filed Dec. 8, 2005 to First Examiner's Report dated May 19, 2004", 36 pgs.
"Australian Application Serial No. 80032/00, Second Examiner's Report dated Jan. 3, 2006", 3 pgs.
"Brazilian Application Serial No. 1120210207082, Office Action dated Dec. 22, 2021", with machine translation, 2 pgs.
"Brazilian Application Serial No. 1120210207082, Response filed Feb. 25, 2022 to Office Action dated Dec. 22, 2021", with machine translation, 4 pgs.
"Calbichem(r) Eicosapentaenoic Acid, EPA; 20:5 w-3; 5,8, 11, 14, 17-Eicosapentaenoic Acid", Catalog No. 324875, (Dec. 7, 1998), 2 pgs.
"Calbiochem(r) MG-132, Carbobenzoxy-L-leucyl-L-leucinal", Catalog No. 474790, (Oct. 15, 1999), 2 pgs.
"Calbiochem(r) Simvastatin, MK-733", Catalog No. 567020, (Oct. 25, 2001), 2 pgs.
"Calbiochem(r) Aminoglycoside antibiotic. Inhibits myeloperoxidase-dependent oxidant cell injury", Tobramycin, Free Base, Catalog No. 614005, (Aug. 26, 1999), 1 pg.
"Calbiochem(r) Camptothecin, Camptotheca acuminata (S)-(+)-Camptothecin; 4-Ethyl-4-hydroxy-1H-pyrano[3', 4': 6,7] indolizino [1,2-b] quinoline-3, 14 (4H, 12H) dione", Catalog No. 208925, (Oct. 2, 2000), 2 pgs.

"Calbiochem(r) Doxorubicin, Hydrochloride Adriamycin; 14-Hydroxydaunomycin, HCl", Catalog No. 324380, (Oct. 21, 1998), 2 pgs.
"Canadian Application Serial No. 2,328,447, Official Action dated Feb. 7, 2005", 2 pgs.
"Canadian Application Serial No. 2,328,447, Response filed Aug. 8, 2005 to Official Action dated Feb. 7, 2005", 15 pgs.
"Canadian Application Serial No. 2,376,400, Office Action dated Apr. 7, 2008", 4 pgs.
"Canadian Application Serial No. 2,376,400, Official Action dated Jan. 5, 2010", 3 pgs.
"Canadian Application Serial No. 2,376,400, Official Action dated Apr. 7, 2008", 4 pgs.
"Canadian Application Serial No. 2,376,400, Response filed Oct. 7, 2008 to Official Action dated Apr. 7, 2008", 49 pgs.
"Canadian Application Serial No. 2,376,400, Response filed Oct. 7, 2008 to Office Action dated Apr. 7, 2008", 49 pgs.
"Canadian Application Serial No. 2,386,546, Office Action dated Jun. 30, 2009", 4 pgs.
"Canadian Application Serial No. 2,520,028, Office Action dated Jan. 19, 2011", 3 pgs.
"Canadian Application Serial No. 2,634,670 , Response filed Sep. 30, 2013 to Office Action dated May 17, 2013", 53 pgs.
"Canadian Application Serial No. 2,634,670, Office Action dated Feb. 3, 2014", 3 pgs.
"Canadian Application Serial No. 2,634,670, Office Action dated Feb. 17, 2015", 6 pgs.
"Canadian Application Serial No. 2,634,670, Office Action dated May 17, 2013", 4 pgs.
"Canadian Application Serial No. 2,634,670, Voluntary Amendment and Submission of Sequence Listing filed Dec. 24, 2008", 19 pgs.
"Canadian Application Serial No. 2,634,670, Voluntary Amendment filed Dec. 20, 2011", 7 pgs.
"Canadian Application Serial No. 2,909,085, Office Action dated Feb. 16, 2021", 4 pgs.
"Canadian Application Serial No. 2,909,085, Office Action dated Feb. 17, 2022", 3 pgs.
"Canadian Application Serial No. 2,909,085, Office Action dated Apr. 2, 2020", 5 pgs.
"Canadian Application Serial No. 2,909,085, Response filed Jun. 11, 2021 to Office Action dated Feb. 16", 77 pgs.
"Canadian Application Serial No. 2,909,085, Response filed Jul. 30, 2020 to Office Action dated Apr. 2, 2020", 29 pgs.
"Canadian Application Serial No. 2386546, Response filed Oct. 14, 2008 to Office Action dated Apr. 14, 2008", 20 pgs.
"Canadian Application Serial No. 2386546,, Office Action dated Apr. 14, 2008", 3 pgs.
"Canadian Application Serial No. 2909085, Voluntary Amendment filed Sep. 6, 2019", 4 pgs.
"Canadian Application Serial No. 3,016,985, Examiner's Rule 30(2) Requisition dated Jun. 28, 2019", 3 pgs.
"Canadian Application Serial No. 3,016,985, Office Action dated Sep. 23, 2020", 7 pgs.
"Canadian Application Serial No. 3,016,985, Office Action dated Oct. 8, 2021", 6 pgs.
"Canadian Application Serial No. 3,016,985, Response filed Jan. 22, 2021 to Office Action dated Sep. 23, 2020", 14 pgs.
"Canadian Application Serial No. 3,016,985, Response filed Dec. 24, 2019 to Examiner's Rule 30(2) Requisition dated Jun. 28, 2019", 40 pgs.
"Canadian Application Serial No. 3,016,985, Response filed Apr. 7, 2022 to Office Action dated Oct. 8, 2021", 11 pgs.
"Canadian Application Serial No. 3,016,985, Voluntary Amendment filed Apr. 12, 2022", 12 pgs.
"Cancer Research", Contribution to Society, http://www.bikaken. or.jp/mcrf_e/contributiion, (Dec. 4, 2000), 2 pages.
"Carbiochem(r) Lovastatin, Mevinolin; MK-803", Catalolg No. 438185, (Jun. 29, 2001), 2 pgs.
"Chinese Application Serial No. 202080043595.2, Notification to Make Rectification dated Dec. 29, 2021", w/o English Translation, 2 pgs.
"DNA Vector-Based siRNA", http://www.genscript.com/rnai_intro. html, (observed Mar. 9, 2004), 3 pgs.

(56) References Cited

OTHER PUBLICATIONS

"Drugs for Selection of Genetic Markers Reagents for positive and negative selection of Genes involved in Nucleotide Metabolism", Calbiochem, (Mar., 2002), 6 pages.
"Enzyme database entry for EC No. 3.4.22", [online}. Retrieved from the Internet: <http://ca.expasy.org/enzyme/3.4.22>, (Jun. 19, 2007), 2 pgs.
"Epoxomicin—a potent and selective proteasome inhibitor", Affiniti Research Products Limited, 2 pages.
"Eurasian Application Serial No. 201892006, Office Action dated Jul. 1, 2021", w/ English Translation, 5 pgs.
"Eurasian Application Serial No. 201892006, Response filed Nov. 24, 2021 to Office Action dated Jul. 1, 2021", w/ English claims, 10 pgs.
"European Application Serial No. 05778984.4, Office Action dated Jul. 20, 2007", 2 pgs.
"European Application Serial No. 005778984.4, Communication dated Jul. 20, 2007", 2 pgs.
"European Application Serial No. 005778984.4, Response filed Mar. 4, 2008 to Communication dated Jul. 20, 2007", 28 pgs.
"European Application Serial No. 00944624.6, Main Request, First Auxiliary Request and Second Auxiliary Request filed Sep. 29, 2008", 67 pgs.
"European Application Serial No. 00944624.6, Office Action Aug. 5, 2003", 3 pgs.
"European Application Serial No. 00944624.6, Office Action dated Mar. 4, 2005", 5 pgs.
"European Application Serial No. 00944624.6, Response and Further Auxiliary Requests filed Oct. 27, 2008 to Primary Examiner's Telephonic Comments", 122 pgs.
"European Application Serial No. 00944624.6, Response filed Feb. 16, 2004 to Office Action dated Aug. 5, 2003", 25 pgs.
"European Application Serial No. 00944624.6, Response filed Aug. 26, 2005 to Office Action dated Mar. 4, 2005", 31 pgs.
"European Application Serial No. 00970689.6, Communication dated Nov. 19, 2003", 4 pgs.
"European Application Serial No. 00970689.6, Communication dated Dec. 19, 2005", 7 pgs.
"European Application Serial No. 00970689.6, Office Action dated Sep. 13, 2007", 5 pgs.
"European Application Serial No. 00970689.6, Office Action dated Dec. 29, 2008", 5 pgs.
"European Application Serial No. 00970689.6, Response filed Apr. 24, 2008 to Communication dated Sep. 13, 2007", 39 pgs.
"European Application Serial No. 00970689.6, Response filed Aug. 9, 2004 to Communication dated Nov. 19, 2003", 10 pgs.
"European Application Serial No. 00970689.6, Response dated Jul. 27, 2006 to Examination Report dated Dec. 19, 2005", 51 pgs.
"European Application Serial No. 02749934.2, Communication dated Mar. 12, 2004", 2 pgs.
"European Application Serial No. 02749934.2, Communication dated Nov. 12, 2004", 3 pgs.
"European Application Serial No. 02749934.2, Response filed Jan. 7, 2005 to Communication dated Nov. 12, 2004", 1 pg.
"European Application Serial No. 02749934.2, Response filed Apr. 21, 2004 to Communication dated Mar. 12, 2004", 9 pgs.
"European Application Serial No. 04749597.3, Communication dated May 13, 2008", 5 pgs.
"European Application Serial No. 04749597.3, Office Action Nov. 20, 2006", 3 pgs.
"European Application Serial No. 04749597.3, Office Action dated Mar. 28, 2006", 9 pgs.
"European Application Serial No. 04749597.3, Office Action Received dated May 13, 2008", 5 pgs.
"European Application Serial No. 04749597.3, Response filed Sep. 6, 2007 to Office Action dated Nov. 20, 2006", 6 pgs.
"European Application Serial No. 04749597.3, Response filed Oct. 6, 2006 to Office Action dated Mar. 28, 2006", 28 pgs.
"European Application Serial No. 04749619.5 Office Action dated Nov. 9, 2009", 3 pgs.
"European Application Serial No. 04749619.5, Communication dated Apr. 14, 2008", 5 pgs.
"European Application Serial No. 04749619.5, Communication dated Sep. 13, 2007", 1 pg.
"European Application Serial No. 04749619.5, Communication Noting Loss of Rights dated Nov. 28, 2008", 1 pg.
"European Application Serial No. 04749619.5, Office Action dated Mar. 11, 2009", 4 pgs.
"European Application Serial No. 04749619.5, Office Action dated Mar. 28, 2006", 8 pgs.
"European Application Serial No. 04749619.5, Office Action dated Nov. 20, 2006", 4 pgs.
"European Application Serial No. 04749619.5, Response filed Feb. 6, 2009 to Communication dated Nov. 28, 2008", 14 pgs.
"European Application Serial No. 04749619.5, Response filed Sep. 7, 2007 to Office Action dated Nov. 20, 2006", 28 pgs.
"European Application Serial No. 04749619.5, Response filed Sep. 21, 2009 to Office Action dated Mar. 11, 2009", 19 pgs.
"European Application Serial No. 04749619.5, Response filed Oct. 4, 2007 to Communication dated Sep. 13, 2007", 3 pgs.
"European Application Serial No. 04749619.5, Response filed Oct. 17, 2006 to Office Action dated Mar. 28, 2006", 17 pgs.
"European Application Serial No. 04749619.5, Summons to Attend Oral Proceedings dated Jun. 16, 2010", 5 pgs.
"European Application Serial No. 05778984.4, Invitation pursuant to Article 94(3) dated Aug. 28, 2008", 5 pgs.
"European Application Serial No. 05778984.4, Response filed Feb. 26, 2009 to Communication dated Aug. 28, 2008", 21 pgs.
"European Application Serial No. 06849005.1, Office Action dated Apr. 21, 2010", 10 Pgs.
"European Application Serial No. 06849005.1, Office Action dated May 15, 2009", 4 pgs.
"European Application Serial No. 06849005.1, Response filed Jan. 17, 2012 to Summons dated Nov. 14, 2011", 13 pgs.
"European Application Serial No. 06849005.1, Response filed Aug. 1, 2011 to Office Action dated Mar. 22, 2011", 16 pgs.
"European Application Serial No. 06849005.1, Response filed Nov. 1, 2010 to Office Action dated Apr. 21, 2010", 17 pgs.
"European Application Serial No. 06849005.1, Response filed Nov. 24, 2009 tp Office Action dated May 15, 2009", 16 pgs.
"European Application Serial No. 06849005.1, Summons dated Nov. 14, 2011", 16 pgs.
"European Application Serial No. 07075464.3, Office Action dated May 7, 2008", 6 pgs.
"European Application Serial No. 07075464.3, Office Action dated Sep. 29, 2009", 8 pgs.
"European Application Serial No. 07075464.3, Partial European Search Report dated Oct. 2, 2007", 13 pgs.
"European Application Serial No. 07075464.3, Response filed Feb. 26, 2009 to Communication dated May 7, 2008", 12 pgs.
"European Application Serial No. 17712339.5, Communication Pursuant to Article 94(3) EPC dated Aug. 20, 2019", 5 pgs.
"European Application Serial No. 17712339.5, Communication Pursuant to Article 94(3) EPC dated Oct. 20, 2020", 4 pgs.
"European Application Serial No. 17712339.5, Response filed Feb. 24, 2021 to Communication Pursuant to Article 94(3) EPC dated Oct. 20, 2020", 10 pgs.
"European Application Serial No. 17712339.5, Response Filed May 2, 2019 to Communication pursuant to Rules 161(2) and 162 EPC dated Oct. 23, 2018", 14 pgs.
"European Application Serial No. 17712339.5, Response filed Dec. 23, 2019 to Communication Pursuant to Article 94(3) EPC dated Aug. 20, 2019", 9 pgs.
"European Application Serial No. 99924404.9, Response filed Jun. 22, 2006 to Communication dated Feb. 27, 2006", 1 pg.
"European Application Serial No. 99924404.9, Communication dated Feb. 27, 2006", 3 pgs.
"European Application Serial No. 99924404.9, Communication Pursuant to Article 96(2) EPC dated Feb. 27, 2006", 3 pgs.
"European Application Serial No. 99924404.9, Communication Pursuant to Article 96(2) dated Jun. 18, 2003", 3 pgs.
"European Application Serial No. 99924404.9, EP Communication Pursuant to Article 96(2) EPC dated Oct. 7, 2004", 3 pgs.

(56) References Cited

OTHER PUBLICATIONS

"European Application Serial No. 99924404.9, Response filed Apr. 8, 2004 to Communication dated Feb. 3, 2004", 13 pgs.

"European Application Serial No. 99924404.9, Response filed Apr. 15, 2005 to Communication dated Oct. 7, 2004", 23 pgs.

"European Application Serial No. EP 07075464, Partial European Search Report dated Sep. 19, 2007", 12 pgs.

"European Application Serial No. 06849005.1, Office Action dated Mar. 22, 2011", 11 Pgs.

"Indian Application Serial No. 10078/DELNP/2015, First Examination Report dated Mar. 12, 2020", w/ English Translation, 8 pgs.

"International Application Serial No. PCT/US 00/15700, International Search Report dated Dec. 21, 2000", 9 pgs.

"International Application Serial No. PCT/US 00/15700, Written Opinion dated Aug. 1, 2001", 7 pgs.

"International Application Serial No. PCT/US00/15700, International Preliminary Examination Report dated Sep. 20, 2001", 7 pgs.

"International Application Serial No. PCT/US00/27863, International Search Report dated Mar. 19, 2001", 8 pgs.

"International Application Serial No. PCT/US00/27863, Written Opinion dated Sep. 24, 2001", 7 pgs.

"International Application Serial No. PCT/US02/21926, International Search Report dated Sep. 11, 2003", 8 pgs.

"International Application Serial No. PCT/US02/21926, PCT International Search Report dated Sep. 11, 2003", 8 pgs.

"International Application Serial No. PCT/US02/21926, Written Opinion dated Jul. 14, 2004", 5 pgs.

"International Application Serial No. PCT/US2004/009950, International Preliminary Report on Patentability dated Mar. 31, 2003", 15 pgs.

"International Application Serial No. PCT/US2004/009950, International Preliminary Report on Patentability dated Oct. 13, 2005", 15 pgs.

"International Application Serial No. PCT/US2004/009950, International Search Report dated Mar. 8, 2005", 8 pgs.

"International Application Serial No. PCT/US2004/009950, Written Opinion dated Mar. 8, 2005", 15 pgs.

"International Application Serial No. PCT/US2004/010045, International Preliminary Report on Patentability dated Oct. 13, 2005", 14 pgs.

"International Application Serial No. PCT/US2004/010045, International Search Report dated Jan. 10, 2005", 6 pgs.

"International Application Serial No. PCT/US2004/010045, Written Opinion dated Jan. 10, 2005", 15 pgs.

"International Application Serial No. PCT/US2005/015315, International Search Report dated Feb. 2, 2007", 7 pgs.

"International Application Serial No. PCT/US2005/015315, International Search Report dated Feb. 7, 2007", 7 pgs.

"International Application Serial No. PCT/US2005/015315, Invitation to Pay Additional Fees and Partial Search Reportt", 6 pgs.

"International Application Serial No. PCT/US2005/015315, Written Opinion dated Feb. 7, 2007", 10 pgs.

"International Application Serial No. PCT/US2006/049424, International Preliminary Report on Patentability dated Jul. 10, 2008", 17 pgs.

"International Application Serial No. PCT/US2006/049424, International Search Report dated Nov. 26, 2007", 11 pgs.

"International Application Serial No. PCT/US2006/049424, Written Opinion dated Nov. 26, 2007", 17 pgs.

"International Application Serial No. PCT/US2007/010434, International Search Report dated Oct. 10, 2007", 11 pgs.

"International Application Serial No. PCT/US2007/010434, International Search Report dated Dec. 5, 2007", 11 pgs.

"International Application Serial No. PCT/US2007/010434, Written Opinion dated Dec. 5, 2007", 19 pgs.

"International Application Serial No. PCT/US2017/021124, International Preliminary Report on Patentability dated Sep. 20, 2018", 7 pgs.

"International Application Serial No. PCT/US2017/021124, International Search Report dated May 22, 2017", 6 pgs.

"International Application Serial No. PCT/US2017/021124, Written Opinion dated May 22, 2017", 5 pgs.

"International Application Serial No. PCT/US2018/013634, International Preliminary Report on Patentability dated Jul. 25, 2019", 12 pgs.

"International Application Serial No. PCT/US2018/013634, International Search Report dated Jun. 18, 2018", 9 pgs.

"International Application Serial No. PCT/US2018/013634, Invitation to Pay Add'l Fees and Partial Search Report dated Apr. 17, 2018", 14 pgs.

"International Application Serial No. PCT/US2018/013634, Written Opinion dated Jun. 18, 2018", 12 pgs.

"International Application Serial No. PCT/US2019/022106, International Preliminary Report on Patentability dated Sep. 24, 2020", 10 pgs.

"International Application Serial No. PCT/US2019/022106, International Search Report dated Sep. 12, 2019", 8 pgs.

"International Application Serial No. PCT/US2019/022106, Invitation to Pay Additional Fees dated Jul. 17, 2019", 10 pgs.

"International Application Serial No. PCT/US2019/022106, Written Opinion dated Sep. 12, 2019", 8 pgs.

"International Application Serial No. PCT/US2020/028264, International Preliminary Report on Patentability dated Oct. 28, 2021", 10 pgs.

"International Application Serial No. PCT/US2020/028264, International Search Report dated Aug. 5, 2020", 7 pgs.

"International Application Serial No. PCT/US2020/028264, Written Opinion dated Aug. 5, 2020", 8 pgs.

"International Application Serial No. PCT/US2020/028269, International Preliminary Report on Patentability dated Oct. 28, 2021", 9 pgs.

"International Application Serial No. PCT/US2020/028269, International Search Report dated Aug. 7, 2020", 7 pgs.

"International Application Serial No. PCT/US2020/028269, Written Opinion dated Aug. 7, 2020", 7 pgs.

"International Application Serial No. PCT/US2021/039860, International Search Report dated Jan. 24, 2022", 12 pgs.

"International Application Serial No. PCT/US2021/039860, Invitation to Pay Additional Fees dated Nov. 29, 2021", 20 pgs.

"International Application Serial No. PCT/US2021/039860, Written Opinion dated Jan. 24, 2022", 15 pgs.

"International Application Serial No. PCT/US99/11197, International Search Report dated Sep. 22, 1999", 9 pgs.

"International Application Serial No. PCT/US99/11197, Written Opinion dated Mar. 13, 2000", 11 pgs.

"Israel Application Serial No. 241954, Office Action dated Dec. 5, 2019", w/ English Translation, 6 pgs.

"Israel Application Serial No. 241954, Response filed Feb. 7, 2019 to Office Action dated Oct. 9, 2018", w/ English Translation, 14 pgs.

"Israel Application Serial No. 261642, Notification of Defects in Patent Application dated Dec. 26, 2021", w/ English Translation, 8 pgs.

"Japanese Application Serial No. 2000-549752, Notice of Rejection dated Feb. 10, 2009", (w/ English Translation), 10 pgs.

"Japanese Application Serial No. 2001-501645, Office Action dated Jun. 8, 2010", With English Claims, 4 pgs.

"Japanese Application Serial No. 2001-501645, Office Action Response filed Dec. 7, 2010", 8 pgs.

"Japanese Application Serial No. 2001-528616, Office Action dated Jun. 8, 2010", 4 pgs.

"Japanese Application Serial No. 2006-509588, Office Action dated Mar. 2, 2010", With English Translation, 14 pgs.

"Japanese Application Serial No. 2008-548723, Office Action dated Apr. 3, 2012", (w/ English Translation), 9 pgs.

"Japanese Application Serial No. 2016-507610, Notification of Reasons for Refusal dated Jan. 24, 2019", w/ English translation, 6 pgs.

"Japanese Application Serial No. 2016-507610, Response filed Mar. 6, 2019 to Notification of Reasons for Refusal dated Jan. 24, 2019", with machine Translation, 10 pgs.

"Japanese Application Serial No. 501645/01, Preliminary Amendment filed May 31, 2007", 12 pgs.

(56) References Cited

OTHER PUBLICATIONS

"Japanese Application Serial No. 501645/01, Response filed Jan. 10, 2012 to Final Office Action dated Sep. 29, 2011", 11 pgs.
"Japanese Application Serial No. 50164501—Final Rejection filed Sep. 6, 2011", 6 pgs.
"Japanese Application Serial No. 509588/06, Final Office Action dated Nov. 16, 2010", 1 pg.
"Japanese Application Serial No. 511645/01, Final Office Action dated Sep. 6, 2011", 6 pgs.
"Japanese Application Serial No. JP2006-509588, Amended Claims filed Mar. 22, 2007", (w/ English Translation of Claims), 28 pgs.
"LDP-341", Millennium Pharmaceuticals, (Jul. 18, 2001) http://www.biospace.com/ct/detail.cfm?ClinicalID=266404, 1 page.
"Mexican Application Serial No. MX/a/2021Z012681, Office Action dated Nov. 16, 2021", with machine translation, 9 pgs.
"Mexican Application Serial No. MX/a/2021/012681, Response filed Mar. 9, 2022", with machine translation, 129 pgs.
"Mexican Application Serial No. MX/a/2021/012681, Voluntary Amendment filed Apr. 19, 2022", with English translation of claims, 10 pgs.
"Mexican Application Serial No. MX/a/2021/012682, Voluntary Amendment filed Apr. 19, 2022", with English translation of claims, 10 pgs.
"New Zealand Application Serial No. 713509, First Examiner Report dated Nov. 14, 2019", 7 pgs.
"PCT Application Serial No. PCT/US2005/015315, International Preliminary Report on Patentability, and Written Opinion, dated Feb. 28, 2007", (Feb. 28, 2007), 11 pages.
"PCT Application Serial No. PCT/US99/11197, Written Opinion dated Mar. 13, 2000", 11 pgs.
"Polymer Vectors Endosomal release and cytoplasmic delivery", Endosomal Release, http://web.bham.ac.uk/can4psd4/nonviral/endosome.html, (Jun. 3, 2001), 1.
"Product Data Sheet", Moravek Biochemicals, Inc., M-1535, Ritonavir, (Jul. 12, 2001), 1 page.
"Product Information", Sigma, Cyclosporin A, Sigma Product No. C3662, (Oct. 28, 1996), 3 pages.
"Product Information", Sigma, Bleomycin Sulfate, Sigma Prod. No. B5507, (Nov. 25, 1996), 2 pages.
"Proteasome Inhibitors", Peptides International, Inc., (Apr. 16, 2001), 1-2.
"South African Application Serial No. 2015/07946, Voluntary Amendment filed Jul. 24, 2020", 21 pgs.
"Tannic Acid, A.C.S. reagent", Sigma, (Jan. 20, 2001) www.sigma-aldrich.com/sacatolog.nsf/productlookup/Aldrich403040?OpenDocument, 1 page.
Abe, Y, et al., "Cytotoxic mechanisms by M239V presenilin 2, a little-analyzed Alzheimer's disease-causative mutant", J. Neurosci Res. 77(4), Abstract Only, (Aug. 2004), 583-95.
Abramov, A. Y, et al., "Beta-amyloid peptides induce mitochondrial dysfunction and oxidative stress in astrocytes and death of neurons through activation of NADPH oxidase.", J Neurosci., 24(2), (Jan. 14, 2004), 565-75.
Abramov, A. Y., et al., "The role of an astrocytic NADPH oxidase in the neurotoxicity of amyloid beta peptides", Philosophical Transactions of The Royal Society B, 360, (2005), 2309-2314.
Adams, J., et al., "Proteasome inhibition: a new strategy in cancer treatment.", Invest New Drugs, 18(2), (May 2000), 109-21.
Adams, Julian, et al., "Chapter 28. Novel Inhibitors of the Proteasome and Their Theraputic Use in Inflammation", Annual Reports in Medicinal Chemistry, Academic Press, Inc., (1996), 279-288.
Adams, Julian, "Proteasome inhibition: a novel approach to cancer therapy", Trends in Molecular Medicine, 8(4), (2002), S49-S54.
Afione, S. A., et al., "In Vivo Model of Adeno-Associated Virus Vector Persistence and Rescue", Journal of Virology, 70(5), (May 1996), 3235-3241.
Aitken, M L, et al., "A Phase I Study of Aerosolized Administration of tgAAVCF to Cystic Fibrosis Subjects with Mild Lung Disease", Hum Gene Ther 12, (2001), 1907-1916.

Alavijeh, Mohammad S, et al., "Drug Metabolism and Pharmacokinetics, the Blood-Brain Barrier, and Central Nervous Systems Drug Discovery", The Journal of the American Societ for Experimental NeuroTherapeutics vol. 2, (Oct. 2005), 554-571.
Alexander, I E., et al., "Effects of Gamma Irradiation on the Transduction of Dividing and Nondividing Cells in Brain and Muscle of Rats by Adeno-Associated Virus Vectors", Human Gene Therapy, 7(7), (May 1, 1996), 841-850.
Alexander, Ian E., et al., "DNA-Damaging Agents Greatly Increase the Transduction of Nondividing Cells by Adeno-Associated Virus Vectors", Journal of Virology, 68(12), (Dec., 1994), 8282-8287.
Ali, R. R., et al., "Gene transfer into the mouse retina mediated by an adeno-associated viral vector", Human Molecular Genetics, 5 (5), (1996), 591-594.
Allander, Tobias, et al., "Cloning of a human parvovirus by molecular screening of respiratory tract samples", PNAS, 102(36), (2005), 12891-12896.
Almond, J. B., et al., "The proteasome: a novel target for cancer chemotherapy", Leukemia, 16, (2002), 443-443.
Andre, Patrice, et al., "An inhibitor of HIV-1 protease modulates proteasome activity, antigen presentation, and T cell responses.", Proc Natl Acad Sci U S A., 95(22), (Oct. 27, 1998), 13120-13124.
Arcamone, F M, "From the Pigments of the Actinomycetes to Third Generation Antitumor Anthracyclines", Biochimie (Paris), 80(3), (Mar. 1998), 201-206.
Arnold, John, et al., "Human Bocavirus Prevalence and Clinical Spectrum at a Childrens Hospital", Clin Infect Dis. 43, (2006), 283-288.
Audige, A., et al., "Epithelial sodium channel (ENaC) subunit mRNA and protein expression in rats with puromycin aminonucleoside-induced nephrotic syndrome.", Clincial Sci., 104(4), (2003), 389-395.
Auerbach, S. D., et al., "Human Amiloride-Sensitive Epithelial Na+ Channel y Subunit Promoter: Functional Analysis and Identification of a Polypurine-Polypyrimidine Tract With the Potential for Triplex DNA Formation", Biochem. J., 347, (2000), 105-114.
Baines, D. L., et al., "Effect of LPS-Induced NF-kB Activity on the Transcriptional Response of a 5' Flanking Region of the alphaENaC Gene", Experimental Biology 2003—Translating the Genome, Abstract No. 5860 (http://www.biosis-select.org/faseb/data/FASEB005860.html, (2003), 1 pg.
Banerjee, D., et al., "The Treatment of Respiratory Pseudomonas Infection in Cystic Fibrosis: What Drug and Which Way?", Drugs, 60(5), (Abstract Only), (Nov. 2000), 1 pg.
Bank, U., "Review: Peptidases and Peptidase Inhibitors in the Pathogenesis of Diseases", Cellular Peptidases in Immune Functions and Diseases 2, (Edited by Jurgen Langner, et al., Kluwer Academic / Plenum Publishers), (2000), 349-378.
Bartlett, J S., et al., "Targeted adeno-associated virus vector transduction of nonpermissive cells mediated by a bispecific F(ab'gamma)2 antibody.", Nature Biotechnology, 17, (1999), 181-186.
Bartlett, Jeffrey S., et al., "Infectious entry pathway of adeno-associated virus and adeno-associated virus vectors", Journal of Virology, 74(6), (Mar. 2000), 2777-2785.
Bartoli, M., et al., "Mannosidase I inhibition rescues the human alpha-sarcoglycan R77C recurrent mutation.", Hum Mol Genet., 17(9), (May 1, 2008), 1214-21.
Baruchel, S., et al., "The role of oxidative stress in disease progression in individuals infected by the human immunodeficiency virus.", J LeukocBiol., 52(1), (Jul., 1992), 111-4.
Basak, S, et al., "Infectious Entry Pathways for Canine Parvovirus", Virology, 186(2), (Feb. 1992), 368-376.
Bennett, J., et al., "Real-Time, Noninvasive In Vivo Assessment of Adeno-Associated Virus-Mediated Retinal Transduction", Investigative Ophthalmology & Visual Science, 38 (13), (Dec. 1997), 2857-2863.
Berns, K. I., et al., "Biology of Adeno-associated Virus", In: Current Topics in Microbiology and Immunology, 218, Springer-Verlag, Berlin: R.W. Compans, et al., (Eds.), (1996), 1-23.
Berns, K. I., "Parvovirus Replication", Microbiological Reviews, 54 (3), (Sep. 1990), pp. 316-329.
Beutler, K. T., et al., "Long-Term Regulation of ENaC Expression in Kidney by Angiotensin II", Hypertension, 41, (2003), 1143-1150.

(56) References Cited

OTHER PUBLICATIONS

Bies, J., et al., "Oncogenic activation of c-Myb by Carboxyl-Terminal truncation leads to Decreased Proteolysis by the Ubiquitin-26S proteasome pathway", Oncogene, 14(2), Abstract, (Jan. 16, 1997), 1 page.
Billington, D., et al., "Dissection of hepatic receptor-mediated endocytic pathways using self-generated gradients of iodixanol (Optiprep).", Anal. Biochem., 258(8), (1998), 251-258.
Blits, B., et al., "Adeno-associated viral vector-mediated neurotrophin gene transfer in the injured adult rat spinal cord improves hind-limb function", Neuroscience,118(1), (2003), 271-81.
Bohenzky, R. A., et al., "Interactions Between the Termini of Adeno-Associated Virus DNA", Journal of Molecular Biology, 206, (1989), 91-100.
Bohenzky, R. A., et al., "Replication of Adeno-Associated Virus Genomes With Chimeric Termini", ICN / UCLA Symposium—Viral DNA Replication, (1987), 20 pgs.
Bohenzky, R. A., et al., "Sequence and Symmetry Requirements Wihtin the Internal Palindromic Sequences of the Adeno-Associated Virus Terminal Repeat", Virology, 166, (1988), 316-327.
Bohl, D., et al., "Control of erythropoietin delivery by doxycycline in mice after intramuscular injection of adeno-associated vector.", Blood, 92(5), (1998), 1512-1517.
Bok, D., "Gene Therapy of Retinal Dystrophies: Achievements, Challenges and Prospects", Novartis Foundation Symposium 255—Retinal Dystrophies: Functional Genomics to Gene Therapy, John Wiley & Sons, Ltd., (2004), 4-16; 177-178.
Bokkala, Shaila, et al., "Angiotensin II-induced Down-regulation of Inositol Trisphosphate Receptors in WB Rat Liver Epithelial Cells", Journal of Biological Chemistry, 272(19), (May 9, 1997), 12454-12461.
Bonacorsi, Stephane, et al., "Comparative in vitro activities of meropenem, imipenem, temocillin, piperacillin, and ceftazidime in combination with tobramycin, rifampin, or ciprofloxacin against Burkholderia cepacia isolates from patients with cystic fibrosis.", Antimicrobial Agents and Chemotherapy, 43(2), (Feb., 1999), 213-217.
Booth, R. E., et al., "Targeted Degradation of ENaC in Response to PKC Activation of the ERK1/2 Cascade", Am. J. Physiol. Renal Physiol., 284, (2003), F938-F947.
Brand, Stephen, et al., "Role of the proteasome in rat indomethacin-induced gastropathy", Gastroenterology, 116(4), (1999), 865-873.
Bravo, Laura, "Polyphenols: chemistry, dietary sources, metabolism, and nutritional significance", Nutrition Reviews, 56(11), (Nov., 1998), 317-333.
Brister, J. R., et al., "Rep-Mediated Nicking of the Adeno-Associated Virus Origin Requires Two Biochemical Activities, DNA Helicase Activity and Transesterification", Journal of Virology, 73(11), (1999), 9325-9336.
Brooijmans, N., et al., "Molecular Recognition And Docking Algorithms", Annu. Rev. Biophys. Biomol. Struct., vol. 32, (2003), 335-373.
Brotz, H., "The Lantibiotic Mersacidin Inhibits Peptidoglycan Biosynthesis and the Level of Transglycosylation", Eur. J. Biochem., 246(1), (1997), 193-199.
Bruno, T., et al., "Levels of Expression of hRPB11, a core subassembly subunit of human RNA polymerase II, affect doxorubicin sensitivity and cellular differentiation", FEBS Letters 427, (1998), 241-246.
Bubien, J. K., et al., "Expression and regulation of normal and polymorphic epithelial sodium channel by human lymphocytes", J. Biol. Chem., 276(11), (2001), 8557-8566.
Buffinton, G. D, et al., "Oxidative stress in lungs of mice infected with influenza A virus", Free Radic Res Commun., 16(2), (1992), 99-110.
Bugg, C., et al., "SRI6975 Increases Adenovirus Mediated Gene Transfer Through the Apical Surface of Polarized MDCK Cell Monolayers", Cystic Fibrosis Foundation: 2000 North American CF Conference, (Nov. 2000), 1.
Cai, J., et al., "Inhibition of influenza infection by glutathione.", Free Radic Biol Med., 34(7), (Apr. 1, 2003), 928-36.
Cameron, "Recent Advance in Transgenic Technology", Molec. Biol. Vol 7, (1997), 253-265.
Cantin, Andre M, et al., "Aerosolized Prolastin Suppresses Bacterial Proliferation in a Model of Chronic Pseudomonas aeruginosa Lung Infection", American Journal of Respiratory and Critical Care Medicine, vol. 160, (1999), 1130-1135.
Capecchi, M. R, "Altering the Genome by Homologous Recombination", Science, (244), (1989), 1288-1292.
Carter, B. J., et al., "Chapter 11—Aav Dna Replication, Integration, and Genetics", In: Handbook of Parvoviruses, vol. 1., Tijssen, P., Editor, CRC Press, Inc. (Boca Raton, FL), (1992), 169-226.
Carter, Brian J, "Adeno-Associated Virus Vectors in Clinical Trials", Human Gene Therapy, 16(5), (2005), 541-550.
Carter, P. J., et al., "Adeno-Associated Viral Vectors as Gene Delivery Vehicles (Review)", International Journal of Molecular Medicine, 6(1), (2000), 17-27.
Cassivi, et al., "Transgene Expression After Adenovirus-Mediated Retransfection of Rat Lungs Is Increased and Prolonged by Transplant Immunosuppression", The Journal of Thoracic and Cardiovascular Surgery, Mosby-Year Book, Inc., St. Louis, MO, US, vol. 117, No. 1, (Jan. 1, 1999), 1-7.
Chao, H., et al., "Several Log Increase in Therapeutic Transgene Delivery by Distinct Adeno-Associated Viral Serotype Vectors", Molecular Therapy, 2(6), (2000), 619-623.
Chiorini, J. A., et al., "Cloning and Characterization of Adeno-Associated Virus Type 5", Journal of Virology, 73(2), (1999), 1309-1319.
Chiorini, J. A., et al., "Determination of Adeno-Associated Virus Rep68 and Rep78 Binding Sites by Random Sequence Oligonucleotide Selection", Journal of Virology, 69(11), (1995), 7334-7338.
Chiorini, J. A., et al., "Sequence Requirements for Stable Binding and Function of Rep68 on the Adeno-Associated Virus Type 2 Inverted Terminal Repeats", Journal of Virology, 68(11), (1994), 7448-7457.
Chu, Q, et al., "Binding and uptake of Cationic Lipid: pDNA Complexes by Polarized Airway Epithelial Cells", Human Gene Therapy, 10, (1999), pp. 25-36.
Chung, King-Thom, et al., "Tannis and Human Health: A Review", Critical Reviews in Food Science and Nutrition, 38(6), (1998), 421-464.
Cifuentes, M. E., et al., "Targeting reactive oxygen species in hypertension", Current Opinion in Nephrology and Hypertension, 15, (2006), 179-186.
Clark, J., et al., "A Future for Transgenic Livestock", Nature Reviews Genetics, 4, (2003), 825-833.
Clark, K. R., et al., "Recombinant Adeno-Associated Viral Vectors Mediate Long-Term Transgene Expression in Muscle", Human Gene Therapy, 8, (Apr. 10, 1997), pp. 659-669.
Conrad, C. K., et al., "Safety of single-dose administration of an adeno-associated virus (AAV)-CFTR vector in the primate lung", Gene Therapy, 3(8), (Aug. 1996), 658-668.
Cooney, Ashley, et al., "Cystic Fibrosis Gene Therapy: Looking Back, Looking Forward", Genes, vol. 9, No. 11, (Nov. 7, 2018).
Coonrod, A, et al., "On the mechanism of DNA transfection: efficient gene transfer without viruses", Gene Therapy, 4(12), (1997), 1313-1321.
Croyle, Maria, et al., "Development of novel formulations that enhance adenoviral-mediated gene expression in the lung in vitro and in vivo.", Molecular Therapy, 4(1), (Jul. 2001), 22-28.
Denby, L., et al., "Adeno-associated virus (AAV)-7 and -8 poorly transduce vascular endothelial cells and are sensitive to proteasomal degradation.", Gene Ther., 12(20), (Oct., 2005), 1534-8.
Desai, Shyamal, et al., "Ubiquitin-dependent Destruction of Topoisomerase I Is Stimulated by the Antitumor Drug Camptothecin", Journal of Biological Chemistry, 272(39), (Sep. 26, 1997), 24159-24164.
Dietrich, Cornelia, et al., "p53-dependent cell cycle arrest induced by N-acetyl-L-leucinyl-L-leucinyl-L-norleucinal in platelet-derived growth factor-stimulated human fibroblasts.", Proc Natl Acad Sci U S A., 93(20), (1996), 10815-10819.

(56) References Cited

OTHER PUBLICATIONS

Ding, W., et al., "Second-Strand Genome Conversion of Adeno-Associated Virus Type 2 (AAV-2) and AAV-5 is Not Rate Limiting Following Apical Infection of Polarized Human Airway Epithelia", Journal of Virology, 77(13), (2003), 7361-7366.
Ding, Wei, et al., "Proteasome Inhibitor LLnL (MG101) Augments AAV5 Transduction in Polarized Human Airway Epithelia", American Society of Gene Therapy, Abstracts of Scientific Presentations-Abstract No. 571, (Jun. 5, 2002), 1 page.
Dishart, Kate, et al., "Recombinant Adeno-Associated Virus-2 as a Candidate Gene Delivery Vector for Vein Grafts", American Society of Gene Therapy, Abstracts of Scientific Presentations-Abstract No. 1107, (Jun. 5, 2002), 1 page.
Djaldetti, M., et al., "SEM observations on the effect of anthracycline drugs on cultured newborn rat cardiomyocytes (Abstract Only)", Basic Res Cardiol., vol. 6, (1988), 627-7.
Doll, R. F, et al., "Comparison of promoter strengths on gene delivery into mammalian brain cells using AAV vectors", Gene Therapy, 3(5), (1996), 437-447.
Dollard, S. C, et al., "Enhanced responsiveness to nuclear factor kappa B contributes to the unique phenotype of simian immunodeficiency virus variant SIVsmmPBj14.", J Virol., 68(12), (Dec., 1994), 7800-9.
Donaldson, S. H., et al., "Regulation of the Epithelial Sodium Channel by Serine Proteases in Human Airways", The Journal of Biological Chemistry, 277(10), (2002), 8338-8345.
Dou, Q. P, et al., "Proteasome inhibitors as potential novel anticancer agents", Drug Resist Updat., 2(4), (Aug., 1999), 215-223.
Douar, A., et al., "Intracellular trafficking of adeno-associated virus vectors: routing to the late endosomal compartment and proteasome degradation.", J Virol., 75(4), (Feb., 2001), 1824-33.
Douar, Anne-Marie, et al., "Intracellular Trafficking of Adeno-Associated Virus Vectors: Routing to the Late Endosomal Compartment and Proteasome", Journal of Virology, Feb. 2011, p. 1824-1833; vol. 75, No. 4, 1824-1833.
Droge, W., et al., "HIV-induced cysteine deficiency and T-cell dysfunction—a rationale for treatment with N-acetylcysteine", Immunol Today., 13(6), (Jun., 1992), 211-4.
Duan, D, et al., "Response to "Polarity Influences the Efficiency of Recombinant Adenoassociated Virus Infection in Differentiated Airway Epithelia"", Human Gene Therapy, 10, (1999), 1553-1557.
Duan, D., "A New Dual-Vector Approach to Enhance Recombinant Adeno-Associated Virus-Mediated Gene Expression Through Intermolecularcis Activation", Nature Medicine, 6(5), (2000), 595-598.
Duan, D., et al., "Chapter 15: Trans-Splicing Vectors Expand the Packaging Limits of Adeno-Associated Virus for Gene Therapy Applications", Methods in Molecular Medicine, vol. 76: Viral Vectors for Gene Therapy: Methods and Protocols, (2003), 287-307.
Duan, D., et al., "Chapter 3—Adeno-Associated Virus", In: Lung Biology in Health and Disease, vol. 169—Gene Therapy in Lung Disease, Albelda, S. M., Editor, Marcel Dekker, Inc., (2002), 51-92.
Duan, D., et al., "Chapter 3—Dual Vector Expansion of the Recombinant AAV Packaging Capacity", In: Methods in Molecular Biology, vol. 219: Cardiac Cell and Gene Transfer, Metzger, J. M., Editor, Human Press, Inc., Totowa, NJ, (2003), 29-51.
Duan, D., "Consequences of DNA-Dependent Protein Kinase Catalytic Subunit Deficiency on Recombinant Adeno-Associated Virus Genome Circularization and Heterodimerization in Muscle Tissue", Journal of Virology, 77(8), (2003), 4751-4759.
Duan, D., et al., "Endosomal processing limits gene transfer to polarized airway epithelia by adeno-associated virus", J Clin Invest., 105(11), (Jun., 2000), 1573-87.
Duan, D., et al., "Enhancement of Muscle Gene Delivery with Pseudotyped Adeno-Associated Virus Type 5 Correlates With Myoblast Differentiation", Journal of Virology, 75(16), (2001), 7662-7671.
Duan, D., et al., "Expanding AAV Packaging Capacity with Trans-splicing or Overlapping Vectors: A Quantitative Comparison", Molecular Therapy, 4(4), http://www.idealibrary.com, (2001), 383-391.
Duan, D., "Formation of Adeno-Associated Virus Circular Genomes is Differentially Regulated by Adenovirus E4 ORF6 and E2a Gene Expression", Journal of Virology, 73(1), (Jan. 1999), 161-169.
Duan, D., "Polarity Influences the Efficiency of Recombinant Adenoassociated Virus Infection in Differentiated Airway Epithelia", Human Gene Therapy, 9, (Dec. 10, 1998), 2761-2776.
Duan, D., et al., "Structural and Functional Heterogeneity of Integrated Recombinant AAV Genomes", Virus Research, 48(1), (Jan. 1997), 41-56.
Duan, Dongsheng, et al., "Circular intermediates of recombinant adeno-associated virus have defined structural characteristics responsible for long-term episomal persistence in muscle tissue", Journal of Virology, 72(11), (Nov., 1998), 8568-77.
Duan, Dongsheng, et al., "Dynamin is required for recombinant adeno-associated virus type 2 infection", Journal of Virology, 73(12), (Dec. 1999), 10371-10376.
Duan, Dongsheng, et al., "Polarity Influences the Efficiency of Recombinant Adenoassociated Virus Infection in Differentiated Airway Epithelia", Human Gene Therapy vol. 9, (Dec. 1998), 2761-2776.
Duan, Dongsheng, et al., "Structural Analysis of adeno-associated virus transduction circular intermediates", Virology, 261(1), (Aug. 15, 1999), 8-14.
Ecelbarger, C. A., et al., "Regulation of the Abudance of Renal Sodium Transporters and Channels by Vasopressin", Experimental Neurology, 171, (2001), 227-234.
Eck, Stephen L, et al., "Chapters: Gene-Based Therapy", Goodman & Gilman's The Pharmacological Basis of Therapeutics, 9th Edition, McGraw-Hill, New York, NY, (1996), 77-101.
Elliott, P J, et al., "Recent Advances in Understanding Proteasome Function", Current Opinion in Drug Discovery and Development, 5 (2), ISSN: 1367-6733, (1999), 484-490.
Elmarakby, A., et al., "NADPH oxidase inhibition attenuates oxidative stress but not hypertension produced by chronic ET-1", Hypertension, 45(2), (Feb., 2005), 283-7.
Engelhardt, J., et al., "Adeno-Associated Virus Vectors", U.S. Appl. No. 60/086,166 filed May 20, 1998.
Engelhardt, J., et al., "Compounds and Methods for Pharmico-Gene Therapy of Epithelial Sodium Channel Associated Disorders", U.S. Appl. No. 10/815,557 filed Mar. 31, 2004, 137 pgs.
Engelhardt, J., et al., "Compounds and Methods to Enhance Adenoassociated Virus Transduction", U.S. Appl. No. 60/138,188 filed Jun. 8, 1999, (Jun. 8, 1999), 102 pgs.
Engelhardt, J., et al., "Compounds and Methods To Enhance rAAV Transduction", U.S. Appl. No. 10/815,262 filed Mar. 31, 2004, 156 pgs.
Engelhardt, J. F., et al., "Direct gene transfer of human CFTR into human bronchial epithelia of xenografts with E1-deleted adenoviruses", Nature Genetics, 4(1), (1993), 27-34.
Engelhardt, J. F., "The Lung as a Metabolic Factory for Gene Therapy", The Journal of Clinical Investigation, 110(4), (2002), 429-432.
Engelhardt, John, et al., "Adeno-Associated Virus Vectors", U.S. Appl. No. 09/276,625 filed Mar. 25, 1999, (Mar. 25, 1999), 122 pgs.
Engelhardt, John, et al., "Adeno-Associated Virus Vectors", U.S. Appl. No. 10/054,665 filed Jan. 22, 2002, 138 pgs.
Engelhardt, John, et al., "Compounds and Methods To Enhance Adenoassociated Virus Transduction", U.S. Appl. No. 60/138,188 filed Jun. 8, 1999.
Engelhardt, John, et al., "Compounds and Methodsd to Enhance Adenoassociated Virus Transduction", U.S. Appl. No. 60/201,089 filed May 2, 2000.
Engelhardt, John, et al., "Enhancement of Muscle Gene Delivery With Pseudotyped AAV-5 Correlates With Myoblast Differentiation", U.S. Appl. No. 60/305,204 filed Jul. 13, 2001.
Englehardt, John, et al., "Adeno-Associated Virus Vectors and Uses Thereof", U.S. Appl. No. 09/684,554 filed Oct. 6, 2000, 141 pgs.
Englehardt, John, "Compounds and Methods for Pharmico-Gene Therapy of Epithelial Sodium Channel Associated Disorders", U.S. Appl. No. 60/512,347 filed Oct. 16, 2003.
Englehardt, John, et al., "Compounds and Methods To Enhance rAAV Transduction", U.S. Appl. No. 60/459,323 filed Mar. 31, 2003.

(56) References Cited

OTHER PUBLICATIONS

Englehardt, John, et al., "Compounds and Methods To Enhance rAAV Transduction", U.S. Appl. No. 09/689,136 filed Oct. 12, 2000, (, 138 pgs.
Englehardt, John, et al., "Pseudotyped Adeno-Associated Viruses and Uses Thereof", U.S. Appl. No. 10/194,421 filed Jul. 12, 2002.
Everett, R D., et al., "A viral activator of gene expression functions via the ubiquitin-proteasome pathway", The EMBO Journal, 17 (24), (1998), pp. 7161-7169.
Excoffon, Katherine J. D. A, et al., "Directed Evolution of Adeno-Associated Virus to an Infectious Respiratory Virus", Proceedings of the National Academy of Sciences, vol. 106, No. 10, (Mar. 10, 2009), 3865-3870.
Fakhiri, Julia, et al., "Novel Chimeric Gene Therapy Vectors Based on Adeno-Associated Virus and Four Different Mammalian Bocaviruses", Molecular Therapy: Methods & Clinical Development vol. 12, (Mar. 2019), 202-222.
Fallin, R. A., et al., "PMA-lnduced Inhibition of Amiloride-Sensitive Sodium Absorption is Partially Mediated by ERK1/2 Activation", The FASEB Journal, 17(5) (Abstracts Part II), Abstract No. 585-19, (2003), A915.
Fasbender, Al, et al., "Complexes of adenovirus with polycationic polymers and cationic lipids increase the efficiency of gene transfer in vitro and in vivo", The Journal of Biological Chemistry, 272 (10), (Mar. 7, 1997), 6479-6489.
Fasbender, Al, et al., "Complexes of Adenovirus with Polycationic Polymers and Cationic Lipids Increase the Efficiency of Gene Transfer in Vitro and in Vivo", Journal of Biological Chemistry vol. 272, No. 10, (Mar. 1997), 6479-6489.
Fayadat, Laurence, et al., "Degradation of Human Thyroperoxidase in the Endoplasmic Reticulum Involves Two Different Pathways Depending on the Folding State of the Protein", Journal of Biological Chemistry, 275(21), (May 26, 2000), 15948-15954.
Fehilly, Carole B, et al., "Interspecific chimaerism between sheep and goat", Nature vol. 307, (Feb. 16, 1984.), 634-6.
Fenteany, G, et al., "Inhibition of proteasome activities and subunit-specific amino-terminal threonine modification by lactacystin", Science, 268(5211), (1995), 726-731.
Fenteany, Gabriel, et al., "Lactacystin, Proteasome Function, and Cell Fate", Journal of Biological Chemistry, 273(15), (Apr. 10, 1998), 8545-8548.
Ferrari, F K., et al., "Second-Strand Synthesis Is a Rate-Limiting Step for Efficient Transduction by Recombinant Adeno-Associated Virus Vectors", Journal of Virology, 70(5), (1996), 3227-3234.
Ferrari, Forrest, et al., "Second-Strand Synthesis Is a Rate-Limiting Step for Efficient Transduction by Recombinant Adneo-Associated Virus Vectors", Journal of Virology vol. 70, No. 5, (3227-3234), May 1996.
Figueiredo-Pereira, Maria E, et al., "The antitumor drug aclacinomycin A, which inhibits the degradation of ubiquitinated proteins, shows selectivity for the chymotrypsin-like activity of the bovine pituitary 20 S proteasome", Journal of Biological Chemistry, 271(28), (Jul. 12, 1996), 16455-16459.
Finn, J. D, et al., "Proteasome inhibitors decrease AAV2 capsid derived peptide epitope presentation on MHC class I following transduction", Mol Ther., 18(1), (Jan., 2010), 135-42.
Finn, Jonathan D., et al., "Proteasome Inhibitors Decrease AAV2 Capsid-Derived Peptide Epitope Presentation on MHC Class I Following Transduction", Molecular Therapy vol. 18 No. 1, 135-142 Jan. 2010, (Jan. 1, 2010), 135-142.
Fisher, K J., et al., "Transduction with recombinant adeno-associated virus for gene therapy is limited by leading-strand synthesis", Journal of Virology, 70(1), (Jan., 1996), 520-532.
Fisher, Krishna, et al., "Recombinant adeno-associated virus for muscle directed gene therapy", Nature Medicine, 3(3), (Mar., 1997), 306-312.
Fisher, Krishna, et al., "Transduction with Recombinant Adeno-Associated Virus for Gene Therapy is Limited by Leading-Strand Synthesis", Journal of Virology vol. 70, No. 5, (1996), 520-532.

Fisher-Adams, G., et al., "Integration of Adeno-Associated Virus Vectors in CD34+ Human Hematopoietic Progenitor Cells After Transduction", Blood, 88 (2), (Jul. 15, 1996), pp. 492-504.
Flotte, T., et al., "A Phase I Study of an Adeno-Associated Virus-CFTR Gene Vector in Adult CF Patients With Mild Lung Disease", Human Gene Therapy, 7(9), (1996), 1145-1159.
Flotte, T. R., et al., "Adeno-Associated Virus Vector Gene Expression Occurs in Nondividing Cells in the Absence of Vector DNA Integration", American Journal of Respiratory Cell and Molecular Biology, 11, (1994), pp. 517-521.
Flotte, T. R., et al., "Chapter 40—Adeno-Associated Viral Vectors for CF Gene Therapy", In: Methods in Molecular Medicine, 70, (2002), 599-608.
Flotte, T. R., "Expression of the Cystic Fibrosis Transmembrane Conductance Regulator from a Novel Adeno-Associated Virus Promoter", The Journal of Biological Chemistry, 268(5), (1993), 3781-3790.
Furst, R., et al., "Atrial natriuretic peptide induces mitogen-activated protein kinase phosphatase-1 in human endothelial cells via Rac1 and NAD(P)H oxidase/Nox2-activation", Circ Res., 96(1), (Jan. 7, 2005), 43-53.
Gabizon, Alberto, "Long-circulating liposomes fordrug delivery in cancer therapy: a review of biodistribution studies in tumor-bearing animals", Advanced Drug Delivery Reviews, (1997), 337-344.
Gabizon, Alberto, et al., "Preclinical Studies with Doxorubicin Encapsulated in Polyethyleneglycol-Coated Liposomes", Journal of Liposome Research, 3(3), (1993), 517-528.
Gadallah, M. F., et al., "Epithelial Sodium Channel-Dependent Hyptertension: An Emerging Syndrome", Journal of the American Society of Nephrology, 10 (Abstracts Issue), Abstract No. A1842, (1999), 365A.
Gadallah, M. F., et al., "Preservation of Renal Function in Patients With Hypertension and Chronic Renal Impairment; Revisited", Journal of the American Society of Nephrology, 10 (Abstracts Issue), Abstract No. A1841, (1999), 365A.
Gao, H., et al., "Critical Role for microglial NADPH Oxidase in Rotenone-induced degeneration of Dopaminergic Neurons", Journal of Neuoscience; 23(15), (Jul. 16, 2003), 6181-6187.
Gao, H. M, et al., "Critical role of microglial NADPH oxidase-derived free radicals in the in vitro MPTP model of Parkinson's disease", FASEB J., 17(13), (Oct., 2003), 1954-6.
Gao, H. M, et al., "Novel anti-inflammatory therapy for Parkinson's disease.", Trends Pharmacol Sci., 24(8), (Aug., 2003), 395-401 pgs.
Gao, Hui-Ming, et al., "Distinct Role for Microglia in Rotenone-Induced Degeneration of Dopaminergic Neurons", Journal of Neuroscience 22(3), (Feb. 1, 2002), 782-790.
Garber, Ken, "Taking Garbage In, Taking Cancer Out?", Science, vol. 295, (Jan. 25, 2002), 612-613.
Ginn, S. L., et al., "Gene therapy clinical trials worldwide to 2012—an update.", J Gene Med, 15(2), (2013), 65-77.
Giraud, C, et al., "Recombinant Junctions Formed by Site-Specific Integration of Adeno-Associated Virus Into an Episome", Journal of Virology, 69(11), (1995), 6917-6924.
Giraud, Catherine, et al., "Recombinant junctions formed by site-specific integration of adeno-associated virus into an episome", Journal of Virology, 69 (11), (Nov., 1995), 6917-6924.
Goldberg, A L., et al., "New insights into proteasome function: from archaebacteria to drug development", Chemistry & Biology, 2(8), (1995), 503-508.
Goncalves, M. A, "Adeno-associated virus: from defective virus to effective vector", Virol J., 2, (May 6, 2005), 17 pgs.
Gormley, K., et al., "Regulation of the Epithelial Sodium Channel by Accessory Proteins", Biochem. J., 371, (2003), 1-14.
Gorvel, J. P, et al., "rab5 controls early endosome fusion in vitro.", Cell, 64(5), (Mar. 8, 1991), 915-25.
Gottlieb, T A., et al., "Actin Microfilaments Play a Critical Role in Endocytosis at the Apical but not the Basolateral Surface of Polarized Epithelial Cells", The Journal of Cell Biology, 120 (3), (1993), pp. 695-710.
Graham, J. M, et al., "Iodixanol—a new density gradient medium for the dissection of the endosomal compartment", Z Gastroenterol., 34 Suppl 3, (1996), 76-8.

(56) References Cited

OTHER PUBLICATIONS

Graham, J., "Purification of peroxisomes using a density barrier in a swinging-bucket rotor.", ScientificWorldJournal, 2, (May 22, 2002), 1400-3.
Graham, J., et al., "The preparation of subcellular organelles from mouse liver in self-generated gradients of iodixanol", Anal. Biochem., 220(2), (1994), 367-73.
Grimm, D., et al., "From Virus Evolution to Vector Revolution: Use of Naturally Occurring Serotypes of Adeno-Associated Virus (AAV) as Novel Vectors for Human Gene Therapy", Current Gene Therapy, 3, (2003), 281-304.
Gross, R., "Clinical problems of optimum bioavailability, in particular in cytostatic therapy (Abstract Only)", Arzneimittelforschung, vol. 26(1 A), (1976), 130-5.
Gruchala, Marcin, et al., "Adeno-Associated Virus-Mediated Gene Transfer into Normal Rabbit Arteries. Assessment of the Tie and CMV Promoters and the Antiproteasome Treatment with MG-132", American Society of Gene Therapy, Abstracts of Scientific Presentations-abstract No. 1110, (Jun. 5, 2002), 1 page.
Gruenberg, J, et al., "Membrane traffic in endocytosis: insights from cell-free assays.", Annu Rev Cell Biol., 5, (1989), 453-81.
Hagstrom, J. N., et al., "Improved Muscle-Derived Expression of Human Coagulation Factor IX From a Skeletal Actin/CMV Hybrid Enhancer/Promoter", Blood, 95(8), (2000), 2536-2542.
Halbert, C. L., "Transduction by Adeno-Associated Virus Vectors in the Rabbit Airway: Efficiency, Persistence, and Readministration", Journal of Virology, 71 (8), (Aug. 1997), pp. 5932-5941.
Hamilton, Bradley A, et al., "Polarized AAVR Expression Determines Infectivity by AAV Gene Therapy Vectors", Gene Therapy, Nature Publishing Group, London, GB, vol. 26, No. 6, (Apr. 8, 2019), 240-249.
Hansen, et al., "Impaired intracellular trafficking of adeno-associated virus type 2 vectors limits efficient transduction of murine fibroblasts", Journal of Virology, (Jan. 2000), 992-996.
Hansen, J., et al., "Adeno-Associated Virus Type 2-Mediated Gene Transfer: Altered Endocytic Processing Enhances Transduction Efficiency in Murine Fibroblasts", Journal of Virology, 75(9), (2001), 4080-4090.
Hansen, J., et al., "Impaired Intracellular Trafficking of Adeno-Associated Virus Type 2 Vectors Limits Efficient Transduction of Murine Fibroblasts", Journal of Virology, 74(2), (2000), 992-996.
Harraz, et al., "SOD1 mutations disrupt redox-sensitive Rac regulation of NADPH oxidase in a familial ALS model", The Journal of Clinical Investigation, vol. 118, No. 2, (Feb. 2008), 659-670.
Hasegawa, S., et al., "Microtubule Involvement in the Intracellular Dynamics for Gene Transfection Mediated by Cationic Liposomes", Gene Therapy, 8, (2001), 1669-1673.
Hashimoto, Y, et al., "Amino- and carboxyl-terminal mutants of presenilin 1 cause neuronal cell death through distinct toxic mechanisms: Study of 27 different presenilin 1 mutants", J Neurosci Res. 75(3), Abstract Only, (Feb. 2004), 417-28.
He, Y, et al., "Minocycline inhibits microglial activation and protects nigral cells after 6-hydroxydopamine injection into mouse striatum", Brain Res. 909(1-2), Abstract Only, (Aug. 2001), 187-93.
Hermonat, Paul, et al., "Use of adeno-associated virus as a mammalian DNA cloning vector: Transduction of neomycin resistance into mammalian tissue culture cells", Proc. Natl. Acad. Sci. USA, vol. 81, (Oct. 1984), 6466-6470.
Herzog, Roland W., et al., "Stable gene transfer and expression of human blood coagulation factor IX after intramuscular injection of recombinant adeno-associated virus", Proceedings of the National Academy of Sciences of the United States of America, 94, (May 1997), 5804-9.
Higgins, D. G., "Clustal: a package for performing multiple sequence alignment on a microcomputer.", Gene, 73(1), (Dec. 15, 1988), 237-44.
Higgins, D. G., "Fast and sensitive multiple sequence alignments on a microcomputer.", Comput Appl Biosci, 5(2), (Apr., 1989), 151-153.

Hong, J., et al., "Identification of SRI6975, A Compound that Enhances Adenovirus-Mediated Gene Expression in Polarized Epithelial Cells", Cystic Fibrosis Foundation: 2000 North American CF Conference, (Nov. 2000), 1-2.
Hosseini, Hassan, et al., "Protection against experimental autoimmune encephalomyelitis by a proteasome modulator", Journal of Neuroimmunology, 188, (2001), 233-244.
Houdebine, L., "Production of Pharmaceutical Proteins From Transgenic Animals", Journal of Biotechnology, vol. 34, France, (1994), 269-287.
Hsu, A., et al., "Ritonavir. Clinical pharmacokinetics and interactions with other anti-HIV agents", Clin Pharmacokinet, 35(6), abstract, (Dec. 1998), 1 page.
Hsy, Py, et al., "Effect of Polyethylenimine On Recombinant Adeno-associated Virus Mediated Insulin Gene Therapy", 1. J Gene Med. Oct. 2005;7(10):1311-21—School of Pharmacy, College of Medicine, National Taiwan University, 1, Jen-Ai Road, Section 1, Taipei 100 Taiwan, (Oct. 7, 2005), 1311-21.
Huang, L., et al., "Efficient lipofection with cisplatin-resistant human tumor cells", Cancer Gene Therapy, vol. 3, No. 2, (1996), 107-112.
Hummler, E., et al., "Genetic Disorders of Membrane Transport —V. The Epithelial Sodium Channel and its Implication in Human Diseases", American Journal of Physiology, Gastrointensinal and Liver Physiology, 276, (1999), G567-G571.
Hunziker, et al., "Review—Perspectives: toward a peptide-based vaccine against hepatitis C virus", Molecular Immunol, 38, (2001), 475-484.
Iqbal, Mohamed, et al., "Potent Inhibitors of Proteasome", Journal of Medicinal Chemistry, vol. 38, No. 13, (1995), 2276-2277.
Itani, O. A., et al., "Cycloheximide Increases Glucocorticoid-Stimulated alpha-ENaC mRNA in Collecting Duct Cells by p38 MAPK-dependent Pathway", Am. J. Physiol. Renal Physiol., 284, (2002), F778-F787.
Jennings, K., et al., "Proteasome inhibition enhances AAV-mediated transgene expression in human synoviocytes in vitro and in vivo", Mol Ther., 11(4), (Apr., 2005), 600-7.
Jensen, T J., et al., "Multiple Proteolytic Systems, Including the Proteasome, Contribute to CFTR Processing", Cell, 83, (1995), pp. 129-135.
Jiang, Q., et al., "Cellular Heterogenecity of CFTR Expression and Function in the Lung: Implications for Gene Therapy of Cystic Fibrosis", European Journal of Human Genetics, 6(1), (Jan. 1998), 12-31.
Jiang, Q., et al., "Cellular Heterogeneity of CFTR Expression and Function in the Lung: Implications for Gene Therapy of Cystic Fibrosis", European Journal of Human Genetics, 6, (Jan. 1998), 12-31.
Johannesson, T., et al., "[Neurodegenerative diseases, antioxidative enzymes and copper. A review of experimental research.]", Laeknabladid, 89(9), (Sep. 2003), 659-671.
Johnson, J. S., et al., "Enhancement of Adeno-Associated Virus Infection by Mobilizing Capsids into and Out of the Nucleolus", Journal of Virology, 83(6), (2009), 2632-2644.
Johnson, L. G, et al., "Efficiency of gene transfer for restoration of normal airway epithelial function in cystic fibrosis", Nature Genetics 2, (1992), 21-25.
Jorgensen, M. J., et al., "Expression of Completely y-Carboxylated Recombinant Human Prothrombin", The Journal of Biological Chemistry, 262(14), (1987), 6729-6734.
Kamynina, E., et al., "Concerted Action of ENaC, Nedd4-2, and Sgk1 in Transepithelial Na+ Transport", Am. J. Physiol. Renal Physiol., 283, (2002), F377-F387.
Kannan, R., et al., "Impairment of conjunctival glutathione secretion and ion transport by oxidative stress in an adenovirus type 5 ocular infection model of pigmented rabbits.", Free Radic Biol Med., 37(2), (Jul. 15, 2004), 229-38.
Kaplan, Johanne M., et al., "Potentiation of gene transfer to the mouse lung by complexes of adenovirus vector and polycations improves therapeutic potential", Human Gene Therapy, vol. 9, No. 10, XP000972242, (Jul. 1, 1998), 1469-1479.

(56) References Cited

OTHER PUBLICATIONS

Kaplitt, M. G., "Long-Term Gene Expression and Phenotypic Correction Using Adeno-Associated Virus Vectors in the Mammalian Brain", Nature Genetics, 8(2), (Oct. 1994), 148-154.
Kapoor, A., et al., "Human bocaviruses are highly diverse, dispersed, recombination prone, and prevalent enteric infections", J Infect Dis. 201(11), (Jun. 2010), 1633-1643.
Kappell, Catherine A., et al., "Regulating gene expression in transgenic animals", Current Opinion in Biotechnology vol. 3, (1992), 548-553.
Kapturczak, M. H, et al., "Adeno-Associated Virus (AAV) as a Vehicle for Therapeutic Gene Delivery : Improvements in vector Design and Viral Production Enhance Potential to prolong Graft Survival in Pancreatic Islet Cell Transplantation for the Reversal of Type I Diabetes", Current Molecular Medicine, (2001), 245-258.
Kay, M. A., et al., "Evidence for Gene Transfer and Expression of Factor IX in Haemophilia B Patients Treated With an AAV Vector", Nature Genetics, 24, (2000), 257-261.
Kazi, A., et al., "Inhibition of the Proteasome Activity, a Novel Mechanism Associated with the Tumor Cell Apoptosis-Inducing Ability of Genistein", Biochemical Pharmacology, 66, (2003), 965-976.
Kearns, W. G., et al., "Recombinant Adeno-Associated Virus (AAV-CFTR) Vectors do not Integrate in a Site-Specific Fashion in an Immortalized Epithelial Cell Line", Gene Therapy, 3, (1996), 748-755.
Kellenberger, et al., "Epithelial Sodium Channel/Degenerin Family of Ion Channels: A Variety fo Functions fora Shared Structure", Physiological Review, 82, (2002), 735-767.
Kessler, P D, et al., "Gene delivery to skeletal muscle results in sustained expression and systemic delivery of a therapeutic protein", Proceedings of the National Academy of Sciences of the United States of America, 93(24), (Nov. 26, 1996), 14082-7.
Kessler, P., et al., "Sodium Butyrate Greatly Enhances the efficiency of Viral Transduction in Adult Ventricular Cardiomyocytes by Adeno-associated Viral Vectors", Circulation 92(8), (Oct. 15, 1995), 296.
Kim, Koanhoi, "Proteasome Inhibitors Sensitize Human Vascular Smooth Muscle Cells to Fas (CD95)—Mediated Death", Biochemical and Biophysical Research Communications, vol. 281, No. 2, (2001), 305-310.
Kim, Kyung Bo, et al., "Proteasome Inhibition by the Natural Products Epoxomicin and Dihydroeponemycin: Insights into Specificity and Potency", Bioorganic & Medicinal Chemistry Letters, (1999), 3335-3340.
Kiyomiya, K., et al., "The role of the proteasome in apoptosis induced by anthracycline anticancer agents", Int. J. Oncol., 20(6), abstract, (Jun. 2002), 1 page.
Kiyomiya, K., et al., "The role of the proteasome in apoptosis induced by anthracycline anticancer agents.", Int J Oncol., 20(6), (Jun., 2002), 1205-9.
Kiyomiya, Ken-Ichi, et al., "Mechanism of specific nuclear transport of adriamycin: the mode of nuclear translocation of adriamycin-proteasome complex", Cancer Res., 61(6), (Mar. 15, 2001), 2467-71.
Kiyomiya, Ken-Ichi, "The role of the proteasome in apoptosis induced by anthracycline anticancer agents", International Journal of Oncology, 20(6), Preliminary Report on Patentability, (Jun., 2002), 1205-9.
Kiyomiya, K-I, et al., "Proteasome is a Carrier to Translocate Doxorubicin From Cytoplasm into Nucleus", Life Sciences, 62(20), (1998), 1853-1860.
Kloetzel, P M., "The Proteasome system: a neglected tool for improvement of novel therapeutic strategies?", Gene Therapy, 5, (1998), pp. 1297-1298.
Kotin, R. M., et al., "Characterization of a preferred site on human chromosome 19q for integration of adeno-associated virus DNA by non-homologous recombination", The EMBO Journal, 11 (13), (1992), pp. 5071-5078.

Kumar, Gita, "Side-stepping the side effects", BioCentury, The Bernstein Report on BioBusiness, (Dec. 17, 2001), 7.
Lambeth, J. D., "Nox enzymes and the biology of reactive oxygen", Nature Reviews, Immunology,4(3), (2004), 181-189.
Lebkowski, J., "Adeno-Associated Virus: a Vector System for Efficient Introduction and Integration of DNA into a Variety of Mammalian Cell Types", Molecular and Cellular Biology, 8(10), (Oct. 1988), 3988-3996.
Lechardeur, D., et al., "Intracellular Barriers to Non-Viral Gene Transfer", Curr. Gene Therapy, 2, (2002), 183-194.
Lee, D. H, et al., "Proteasome inhibitors: valuable new tools for cell biologists", Trends Cell Biol., 8(10), (Oct., 1998), 397-403.
Lee, Do Hee, et al., "Selective Inhibitors of the Proteasome-dependent and Vacuolar Pathways of Protein Degradation in *Saccharomyces cerevisiae*", Journal of Biological Chemistry, (Nov. 1, 1996), 27280-27284.
Lee, Do Hee, et al., "The Proteasome Inhibitors and Their Uses", Proteasomes: The World of Regulatory Proteolysis, (2000), 154-175.
Lee, K., et al., "Shuttle PCR-based cloning of the infectious adeno-associated virus type 5 genome", Journal of Virological Methods, 111(2), (Aug. 2003), 75-84.
Lee, Sang Goo, et al., "Enhancement of adenoviral transduction with polycationic liposomes in vivo", Cancer Gene Therapy, vol. 7, No. 10, (2000), 1329-1335.
Lefebvre, R. B., et al., "Conformation Takes Precedence Over Sequence in Adeno-Associated Virus DNA Replication", Molecular and Cellular Biology, 4(7), (1984), 1416-1419.
Li, et al., "Cloned ferrets produced by somatic cell nuclear transfer", Dev. Biol vol. 293, Iss. 2, (2006), 439-448.
Li, et al., "Progress toward generating a ferret model of cystic fibrosis by somatic cell nuclear transfer", Reprod. Biol. and Endocrinology vol. 1, (2003), 1-8.
Li, M., et al., "Macrophage colony stimulatory factor and interferon-gama trigger distinct mechanisms for augmentation of beta-amyloid-induced microglia-mediated neurotoxicity", J. Neurochem 91(3), Abstract Only, (Nov. 2004), 1 pg.
Li, Q., et al., "Nox2 and Rac1 regulate H2O2-dependent recruitment of TRAF6 to endosomal interleukin-1 receptor complexes", Mol Cell Biol., 26(1), (Jan., 2005), 140-54.
Liang, E., et al., "Oligonucleotide delivery: a cellular prospective", Pharmazie, vol. 54,No. 8, XP000965598, (Aug. 1999), 559-566.
Lin, H. C, et al., "Prediction of tyrosine sulfation sites in animal virus", Biochemical And Biophysical Research Communications,312(4), (Dec. 26, 2003), 1154-1158.
Lin, S, et al., "Delivery of a Novel AAV, AV.T165-CFTR, to Human Bronchial Epithelial Cells from Patients with Cystic Fibrosis Augments Functional Recovery of Chloride Conductance", Pediatric Pulmonology; 33rd Annual North American Cystic Fibrosis Conference Oct. 31, 2019 to Nov. 2, 2019 Nashville, TN, John Wiley & Sons, Inc, US, vol. 54, No. Supplement 2, (Oct. 1, 2019), p. 218.
Linden, R. M., et al., "Site-specific integration by adeno-associated virus", PNAS, 93, (Oct. 1994), pp. 11288-11294.
Linden, R. M., et al., "The Recombinant Signals for Adeno-Associated Virus Site-Specific Integration", Proc. Natl. Acad. Sci. USA, 93, (Jul. 1996), 7966-7972.
Loguercio, C., et al., "Oxidative stress in viral and alcoholic hepatitis.", Free Radic Biol Med., 34(1), (Jan. 1, 2003), 1-10.
Lu, Wei, et al., "HIV protease inhibitors restore impaired T-cell proliferative response in vivo and in vitro: a viral-suppression-independent mechanism", Blood, vol. 96, No. 1, (Jul. 1, 2000), 250-258.
Lu, X., et al., "Synthesis and biological evaluations of novel apocynin analogues", Eur J Med Chem., 46(7), (Jul., 2011), 2691-8.
Lull, M. E, et al., "Chronic apocynin treatment attenuates beta amyloid plaque size and microglial No. in hAPP(751)(SL) mice", PLoS One, 6(5), (2011), e20153.
Luo, Hongyu, et al., "A Proteasome Inhibitor Effectively Prevents Mouse Heart Allograft Rejection", Transplantation, vol. 72, No. 2, (Jul. 27, 2001), 196-202.
Ma, Xiaoming, et al., "Detection of Human Bocavirus in Japanese Children with Lower Respiratory Tract Infections", J Clin Microbiol, 44, (2006), 1132-1134.

(56) References Cited

OTHER PUBLICATIONS

Ma, Y., et al., "p53-Independent Down-Regulation of Mdm2 in Human Cancer Cells Treated with Adriamycin", Molecular Cell Biology Research Communications, 3(2), (Feb., 2000), 122-128.

Macías-Pérez, Martha Edith, et al., "Ethers and Esters Derived Rom Apocynin Avoid the Interaction Between p47phox and p22phox Subunits of Nadph Oxidase: Evaluation in Vitro and in Silico", (Biosci. Rep., 33: e00055 (2013)), (2013), 605-616.

Mah, C, et al., "Adeno-Assodated Virus Type 2-Mediated Gene Transfer: Role of Epidermal Growth Factor Receptor Protein Tyrosine Kinase in Transgene Expression", Journal of Virology, 72 (12), (1998), pp. 9835-9843.

Mah, C., et al., "Improved Method of Recombinant AAV2 Delivery for Systemic Targeted Gene Therapy", Molecular Therapy, 6(1), (2001), 106-112.

Maitra, R., et al., "Increased Functional Cell Surface Expression of CFTR and deltaF508-CFTR by the Anthracycline doxorubicin", Am. J. Physiol. Cell Physiol., 280, (May 2001), C1031-C1037.

Malik, B., et al., "ENaC Degradation in A6 Cells by the Ubiquitin-Proteosome Proteolytic Pathway", The Journal of Biological Chemistry, 276(16), (Apr. 20, 2001), 12903-12910.

Marshall, E., "Gene Therapy's Growing Plans", Science 269(5227), (1995), 1050-1055.

Mastroianni, Claudio M, et al., "Ex Vivo and In Vitro Effect of Human Immunodeficiency Virus Protease Inhibitors on Neutrophil Apoptosis", Journal of Infectious Diseases (182), (Nov. 2000), 1536-1539.

Matalon, S., et al., "Lung Edema Clearance: 20 Years of Progress—Invited Review: Biophysical Properties of Sodium Channels in Lung Alveolar Epithelial Cells", J. Appl. Physiol., 93, (2002), 1852-1859.

Mattsson, Karin, et al., "Proteins associated with the promyelocytic leukemia gene product (PML)-containing nuclear body move to the nucleolus upon inhibition of proteaseome-dependent protein degradation", Proc. National Academy of Science, vol. 98, No. 3, (Jan. 30, 2001), 1012-1017.

McAuliffe, O., et al., "Lantibiotics: Structure, Biosynthesis and Mode of Action", FEMS Microbiology Reviews, 25(3), (2001), 285-308.

McCarty, D. M., et al., "Identification of Linear DNA Sequences That Specifically Bind the Adeno-Associated Virus Rep Protein", Journal of Virology, 68(8), (1994), 4988-4997.

McCarty, D. M., et al., "Interaction of the Adeno-Associated Virus Rep Protein With a Sequence Within the A Palindrome of the Viral Terminal Repeat", Journal of Virology, 68(9), (1994), 4998-5006.

McFadden, G., "Even viruses can learn to cope with stress.", Science, 279(5347), (Jan. 2, 1998), 40-1.

McLaughlin, Susan K., et al., "Adeno-associated virus general transduction vectors: analysis of proviral structures", Journal of Virology, 62 (6), (Jun. 1988), pp. 1963-1973.

Meng, L., et al., "Epoxomicin, a potent and selective proteasome inhibitor, exhibits in vivo antiinflammatory activity.", Proc Natl Acad Sci USA., 96(18), (Aug. 31, 1999), 10403-8.

Meng, Lihao, et al., "Eponemycin Exerts Its Antitumor Effect through the Inhibition of Proteasome Function", Cancer Research, vol. 59, (Jun. 15, 1999), 2798-2801.

Meng, Lihao, et al., "Epoxomicin, a potent and selective proteasome inhibitor, exhibits in vivo antiinflammatory activity", Proc Natl Acad Sci U S A, 96(18), (Aug. 31, 1999), 10403-8.

Meyer, Stephanie, et al., "Cyclosporine A is an uncompetitive inhibitor of proteasome activity and prevents NF-kB activation", Federation of European Biochemical Societies, (1997), 354-358.

Mihm, S., et al., "Inhibition of HIV-1 replication and NF-kappa B activity by cysteine and cysteine derivatives.", AIDS, 5(5), (May 1991), 497-503.

Mikulski, S. M, et al., "Enhanced in vitro cytotoxicity and cytostasis of the combination of onconase with a proteasome inhibitor", Int J Oncol., 13(4), (Oct., 1998), 633-44.

Mingozzi, Federico, et al., "Pharmacological Modulation of Humoral Immunity in a Nonhuman Primate Model of AAV Gene Transfer for Hemophilia B", Molecular Therapy, vol. 20, No. 7, (May 8, 2012), 1410-1416.

Mirshahi, M., et al., "Paradoxical Effects of Mineralocorticoids on the Ion Gated Sodium Channel in Embryologically Diverse Cells", Biochemical and Biophysical Research Communications, 270, (2000), 811-815.

Mitsiades, Constantine, et al., "TRAIL/Apo2L ligand selectively induces apoptosis and overcomes drug resistance in multiple myeloma: theraputic applications", Blood, vol. 98, No. 3, (Aug. 1, 2001), 795-804.

Monahan, P E, et al., "Proteasome inhibitors enhance gene delivery by AAV virus vectors expressing large genomes in hemophilia mouse and dog models: a strategy for broad clinical application", Mol Ther 18, (2010), 1907-1916.

Mondejar-Lopez, Pedro, et al., "Cystic Fibrosis Treatment: Targeting the Basic Defect", Expert Opinion On Orphan Drugs, vol. 5, No. 2, (Feb. 26, 2017), 181-192.

Mosnaim, Aron, et al., "Degradation Kinetics of Leucine5-Enkephalin by Plasma Samples from Healthy Controls and Various Patient Populations: In Vitro Drug Effects", American Journal of Therapeutics, vol. 7, (2000), 185-194.

Mullins, et al., "Perspectives Series: Molecular Medicine in Genetically Engineered Animals", J. Clin. Invest. Vol. 97, (1996), 1557-1560.

Mullins, et al., "Transgenesis in nonmurine species", Hypertension vol. 22, (1993), 630-633.

Muramatsu, S., et al., "Nucleotide Sequencing and Generation of an Infectious Clone of Adeno-Associated Virus-3", Virology, 221(1), (1996), 208-217.

Murray, R. Z, et al., "Proteasome inhibitors as anti-cancer agents", Anticancer Drugs, 11(6), (Jul., 2000), 407-17.

Musatov, S. A., et al., "Induction of Circular Episomes During Rescue and Replication of Adeno-Associated Virus in Experimental Models of Virus Latency", Virology, 275, (2000), 411-432.

Muzyczka, N., "Use of Adeno-Associated Virus as a General Transduction Vector for Mammalian Cells", In: Current Topics in Microbiology and Immunology, 158, Springer-Verlag, Berlin: R.W. Compans, et al., (Eds.), (1992), pp. 97-129.

Nakai, H., et al., "Helper-Independent and AAV-ITR-Independent Chromosomal Integration of Double-Stranded Linear DNA Vectors in Mice", Molecular Therapy, 7(1), (2003), 101-111.

Nakai, H., et al., "Increasing the Size of rAAV-Mediated Expression Cassettes in vivo by Intermolecular Joining of Two Complementary Vectors", Nature Biotechnology, 18, (2000), 527-532.

Nakai, H., et al., "Recruitment of Single-Stranded Recombinant Adeno-Associated Virus Vector Genomes and Intermolecular Recombination Are Responsible for Stable Transduction of Liver In Vivo", Journal of Virology, 74(20), (2000), 9451-9463.

Nakamura, H., et al., "Redox imbalance and its control in HIV infection", Antioxid Redox Signal., 4(3), (Jun., 2002), 455-64.

Nakayama, M., et al., "Hypomethylation Status of CpG Sites at the Promoter Region and Overexpression of the Human MDR1 Gene in Acute Myeloid Leukemias", Blood, 92(11), (1998), 4296-4307.

Nam, Sangkil, et al., "Tannic Acid Potently Inhibits Tumor Cell Proteasome Activity, Increases p27 and Bax Expression, and Induces G1 Arrest and Apoptosis", Cancer Epidemiology, Biomarkers & Prevention, vol. 10, (Oct. 2001), 1083-1088.

Nathwani, Amit C et al., "Enhancing Transduction of the Liver By Adeno-associated Viral Vectors", Gene Ther. Jan. 2009; 16(1): 60-69. doi:10.1038/gt.2008.137, (Jul. 1, 2009), 60-69.

Nepka, Ch., et al., "Tannins, xenobiotic metabolism and cancer chemo-prevention in experimental animals", European Journal of Drug Metabolism and Pharmacokinetics, vol. 24, No. 2, (1999), 183-189.

Nepka, Charitini, et al., "Chemopreventive activity of very low dose dietary tannic acid administration in hepatoma bearing C3H male mice", Cancer Letters, vol. 141, (1999), 57-62.

Neves, D. D. C., et al., "Differentiation-dependent sensitivity to cell death induced in the developing retina by inhibitors of the ubiquitin-proteasome proteolytic pathway", European Journal of Neuroscience, vol. 13, (2001), 1938-1944.

(56) References Cited

OTHER PUBLICATIONS

Newman, G. W, et al., "Opposing regulatory effects of thioredoxin and eosinophil cytotoxicity-enhancing factor on the development of human immunodeficiency virus 1.", J ExpMed., 180(1), (Jul. 1, 1994), 359-63.
Nicolaus, B. J, "Symbiotic Approach to Drug Design", Decision Making in Drug Research, (Jan. 1, 1983), 173-186.
Nielsen, J., et al., "Spironolactone-Mediated Downregulation of the Epithelial Sodium Channel (eNaC) in Rat Kidney", FASEB Journal, 15(1) (Abstracts Part I), Abstract No. 393.11, (2001), A432.
Niikura, T, et al., "Characterization of V642I-AbetaPP-induced cytoxicity in primary neurons", J. Neruosci Res. 77(1), Abstract Only, (Jul. 2004), 54-62.
Oberdorf, J., et al., "Redundancy of Mammalian Proteasome & Subunit Function during Endoplasmic Reticulum Associated Degradation", Biochemistry; 40(44), (2001), 13397-13405.
Obin, M, et al., "Neurite outgrowth in PC12 cells. Distinguishing the roles of ubiquitylation and ubiquitin-dependent proteolysis", Journal of Biological Chemistry, 274 (17), (Apr. 23, 1999), 11789-11795.
Oda, T., et al., "Oxygen radicals in influenza-induced pathogenesis and treatment with pyran polymer-conjugated SOD.", Science, 244(4907), (May 26, 1989), 974-6.
Ogiso, Y., et al., "Proteasome inhibition circumvents solid tumor resistance to topoisomerase II-directed drugs", Cancer Res., 60(9), (May 1, 2000), 2429-34.
Orkin, S. H., et al., "Report and recommendation of the Panel to Assess the NIH Investment in Research on Gene Therapy", [online], [retrieved Jul. 6, 2007], Retrieved from the Internet: <URL: file://E:\Enablement Rejections\Generally usefu art\wwwnihgov-news-panelrephtm.htm>, (Dec. 7, 1995), 39 pgs.
Palombella, Vito, et al., "Role of the proteasome and NF-kB in streptococcal cell wall-induced polyarthritis", Proc. National Academy of Science USA, vol. 95, (Dec. 1998), 15671-15676.
Paolini, Rossella, et al., "Ubiquitination and degradation of Syk and ZAP-70 protein tyrosine kinases in human NK cells upon CD16 engagement", PNAS, vol. 98, No. 17, (Aug. 14, 2001), 9611-9616.
Pardridge, William M, "Blood-Brain Barrier Drug Targeting: The Future of Brain Drug Development", Molecular Interventions 3(2), (Mar. 2003), 90-105.
Parker, J. S., et al., "Cellular Uptake and Infection by Canine Parvovirus Involves Rapid Dynamin-Regulated Clathrin-Mediated Endocytosis, Followed by Slower Intracellular Trafficking", Journal of Virology, 74(4), (2000), 1919-1930.
Patel, et al., "identification of Yeast DNA Topoisomerase II Mutants Resistant to the Antitumor Drug Doxorubcin: Implications for the Mechanisms of Doxorubicin Action and Cytotoxicity", Pharmacol. 52(4), (1997), 658-666.
Petrov, Victor, et al., "Effect of Protease Inhibitors on Angiotensin-Converting Enzyme Activity in Human T-Lymphocytes", American Journal of Hypertension, vol. 13, No. 5, (May 2000), 535-539.
Phelps, C. J, et al., "Production of alpha 1,3-galactosyltransferase-deficient pigs", Science, 299(5605), (Jan. 17, 2003), 411-4.
Piccinini, M., et al., "The human 26S proteasome is a target of antiretroviral agents", AIDS, 16(5), abstract, (Mar. 29, 2002), 1 page.
Pickles, R J., et al., "Limited Entry of Adenovirus Vectors into Well-Differentiated Airway Epithelium Is Responsible for Inefficient Gene Transfer", Journal of Virology, 72 (7), (1998), pp. 6014-6023.
Plonne, D., et al., "Separation of the intracellular secretory compartment of rat liver and isolated rat hepatocytes in a single step using self-generating gradients of iodixanol.", Anal Biochem., 276(1), (Dec. 1, 1999), 88-96.
Ponnazhagan, S., et al., "Lack of Site-Specific Integration of the Recombinant Adeno-Associated Virus 2 Genomes in Human Cells", Human Gene Therapy, 8, (Feb. 10, 1997), pp. 275-284.
Pratelli, Annamaria, et al., "Host range of Canine minute virus in cell culture", Journal of Veterinary Diagnostic Investigation 24(5), (Jul. 23, 2012), 981-985.

Princiotta, Michael F, et al., "Cells adapted to the proteasome inhibitor 4-hydroxy-5-iodo-3-nitrophenylacetyl-Leu-Leu-leucinal-vinyl sulfone require enzymatically active proteasomes for continued survival", PNAS, vol. 98, No. 2, (Jan. 16, 2001), 513-518.
Prydz, K, et al., "Effects of Brefeldin A on Endocytosis, and Transport to the Golgi Complex in Polarized MDCK Cells", The Journal of Cell Biology, 119 (2), (1992), pp. 259-272.
Puttaraju, M., et al., "Spliceosome-mediated RNA trans-splicing as a tool for gene therapy", Nature Biotechnology, 17 (3), (Mar. 1999), pp. 246-252.
Qing, K., et al., "Adeno-Associated Virus Type 2-Mediated Gene Transfer: Correlation of Tyrosine Phosphorylation of the Cellular Single-Stranded D Sequence-Binding Protein with Transgene Expression in Human Cells In Vitro and Murine Tissues In Vivo", Journal of Virology, 72 (2), (Feb. 1998), pp. 1593-1599.
Qing, K., et al., "Human Fibroblast Growth Factor Receptor 1 is a Co-Receptor for Infection by Adeno-Associated Virus 2", Nature Medicine, 5(1), (Jan. 1999), 71-77.
Qing, K., "Role of Tyrosine Phosphorylation of a Cellular Protein in Adeno-Associated Virus 2-Mediated Transgene Expression", Proc. Natl. Acad. Sci. USA, 94, (Sep. 1997), 10879-10884.
Rabinowitz, Joseph, et al., "Cross-Packaging of a Single Adeno-Associated Virus (AAV) Type 2 Vector Genome into Multiple AAV Serotypes Enables Transduction with Broad Specificity", Journal of Virology, (Jan. 2002), 791-801.
Ramage, A. D., et al., "Improved EBV-Based Shuttle Vector System: Dicistronic mRNA Couples the Synthesis of the Epstein-Barr Nuclear Antigen-1 Protein to Neomycin Resistance", Gene, 197(102), (1997), 83-89.
Rao, Sharmila, et al., "Lovastatin-mediated G1 arrest is through inhibition of the proteasome, independent of hydroxymethyl glutaryl-CoA reductase", Proc. National Academy of Science USA, vol. 96, (Jul. 1999), 7797-7802.
Reich, S. J., et al., "Efficient Trans-Splicing in the Retina Expands the Utility of Adeno-Associated Virus as a Vector for Gene Therapy", Human Gene Therapy, 14, (2003), 37-44.
Rendahl, K. G., et al., "Regulation of Gene Expression in vivo Following Transduction by Two Separate rAAv Vectors", Nature Biotechnology, 16, (1998), 757-761.
Richards, R. Gregg, et al., "E2-lnduced Degradation of Uterine Insulin Receptor Substrate-2: Requirement for an IGF-I-Stimulated, Proteasome-Dependent Pathway", Endocrinology, 142(9), (Sep. 2001), 3842-3849.
Ricour, C., et al., "Human Bocavirus, a Newly Discovered Parvovirus of the Respiratory Tract", International Journal of Clinical and Laboratory Medicine, vol. 63, Issue 5, Abstract only, (2008), 329-334.
Rivett, A. J, et al., "Proteasome inhibitors: from in vitro uses to clinical trials", Journal of Peptide Science, 6(9), (Sep., 2000), 478-488.
Rock, K L., et al., "Inhibitors of the Proteasome Block the Degradation of Most Cell Proteins and the Generation of Peptides Presented on MHC Class I Molecules", Cell, 78, (1994), pp. 761-771.
Ross, G., et al., "Gene Therapy in the United States: A Five-Year Status Report", Human Gene Therapy, 7, (1996), 1781-1790.
Rotin, D., "Regulation of the Epithelial Sodium Channel (ENaC) by Accessory Proteins", Current Opinion in Nephrology and Hypertension, 9, (2000), 529-534.
Rotin, D., et al., "Trafficking and Cell Surface Stability of ENaC", Am. J. Physiol. Renal Physiol., 281, (2001), F391-F399.
Rubanyi, Gabor M., "The Future of Human Gene Therapy", Molecular Aspects of Medicine, 22, (2001), 113-142.
Russell, D W., et al., "DNA synthesis and topoisomerase inhibitors increase transduction by adeno-associated virus vectors", PNAS, 92, (1995), pp. 5719-5723.
Russell, S. J, "Replicating Vectors for Gene Therapy of Cancer: Risks, Limitations and Prospects", European J Cancer, vol. 30A (8), (1994), 1165-1171.
Ryan, J. H., et al., "Sequence Requirements for Binding of Rep68 to the Adeno-Associated Virus Terminal Repeats", Journal of Virology, 70(3), (1996), 1542-1553.

(56) References Cited

OTHER PUBLICATIONS

Saha, D., et al., "The antiangiogenic agent SU5416 down-regulates phorbol ester-mediated induction of cyclooxygenase 2 expression by inhibiting nicotinamide adenine dinucleotide phosphate oxidase activity", Cancer Res., 63(20), (Oct. 15, 2003), 6920-7.
Sakai, H., et al., "Cloning and functional expression of a novel degenerin-like Na+ channel gene in mammals", J. Physiol 519, (1999), 323-333.
Salganik, Max, et al., "Adeno-associated Virus as a Mammalian DNA Vector", Microbiol. Spectr., 3:10.1128, (Aug. 2015), 32 pgs.
Samulski, R. J., et al., "A Recombinant Plasmid from Which an Infectious Adeno-Associated Virus Genome Can Be Excised In Vitro and Its Use To Study Viral Replication", Journal of Virology, 61(10), (Oct. 1987), 3096-3101.
Samulski, R. J., "Adeno-Associated Virus: Integration at a Specific Chromosomal Locus", Current Opinion in Genetics & Development, 3(1), (1993), 74-80.
Samulski, R. J., et al., "Helper-Free Stocks of Recombinant Adeno-Associated Viruses: Normal Integration Does Not Require Viral Gene Expression", Journal of Virology, 63 (9), (Sep. 1989), pp. 3822-3828.
Sanlioglu, et al., "Novel Approaches to Augment Adeno-Associated Virus TYPE-2 Endocytosis and Transduction", Virus Research and Transduction, 104(1), (Aug. 2004), 51-59.
Sanlioglu, S, et al., "Cellular redox state alters recombinant adeno-associated virus transduction through tyrosine phosphatase pathways", Gene Therapy vol. 6, No. 8, (Aug. 1999), pp. 1427-1437.
Sanlioglu, S., et al., "Endocytosis and Nuclear Traffickling of Adeno-Associated Virus Type 2 Are Controlled by Rac1 and Phosphatidylinositol-3 Kinase Activation", Journal of Virology, 74(19), (Oct. 2000), 9184-9196.
Sanlioglu, S., et al., "Lipopoolysaccharide Induces Rac1-Dependent Reactive Oxygen Species Formation and Coordinates Tumor Necrosis Factor-alpha Secretion Through IKK Regulation of NF-kB", The Journal of Biological Chemistry, 276(32), (2001), 30188-30198.
Sanlioglu, S., "Loss of ATM Function Enhances Recombinant Adeno-Associated Virus Transduction and Integration Through Pathways Similar to UV Irradiation", Virology, 268, (2000), 68-78.
Sanlioglu, S., et al., "Rate Limiting Steps of AAV Transduction and Implications for Human Gene Therapy", Current Gene Therapy, 1, (2001), 137-147.
Sanlioglu, S., et al., "Two Independent Molecular Pathways for Recombinant Adeno-Associated Virus Genome Conversion Occur After UV-C and E4orf6 Augmentation of Transduction", Human Gene Therapy, 10(4), (1999), 591-602.
Sasaki, T., et al., "Inhibitory Effect of di- and Tripeptidyl Aldehydes on Calpains and Cathepsins", Journal of Enzyme Inhibition, 3(3), (1990), 195-201.
Schaefer, et al., "Molecular cloning, functional expression and chromosomal localization of an amiloride-sensitive Na+ channel from human small intestine", FEBS Letters 471, (2000), 205-210.
Schlabach, Michael R, et al., "Synthetic design of strong promoters", Proceedings of the National Academy Of Sciences, vol. 107, No. 6, (Feb. 9, 2010), 2538-2543.
Schnepp, B. C., et al., "Genetic Fate of Recombinant Adeno-Associated Virus Vector Genomes in Muscle", Journal of Virology, 77(6), (2003), 3495-3504.
Schreck, R., et al., "Antioxidants selectively suppress activation of NF-kappa B by human T-cell leukemia virus type I Tax protein", J Virol., 66(11), (Nov., 1992), 6288-93.
Schwartz, Donald, et al., "The neutral cysteine protease bleomycin hydrolase is essential for epidermal integrity and bleomycin resistance", Proc. National Academy of Science USA, vol. 96, (Apr. 1999), 4680-4685.
Schwartz, O, et al., "Antiviral Activity of the Proteasome on Incoming Human Immunodeficiency Virus Type 1", Journal of Virology, 72 (5), (1998), pp. 3845-3850.
Schwarz, K., "Oxidative stress during viral infection: a review.", Free Radic Biol Med., 21(5), (1996), 641-9.

Schwarz, Katrin, et al., "The Selective Proteasome Inhibitors Lactacystin and Epoxomicin can be used to either Up- or Down-Regulate Antigen Presentation at Nontoxic Doses", Journal of Immunology, (2000), 6147-6157.
Schwarzbach, M., et al., "Sensitization of Sarcoma cells to doxorubicin treatment by concomitant wild-type adeno-associated virus type 2(AAV-2) infection", Oncology,20, (2002), 1211-1218.
Sen, S, et al., "Characterisation of gene transfer to vascular cell lines using adenoassociated virus (AAV Serotype-2)", Endocrine Abstracts, 4 DP31; Dept, of medicine, National Univ, of Ireland, Galway, Ireland; 2The Ohio State Univ. School of Medicine and Molecular Virology, Columbus, Ohio, USA, (2002), 1 pg.
Serwer, et al., "Systemic and Local Drug Delivery for Treating Diseases of the Central Nervous System in Rodent Models", Jove, vol. 42, (2010), 1-6.
Shah, S. A., et al., "26S Proteasome Inhibition Induces Apoptosis and Limits Growth of Human Pancreatic Cancer", Journal of Cellular Biochemistry, vol. 82, (2001), 110-122.
Sharma, A, et al., "Pig cells that lack the gene for alpha1-3 galactosyltransferase express low levels of the gal antigen", Transplantation, 75(4), (Feb. 27, 2003), 430-6.
Shay, David, et al., "Bronchiolitis-Associated Hospitalizations Among US Children, 1980-1996", JAMA, vol. 282, No. 15, (1999), 1440-1446.
Shisler, J. L, et al., "Ultraviolet-induced cell death blocked by a selenoprotein from a human dermatotropic poxvirus", Science,279(5347), (Jan. 2, 1998), 102-5.
Sloots, Theo, et al., "Evidence of human coronavirus HKU1 and human bocavirus in Australian Children", J Clin Virol, 35, (2006), 99-102.
Smith, Andrew, et al., "The Role of the Epidermal Growth Factor Receptor in Recombinant Adeno-Associated Virus Type-2 Mediated Transgene Expression in Lung Epithelial Cells", Molecular Therapy, 5(5), abstract, (May 2002), S186.
Smith, H., et al., "Effect of a cancer cachectic factor on protein synthesis/degradation in murine C2C12 myoblasts: modulation by eicosapentaenoic acid", Cancer Res., 59(21), abstract, (Nov. 1999), 1 page.
Snyder, P. M., et al., "Serum and Glucocorticoid-Regulated Kinase Modulates Nedd4-2-Mediated Inhibition of the Epithelial NA+ Channel", The Journal of Biological Chemistry, 277(1), (2002), 5-8.
Snyder, R. O., et al., "Features of the Adeno-Associated Virus Origin Involved in Substrate Recognition by the Viral Rep Protein", Journal of Virology, 67(10), (1993), 6096-6104.
Snyder, R. O., et al., "Persistent and therapeutic concentrations of human factor IX in mice after hepatic gene transfer of recombinant AAV vectors", Nature Genetics, 16, (Jul. 1997), pp. 270-276.
Son, K, et al., "Factors influencing the drug sensitization of human tumor cells for in situ lipofection", Gene Therapy (3), (1996), 630-634.
Son, Kyonghee, et al., "Exposure of human ovarian carcinoma to cisplatin transiently sensitizes the tumor cells for liposome-mediated gene transfer", Proc. National Academy of Science USA, vol. 91, (Dec. 1994), 12669-12672.
Son, Kyonghee, et al., "Nitric oxide-mediated tumor cell killing of cisplatin-based interferon-y gene therapy in murine ovarian carcinoma", Cancer Gene Therapy, vol. 7, No. 10, (2000), 1324-1328.
Sonntag, Florian, et al., "Adeno-associated Virus Type 2 Capsids with Externalized VP1/VP2 Trafficking Domains Are Generated Prior to Passage through the Cytoplasm and Are Maintained until Uncoating Occurs", Journal of Virology, vol. 80, No. 22, (Nov. 2006), 11040-11054.
Spindler, B., et al., "Characterization of Early Aldosterone-induced RNAs identified in A6 Kidney Epithelia", Pfluegers Archiv, vol. 434, Springer Verlag, Berlin, DE XP001025924 ISSN: 0031-6768, (1997), 323-331.
Srivastava, C. H., et al., "Construction of a Recombinant Human Parvovirus B19: Adeno-Associated Virus 2 (AAV) DNA Inverted Terminal Repeats are Functional in an AAV-B19 Hybrid Virus", Proc. Natl. Acad. Sci USA, 86(20), (1989), 8078-8082.
Staub, O., "Chapters Regulation of ENaC by Interacting Proteins and by Ubiquitination", Current Topics in Membranes, 47—Amiloride-

(56) References Cited

OTHER PUBLICATIONS

Sensitive Sodium Channels—Physiology and Functional Diversity, Edited by Dale J. Benos, Academic Press, Publisher, (1999), 65-87.
Staub, O., "Regulation of Stability and Functional of the Epithelial Na+ Channel (ENaC) by Ubiquitination", The EMBO Journal, 16(21), (1997), 6325-6336.
Stockand, J. D., et al., "Targeted Degradation of the Epithelial Na Channel (ENaC) in Response to PKC Activation of the MAPK 1/2 Cascade", The FASEB Journal, 17(5), Abstracts (Part II), (Abstract No. 585.7), (2003), A913.
Stokes, J. B., "Regulation of rENac mRNA by Dietary NaCl and Steroids: Organ, Tissue, and Steroid Heterogeneity", American Journal of Physiology, Cell Physiology, 274, (1998), C1699-C1707.
Stutts, M. J, et al., "Cystic fibrosis transmembrane conductance regulator inverts protein kinase A-mediated regulation of epithelial sodium channel single channel kinetics.", J. Biol. Chem., 272(22), (1997), 14037-14040.
Summerford, C., et al., "alphaVbeta5 integrin: a co-receptor for adeno-associated virus type 2 infection", Nature Medicine, 5 (1), (Jan. 1999), 78-82.
Summerford, C., et al., "Membrane-Associated Heparan Sulfate Proteoglycan Is a Receptor for Adeno-Associated Virus Type 2 Virions", Journal of Virology, 72 (2), (Feb. 1998), pp. 1438-1445.
Sun, A. Y, et al., "Botanical phenolics and brain health", Neuromolecular Med., 10(4), (2008), 259-74.
Swinney, David C, et al., "Targeting protein ubiquitination for drug discovery. What is in the drug discovery toolbox?", DDT, vol. 6, No. 5, (Mar. 2001), 244-250.
Tajima, Kimihisa, et al., "The proteasome inhibitor MG132 promotes accumulation of the steroidogenic acute regulatory protein (StAR) and steriodogenesis", Federation of European Biochemical Societies, 490, (Jan. 24, 2001), 59-64.
Tang, Y, "435: Immunosuppressants improve the transduction of AAV2.5T after repeat dosing of ferret lungs", Pediatric Pulmonology; 34TH Annual North American Cystic Fibrosis Conference; Oct. 7, 2020 to Oct. 23, 2020; Phoenix, AZ, USA, John Wiley & Sons, Inc, US, vol. 55, No. SUPPL 2, (Oct. 1, 2020), p. 208.
Tang, Y, et al., "Study of the Neutralizing Antibody after rAAV. TL65 Transduction in Ferret Airway", Pediatric Pulmonology; 33RD Annual North American Cystic Fibrosis Conference, Nashville, TN, John Wiley & Sons, Inc, US, vol. 54, No. Supplement 2, (Oct. 1, 2019), p. 325.
Tenenbaum, et al., "Cellular contaminants of adeno-associated virus vector stocks can enhance transduction", Gene Therapy, 6, (1999), 1045-1053.
Tenenbaum, et al., "Evaluation of Risks Related to the Use of Adeno-Associated Virus-Based Vectors", Current Gene Therapy, 3, (2003), 545-565.
Teodori, L., et al., "Reduction of 1-beta-D-arabinofuranosylcytosine and adriamycin cytotoxicity following cell cycle arrest by anguidine", Cancer Res., 41(4), abstract, (Apr. 1981), 1 page.
Teoh, M. L, et al., "Tumorigenic poxviruses up-regulate intracellular superoxide to inhibit apoptosis and promote cell proliferation", J Virol., 79(9), (May 2005), 5799-811.
Teramoto, S., "Factors influencing adeno-associated virus-mediated gene transfer to human cystic fibrosis airway epithelial cells: comparison with adenovirus vectors", Journal of Virology, 72(11), (Nov., 1998), 8904-8912.
Teramoto, S., et al., "Factors influencing adeno-associated virus-mediated gene transfer to human cystic fibrosis airway epithelial cells: comparison with adenovirus vectors.", J Virol., 72(11), (Nov., 1998), 8904-12.
Thakur, et al., "Strategies for ocular siRNA delivery: Potential and limitations of non-viral nanocarriers", Journal of Biological Engineering, 6, (2012), 1-7.
Thomas, C. P., et al., "Genomic Organization of the 5' End of Human B-ENaC and Preliminary Characterization of its Promoter", Am. J. Physiol. Renal Physiol. 282, (2002), F898-F909.
Thrasher, a J, et al., "Generation of recombinant adeno-associated virus (rAAV) from an adenoviral vector and functional reconstitution of the NADPH-oxidase", Gene Therapy, Macmillan Press Ltd., Basinstoke, GB, Vo. 2, 1995, pp. 481-485, XP000651495, (1995), 5.
Touyz, R. M, et al., "Expression of a functionally active gp91phox-containing neutrophil-type NAD(P)H oxidase in smooth muscle cells from human resistance arteries: regulation by angiotensin II", Circ Res., 90(11), (Jun. 14, 2002), 1205-13.
Trischler, M., et al., "Biochemical analysis of distinct Rab5- and Rab11-positive endosomes along the transferrin pathway.", J Cell Sci., 112 ( Pt 24), (Dec., 1999), 4773-4783.
Unzu, Carmen, et al., "Transient and intensive pharmacological immunosuppression fails to improve AAV-based liver gene transfer in nonhuman primates", Journal of Translational Medicine, Biomed Central, vol. 10, No. 1, (Jun. 15, 2012).
van den Worm, E., et al., "Apocynin: A Lead-Compound for New Respiratory Burst Inhibitors", van den Worm thesis, Chapter 3, entitled Apocynin: a lead compound for new respiratory burst inhibitors? (2001)), (2001), 49-58.
van den Worm, E et al., "Effects of Methoxylation of Apocynin and Analogs On the Inhibition of Reactive Oxygen Species Production By Stimulated Human Neutrophils", Eur J Pharmacol. Dec. 21, 2001;433(2-3):225-30 (Abstract), (Dec. 21, 2001), 1 pg.
van den Worm, E., et al., "Effects of methoxylation of apocynin and analogs on the inhibition of reactive oxygen species production by stimulated human neutrophils", Euro. Jour, of pharm.;433(2-3), (Dec. 21, 2001), 225-230 Pgs.
van Kerkhof, Peter, et al., "Proteasome Inhibitors Block a Late Step in Lysosomal Transport of Selected Membrane but not Soluble Proteins", Molecular Biology of the Cell, vol. 12, (Aug. 2001), 2556-2566.
Verma, I. M., et al., "Gene Therapy—Promises, Problems and Prospects", Nature, 389, (1997), 239-242.
Vihinen-Ranta, M, et al., "Intracellular Route of Canine Parvovirus Entry", Journal of Virology, 72 (1), (1998), pp. 802-806.
Villani, P., et al., "Antiretrovirals: Simultaneous determination of five protease inhibitors and three nonnucleoside transcriptase inhibitors in human plasma by a rapid high-performance liquid chromatography-mass spectrometry assay", The Drug Monit., 23(4), abstract, (Aug. 2001), 1 page.
Voinea, et al., "Designing of Intelligent liposomes for efficient delivery of drugs", J. cell. Mol. Med. 6(4), (2002), 465-474.
Wagner, J. A., et al., "A Phase 1/ll Study of tgAAV-CF for the Treatment of Chronic Sinusitis in Patients With Cystic Fibrosis", Human Gene Therapy, 9(6), (1998), 889-909.
Wagner, J. A., et al., "Safety and Biological Efficacy of an Adeno-Associated Virus Vector-Cystic Fibrosis Transmembrane Regulator (AAV-CFTR) in the Cystic Fibrosis Maxillary Sinus", The Laryngoscope, 109(2, Part 1), (1999), 266-274.
Wall, R. J., "Transgenic Livestock: Progress and Prospects for the Future", Theriogenology, 45, (1996), 57-68.
Walsh, C. E., "Phenotypic Correction of Fanconi Anemia in Human Hematopoietic Cells with a Recombinant Adeno-associated Virus Vector", The Journal of Clinical Investigation, 94(4), (Oct. 1994), 1440-1448.
Walters, R W., et al., "Basolateral localization of fiber receptors limits adenovirus infection from the apical surface of airway epithelia", The Journal of Biological Chemistry, 274(15), (Apr. 9, 1999), 10219-10226.
Walters, R W., et al., "Incorporation of Adeno-Associated Virus in a Calcium Phosphate Coprecipitate Improves Gene Transfer to Airway Epithelia In Vitro and In Vivo", Journal of Virology, 74 (1), (2000), 535-540.
Wang, Jiali, et al., "Identification of a novel bocaparvovirus in a wild squirrel in Kunming, Yunnan Province, China", Archives of Virology 165, (2020), 1469-1474.
Wang, Kaiyu, et al., "Improvement of Pharmacokinetics Behavior of Apocynin by Nitrone Derivatization: Comparative Pharmacokinetics of Nitrone-Apocynin and Its Parent Apocynin in Rats", (PLoS One, 8:e70189 (2013)), (2013), 6 pgs.
Wang, Zekun, et al., "Development of a Novel Recombinant Adeno-Associated Virus Production System Using Human Bocavirus 1 Helper Genes", Molecular Therapy: Methods & Clinical Development vol. 11, (Dec. 2018), 40-51.

(56) References Cited

OTHER PUBLICATIONS

Wang, Zekun, et al., "Parvovirus Expresses a Small Noncoding RNA That Plays an Essential Role in Virus Replication", Journal of Virology, vol. 91 Issue 8, (2017), 1-20.

Weitzman, M. D., et al., "Adeno-Associated Virus (AAV) Rep Proteins Mediate Complex Formation Between AAV DNA and its Integration Site in Human DNA", Proc. Nat. Acad. Sci. USA, 91(13), (1994), 5808-5812.

Westfall, T. D., et al., "The Ecto-ATPase Inhibitor ARL 67156 Enhances Parasympathetic Neurotransmission in the Guinea-Pig Urinary Bladder", European Journal of Pharmacology, 329, (1997), 169-173.

Whitehouse, Alison, et al., "Downregulation of Ubiquitin-Dependent Proteolysis by Eicosapentaenoic Acid in Acute Starvation", Biochemical and Biophysical Research Communications, vol. 285, No. 3, (2001), 598-602.

Wickham, T J., et al., "Adenovirus targeted to heparan-containing receptors increases its gene delivery efficiency to multiple cell types", Nature Biotechnology, 14, (1996), pp. 1570-1573.

Wickham, T J., et al., "Targeted Adenovirus Gene Transfer to Endothelial and Smooth Muscle Cells by Using Bispecific Antibodies", Journal of Virology, 70 (10), (1996), pp. 6831-6838.

Woessner, Richard, et al., "Comparison of Three Approaches to Doxorubicin Therapy: Free Doxorubicin, Liposomal Doxorubicin, and B-Glucuronidase-Activated Prodrug (HMR 1826)", Anticancer Research, (2000), 2289-2296.

Wojcik, "Inhibition of the proteasome as a therapeutic approach", Drug Discovery Today, 4 (4), (Apr. 1999), pp. 188-189.

Wojcik, Czary et al., "Lovastatin and simvastatin are modulators of the proteasome", Int J Biochem Cell Biol., 32(9), (Sep., 2000), 957-65.

Working, Peter, et al., "Pharmacological-Toxicological Expert Report (Stealth Liposomal Doxorubicin HCI)", Human & Experimental Toxicology, (1996), 752-785.

Wu, C. W, et al., "Gene Therapy for Detached Retina by Adeno-Associated virus vecto Expressing Glial Line-Derived Neurotrophic Factor", Investigative Ophthalmology and visual science, 43(11), (Nov. 2002), 3480-3488.

Wu, D., et al., "NADPH—oxidase in a transgenic mouse model of familial amyotrophic lateral sclerosis", Society for Neuroscience Abstract Viewer and Iteinerary Planner, 2003, Abstract No. 528-13, URL-http://sf, XP008085727 & 33rd Annual Meeting of the Society of Neuroscience, New Orleans, LA, USA, (Nov. 8-12, 2003), 1 pg.

Wu, D., et al., "NADPH-Oxidase in a transgenic mouse model of familial amyotrophic lateral sclerosis (Abstract)", Program No. 528.12. Abstract Viewer/ltinerary Planner, (2003), 1 pg.

Wu, D., et al., "The inflammatory NADPH oxidase enzyme modulates motor neuron degeneration in amyotrophic lateral sclerosis mice", Proc Natl Acad Sci U S A., 103(32), (Aug. 8, 2006), 12132-7.

Wu, Du Chu, et al., "Blockade of Microglial Activation Is Neuroprotective in the 1-Methyl-4-Phenyl-1,2,3,6-Tetrahydropyridine Mouse Model of Parkison Disease", Journal of Neuroscience, (Mar. 1, 2002), 1763-1771.

Wu, J., "On the role of proteasomes in cell biology and proteasome inhibition as a novel frontier in the development of immunosuppressants.", Am J Transplant., 2(10), (Nov., 2002), 904-12.

Wu, Jihong, et al., "Enhanced transduction and improved photoreceptor survival of retinal degeneration by the combinatorial use of rAAV2 with a lower dose of adenovirus", Vision Research 48, (2008), 1648-1654.

Wu, P., et al., "Adeno-Associated Virus Vector-Mediated Transgene Integration into Neurons and Other Nondividing Cell Targets", Journal of Virology, 72 (7), (Jul. 1998), pp. 5919-5926.

Xia, W., et al., "Presenilin 1 regulates the processing of beta-amyloid precursor protein C-terminal fragments and the generation of amyloid beta-protein in endoplasmic reticulum and Golgi", Biochemistry, 37(47), (Nov. 24, 1998), 16465-71.

Xiao, et al., "Efficient Long-Term Gene Transfer Into Muscle Tissue of Immunocomponent Mice by Adeno-Associated Virus Vector", Journal of Virology, 70(11), (1, Nov. 1996), 8098-8108.

Xiao, W, et al., "Adeno-Associated Virus as a Vector for Liver-Directed Gene Therapy", Journal of Virology, 72 (12), (1998), pp. 10222-10226.

Xiao, X, et al., "A Novel 165-Base-Pair Terminal Repeat Sequence Is the Sole cis Requirement for the Adeno-Associated Virus Life Cycle", J Virol, vol. 71, (1997), 941-948.

Xiao, X., et al., "A Novel 165-Base-Pair Terminal Repeat Sequence Is the Sole cis Requirement for the Adeno-Associated Virus Life Cycle", Journal of Virology, 71(2), (Feb. 1997), 941-948.

Xuefeng, Deng, et al., "DNA Damage Signaling Is Required for Replication of Human Bocavirus 1 DNA in Dividing HEK293 Cells", Journal of Virology, vol. 91 No. 1, (Jan. 1, 2017), 20 pgs.

Xuefeng, Deng, et al., "Replication of an Autonomous Human Parvovirus in Non-dividing Human Airway Epithelium Is Facilitated through the DNA Damage and Repair Pathways", Plos Pathogens vol. 12 No. 1, (U.S. Appl. No. 01/142,016), 25 pgs.

Yalkinoglu, A. O, et al., "Inhibition of N-methyl-N'-nitro-N-nitrosoguanidine-induced methotrexate and adriamycin resistancce in CHO cells by adeno-associated virus type 2", Cancer,45(6), (1990), 1195-1203.

Yamagishi, S., et al., "Nifedipine inhibits tumor necrosis factor-alpha-induced monocyte chemoattractant protein-1 overexpression by blocking NADPH oxidase-mediated reactive oxygen species generation", Drugs Exp Clin Res., 29(4), (2003), 147-52.

Yan, Z, "Trans-splicing vectors expand the utility of adeno-associated virus for gene therapy", Proc Natl Acad Sci U S A, 97(12), (Jun. 6, 2000), 6716-6721.

Yan, Z., et al., "A New Class of Hybrid Adeno-Associated Viral Vectors with Non-Homologous ITRs Improves Directional Recombination and Dual-Vector Reconstitution of Large Transgenes", Molecular Therapy, 9(Suppl. 1), (2004), S5-S6.

Yan, Z., et al., "Distinct classes of proteasome-modulating agents cooperatively augment recombinant adeno-associated virus type 2 and type 5-mediated transduction from the apical surfaces of human airway epithelia", J Virol., 78(6), (Mar., 2004), 2863-74.

Yan, Z., et al., "Inverted terminal repeat sequences are important for intermolecular recombination and circularization of adeno-associated virus genomes", Journal of Virology, 79(1), (Jan. 2005), 364-379.

Yan, Z., "Recombinant AAV-Mediated Gene Delivery Using Dual Vector Heterodimerizatiion", In: Methods in Enzmology, vol. 346: Gene Therapy Methods, Phillips, M. I., Editor, Academic Press, San Diego, CA, (2002), 334-357.

Yan, Z., et al., "Trans-splicing vectors expand the utility of adeno-associated virus for gene therapy", Proceedings of the National Academy of Sciences, 97(12), (Jun. 6, 2000), 6716-6721.

Yan, Z., et al., "Trans-splicing vectors expand the utility of adeno-associated virus for gene therapy.", Proc Natl Acad Sci USA., 97(12), (Jun. 6, 2000), 6716-21.

Yan, Z., et al., "Ubiquitination of Both Adeno-Associated Virus Type 2 and 5 Capsid Proteins Affects the Transduction Efficiency of Recombinant Vectors", Journal of Virology, 76(5), (2002), 2043-2053.

Yan, Ziying, et al., "A Common Theme for Ubiquitination-Dependent Transduction of rAAV Type 2 and 5", American Society of Gene Therapy, Abstracts of Scientific Presentations-Abstract No. 569, (Jun. 5, 2002), 1 page.

Yan, Ziying, et al., "Human Bocavirus Type-1 Capsid Facilitates the Transduction of Ferret Airways by Adeno-Associated Virus Genomes", Human Gene Therapy, vol. 28, No. 8, (2017), 612-625.

Yan, Ziying, et al., "Optimization of Recombinant Adeno-Associated Virus-Mediated Expression for Large Transgenes, Using a Synthetic Promoter and Tandem Array Enhancers", Human Gene Therapy, vol. 26, No. 6, (Jun. 1, 2015), 334-346.

Yang, J., et al., "Concatamerization of Adeno-Associated Virus Circular Genomes Occurs Through Intermolecular Recombination", Journal of Virology, 73(11), (Nov. 1999), 9468-9477.

Yu, J., et al., "The Role of the Methoxyphenol Apocynin, a Vascular Nadph Oxidase Inhibitor, as a Chemopreventative Agent in the Potential Treatment of Cardiovascular Diseases", (Curr. Vasc. Pharmacol., 6:204 (2008), (2008), 14 pgs.

(56) References Cited

OTHER PUBLICATIONS

Zabner, J, et al., "Adenovirus-mediated gene transfer to ciliated airway epithelia requires prolonged incubation time", Journal of Virology, 70(10), (Oct., 1996), 6994-7003.
Zabner, J, et al., "Adenovirus-mediated generation of cAMP-stimulated Cl—transport in cystic fibrosis airway epithelia in vitro: effect of promoter and administration method.", Gene Therapy, 3(5), (1996), 458-465.
Zeitlin, Pamela L, "Novel pharmacologic therapies for cystic fibrosis", Perspective Series on cystic fibrosis 103(4), (Feb. 1999), 447-452.
Zentner, M. D., "The Amiloride-Sensitive Epithelial Sodium Channel a-Subunit is Transcriptionally Down-Regulated in Rat Parotid Cells by the Extracellular Signal-Regulated Protein Kinase Pathway", The Journal of Biological Chemistry, 273(46), (1998), 30770-30776.
Zentner, M. D, et al., "The Amiloride-sensitive epithelial Sodium Channel Alpha subunit is Transcriptionally down regulated in rat parotid cells by the extracellular signal-regulatedprotine Kinase pathway.", The Journal of the Biological Chemistry, vol. 273(46), (1998), 30770-30776.
Zhang, Chi, et al., "Identification and characterization of a novel rodent bocavirus from different rodent species in China", Emerging Microbes & Infections 7:48, (2018), 11 pgs.
Zhang, F, et al., "Proteasome Function is Regulated by Cyclic AMP-dependent Protein Kinase through Phosphorylation of Rpt6", The journal of Biological Chemistry;282(31), (Aug. 3, 2007), 22460-22471.
Zhang, L. N., "Dual Therapeutic Utility of Proteasome Modulating Agents for Pharmaco-Gene Therapy of the Cystic Fibrosis Airway", Molecular Therapy, 10(6), (2004), 990-1002.
Zhou, Liqiao, et al., "Improvement of Transduction Efficiency from Split AAV Vectors", American Society of Gene Therapy, Abstracts of Scientific Presentations-Abstract, (Jun. 5, 2002), 1 page.
Zinn, Eric, et al., "Adeno-associated Virus: Fit to serve", Curr Opin Virol., (Oct. 2014), 13 pgs.
Alberts, B., et al., "", In: Molecular Biology of the Cell, 3rd edition, (1994), 618-626.
Flotte, T R, "(Abstract) Recombinant adeno-associated virus vectors for cystic fibrosis gene therapy", Curr Opin Mol Ther 3(5), pp. 497-502, (2001), 1 pg.
Guido, et al., "", World Journal of Gastroenterology, (2016), 8684-8697.
Iwane, Marika, et al., "(Abstract) Population-based surveillance for hospitalizations associated with respiratory syncytial virus, influenza virus, and parainfluenza viruses among young children,", Pediatrics, 113 (6). Pages 1758-1764, (2004), 2 pgs.
Tweedale, Tony, "[Dioxin-I] Inhibits Estrogen-Induced Breast Cancer Cell Proliferation", Reuters Health, http//lists.essential.org/pipermail/dioxin-I/Week-of-Mon-2000103/000096.html, (Dec. 1999), 1 page.
U.S. Appl. No. 09/276,625 U.S. Pat. No. 6,436,392, filed Mar. 25, 1999, Adeno-Associated Virus Vectors.
U.S. Appl. No. 10/054,665 U.S. Pat. No. 6,897,045, filed Jan. 22, 2002, Adeno-Associated Virus Vectors.
U.S. Appl. No. 11/058,751 U.S. Pat. No. 7,803,622, filed Feb. 15, 2005, Adeno-Associated Virus Vectors.
U.S. Appl. No. 11/890,767, filed Aug. 7, 2007, Adeno-Associated Virus Vectors.
U.S. Appl. No. 09/684,554 U.S. Pat. No. 7,241,447, filed Oct. 6, 2000, Adeno-Associated Virus Vectors and Uses Thereof.
U.S. Appl. No. 11/821,116, filed Jun. 21, 2007, Adeno-Associated Viruses and Uses Thereof.
U.S. Appl. No. 11/890,762, filed Aug. 7, 2007, Adeno-Associated Viruses and Uses Thereof.
U.S. Appl. No. 09/689,136 U.S. Pat. No. 7,122,335, filed Nov. 26, 2002, Compound ad Methods to Enhance rAAV Transduction.
U.S. Appl. No. 11/301,601 U.S. Pat. No. 8,846,030, filed Dec. 13, 2005, Compounds and Methods to Enhance rAAV Transduction.
U.S. Appl. No. 11/890,777, filed Aug. 7, 2007, Compounds and Methods to Enhance rAAV Transduction.
U.S. Appl. No. 10/194,421, filed Jul. 12, 2002, Pseudotyped Adeno-Associated Viruses and Uses Thereof.
U.S. Appl. No. 10/815,262 U.S. Pat. No. 7,749,491, filed Mar. 31, 2004, Compounds and Methods to Enhance rAAV Transduction.
U.S. Appl. No. 11/890,761, filed Aug. 7, 2007, Compounds and Methods to Enhance rAAV Transduction.
U.S. Appl. No. 10/815,557, filed Mar. 31, 2004, Compounds and Methods for Pharmico-Gene Therapy of Epithelial Sodium Channel Associated Disorders.
U.S. Appl. No. 11/890,776, filed Aug. 7, 2007, Compounds and Methods for Pharmico-Gene Therapy of Epithelial Sodium Channel Associated Disorders.
U.S. Appl. No. 10/837,029 U.S. Pat. No. 8,241,622, filed Apr. 30, 2004, Adeno-Associated Virus Vectors with Intravecor Heterologous Terminal Palindromic Sequences.
U.S. Appl. No. 11/890.778, filed Aug. 7, 2007, Adeno-Associated Virus Vectors with Intravector Heterologous Terminal Palindromic Sequences.
U.S. Appl. No. 11/890,786, filed Aug. 7, 2007, Adeno-Assoviated Virus Vectors with Intravector Heterologous Terminal Palindromic Sequences.
U.S. Appl. No. 11/617,491, filed Dec. 28, 2006, Method of Identifying Compouncs Useful to Treat Neuronal Degenerative Diseases.
U.S. Appl. No. 11/890,775, filed Aug. 7, 2007, Method of Identifying Compounds Useful to Treat Neuronal Degenerative Diseases.
U.S. Appl. No. 11/890,778, filed Aug. 7, 2007, Method of Identifying Compounds Useful to Treat Neuronal Degenerative Diseases.
U.S. Appl. No. 11/796,605, filed Apr. 27, 2007, Methods and Compounds to Alter Virus Infection.
U.S. Appl. No. 11/890,787, filed Aug. 7, 2007, Method and Compounds to Alter Virus Infection.
U.S. Appl. No. 12/397,583, filed Mar. 4, 2009, Methods for Cloning Ferrets and Transgenic Ferret Models for Diseases.
U.S. Appl. No. 12/835,102, filed Jul. 13, 2010, Methods for Cloning Ferrets and Transgenic Ferret Models for Diseases.
U.S. Appl. No. 14/782,876 U.S. Pat. No. 9,828,587, filed Oct. 7, 2015, Chimeric Adeno-Assoviated Virus/ Boca Virus Parvovirus Vector.
U.S. Appl. No. 15/822,956 U.S. Pat. No. 10,793,835, filed Nov. 27, 2017, Chimeric Adeno-Assoviated Virus/ Boca Virus Parvovirus Vector.
U.S. Appl. No. 16/082,767, filed Sep. 6, 2018, AAV-Mediated Expression Using a Synthetic Promoter and Enhancer.
U.S. Appl. No. 16/304,064, filed Nov. 21, 2018, cis and trans Requirements for Terminal Resolution of Human Boca Virus I.
U.S. Appl. No. 16/477,762 U.S. Pat. No. 11,142,775, filed Jul. 12, 2018, Bocaparvovirus Amall Noncoding RNA and Uses Thereof.
U.S. Appl. No. 17/470,560, filed Sep. 9, 2021, Bocaparvovirus Small Noncoding RNA and Uses Thereof.
U.S. Appl. No. 16/980,268, filed Sep. 11, 2020, Inductive Regeneration of the Airway by Transcriptional Factoe Modulation of Glandular Myoepithelial Stem Cells.
U.S. Appl. No. 17/603,831, filed Oct. 1, 2021, Composition and Methods for Treatment of Cyctic Fibrosis.
U.S. Appl. No. 17/603,840, filed Oct. 14, 2021, Methods and Compositions for Transgene Expression.
"U.S. Appl. No. 16/082,767, Advisory Action dated May 10, 2022", 3 pgs.
"U.S. Appl. No. 16/082,767, Pre-Appeal Brief Request filed Jul. 12, 2022", 5 pgs.
"U.S. Appl. No. 16/304,064, Response filed May 6, 2022 to Non Final Office Action dated Jan. 6, 2022", 8 pgs.
"Chinese Application Serial No. 202080043595.2, Response filed Mar. 11, 2022", with machine translation, 4 pgs.
"Eurasian Application Serial No. 201892006, Office Action mailed Apr. 29, 2022", w/ English translation, 7 pgs.
"European Application Serial No. 17712339.5, Communication Pursuant to Article 94(3) EPC dated May 12, 2022", 4 pgs.
"European Application Serial No. 20727413.5, Response filed Jun. 20, 2022 to Communication Pursuant to Rules 161(1) and 162 EPC dated Dec. 9, 2021", 10 pgs.

(56) References Cited

OTHER PUBLICATIONS

"European Application Serial No. 20728248.4, Response filed Jun. 20, 2022 to Communication Pursuant to Rules 161(1) and 162 EPC dated Jan. 26, 2022", 9 pgs.
"Israeli Application Serial No. 261642, Response filed Apr. 25, 2022 to Notification of Defects in Patent Application dated Dec. 26, 2021", W/ English Claims, 7 pgs.
"Mexican Application Serial No. MX/a/2018/010842, Office Action dated May 13, 2022", with machine translation, 9 pgs.
"Singaporean Application Serial No. 11202111353Q, Response Filed May 11, 2022 to Request for Examination Notice dated Apr. 4, 2022", W/ English Claims, 18 pgs.
"U.S. Appl. No. 16/304,064, Advisory Action Before Filing of an Appeal Brief dated Dec. 15, 2022", 3 pgs.
"U.S. Appl. No. 16/304,064, Response filed Nov. 18, 2022 to Final Office Action dated Aug. 26, 2022", 7 pgs.
"Chilean Application Serial No. 202102701, Acceptance to Continue Prosecution dated Oct. 19, 2022", with machine translation, 2 pgs.
"Japanese Application Serial No. 2021-561893, Notification of Reasons for Refusal dated Nov. 1, 2022", w/ English Translation, 10 pgs.
"Vietnamese Application Serial No. 1-2021-07262, Response filed Nov. 7, 2022 to Office Action dated Sep. 13, 2022", W/ English Claims, 11 pgs.
"Vietnamese Application Serial No. 1-2021-07263, Response filed Nov. 7, 2022 to Office Action dated Sep. 13, 2022", W/ English Claims, 8 pgs.
U.S. Appl. No. 18/0013,417, filed Dec. 28, 2022, Methods and Compositiond for Administering Recombinant Viral Vectors.
"U.S. Appl. No. 16/082,767, Decision on Pre-Appeal Brief Request for Review dated Aug. 17, 2022", 2 pgs.
"U.S. Appl. No. 16/082,767, Notice of Allowance dated Aug. 22, 2022", 8 pgs.
"U.S. Appl. No. 16/304,064, Final Office Action dated Aug. 26, 2022", 21 pgs.
"Australian Application Serial No. 2020289851, First Examination Report dated Aug. 8, 2022", 4 pgs.
"Canadian Application Serial No. 2,909,085, Response filed Aug. 26, 2022 to Office Action dated Feb. 17, 2022", 12 pages.
"Canadian Application Serial No. 3,174,963, Voluntary Amendment filed Sep. 29, 2022", 10 pgs.
"Chinese Application Serial No. 202080043579.3, Voluntary Amendment filed Jul. 28, 2022", W/English Claims, 23 pgs.
"Chinese Application Serial No. 202080043595.2, Voluntary Amendment filed Oct. 8, 2022", with English claims, 13 pgs.
"Eurasian Application Serial No. 201892006, Response filed Aug. 29, 2022 to Office Action dated Apr. 29, 2022", W/ English Claims, 9 pgs.
"European Application Serial No. 17712339.5, Response filed Sep. 15, 2022 to Communication Pursuant to Article 94(3) EPC dated Sep. 15, 2022", 10 pgs.
"Mexican Application Serial No. MX/a/2018/010842, Response filed Sep. 19, 2022 to Office Action dated May 13, 2022", W/ English Claims, 18 pgs.
"Singapore Application Serial No. 11202111334S, Voluntary Amendment filed Apr. 27, 2022", 10 pgs.
"Vietnamese Application Serial No. 1-2021-07262, Office Action dated Sep. 13, 2022", w/English translation, 2 pgs.
"Vietnamese Application Serial No. 1-2021-07263, Office Action dated Sep. 13, 2022", w/English translation, 2 pgs.
"International Application Serial No. PCT US2021 039860, International Preliminary Report on Patentability dated Jan. 1, 2023", 17 pgs.
"U.S. Appl. No. 16/082,767, Notice of Allowance dated Jan. 26, 2023", 7 pgs.
"Canadian Application Serial No. 3,137,015, Examiners Rule 86(2) Requisition dated Jan. 13, 2023", 5 pgs.
"Canadian Application Serial No. 3,137,078, Examiners Rule 86(2) Requisition dated Jan. 16, 2023", 5 pgs.
"Mexican Application Serial No. MX a 2018 010842, Office Action dated Jan. 3, 2023", with machine translation, 12 pgs.

\* cited by examiner

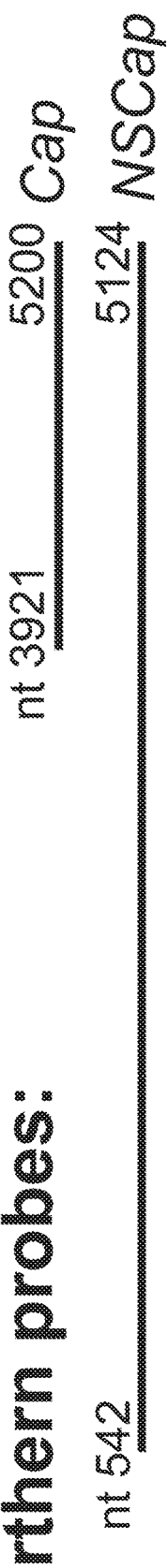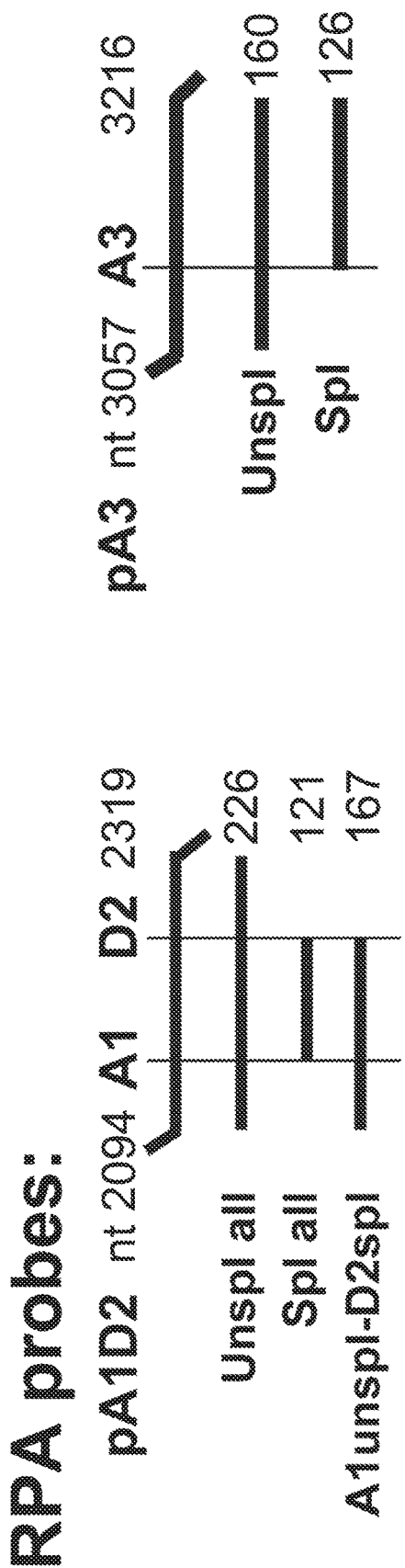
Fig. 1C nt 3146 GTTAAGACGCCACCAATCAAGAGACAGCCAAGAGGGTGGGTGCTGCCCGGATAC
         ―――
         VP1
         3152

AGATACCTGGGACCTTTTCAATCCCACTGGACAACGGCGAACCTGTGAACAACGCT

GACCGGGGCCGCTCAGCTGCACGATCACGCGCATACAGCGCAGCTGATCAAGTCCGGC
                                          ――――――――――
                                          PAS1(3295)

AAAAACCCATACCCTGTACTTTCAAACAAGGCTGACGAAAAAATTCATCGACGATCTG
                       ―――――――
                       PAS2(3329)

AAAGACGATTGGGAGCATTGGGGATCATTGGGAGCTCCTTCTTTTAAGATCAAG
     ―――                                       ――――――――
     3422                                      PAS3(3409)
     VP2

AGAGCAGTGGCCCCCGCTCTCTGGGAAACAAGGAGAGAGCACAGAAAAGGCATTTC
                           ――――――――――
                           PAS4(3440)

TACTTTTGCAAACAGCAATAAGGGCGCCAAAGAAAACAAAGAAATCCGAACCCAAG
                    ――――――――――
                    PAS5(3458)
                    3539
                     |
                    ATG
                    ―――
                    VP3
                    3538

CCTGGGGACTTCCAAAATG

Fig. 2

1. pVP2m1    GUA GCT
2. pVP2m2    GGG CCC
3. pVP2m3    GUG GCC
4. pVP2m4    AAU AUU
5.

Figure 6A:
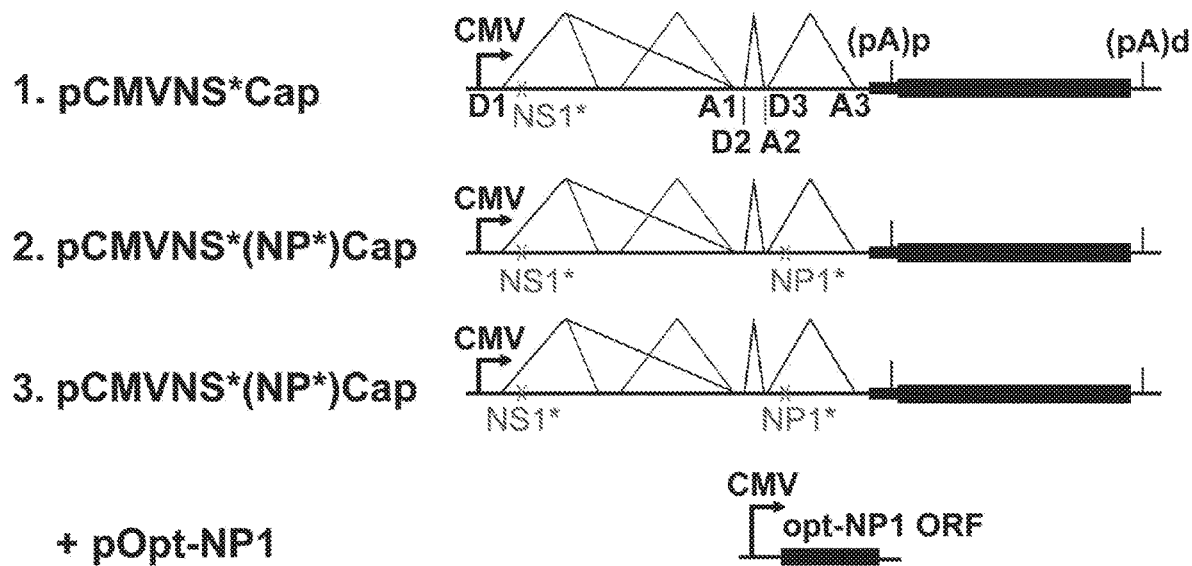

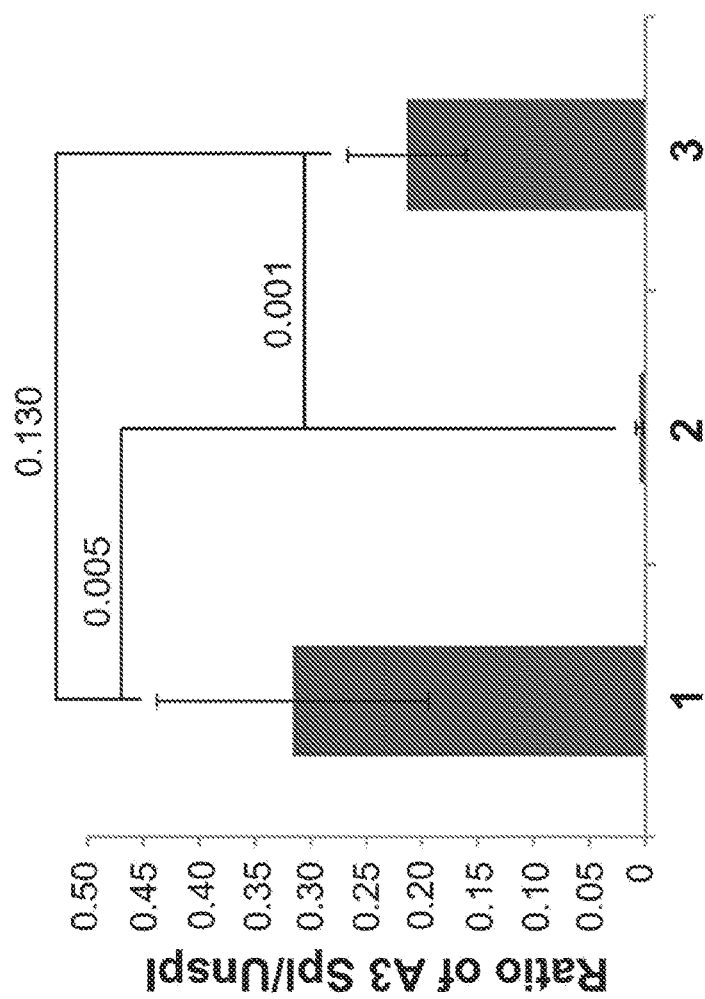
Fig. 6D
Fig. 6C

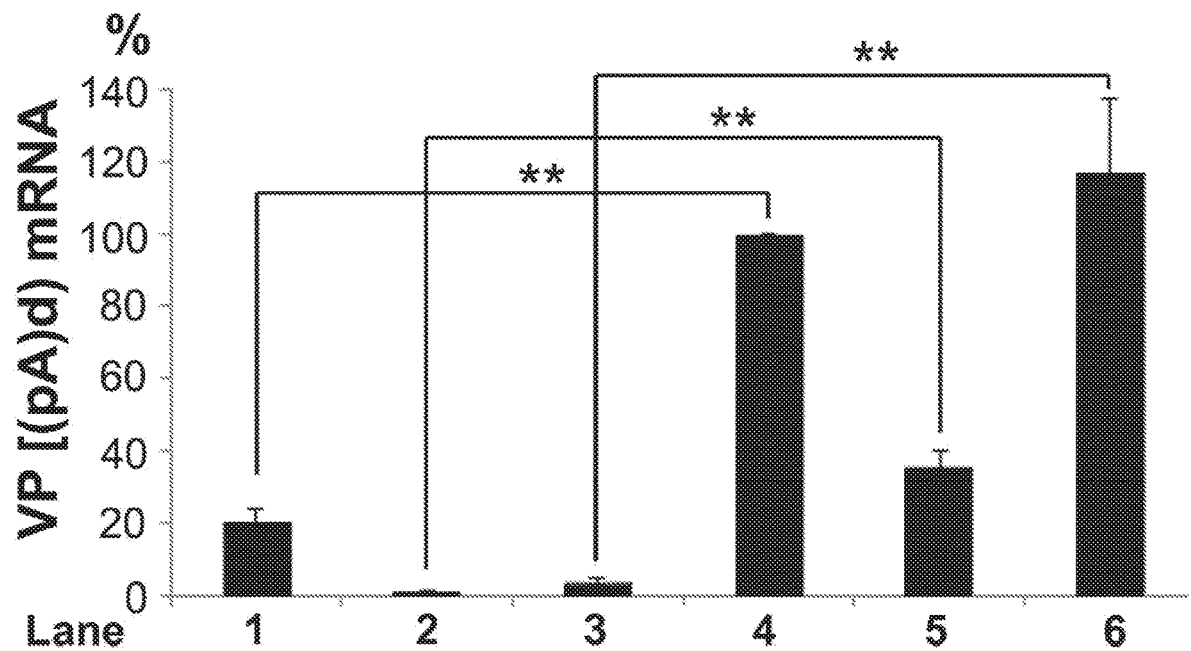
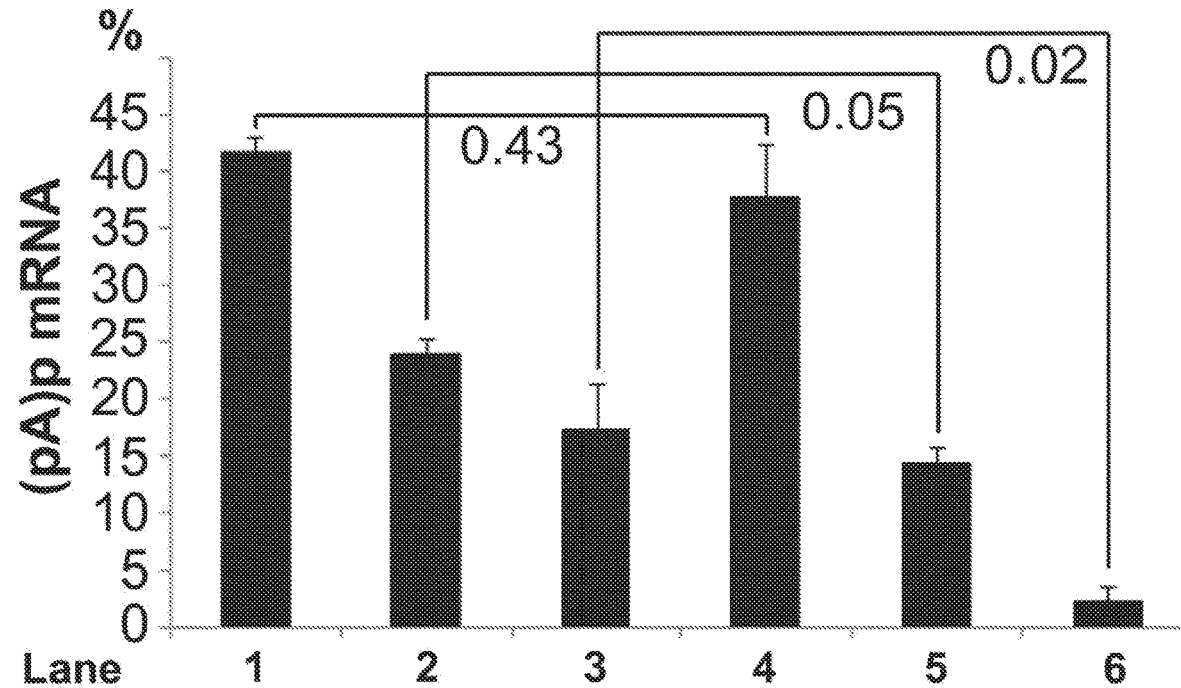
Fig. 7D

ATGAGCTCAGGGAATATGAAGGATAAACACAGATCTTACAAGAGAAAGGGGTCTCTGAACGCGGAGAACGGAA
ACGGCATTGGCAAACAACCATCACAGAAGCAGGAGTCGGTCACCATCCGCCATAGCGGGGAGCGGAGGGTCAG
GGAGCTACCACCAGGAACACCCCATTTCACATCTGAGCAGTGTACCGTAAAACAAGTGACCAGGTGATGA
AGACCCGGGAAAGCACTTCTGGAAAGAAGGACAATAGAACAAACCCTTACACGTGTCTCCCAGCACCGAGCAT
CCAATCCTGAGGCCCCAGGGTGGTGCGGATTCTATTGGCATAGCACCGCATTGCACGCGAGGTACTAACAGTA
TTTCAATGAGATGAAGCAGTTCCAGCAACTGCAAATAAAATGGGGATAATACGGGAGC
TGCTGTTTAATCAGAAGAAGACCCTGACCAGAAATACGGAATATGTTCTGGCATTTCAGAAACAACTCTGATTG
CGAGAGGTGTAATTACTGGGATGATGTATATCGGCGACACCTCGCTAATGTGAGCAGTCAGACTGAAGCCGACGA
AATCACAGACGAGGAGATGCTGTCAGCCGATGCCGATGCCAGCAAT (SEQ ID NO:1)

Figure 12C:
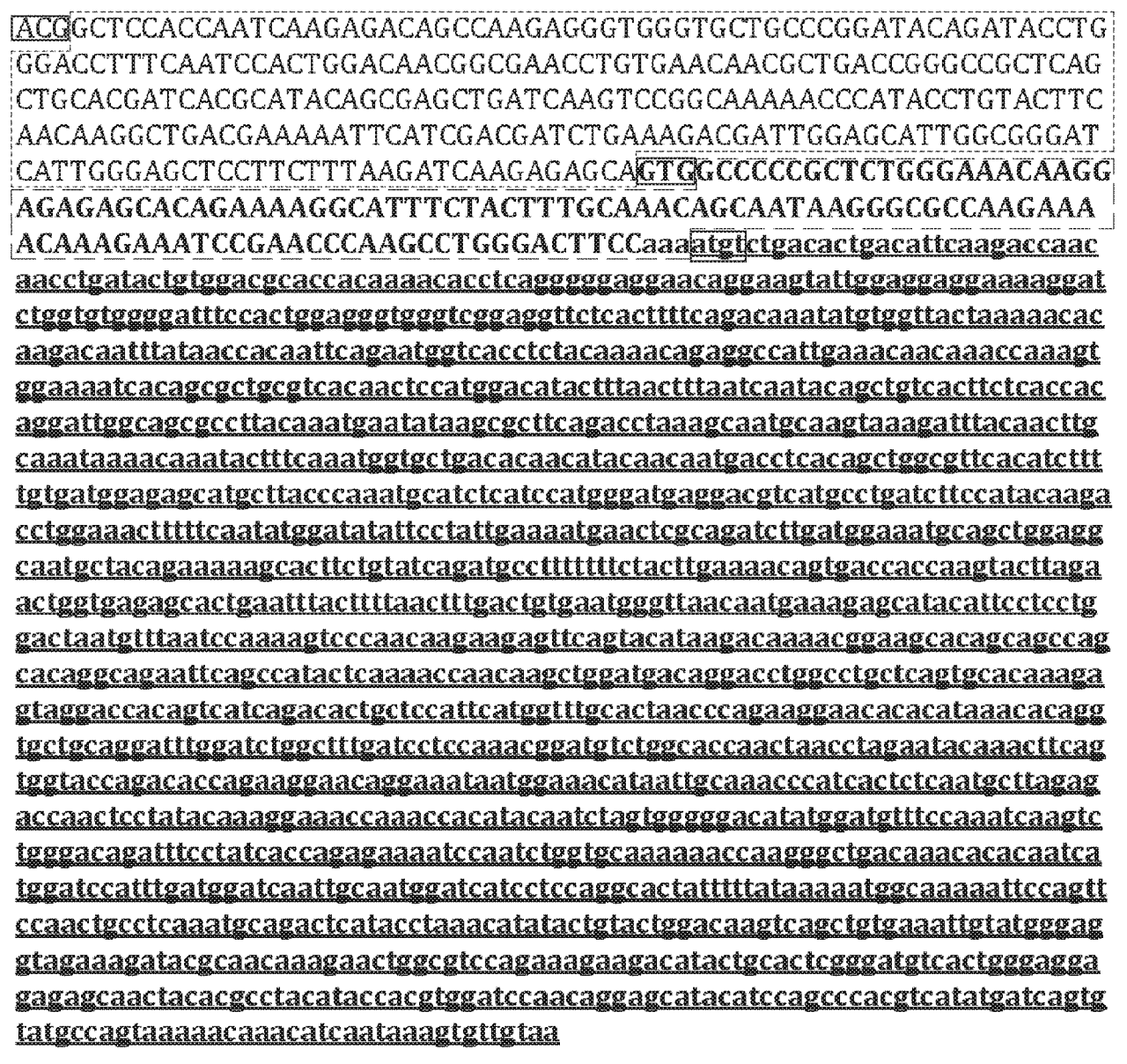

*Fig. 12A*

ACGGCTCCACCAATCAAGAGACAGCCAAGAGGGTGGGTGCTGCCCGGATACAGATACCTG
GGACCTTTCAATCCACTGGACAACGGCGAACCTGTGAACAACGCTGACCGGGCCGCTCAG
CTGCACGATCACGCATACAGCGAGCTGATCAAGTCCGGCAAAAACCCATACCTGTACTTC
AACAAGGCTGACGAAAAATTCATCGACGATCTGAAAGACGATTGGAGCATTGGCGGGAT
CATTGGGAGCTCCTTCTTTAAGATCAAGAGAGCAGTGGCCCCCGCTCTGGGAAACAAGG
AGAGAGCACAGAAAGGCATTTCTACTTTGCAAACAGCAATAAGGGCGCCAAGAAA
ACAAAGAAATCCGAACCCAAGCCTGGGACTTCCAAAATGTCTGACACCGATATCCAG
GACCAGCAGCCCGACACTGTGGATGCCCCTCAGAACACCTCCGGAGGAGGAACAGGC
TCTATCGGAGGAGGGAAGGGGTCTGGAGTGGGCATTAGTACCGGAGGCTGGGTCGG
GGGAAGTCATTTTTCAGACAAGTACGTGGTCACCAAAAACACAAGGCAGTTCATCAC
CACAATTCAGAATGGCCACCTGTATAAAACAGAGGCTATCGAAACTACCAACCAGAG
CGGGAAGTCCCAGCGGTGCGTGACAACTCCTTGGACCTACTTCAACTTTAATCAGTA
CTCTTGTCACTTTAGTCCACAGGATTGGCAGAGACTGACAAATGAGTACAAGCGATT
CCGGCCCAAAGCCATGCAGGTGAAGATCTATAACCTGCAGATCAAGCAGATTCTGTC
TAATGGCGCCGACACCACATACAACAATGATCTGACCGCTGGGGTGCACATCTTCTG
CGACGGAGAGCATGCTTACCCTAACGCAAGCCACCCATGGGACGAAGATGTCATGCC
TGATCTGCCATATAAGACATGGAAACTGTTCCAGTACGGATATATCCCCATTGAGAA
TGAACTGGCAGACCTGGATGGAAACGCAGCAGGAGGGAATGCCACTGAGAAGGCTC
TGCTGTACCAGATGCCTTTCTTTCTGCTGGAAAACTCTGACCATCAGGTGCTGCGAA
CCGGGGAGAGTACTGAATTCACCTTTAATTTCGATTGTGAGTGGGTCAACAATGAA
CGCGCCTATATCCCCCCTGGACTGATGTTTAACCCCAAAGTGCCTACCCGGAGAGTCC
AGTACATCAGGCAGAATGGCTCAACAGCTGCAAGCACTGGGCGCATTCAGCCATATT
CCAAGCCCACCTCTTGGATGACAGGACCTGGACTGCTGAGCGCACAGCGAGTGGGAC
CTCAGTCTAGTGACACAGCCCCATTCATGGTCTGCACTAACCCCGAGGGAACTCACA
TCAATACCGGCGCCGCTGGCTTTGGGAGTGGATTCGATCCACCCTCAGGCTGTCTGG
CACCTACCAACCTGGAGTACAAACTGCAGTGGTATCAGACACCAGAAGGCACTGGGA
ACAATGGGAACATCATTGCCAATCCCTCACTGAGCATGCTGAGGGACCAGCTGCTGT
ACAAGGGAAACCAGACTACCTATAATCTGGTGGGCGACATCTGGATGTTTCCAAACC
AGGTCTGGGATCGCTTCCCAATCACACGAGAGAATCCCATTTGGTGCAAGAAACCTC
GCGCCGACAAGCATACTATCATGGACCCCTTTGATGGGAGCATTGCCATGGATCACC
CTCCAGGAACTATCTTCATTAAGATGGCTAAAATTCCAGTGCCCACCGCAAGTAACG
CCGACTCATACCTGAATATCTATTGCACCGGCCAGGTCTCCTGTGAGATCGTGTGGG
AAGTCAAACGGTACGCTACCAAGAACTGGAGACCCGAGAGGCGCCATACAGCACTGG
GAATGTCACTGGGAGGCGAAAGCAATTACACACCAACTTATCACGTGGACCCCACCG
GCGCCTATATTCAGCCTACTTCTTACGATCAGTGTATGCCAGTCAAAACTAACATCA
ACAAGGTCCTGTAA

Fig. 12C

Fig. 12D

METHODS TO PRODUCE CHIMERIC ADENO-ASSOCIATED VIRUS/BOCAVIRUS PARVOVIRUS

CROSS-REFERENCE TO RELATED APPLICATIONS

This application is a U.S. National Stage Filing under 35 U.S.C. 371 from International Application No. PCT/US2017/017021, filed on Feb. 8, 2017, and published as WO 2017/139381 on Aug. 17, 2017, which application claims the benefit of the filing date of U.S. application Ser. No. 62/292,613, filed on Feb. 8, 2016 and U.S. application Ser. No. 62/453,745, filed on Feb. 2, 2017, the disclosures of which are incorporated by reference herein.

STATEMENT OF GOVERNMENT RIGHTS

This invention was made with government support under grants AI105543 and AI112803 awarded by the National Institutes of Health. The Government has certain rights in the invention.

BACKGROUND

Human bocavirus1 (HBoV1), first identified in 2005 (Allander et al., 2005), belongs to genus *Bocaparvovirus* in the subfamily Parvovirinae of the Parvoviridae family (Cotmore et al., 2014). The genus *Bocaparvovirus* consists of three groups of viruses, namely HBoV1-4, bovine parvovirus 1 (BPV1) and minute virus of canines (MVC/CnMV) (Johnson and Qiu, 2011). HBoV1 causes respiratory tract infection in young children worldwide (Allander et al., 2007; Christensen et al., 2010; Deng et al., 2012; Don et al., 2010; Edner et al., 2011; Kantola et al., 2008; Martin et al., 2015). In vitro, the virus infects only polarized (well-differentiated) human airway epithelium cultured at an air-liquid interface (HAE-ALI) (Dijkman et al., 2009; Huang et al., 2012; Deng et al., 2013; Deng et al., 2014). An infectious clone of HBoV1 (pIHBoV1) was constructed. Transfecting the pIHBoV1 in human embryonic kidney 293 (HEK293) cells results in efficient replication of the HBoV1 genome and production of HBoV1 virions, which are infectious in HAE-ALI (Huang et al., Deng et al., 2013).

The transcription profile of HBoV1 has been studied in transfection of both HBoV1 non-replicating and replicating double-stranded DNA (dsDNA) forms of the viral genome in HEK293 cells (Chen et al., 2010; Shen et al., 2015), as well as during HBoV1 infection of HAE-ALI (Dijkman et al., 2009; Shen et al., 2015). All the viral mRNA transcripts are generated from alternative processing (involving both splicing and polyadenylation) of one HBoV1 precursor-RNA (pre-mRNA), which is transcribed from the P5 promoter (FIG. 1A) (Dijkman et al., 2009; Chen et al., 2010; Shen et al., 2015). The left side of the genome encodes non-structural (NS) proteins, and four major NS proteins (NS1, NS2, NS3, and NS4) are expressed from alternatively spliced mRNA transcripts (Shen et al., 2015). While NS1 is critical to viral DNA replication, NS2 also plays a role during virus replication in infection of HAE-ALI (Shen et al., 2015). The right side of the genome encodes viral capsid proteins from alternatively spliced mRNA transcripts, R6, R7, and R8 mRNAs (FIG. 1A). Of note, HBoV1, like other members of the genus *Bocaparvovirus*, encodes a unique nonstructural protein NP1 from the middle of the genome. NP1 is required for an efficient replication of viral DNA (Huang et al., 2012; Sun et al., 2009).

HBoV1 capsid is capable of cross-genus packaging of a genome of recombinant adeno-associated virus 2 (rAAV2) in HEK293 cells, which generates HBoV1 capsid-pseudotyped 129 rAAV2 vector (rAAV2/HBoV1) (Yan et al., 2013). The chimeric vector can deliver a full-length cystic fibrosis transmembrane conductance regulator (CFTR) gene with a strong promoter to cystic fibrosis (CF) HAE, with demonstrated efficacy in correcting CFTR-dependent chloride transport (Yan et al., 2013). Therefore, the rAAV2/HBoV1-CFTR vector holds much promise for CF gene therapy. However, in the current vector production system, the packaging plasmid pHBoV1NSCap, which carries an HBoV1 non-replicating dsDNA genome (containing the P5 promotor and NS and Cap genes), was used for packaging rAAV2/HBoV1 vector. The efficiency of the vector production is on average 10 times lower than that of the rAAV2 vector packaged by the AAV2 capsid (Yan et al., 2013). It was hypothesized that this lower efficiency is likely due to the unnecessary expression of the HBoV1 NS gene from the packaging plasmid pHBoV1NSCap.

SUMMARY

Chimeric parvovirus vector rAAV/HBoV inherits the safety of rAAV (recombinant adeno-associated virus) and the airway tropism of HBoV (human bocavirus type 1), which provides a solution for the current lack of an efficient vector for airway gene therapy of pulmonary diseases, such as cystic fibrosis, alpha-antitrypsin deficiency, asthma, vaccines, and lung cancer.

This disclosure provides improved methods to produce chimeric AAV/BoV viruses, e.g., using a chimeric parvoviral vector (rAAV2/HBoV1) vector, in which the recombinant adeno-associated virus (rAAV) genome is pseudo-packaged by the human bocavirus 1 (HBoV1) capsid, such as one expressing a full-length cystic fibrosis transmembrane conductance regulator (CFTR) gene that is capable of correcting CFTR81 dependent chloride transport in cystic fibrosis human airway epithelium. Previously, an HBoV1 nonstructural (NS) and capsid (Cap) protein-expressing plasmid, pHBoV1NSCap, was used to package a rAAV2/HBoV1 vector, but yields remain low, e.g., $2 \times 10^{11}$ DNAase-resistant particles (DRPs)/40 150 mm dishes of transfected cells (400-600 DRP/cell), which is about 5% to about 10% the typical yield of rAAV2 production). In order to simplify this packaging plasmid, the involvement of the HBoV1 nonstructural proteins in capsid protein expression was investigated as described below. It was found that NP1, a small NS protein encoded by the middle open reading frame, allows for the expression of the viral capsid proteins (VP1, VP2, and VP3), whereas the other NS proteins (NS1, NS2, NS3, and NS4) are not necessarily required. Systematic analyses of the HBoV1 mRNAs transcribed from the pHBoV1NSCap packaging plasmid and its derivatives in HEK293 cells were performed. By mutating the cis-elements, which function as internal polyadenylation signals in the capsid protein-expressing mRNA, a simple HBoV1 capsid protein gene was constructed that expresses capsid proteins VP1, VP2 and VP3 as efficiently as pHBoV1NSCap and at similar ratios, but independently of the NP1. Thus, mechanistically, it was found that NP1 is required for both the splicing and the read-through of the proximal polyadenylation site of the HBoV1 precursor-mRNA, both of which are essential for the maturation of capsid protein-encoding mRNA. Thus, the present disclosure provides a unique example of how a small viral nonstructural protein facilitates the multifaceted regulation of capsid gene expression. Moreover, a function of HBoV1 NP1 in the regulation of capsid protein expression was identified, which allows for a better packaging system for rAAV/HBoV vector production.

The present invention provides a method of preparing a chimeric virus comprising bocavirus capsid protein (VP) and a recombinant adeno-associated (AAV) viral genome. Any AAV genome may be employed, e.g., any mammalian AAV including any primate AAV, a human or non-human primate AAV, including a chimeric AAV genome such as one having synthetic or chimeric ITRs (see, e.g., U.S. Pat. No. 8,241,622, which is incorporated by reference herein), or formed from AAV DNA from two or more different serotypes, e.g., a chimeric genome having 2 ITRs, each ITR from a different serotype or chimeric ITRs. Any bocavirus or bocavirus genome may be employed in the methods, for example, a human bocavirus or human bocavirus genome. In one embodiment, the method is NP1 dependent, and according to one embodiment, the method comprises providing a mutant bocavirus, e.g., HoBV1, genome that when introduced into cells; i) does not express one or more of NS1, NS2, NS3 or NS4; for example, expresses none of NS1, NS2, NS3, NS4; or expresses only NS1 or NS2 or NS3 or NS4; or expresses any two of NS1, NS2, NS3, NS4, for example, expresses NS3 and NS4; or expresses any three of NS1, NS2, NS3, NS4, for example, expresses NS2, NS3 and NS4, ii) expresses one or more of bocavirus VP1, VP2 or VP3, for example, expresses VP1 and VP2 and VP3, or expresses VP1 and VP2, or expresses VP1 and VP3, or expresses VP2 and VP3, and iii) expresses bocavirus NP1. The method can further include introducing the mutant bocavirus genome and a rAAV vector into cells which do not express one or more of bocavirus NS1, NS2, NS3 or NS4, as defined above thereby producing bocavirus VP, bocavirus NP1 and a rAAV genome; and can further comprise collecting chimeric rAAV/bocavirus. Optionally the collecting of chimeric rAAV/bocavirus can be from the cells or the cell supernatant, for example, where the cells are grown in culture medium.

According to one embodiment the method comprises providing one or more vectors that express one or more of bocavirus VP1, VP2 or VP3; for example, express VP1 and VP2 and VP3, or express VP1 and VP2, or express VP1 and VP3, or express VP2 and VP3, and express bocavirus NP1 but do not express one or more of bocavirus NS1, NS2, NS3 or NS4, for example, expresses none of NS1, NS2, NS3, NS4, or expresses only NS1 or NS2 or NS3 or NS4; or expresses any two of NS1, NS2, NS3, NS4, for example, expresses NS3 and NS4; or expresses any three of NS1, NS2, NS3, NS4, for example, expresses NS2, NS3 and NS4. The method can further comprise expressing the one or more vectors in cells which do not express one or more of bocavirus NS1, NS2, NS3 or NS4, as defined above thereby producing bocavirus VP, bocavirus NP1 and a rAAV genome; and can further comprise collecting chimeric rAAV/bocavirus, optionally the collecting chimeric rAAV/bocavirus can be from the cells or the cell supernatant, for example, where the cells are grown in culture medium The one or more vectors may be integrated into the genome of the cells. The bocavirus can be a human bocavirus or the genome a human bocavirus genome.

According to the invention, the mutant bocavirus genome and a rAAV vector can be introduced into cells thereby producing bocavirus capsid protein (VP) and bocavirus NP1, and a rAAV genome. A mutant BoV genome, e.g., a mutant human BoV genome or a non-human BoV genome, may include one or more insertions, one or more deletions, or one or more nucleotide substitutions, e.g., substitutions that results in an in-frame stop codon or removal of a splice site, or any combination thereof, in order to inhibit or prevent expression of a functional viral protein. The chimeric rAAV/bocavirus virus can then be collected, optionally the collecting chimeric rAAV/bocavirus can be from the cells or the cell supernatant, for example, where the cells are grown in culture medium. According to the invention, the one or more vectors may be integrated into the genome of the cells. According to the invention the bocavirus may be a human bocavirus or the genome may be a human bocavirus genome.

In one embodiment, the rAAV vector comprises an expression cassette encoding a heterologous gene product. In one embodiment, the gene product encodes a therapeutic protein. In one embodiment, the rAAV genome is a rAAV-1, rAAV-2, rAAV-3, rAAV-4, rAAV-5, rAAV-6, rAAV-7, rAAV-8 or rAAV-9 genome. In one embodiment, the gene product is a viral, bacterial, tumor, parasite, or fungal antigen. In one embodiment, the gene product is cystic fibrosis transmembrane conductance regulator, C1 inhibitor gene, C1-INH gene, SERPING gene, β-globin, γ-globin, tyrosine hydroxylase, glucocerebrosidase, aryl sulfatase A, factor VIII, dystrophin, alpha 1-antitrypsin, surfactant protein SP-D, SP-A or SP-C, erythropoietin, HBoV protein, influenza virus protein, RSV protein, a neutralizing antibody or an antigen binding fragment thereof, SARS virus protein, or a cytokine, e.g., IFN-alpha, IFN-gamma, TNF, IL-1, IL-17, or IL-6. In one embodiment, the gene product is cystic fibrosis transmembrane conductance regulator. In one embodiment, the gene product is C1 inhibitor gene, C1-INH gene, or SERPING1 gene. In one embodiment, the DNAase-resistant particles, DRPs, of the chimeric virus which are produced are at least about 5% greater than the DRPs produced of a corresponding chimeric virus where the bocavirus genome also expresses bocavirus NS protein, for example, that expresses all of NS1, NS2, NS3, NS4, or that expresses one or more of NS1, NS2, NS3 or NS4, or that expresses the one or more of NS1, NS2, NS3 or NS4 not expressed by the chimeric virus produced by the methods described herein. In one embodiment, the yield is about 1,000 to about 10,000 DRP/cell, e.g., about 1,500 to about 6,000 DRP/cell. The AAV genome may be stably incorporated into the genome of the cell, e.g., via homologous recombination or random integration.

Also provided is a method of preparing a chimeric virus comprising bocavirus capsid protein and a recombinant adeno-associated (AAV) viral genome, which method is NP1 dependent. The method comprises providing one or more vectors that express one or more of VP1, VP2 or VP3, for example, express VP1 and VP2 and VP3, or express VP1 and VP2, or express VP1 and VP3, or express VP2 and VP3, and express NP1 but do not express one or more of NS1, NS2, NS3 or NS4, for example, expresses none of NS1, NS2, NS3, NS4; or expresses only NS1 or NS2 or NS3 or NS 4; or expresses any two of NS1, NS2, NS3, NS4, for example, expresses NS3 and NS4; or expresses any three of NS1, NS2, NS3, NS4, for example, expresses NS2, NS3 and NS4; expressing the vectors in cells; optionally wherein the cells do not express one or more of bocavirus NS1, NS2, NS3 or NS4, as defined above, and collecting chimeric virus. Optionally the collecting of chimeric virus can be from the cells or the cell supernatant, for example, where the cells are grown in culture medium. In one embodiment, the rAAV vector comprises an expression cassette encoding a heterologous gene product. In one embodiment, the gene product encodes a therapeutic protein. In one embodiment, the rAAV genome is a rAAV-1, rAAV-2, rAAV-3, rAAV-4, rAAV-5, rAAV-6, rAAV-7, rAAV-8 or rAAV-9 genome. In one embodiment, the gene product is a viral, bacterial, tumor, parasite, or fungal antigen. In one embodiment, the gene product is cystic fibrosis transmembrane conductance regulator, C1 inhibitor gene, C1-INH gene, SERPING gene, β-globin, γ-globin, tyrosine hydroxylase, glucocerebrosidase, aryl sulfatase A, factor VIII, dystrophin, alpha 1-antitrypsin, surfactant protein SP-D, SP-A or SP-C, erythropoietin, HBoV protein, influenza virus protein, RSV protein, a neutralizing antibody or an antigen binding fragment thereof, SARS virus protein, or a cytokine, e.g., IFN-alpha, IFN-gamma, TNF, IL-1, IL-17, or IL-6. In one embodiment, the gene product is cystic fibrosis transmembrane conductance regulator. In one embodiment, the gene product is C1 inhibitor gene, C1-INH gene, or SERPING1 gene. In one embodiment, DRP of the chimeric virus is at least about 5% greater than a corresponding chimeric virus where the bocavirus genome also expresses bocavirus NS protein, for example that expresses all of NS1, NS2, NS3, NS4, that also expresses one or more of NS1, NS2, NS3 or NS4, or that expresses the one or more of NS1, NS2, NS3 or NS4 not expressed by the chimeric virus of the invention.

Further provided is a method of preparing a chimeric virus comprising bocavirus capsid protein and a recombinant adeno-associated (AAV) viral genome, which method is independent of bocavirus NP1. In one embodiment, the method comprises providing a mutant bocavirus genome that when introduced into cells expresses one or more of bocavirus NS1, NS2, NS3 or NS4, for example, that expresses only NS1 or NS2 or NS3 or NS4; or expresses any two of NS1, NS2, NS3, NS4, for example, expresses NS3 and NS4; or expresses any three of NS1, NS2, NS3, NS4, for example, expresses NS2, NS3 and NS4, or that expresses all of NS1, NS2, NS3, NS4; or alternatively expresses none of NS1, NS2, NS3, NS4, expresses one or more of bocavirus VP1, VP2 or VP3, for example, expresses VP1 and VP2 and VP3, or expresses VP1 and VP2, or expresses VP1 and VP3, or expresses VP2 and VP3, but does not express bocavirus NP1 or a functional bocavirus NP1, wherein optionally the coding region for the one or more of the VP1, VP2 or VP3 is codon optimized (SEQ ID Nos. 2-3). In one embodiment, the mutant genome expresses VP1, VP2 and VP3. In one embodiment, the method includes providing a mutant bocavirus genome that when introduced into cells does not express any of bocavirus NS1, NS2, NS3 or NS4, expresses one or more of bocavirus VP1, VP2 or VP3, for example, expresses VP1 and VP2 and VP3, or expresses VP1 and VP2, or expresses VP1 and VP3, or expresses VP2 and VP3, but does not express bocavirus NP1 or a functional bocavirus NP1, wherein optionally the coding region for the one or more of the VP1, VP2 or VP3 is codon optimized (SEQ ID Nos. 2-3). In one embodiment, the method includes providing one or more vectors that when introduced to cells express one or more of bocavirus VP1, VP2 or VP3, but do not express bocavirus NP1 or a functional bocavirus NP1 or any of NS1, NS2, NS3 or NS4, wherein optionally the coding region for the one or more of the VP1, VP2 or VP3 is codon optimized (SEQ ID Nos. 2-3). Optionally or additionally, the mutant genome and a rAAV vector are introduced into cells that do not express NP1 in trans, for example, the method can further comprise introducing the mutant bocavirus genome and a rAAV vector into cells that do not express bocavirus NP1 in trans, thereby producing bocavirus nonstructural proteins NS1, NS2, NS3 or NS4, capsid proteins and a rAAV genome. The method can further comprise collecting the chimeric virus or chimeric rAAV/bocavirus, and optionally the collecting can be from the cells or the cell supernatant, for example, where the cells are grown in culture medium. In one embodiment, the promoter that expresses bocavirus proteins is not a bocavirus promoter, e.g., not a HBoV promoter. The bocavirus can be human bocavirus. In one embodiment, the rAAV vector comprises an expression cassette encoding a heterologous gene product. In one embodiment, the rAAV genome is a rAAV-1, rAAV-2, rAAV-3, rAAV-4, rAAV-5, rAAV-6, rAAV-7, rAAV-8 or rAAV-9 genome wherein the gene product encodes a therapeutic protein. In one embodiment, the gene product is a viral, bacterial, tumor, parasite, or fungal antigen. In one embodiment, the gene product is cystic fibrosis transmembrane conductance regulator, C1 inhibitor gene, C1-INH gene, SERPING1 gene, β-globin, γ-globin, tyrosine hydroxylase, glucocerebrosidase, aryl sulfatase A, factor VIII, dystrophin, alpha 1-antitrypsin, surfactant protein SP-D, SP-A or SP-C, erythropoietin, HBoV protein, influenza virus protein, RSV protein, a neutralizing antibody or an antigen binding fragment thereof, SARS virus protein, or a cytokine, e.g., IFN-alpha, IFN-gamma, TNF, IL-1, IL-17, or IL-8. In one embodiment, the gene product is cystic fibrosis transmembrane conductance regulator. In one embodiment, the gene product is C1 inhibitor gene, C1-INH gene, or SERPING1 gene. In one embodiment, the DRP of the chimeric virus is at least about 5% greater than a corresponding chimeric virus with a bocavirus genome that also expresses bocavirus NS protein, for example that expresses all of NS1, NS2, NS3 NS4, that also expresses one or more of NS1, NS2, NS3 or NS4, or that expresses the one or more of NS1, NS2, NS3 or NS4 not expressed by the chimeric virus of the invention. According to one embodiment of the method of the invention neither the cells nor the mutant genome provides for expression of any of bocavirus NS1, NS2, NS3 or NS4.

In one embodiment, the invention also provides a method of preparing a chimeric virus comprising bocavirus capsid protein and a recombinant adeno-associated (AAV) viral genome which method is independent of bocavirus NP1. In one embodiment, the method comprises providing one or more vectors that when introduced to cells express one or more of NS1, NS2, NS3 or NS4, for example, that expresses only NS1 or NS2 or NS3 or NS 4; or expresses any two of NS1, NS2, NS3, NS4, for example, expresses NS3 and NS4; or expresses any three of NS1, NS2, NS3, NS4, for example, expresses NS2, NS3 and NS4, or that expresses all of NS1, NS2, NS3, NS4, or alternatively do not express any of NS1, NS2, NS3, NS4; express one or more of bocavirus VP1, VP2 or VP3, for example, express VP1 and VP2 and VP3, or express VP1 and VP2, or express VP1 and VP3, or express VP2 and VP3, but do not express bocavirus NP1 or a functional bocavirus NP1, wherein the coding region for the one or more of the bocavirus VP1, VP2 or VP3 may be codon optimized. In one embodiment, the method includes providing one or more vectors that when introduced to cells express one or more of bocavirus VP1, VP2 or VP3, but do not express bocavirus NP1 or a functional bocavirus NP1 or any of NS1, NS2, NS3 or NS4. In one embodiment, the one or more vectors express VP1, VP2 and VP3. In one embodiment, the coding region for the one or more of the bocavirus VP1, VP2 or VP3 is codon optimized. Those vectors and a rAAV vector are expressed in cells that do not express NP1 in trans thereby, producing bocavirus capsid protein and a rAAV genome; and chimeric virus is collected. For example the method can further comprise expressing the one or more vectors and a rAAV vector in cells that do not express NP1 in trans, thereby producing bocavirus nonstructural proteins NS1, NS2, NS3 or NS4 capsid protein and a rAAV genome;

and collecting chimeric rAAV/bocavirus, optionally the collecting chimeric virus can be collecting from the cells or the cell supernatant, for example where the cells are grown in culture medium. The method can further comprise that the one or more vectors are integrated into the genome of the cell and can additionally or alternatively comprise that neither the cells nor the one or more vectors provides for expression of any of bocavirus NS1, NS2, NS3 or NS4.

According to some embodiments of the invention, the promoter that expresses bocavirus proteins is not a bocavirus promoter.

According to a further aspect of the invention there is provided an isolated mutant bocavirus genome that when introduced to cells does not express one or more of bocavirus NS1, NS2, NS3 or NS4, for example, expresses none of NS1, NS2, NS3, NS4; or expresses only NS1 or NS2 or NS3 or NS 4; or expresses any two of NS1, NS2, NS3, NS4, for example, expresses NS3 and NS4; or expresses any three of NS1, NS2, NS3, NS4, for example, expresses NS2, NS3 and NS4; expresses bocavirus VP1, VP2 and VP3; and expresses bocavirus NP1. Optionally the promoter that expresses bocavirus proteins is not a bocavirus promoter.

Figure 1B:
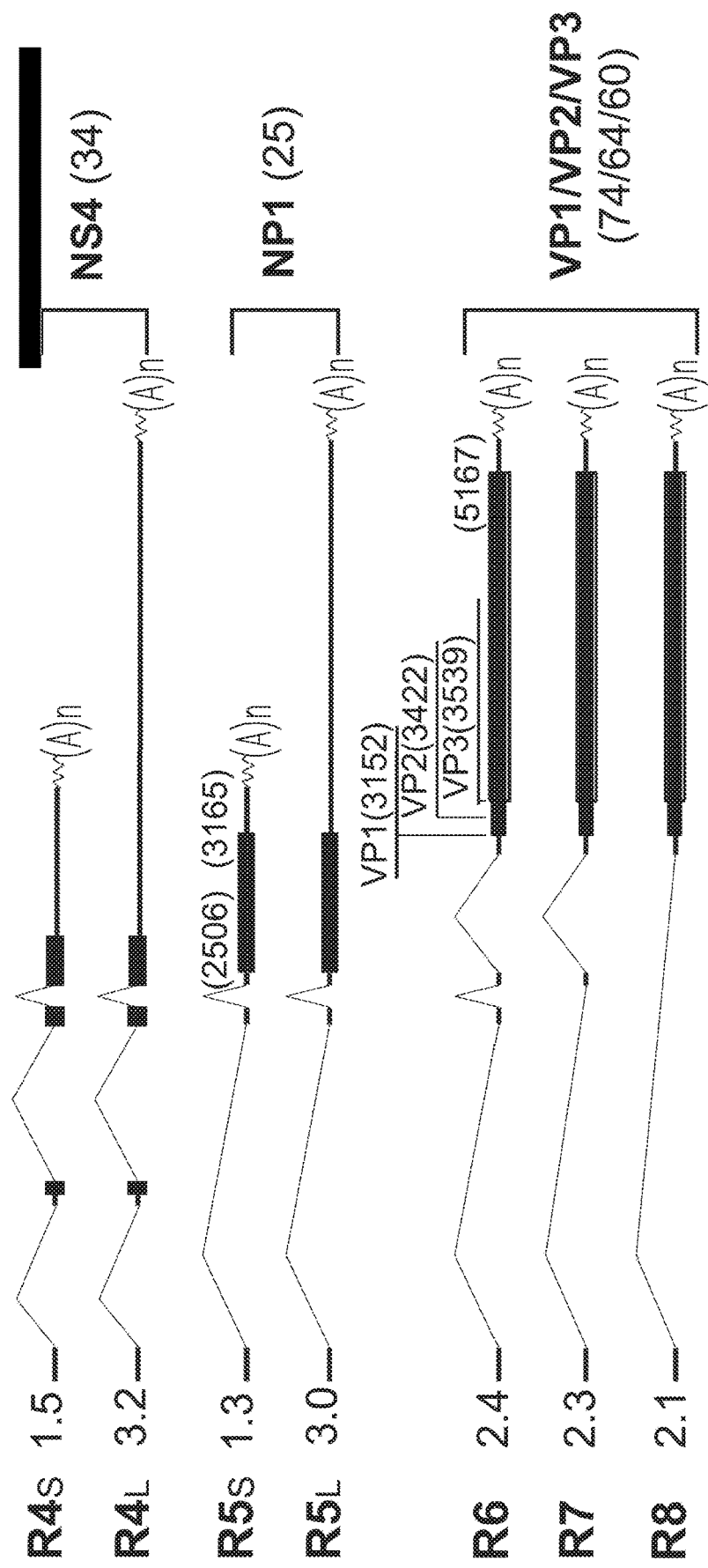

According to a further aspect of the invention there is provided an isolated mutant bocavirus genome that when introduced to cells i) expresses one or more of bocavirus NS1, NS2, NS3 or NS4, for example, that expresses only NS1 or NS2 or NS3 or NS 4; or expresses any two of NS1, NS2, NS3, NS4, for example, expresses NS3 and NS4; or expresses any three of NS1, NS2, NS3, NS4, for example, expresses NS2, NS3 and NS4, or that expresses all of NS1, NS2, NS3, NS4, ii) expresses bocavirus VP1, VP2 and VP3; and ii) does not express bocavirus NP1 or a functional bocavirus NP1. Optionally the promoter that expresses bocavirus proteins is not a bocavirus promoter.

According to a further aspect of the invention there is provided an isolated mutant bocavirus genome that when introduced to cells i) does not express any of bocavirus NS1, NS2, NS3 or NS4; ii) expresses bocavirus VP1, VP2 and VP3; and iii) does not express bocavirus NP1 or a functional bocavirus NP1. Optionally the promoter that expresses bocavirus proteins is not a bocavirus promoter.

According to a further aspect of the invention there is provided an isolated mutant bocavirus genome and bocavirus protein expression vector(s). A mutant BoV genome, e.g., a mutant human BoV genome or a non-human BoV genome, may include one or more insertions, one or more deletions, or one or more nucleotide substitutions, e.g., substitutions that results in an in-frame stop codon or removal of a splice site, or any combination thereof, in order to inhibit or prevent expression of a functional viral protein. In one embodiment, there is provided an expression vector comprising a codon optimized open reading frame for bocavirus NP1, or bocavirus VP1, VP2 or VP3, or a portion thereof. The open reading frame for NP1 can encode a protein with at least 80%, 85%, 90%, 95%, 98% or more identity to the protein encoded by SEQ ID NO:1, that is, NP1 useful in the methods may be a protein with at least 80%, 85%, 90%, 95%, 98% or more identity to the protein encoded by SEQ ID NO:1. The open reading frame for bocavirus VP1, VP2 and VP3 can encode proteins with at least 80%, 85%, 90%, 95%, 98% or more identity to the protein encoded by any one of SEQ ID Nos. 2-3, e.g., bocavirus VP1, VP2 and VP3 useful in the methods may be a protein with at least 80%, 85%, 90%, 95%, 98% or more identity to the protein encoded by any one of SEQ ID Nos. 2-3. Coding regions for NP1 and capsid proteins from AAVs, e.g., other than AAV2, may likewise by codon optimized. According to one embodiment the expression vector comprises a heterologous promoter linked to the open reading frame.

BRIEF DESCRIPTION OF FIGURES

FIGS. 1A-C. Genetic map of HBoV1 and the probes used. A-B) The expression profile of HBoV1 mRNAs and their encoded proteins are shown with transcription landmarks and boxed open reading frames (ORFs). The numbers are nucleotide (nt) numbers of the HBoV1 full-length genome (GenBank accession no.: JQ923422). Major species of HBoV1 mRNA transcripts that are alternatively processed are shown with their sizes in kilobases (kb) (minus a poly A tail of about 150 nts), which were concluded from multiple studies in HBoV1 DNA transfection of HEK293 cells and in HBoV1 infection of polarized human airway epithelium (Dijkman et al., 2009; Chen et al., 2010; Shen et al., 2015). Viral proteins detected in both transfected and infected cells are shown side by side at the right. P5, P5 promoter; D, 5' splice donor site; A, 3' splice acceptor site; (pA)p and (pA)d, proximal and distal polyadenylation sites, respectively; LEH/REH, left/right end hairpin. C) Probes used for Northern blot analysis are depicted with the nucleotide numbers. Probes used for RNAse protection assay (RPA) are diagrammed with the sizes of their detected bands.

FIG. 2. DNA sequence of silent mutations in the (pA)p sites (SEQ ID NO:5). Nucleotide sequences between the VP1 and VP3 start codons were silently mutated to eliminate potentially used (cryptic) polyadenylation signals (PAS: AAUAAA), but still retain the same coding sequence as the wild type. The mutated sequence is shown with locations of the 5 PASs (dashed underline). The VP1 start codon was mutated from ATG to ACG, together with a weak Kozak signal (GTT AAG), and retained VP2 start codon GTG.

FIGS. 3A-B. VP2 is translated from a non-canonical translation initiation codon. A) Diagrams of pHBoV1NSCap-based mutants. The parent pHBoV1NSCap plasmid is diagrammed with transcription, splicing, and polyadenylation units shown, together with the mutants that carry various mutations at the GUG and GCU codons (nt 3,422-3,427) of the HBoV1 genome, as shown. B) Western blot analysis of capsid proteins. HEK293 cells were transfected with plasmids as indicated. The lysates of transfected cells were analyzed by Western blotting using an anti-VP antibody, and was reprobed with anti-β-actin. The identities of the detected bands are indicated at the left of the blot. Arrow shows the novel VP2 protein, which was denoted previously by an asterisk (*) (Shen et al., 2015). Control, without transfection.

FIGS. 4A-D. HBoV1 VP cDNA constructs did not express capsid proteins. A) Diagrams of HBoV1 VP cDNA constructs. pHBoV1NSCap is diagramed with transcription, splicing, and polyadenylation units shown. pCMVCap1-3 and pCMVR6-8cDNA that contain various sequences of the 5' untranslational region (UTR) and 3'UTR and the VP1/2/3 ORF are diagramed with the junction of the 5' and 3' splice sites or the heterogeneous Epo intron 4 (Epo In4) as shown. B) Western blot analysis of capsid proteins. HEK293 cells were transfected with plasmids as indicated. The lysates of transfected cells were analyzed by Western blotting using an anti-VP antibody, and were reprobed with anti-β-actin. The lysates were also analyzed by Western blotting using an anti-HA antibody for detecting the C-terminal HA-tagged mCherry. The identities of the detected bands are indicated at the left of the blot. C) Northern blot analysis of cytoplasmic VP mRNAs. HEK293 cells were transfected with plasmids as indicated. Cytoplasmic RNA prepared from each transfection was analyzed by Northern blotting using the Cap probe, which specifically detects VP mRNA (FIG. 1B). EB stained 18S rRNA bands are shown, and the VP mRNA bands are indicated. Asterisk (*) denotes various NS-encoding mRNAs. A RNA ladder (M) was used as a size marker. D) Quantification of VP mRNA expression. The bands of VP mRNA in each lane of panel C were quantified and normalized to the level of 18S rRNA. The signal intensity of the VP mRNA band in lane 1 was arbitrally set as 100%. Relative intensity was calculated for the bands in other lanes. Means and standard deviations were calculated from at least three independent experiments.

FIGS. 5A-D. Knockout of NP1 abolished VP mRNA production and capsid protein expression. A) Diagrams of HBoV1 NSCap gene constructs. pHBoV1NSCap and its derivatives are diagramed with replacement of the CMV promoter and bGHpA signal and knockout of the NS1 and NP1 as shown. B) Western blot analysis of capsid proteins. HEK293 cells were transfected with plasmids as indicated. Cell lysates were analyzed by Western blotting using an anti-VP antibody. The blot was reprobed with anti-β-actin. The lysates were also analyzed by Western blotting using anti-NP1 and anti-HA antibodies. The identities of detected proteins are shown at the left of the blot. C) Northern blot analysis of cytoplasmic VP mRNAs. HEK293 cells were transfected with plasmids as indicated. Cells were harvested and extracted for cytoplasmic RNA at 2 days post-transfection. The cytoplasmic RNA samples were analyzed by Northern blotting using the Cap probe. EB-stained 18S rRNA and detected VP mRNA are indicated. Asterisk (*) denotes various NS-encoding mRNAs. D) Western blot analysis of NS proteins. The same lysates prepared for panel B were analyzed by Western blotting using an anti-NS1C antibody. The identities of detected proteins are shown at the left of the blot.

FIGS. 6A-H. NP1 complementation rescued VP mRNA production and capsid proteins expression. A) Diagrams of HBoV1 NSCap constructs. pCMVNS*Cap and pCMVNS*(NP*)Cap are diagramed, along with the pOpt-NP1 plasmid that expresses NP1 from a codon-optimized NP1 ORF (SEQ ID NO:1). (B) RPA analysis of viral RNAs spliced at the A1. D2 and A3 splice sites. Ten μg of total RNA isolated at 2 days post-transfection from HEK293 cells transfected with plasmids as indicated, was protected by both the pA1D2 and pA3 probes. Lane M, 32P-labeled RNA markers (Qiu et al., 2002), with sizes indicated to the left. The origins of the protected bands in the lanes are indicated to the left and right for pA1D2 and pA3 probes, respectively. Spl, spliced RNAs; Unspl, unspliced RNAs. C) Quantification of the mRNAs spliced at the A3 splice acceptor. The bands of both spliced and unspliced RNAs in lanes 4-6 of panel B were quantified. The ratio of spliced vs. unspliced RNA (A3 Spl/Unspl) was calculated and is shown with means and standard deviations from three independent experiments. Numbers shown are P values calculated using a two-tailed Student's t test. D) Northern blot analysis of cytoplasmic VP mRNAs. HEK293 cells were transfected with plasmids as indicated, and were harvested at two days post-transfection. Cytoplasmic RNA was extracted, and the RNA samples were analyzed by Northern blotting using the Cap probe. EB-stained 18S rRNA and VP mRNA are indicated. Asterisk (*) denotes various NS-encoding mRNAs. E) Western blot analysis of capsid proteins. Transfected cells were harvested and lysed at 2 days post-transfection. The lysates were analyzed by Western blotting using an anti-VP antibody. The blot was reprobed with anti-β-actin. The lysates were also analyzed by Western blotting using anti-NP1 and anti-HA antibodies. The identities of detected proteins are shown at the left of the blot. F)-H) VP mRNA was exported from the nucleus to cytoplasm efficiently and was stable. F) Northern blot analysis. HEK293 cells were transfected with plasmids as indicated with or without co-transfection of the pOpt-NP1. The same numbers of cells were harvested and extracted for both total and cytoplasmic RNA. RNA samples were analyzed by Northern blotting using the Cap probe. EB-stained 18S rRNA and VP mRNA are indicated. Asterisk (*) denotes various NS617 encoding mRNAs. G) Quantification of VP mRNAs on Northern blots. The bands of VP mRNA in each lane of panel F were quantified and normalized to the level of 18S rRNA. The intensity of the VP mRNA band in lane 1 was arbitrally set as 100%. Relative VP mRNA level was calculated for the bands in other lanes. Means and standard deviations are quantified from three independent experiments. P values shown are calculated using a two-tailed Student's t-test. ND, not detectable. (H) RNA stability assay. HEK293 cells were transfected with pCMVNS*Cap. At 2 days post-infection, cells were treated with actinomycin D at 5 μg/mL for hours (hrs p.t.) as indicated. The treated cells were harvested and extracted for total RNA. The RNA samples were analyzed by Northern blotting using the NSCap probe (FIG. 1B). EB-stained 18S rRNA bands are shown. Indicated bands are detected VP mRNA at about 2.5 kb, which is likely the R6 mRNA that is polyadenylated at the (pA)d site, and (pA)p mRNA at about 1.5 kb, which is the R5s mRNA that is polyadenylated at the (pA)p site (FIG. 1A). Asterisk (*) denotes various NS-encoding mRNAs. Control, total RNA of non-transfected cells.

FIGS. 7A-E. NP1 increased VP mRNA production independent of RNA splicing at the A3 splice acceptor. A) Diagrams of HBoV1 intron deletion/exchange constructs. Plasmids pCMVNS*(ln3Δ)Cap, pCMVEpoln14(ln3Δ)Cap and pCMVEpoln124Cap are diagrammed with replaced introns shown. B) Western blot analysis of capsid proteins. HEK293 cells were transfected with plasmids as indicated. Cells were harvested and lysed at 2 days post-transfection. The lysates were analyzed by Western blotting using an anti-VP antibody and reprobed with anti-β-actin. The lysates were also analyzed by Western blotting using anti-NP1 and anti-HA antibodies. C) Northern blot analysis of VP mRNAs. HEK293 cells were transfected with plasmids as indicated. Cells were harvested and extracted for total RNA at 2 days post-transfection. The total RNA samples were analyzed by Northern blotting using the NSCap probe. EB-stained 18S rRNA bands are shown. Detected bands of VP mRNA and (pA)p mRNA are indicated. Asterisk (*) denotes various NS-encoding mRNAs. Lane M, an RNA ladder marker. D) Quantification of VP mRNAs on Northern blots. The bands of VP mRNA and (pA)p mRNA in each lane of panel C were quantified and normalized to the level of 18S rRNA, respectively. The intensity of the VP mRNA band in lane 4 was arbitrally set as 100%. Relative intensities were calculated for the bands in other lanes. Means and standard deviations are calculated from three independent experiments. P values shown are calculated using a two-tailed Student's t test. Asterisks (**) denote P<0.01. E) Determination of the usage of the A1, D2, and A3 splice sites using RPA. Ten μg of total RNA isolated at two days post-transfection from HEK293 cells transfected with plasmids as indicated, was protected by the pA1D2 and pA3 probes or their homology counterparts, as indicated. Lane M, 32P-labeled RNA markers (Qiu et al., 2002), with sizes indicated to the left. The origins of the protected bands are shown with sizes. Spl, spliced RNAs; Unspl, unspliced RNAs.

FIGS. 8A-D. NP1 increased VP mRNA production from cDNA constructs. A) Diagrams of HBoV1 cDNA constructs. HBoV1 cDNA constructs are diagrammed along with the pCMVNS*(NP*)Cap control. B) Northern blot analysis of VP and (pA)p mRNAs. HEK293 cells were transfected with plasmids as indicated. Cells were harvested and extracted for total RNA at 2 days post-transfection. The RNA samples were analyzed by Northern blotting using the NSCap probe. EB-stained 18S rRNA bands of each sample are shown. The identities of detected bands are indicated. Asterisk (*) denotes various NS-encoding mRNAs. C) Quantification of VP and (pA)p mRNAs on Northern blots. The bands of VP mRNA and (pA)p mRNA in each lane of panel B were quantified and normalized to the level of 18S rRNA. The intensity of the VP mRNA band in lane 8 was arbitrarily set as 100%. Relative intensity was calculated for the bands in other lanes. Means and standard deviations are calculated from three independent experiments. P values shown are calculated using a two-tailed Student's t test. Asterisks (**) indicate P<0.01. ND, not detectable. D) Western blot analysis of capsid proteins. HEK293 cells were transfected with plasmids as indicated. Cells were harvested and lysed at 2 days post-transfection. The lysates were analyzed by Western blotting using an anti-VP antibody. The blot was reprobed using an anti-β-actin antibody. The lysates were also analyzed by Western blotting using an anti-HA antibody.

FIGS. 9A-D. Mutation of the (pA)p sites enables VP mRNA production and capsid protein expression in the absence of NP1. A) Diagrams of HBoV1 NSCap and cDNA constructs. HBoV1 NS and Cap genes and cDNA constructs are diagrammed along with the pCMVNS*(NP*)Cap control. B) Northern blot analysis of VP and (pA)p mRNAs. HEK293 cells were transfected with plasmids as indicated. The total RNA samples were analyzed by Northern blotting using the NSCap probe. EB-stained 18S rRNA bands are shown. Detected bands of VP and (pA)p mRNAs are indicated to the left of the blot. Asterisk (*) denotes various NS-encoding mRNAs. C) Quantification of VP and (pA)p mRNAs on Northern blots. The bands of VP and (pA)p mRNAs in each lane in panel B were quantified and normalized to 18S rRNA. The intensity of the VP mRNA band in lane 1 was arbitrarily set as 100%. Relative intensity was calculated for the bands of both VP and (pA)p mRNAs in other lanes. Means and standard deviations are calculated from three independent experiments. P values shown are calculated using a two-tailed Student's t test. Asterisks (*) indicate P<0.01. D) Western blot analysis of capsid proteins. HEK293 cells were transfected with plasmids as indicated. Cell lysates of each transfection were analyzed by Western blotting using an anti-VP antibody. The blot was reprobed with an anti-f-actin antibody. The lysates were also analyzed by Western blotting using an anti-HA antibody for mCherry expression.

Figure 10A:
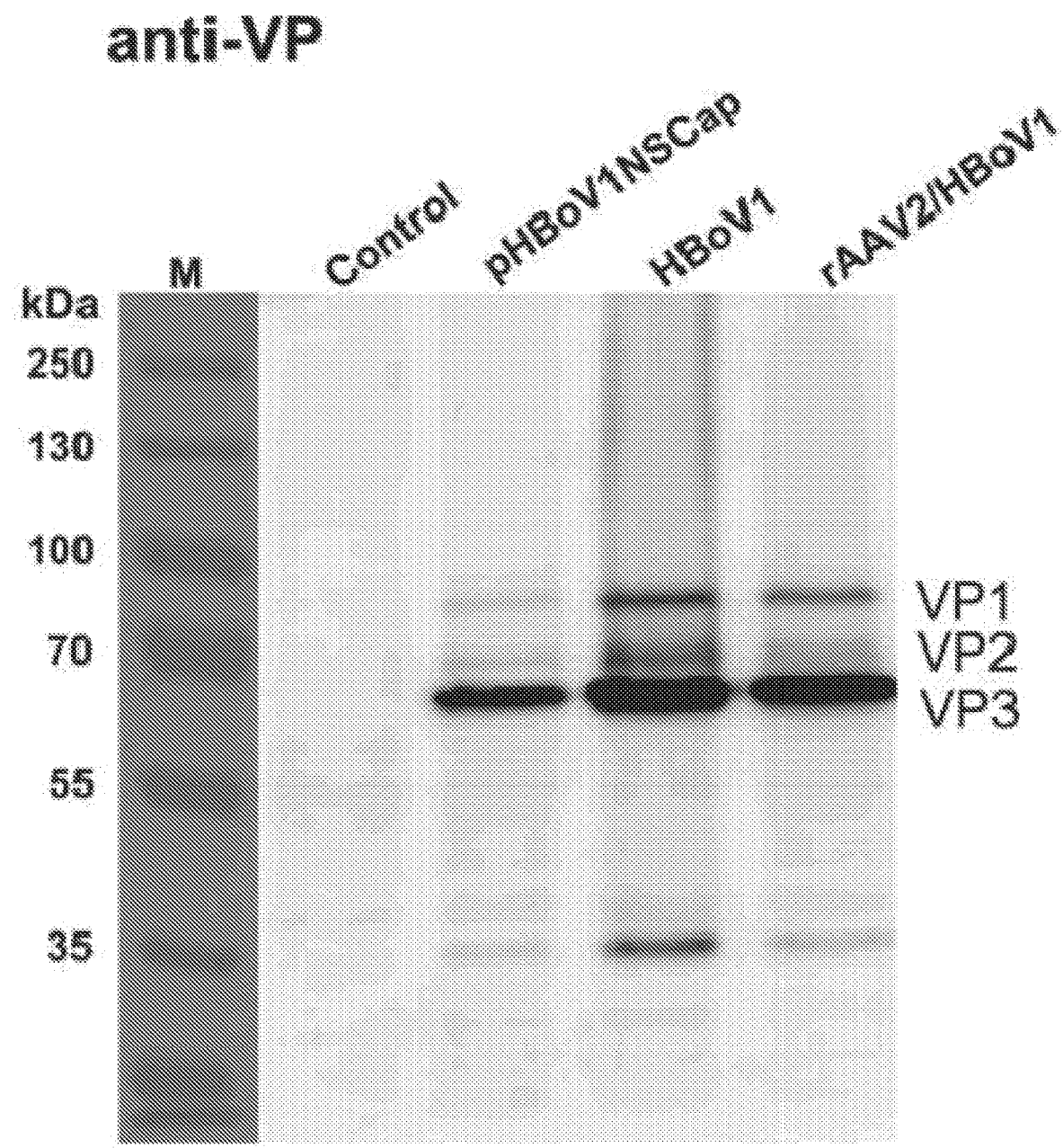
Figure 10B:
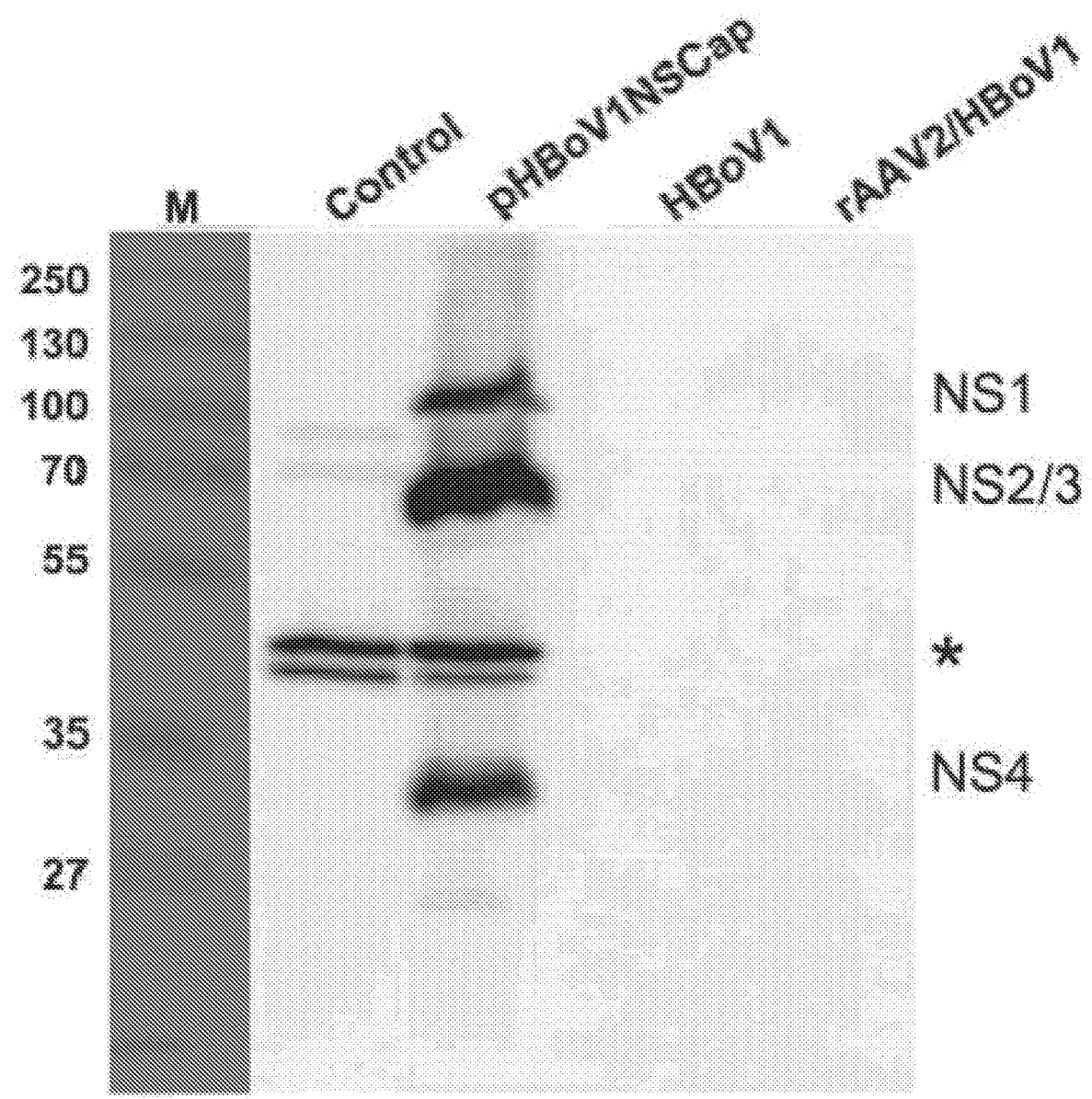
Figure 10C:
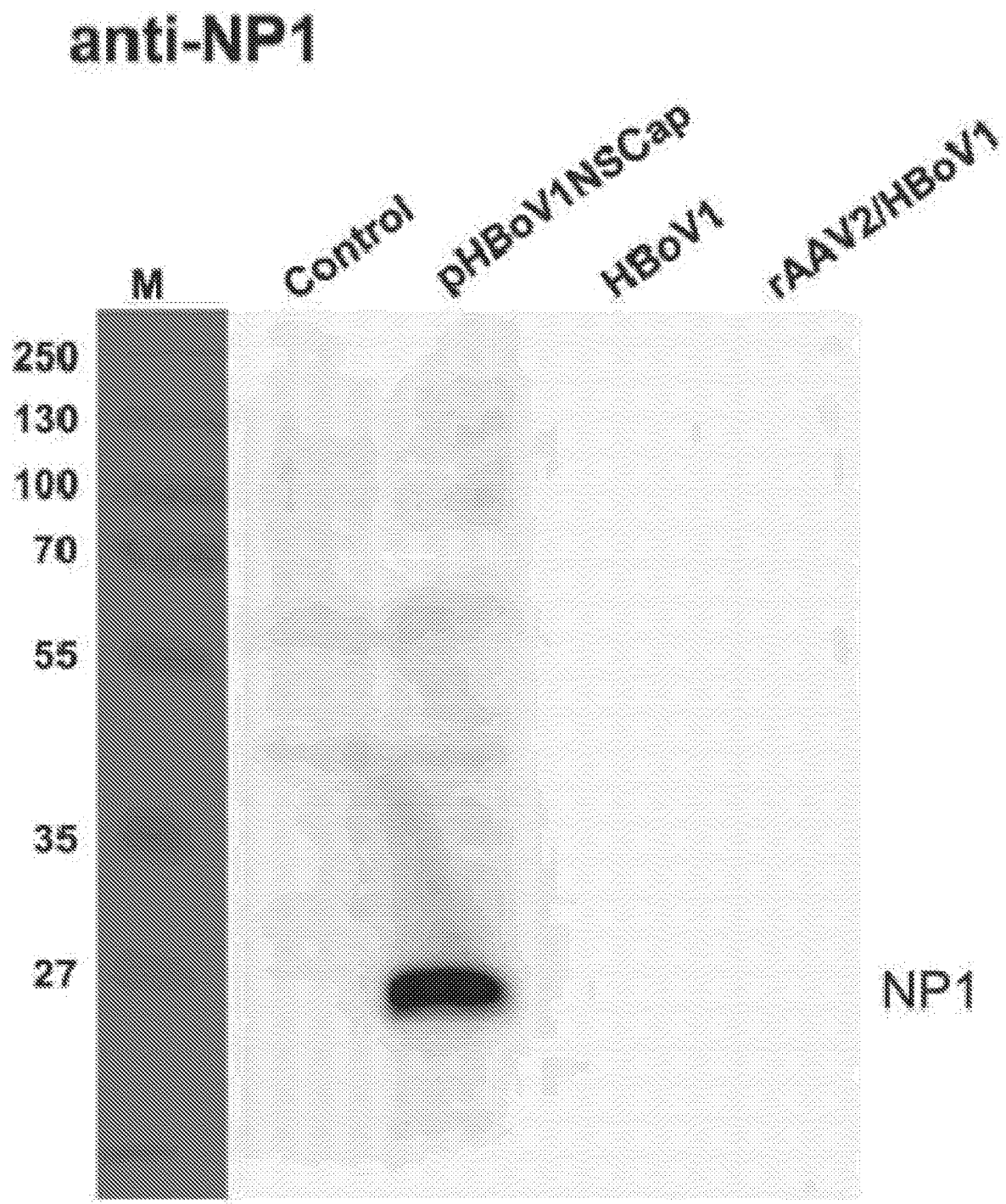

FIGS. 10A-C. Both purified wild type HBoV1 virions and purified rAAV2/HBoV1 vectors do not contain any non-structural proteins (NS1, NS2, NS2, NS4 and NP1). 8×10$^9$ DPR (DNAse I digestion resistant particles) of wild type of HBoV1 (HBoV1) and rAAV2/HBoV1 vector rAAV2/HBoV1), which were purified by CsCl density-gradient centrifugation, were lyzed and separated on SDS-10% PAGE. After transferring, the blots were probed using anti-HBoV1 VP (Panel A) and anti-NS1 C-terminus (Panel B), respectively. The blot shown in panel B was reprobed with anti-HBoV1 NP1 (Panel C). An amount of 0.5 million of 293 cells transfected with pHBV1NSCap plasmid (pHBoV1NSCap) or not transfected (Control) were lyzed and analyzed as positive and negative controls, respectively. The identity of each band detected is indicated to the right side of the blots. A lane with protein markers is shown with their respective sizes to the left side of the blot. Asterisk indicates non-specific bands.

Figure 11:
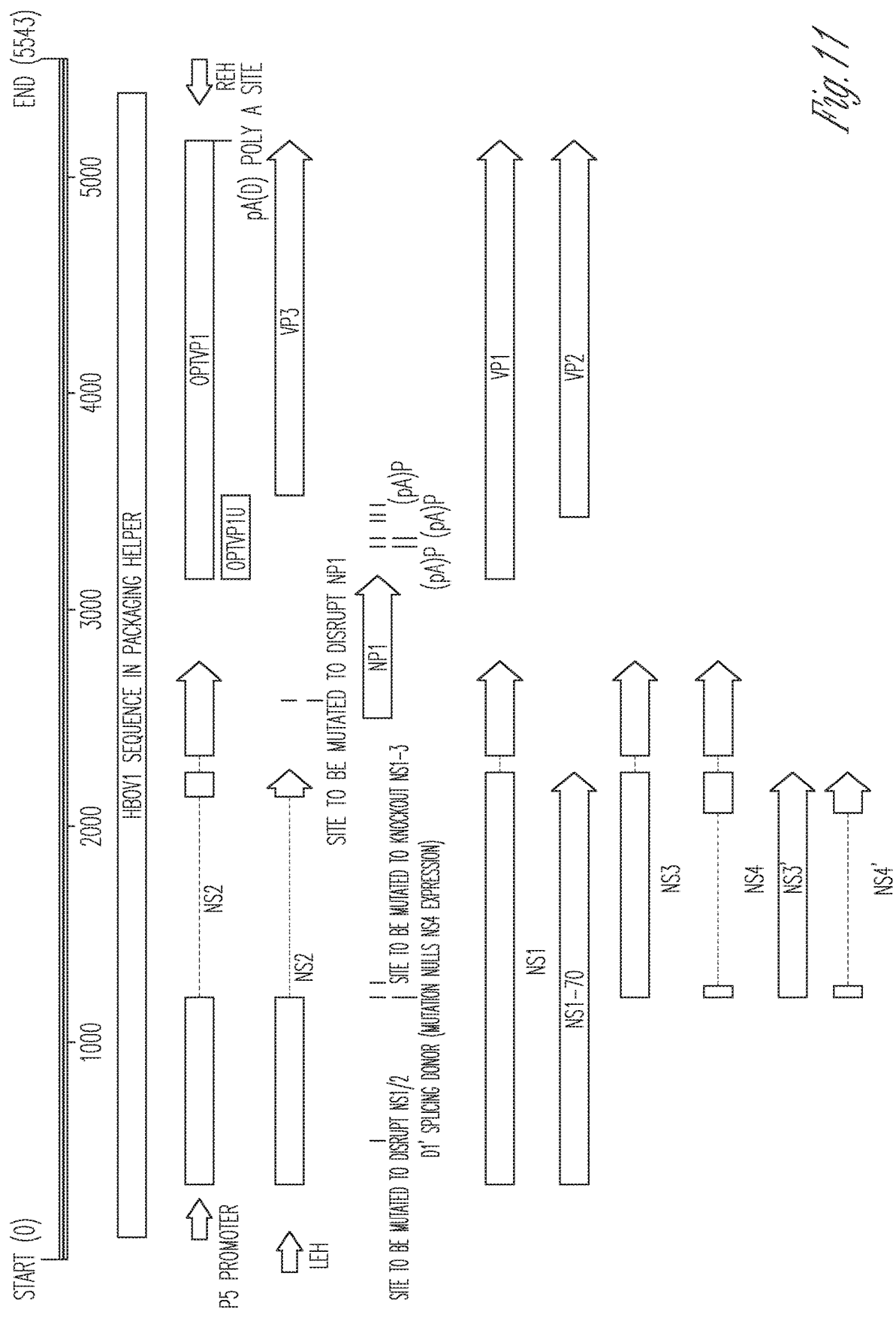

FIG. 11. HBoV1 Genome Structure and Elements Used in rAAV/HBoV1 Helpers. LEH and REH represent the left and right end hairpin sequence at the termini of HBoV1 genome (GeneBank Accession no: JQ923422, which is incorporated by reference herein). NS1, NS2, NS3, NS4, NP1 are the non-structural protein: VP1, VP2 and VP3 are the capsid protein. All the HBoV1 encoded viral proteins are processed from a single preRNA transcribed from P5 promoter. (pA)p and (pA)d indicated the proximal and distal polyadenylation sites, respectively. NP1 plays a role for VP encoded mRNA splicing and read through the (pA)p sides. LEH and REH deleted HBoV1 genome is used as the prototype packaging helper, pHBoVNScap for rAAV2/HBoV1 vector production. Sites to be mutated to in-frame stop codon for early termination of the non-structural protein expression are marked in red. Mutation at the D1' splicing donor prevents NP1 expression. Codon optimization of the HBoV1 capsid protein reading frame removes the five (pA)p sides in the unique region of the 5' end of VP1 and VP2. OptVP1 or OptVP1U indicate regions of codon optimization of the full capsid coding sequence or only at the VP1/2 5' unique region. An optimized Kozak sequence (GTT AAG ACG) is used in optVP1 and optVP1U to express VP1, and with the GUG codon for VP2 remaining intact, in order to obtain an appropriate ratio of the VP1:VP2:VP3.

FIGS. 12A-D. Optimized Sequences. A) Optimized NP1 sequence (SEQ ID NO:1). B) Optimized VP sequence (SEQ ID NO:2). Translation starts at an alternative start codon ACG of VP1, GTG for VP2, and ATG for VP3 (solid line box). VP1-3 are encoded in the same OFR; the short dashed line box shows the unique region of VP1, the long dashed line box shows the unique region of VP2. Bold: VP2; bold and underlined: VP3. Upper Cases: codon optimized. C) Optimized VP sequence (SEQ ID NO:3). Translation starts at an alternative start codon ACG of VP1, GTG for VP2, and ATG for VP3 (solid line box). VP1-3 are encoded in the same OFR; the short dashed line box shows the unique region of VP1, the long dashed line box shows the unique region of VP2. Bold: VP2; bold and underlined: VP3. Upper Cases: codon optimized, lower cases: original coding sequence in the HBoV1 genome. D) Exemplary wild-type VP sequence (SEQ ID NO:4). Translation starts at ATG for VP1, an alternative start codon GTG for VP2, and ATG for VP3 (solid line box). VP1-3 are encoded in the same OFR; the short dashed line box shows the unique region of VP1, the long dashed line box shows the unique region of VP2. Bold: VP2; bold and underlined: VP3.

DETAILED DESCRIPTION

Definitions

A "vector" as used herein refers to a macromolecule or association of macromolecules that comprises or associates with a polynucleotide and which can be used to mediate delivery of the polynucleotide to a cell, either in vitro or in vivo. Illustrative vectors include, for example, plasmids, viral vectors, liposomes and other gene delivery vehicles. The polynucleotide to be delivered, sometimes referred to as a "target polynucleotide" or "transgene," may comprise a coding sequence of interest in gene therapy (such as a gene encoding a protein of therapeutic or interest), a coding sequence of interest in vaccine development (such as a polynucleotide expressing a protein, polypeptide or peptide suitable for eliciting an immune response in a mammal), and/or a selectable or detectable marker.

"AAV" is adeno-associated virus, and may be used to refer to the naturally occurring wild-type virus itself or derivatives thereof. The term covers all subtypes, serotypes and pseudotypes, and both naturally occurring and recombinant forms, except where required otherwise. As used herein, the term "serotype" refers to an AAV which is identified by and distinguished from other AAVs based on capsid protein reactivity with defined antisera, e.g., there are nine serotypes of primate AAVs, AAV-1 to AAV-9, although there are many related AAVs. For example, serotype AAV2 is used to refer to an AAV which contains capsid proteins encoded from the cap gene of AAV 2 and a genome containing 5' and 3' ITR sequences from the same AAV2 serotype. For each example illustrated herein the description of the vector design and production describes the serotype of the capsid and 5'-3' ITR sequences. The abbreviation "rAAV" refers to recombinant adeno-associated virus, also referred to as a recombinant AAV vector (or "rAAV vector"). Any AAV may be employed in the production of chimeras, including both human and nonhuman primate AAVs.

BoV is bocavirus, and may be used to refer to the naturally occurring wild-type virus itself or derivatives thereof. The term covers all subtypes, serotypes and pseudotypes, and both naturally occurring and recombinant forms, except where required otherwise. As used herein, the term "serotype" refers to a BoV, which is identified by and distinguished from other BoVs based on capsid protein reactivity with defined antisera, e.g., there are four known serotypes of human bocavirus (HBoV), HBoV1, HBoV2, HBoV3, and HBoV4. However, included in BoV are serotypes derived from other non-human mammals such as swine BoV. Like for AAV, different serotypes of HBoV and BoV can have different tropisms that infect different cell types and organs.

rAAV/HBoV is a chimeric vector which is composed of HBoV capsids and a rAAV genome. In such a chimeric virus there is no genetic information from HBoV within the genome. The rAAV genome may be from any serotype of AAV.

rAAV/BoV is a chimeric vector which is composed of a non-human BoV capsids and a rAAV genome. In such a chimeric virus there is no genetic information from BoV within the genome. The rAAV genome may be from any serotype of AAV.

Tropism as used herein, is a term referring to the ability of a particular viral serotype to productively infect cells of differing phenotypes or organs to deliver their genomic information to the nucleus.

"Transduction" or transducing as used herein, are terms referring to a process for the introduction of an exogenous polynucleotide, e.g., a transgene in rAAV vector, into a host cell leading to expression of the polynucleotide, e.g., the transgene in the cell. The process includes one or more of 1) endocytosis of the chimeric virus, 2) escape from endosomes or other intracellular compartments in the cytosol of a cell, 3) trafficking of the viral particle or viral genome to the nucleus, 4) uncoating of the virus particles, and generation of expressive double stranded AAV genome forms, including circular intermediates. The rAAV expressible double stranded form may persist as a nuclear episome or optionally may integrate into the host genome. The alteration of any or a combination of endocytosis of the chimeric virus after it has bound to a cell surface receptor, escape from endosomes or other intracellular compartments to the cytosol of a cell, trafficking of the viral particle or viral genome to the nucleus, or uncoating of the virus particles, and generation of expressive double stranded AAV genome forms, including circular intermediates, by an agent of the invention, e.g., a proteasome inhibitor, may result in altered expression levels or persistence of expression, or altered trafficking to the nucleus, or altered types or relative numbers of host cells or a population of cells expressing the introduced polynucleotide. Altered expression or persistence of a polynucleotide introduced via the chimeric virus can be determined by methods well known to the art including, but not limited to, protein expression, e.g., by ELISA, flow cytometry and Western blot, measurement of and DNA and RNA production by hybridization assays, e.g., Northern blots, Southern blots and gel shift mobility assays. The agents of the invention may alter, enhance or increase viral endocytosis, escape from endosomes or other intracellular cytosolic compartments, and trafficking into or to the nucleus, uncoating of the viral particles in the nucleus, and/or increasing concatamerization or generation of double stranded expressible forms of the rAAV genome in the nucleus, so as to alter expression of the introduced polynucleotide, e.g., a transgene in a rAAV vector, in vitro or in vivo. Methods used for the introduction of the exogenous polynucleotide include well-known techniques such as transfection, lipofection, viral infection, transformation, and electroporation, as well as non-viral gene delivery techniques. The introduced polynucleotide may be stably or transiently maintained in the host cell.

"Gene delivery" refers to the introduction of an exogenous polynucleotide into a cell for gene transfer, and may encompass targeting, binding, uptake, transport, localization, replicon integration and expression.

"Gene transfer" refers to the introduction of an exogenous polynucleotide into a cell which may encompass targeting, binding, uptake, transport, localization and replicon integration, but is distinct from and does not imply subsequent expression of the gene.

"Gene expression" or "expression" refers to the process of gene transcription, translation, and post-translational modification.

A "detectable marker gene" is a gene that allows cells carrying the gene to be specifically detected (e.g., distinguished from cells which do not carry the marker gene). A large variety of such marker genes are known in the art.

A "selectable marker gene" is a gene that allows cells carrying the gene to be specifically selected for or against, in the presence of a corresponding selective agent. By way of illustration, an antibiotic resistance gene can be used as a positive selectable marker gene that allows a host cell to be positively selected for in the presence of the corresponding antibiotic. A variety of positive and negative selectable markers are known in the art, some of which are described below.

An "rAAV vector" as used herein refers to an AAV vector comprising a polynucleotide sequence not of AAV origin (i.e., a polynucleotide heterologous to AAV), typically a sequence of interest for the genetic transformation of a cell. In preferred vector constructs of this invention, the heterologous polynucleotide is flanked by one or two AAV inverted terminal repeat sequences (ITRs). The term rAAV vector encompasses both rAAV vector particles and rAAV vector plasmids.

A "Chimeric virus" or "Chimeric viral particle" refers to a viral particle composed of at least one capsid protein and an encapsidated polynucleotide, which is from a different virus.

A "helper virus" for AAV refers to a virus that allows AAV (e.g., wild-type AAV) to be replicated and packaged by a mammalian cell. A variety of such helper viruses for AAV are known in the art, including adenoviruses, herpes viruses and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC.

An "infectious" virus or viral particle is one that comprises a polynucleotide component, which it is capable of delivering into a cell for which the viral species is trophic. The term does not necessarily imply any replication capacity of the virus.

The term "polynucleotide" refers to a polymeric form of nucleotides of any length, including deoxyribonucleotides or ribonucleotides, or analogs thereof. A polynucleotide may comprise modified nucleotides, such as methylated or capped nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment of the invention described herein that is a polynucleotide encompasses both the double-stranded form and each of two complementary single-stranded forms known or predicted to make up the double-stranded form.

A "transcriptional regulatory sequence" or "TRS," as used herein, refers to a genomic region that controls the transcription of a gene or coding sequence to which it is operably linked. Transcriptional regulatory sequences of use in the present invention generally include at least one transcriptional promoter and may also include one or more enhancers and/or terminators of transcription.

"Operably linked" refers to an arrangement of two or more components, wherein the components so described are in a relationship permitting them to function in a coordinated manner. By way of illustration, a transcriptional regulatory sequence or a promoter is operably linked to a coding sequence if the TRS or promoter promotes transcription of the coding sequence. An operably linked TRS is generally joined in cis with the coding sequence, but it is not necessarily directly adjacent to it.

"Heterologous" means derived from a genotypically distinct entity from that of the rest of the entity to which it is compared. For example, a polynucleotide introduced by genetic engineering techniques into a different cell type is a heterologous polynucleotide (and, when expressed, can encode a heterologous polypeptide). Similarly, a TRS or promoter that is removed from its native coding sequence and operably linked to a different coding sequence is a heterologous TRS or promoter.

"Packaging" as used herein refers to a series of subcellular events that results in the assembly and encapsidation of a viral vector. Thus, when a suitable vector is introduced into a packaging cell line under appropriate conditions, it can be assembled into a viral particle. Functions associated with packaging of viral vectors are described herein and in the art.

A "terminator" refers to a polynucleotide sequence that tends to diminish or prevent read-through transcription (i.e., it diminishes or prevent transcription originating on one side of the terminator from continuing through to the other side of the terminator). The degree to which transcription is disrupted is typically a function of the base sequence and/or the length of the terminator sequence. In particular, as is well known in numerous molecular biological systems, particular DNA sequences, generally referred to as "transcriptional termination sequences," are specific sequences that tend to disrupt read-through transcription by RNA polymerase, presumably by causing the RNA polymerase molecule to stop and/or disengage from the DNA being transcribed. Typical examples of such sequence-specific terminators include polyadenylation ("polyA") sequences, e.g., SV40 polyA. In addition to or in place of such sequence-specific terminators, insertions of relatively long DNA sequences between a promoter and a coding region also tend to disrupt transcription of the coding region, generally in proportion to the length of the intervening sequence. This effect presumably arises because there is always some tendency for an RNA polymerase molecule to become disengaged from the DNA being transcribed, and increasing the length of the sequence to be traversed before reaching the coding region would generally increase the likelihood that disengagement would occur before transcription of the coding region was completed or possibly even initiated. Terminators may thus prevent transcription from only one direction ("uni-directional" terminators) or from both directions ("bi-directional" terminators), and may be comprised of sequence-specific termination sequences or sequence-non-specific terminators or both. A variety of such terminator sequences are known in the art; and illustrative uses of such sequences within the context of the present invention are provided below.

"Host cells," "cell lines," "cell cultures," "packaging cell line" and other such terms denote higher eukaryotic cells, e.g., mammalian cells, such human cells, useful in the present invention. These cells can be used as recipients for recombinant vectors, viruses or other transfer polynucleotides, and include the progeny of the original cell that was transduced. It is understood that the progeny of a single cell may not necessarily be completely identical (in morphology or in genomic complement) to the original parent cell.

A "therapeutic gene," "prophylactic gene," "target polynucleotide," "transgene," "gene of interest" and the like generally refer to a gene or genes to be transferred using a vector. Typically, in the context of the present invention, such genes are located within the rAAV vector (which vector is flanked by inverted terminal repeat (ITR) regions and thus can be replicated and encapsidated into rAAV particles). Target polynucleotides can be used in this invention to generate rAAV vectors for a number of different applications. Such polynucleotides include, but are not limited to: (i) polynucleotides encoding proteins useful in other forms of gene therapy to relieve deficiencies caused by missing, defective or sub-optimal levels of a structural protein or enzyme; (ii) polynucleotides that are transcribed into antisense molecules; (iii) polynucleotides that are transcribed into decoys that bind transcription or translation factors; (iv) polynucleotides that encode cellular modulators such as cytokines; (v) polynucleotides that can make recipient cells susceptible to specific drugs, such as the herpes virus thymidine kinase gene; and (vi) polynucleotides for cancer therapy, such as E1A tumor suppressor genes or p53 tumor suppressor genes for the treatment of various cancers. To effect expression of the transgene in a recipient host cell, it is operably linked to a promoter, either its own or a heterologous promoter. A large number of suitable promoters are known in the art, the choice of which depends on the desired level of expression of the target polynucleotide; whether one wants constitutive expression, inducible expression, cell-specific or tissue-specific expression, etc. The rAAV vector may also contain a selectable marker.

A "gene" refers to a polynucleotide containing at least one open reading frame that is capable of encoding a particular protein after being transcribed and translated.

"Recombinant," as applied to a polynucleotide means that the polynucleotide is the product of various combinations of cloning, restriction and/or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter. Promoters include AAV promoters, e.g., P5, P19, P40 and AAV ITR promoters, as well as heterologous (to parvovirus) promoters, e.g., a CMV promoter, a beta-actin promoter, a RSV-LTR or an ubiquitin promoter.

An "expression vector" is a vector comprising a region which encodes a polypeptide of interest, and is used for effecting the expression of the protein in an intended target cell. An expression vector also comprises control elements operatively linked to the encoding region to facilitate expression of the protein in the target. The combination of control elements and a gene or genes to which they are operably linked for expression is sometimes referred to as an "expression cassette," a large number of which are known and available in the art or can be readily constructed from components that are available in the art.

"Genetic alteration" refers to a process wherein a genetic element is introduced into a cell other than by mitosis or meiosis. The element may be heterologous to the cell, or it may be an additional copy or improved version of an element already present in the cell. Genetic alteration may be effected, for example, by transfecting a cell with a recombinant plasmid or other polynucleotide through any process known in the art, such as electroporation, calcium phosphate precipitation, or contacting with a polynucleotide-liposome complex. Genetic alteration may also be effected, for example, by transduction or infection with a DNA or RNA virus or viral vector. The genetic element may be introduced into a chromosome or mini-chromosome in the cell; but any alteration that changes the phenotype and/or genotype of the cell and its progeny is included in this term.

A cell is said to be "stably" altered, transduced or transformed with a genetic sequence if the sequence is available to perform its function during extended culture of the cell in vitro. In some examples, such a cell is "inheritably" altered in that a genetic alteration is introduced which is also inheritable by progeny of the altered cell.

The terms "polypeptide" and "protein" are used interchangeably herein to refer to polymers of amino acids of any length. The terms also encompass an amino acid polymer that has been modified; for example, disulfide bond formation, glycosylation, acetylation, phosphorylation, lipidation, or conjugation with a labeling component. Polypeptides such as "CFTR" and the like, when discussed in the context of gene therapy and compositions therefor, refer to the respective intact polypeptide, or any fragment or genetically engineered derivative thereof, that retains the desired biochemical function of the intact protein. Similarly, references to CFTR, and other such genes for use in gene therapy (typically referred to as "transgenes" to be delivered to a recipient cell), include polynucleotides encoding the intact polypeptide or any fragment or genetically engineered derivative possessing the desired biochemical function.

An "isolated" plasmid, virus, or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture.

A preparation of AAV is said to be "substantially free" of helper virus if the ratio of infectious AAV particles to infectious helper virus particles is at least about $10^2:1$; e.g., at least about $10^4:1$, including at least about $10^6:1$ or at least about $10^8:1$. Preparations may also be free of equivalent amounts of helper virus proteins (i.e., proteins as would be present as a result of such a level of helper virus if the helper virus particle impurities noted above were present in disrupted form). Viral and/or cellular protein contamination can generally be observed as the presence of Coomassie blue staining bands on SDS gels (e.g., the appearance of bands other than those corresponding to the AAV capsid proteins VP1, VP2 and VP3).

"Efficiency" when used in describing viral production, replication or packaging refers to useful properties of the method: in particular, the growth rate and the number of virus particles produced per cell. "High efficiency" production indicates production of at least 100 viral particles per cell; e.g., at least about 10,000 or at least about 100,000 particles per cell, over the course of the culture period specified.

The practice of the present invention will employ, unless otherwise indicated, conventional techniques of molecular biology, virology, microbiology, recombinant DNA, and immunology, which are within the skill of the art. Such techniques are explained fully in the literature. See, e.g., Sambrook et al., 1989; Gait, 1984; Freshney, 1987; the series *Methods in Enzymology* (Academic Press, Inc.); Miller et al., 1987; Weir et al., 1996; Ausubel et al., 1998; Coligan et al., 1991; Coligan et al., 1995; and Scopes 1994.

I. Chimeric Viruses

Human airway epithelial cells are highly resistant to infection by most viral vectors included the adeno-associated virus (rAAV), the most widely used gene therapy vector in clinical trials. Human *Bocavirus* 1 (HBoV1), an autonomous human parvovirus which is likely an etiological agent of acute respiratory tract infections (ARTI) associated with wheezing in infants and young children (Allander et al., 2007; Christensen et al., 2010; Deng et al., 2012; Don et al., 2010), efficiently infects HAE from the apical membrane, resulting in replication of progeny viruses and cytopathology (Huang et al., 2012a). Impressively, HBoV1 infection of HAE at extremely low multiplicities of infection (MOI) of 10⁻³ DNAse-resistant particles (DRP) per cell results in a productive infection (see Example 2). Recently, the full-length 5543-nt HBoV1 complete genome (including terminal palindromic sequences at both ends) was cloned, and cell culture systems for HBoV1 production have been established (Example 1). Given the high efficiency of HBoV1 infection from the apical surface of HAE, HoBV1 was hypothesized to be suitable for engineering recombinant vectors for human airway gene therapy.

HBoV1 is a relative of AAV and other Parvoviridae family members. HBoV1 belongs to the genus *Bocavirus*, while AAV is in the genus *Dependovirus* (Tijssen et al., 2011). HBoV1 and AAV are both small single-stranded DNA viruses, but 90% of encapsidated HBoV1 genomes are of the minus strand, while for AAV, an equal ratio of plus and minus strands are encapsidated (Schildgen et al., 2012). These two viruses differ greatly in their lytic phase life cycle; AAV requires co-infection with a helper virus, while HBoV1 autonomously replicates progeny in permissive cells (Huang et al., 2012a; Dijkman et al., 2009). The HBoV1 genome size is 5543 nt, 18.5% (863 nt) larger than that of AAV2 (4679-nt), and its structural features include asymmetrical hairpins with unique palindromic sequences at 5' (140 nt) and 3' (200 nt) termini, which are involved in replication and encapsidation, and a single P5 promoter that transcribes all viral structural and non-structural proteins (Huang et al., 2012; Chen et al., 2010). This is in contrast to the inverted terminal repeats and multiple internal promoters found in AAV genomes. HBoV1 capsid surface topology possesses common features with other parvoviruses (icosahedral capsid), and is most closely similar to human parvovirus B19 (Gurda et al., 2010). Uke the cloned AAV genome, a plasmid that encodes the HBoV1 proviral genome is infectious and can be used to produce infectious particles through transfection into HEK 293 cells without the need for helper virus co-infection.

Cross-genera pseudopackaging between Parvoviridae was first established when a rAAV genome was encapsidated into a human parvovirus B19 capsid (Ponnazhagan et al., 1998). This resultant cross-genera chimera was able to deliver the rAAV genome into human bone marrow cells that are resistant to rAAV infection (Ponnazhagan et al., 1998). One important feature of the HBoV1 virus is that its genome autonomously replicates in permissive cells, in contrast to rAAV, which is a dependent parvovirus and needs helper virus coinfection for replication.

With the success in trans-complementation for rHBoV1 vector production, a so-called replicative rHBoV1 vector was developed by retaining the coding sequences for HBoV1 rep genes but replacing the structural gene by a transgene. This type of vector can deliver a high level of therapeutic gene expression in the airway cells for the therapy such as CF, AAT deficiency, COPD, or lung cancers. Such a replicating HBoV1 vector could have high utility as a vaccine against WT HBoV1 infections.

Another vector developed was an AAV2/HBoV1 chimeric virus, which packages a rAAV2 genome into a HBoV1 capsid particle. The vector was also produced in HEK293 cells with a procedure similar for rAAV vector, but the capsid genes are substituted by HBoV1 capsids. This AAV/HBoV1 vector combines both the advantages of AAV and HBoV1 transduction biology, with less safety concerns than the rHBoV1 vector since rAAV vector genomes have been extensively studied in many pre-clinical research and clinical trials, but higher airway cell tropism than rAAV. More importantly, the large HBoV1 package capacity makes it possible to encapsidate an oversized rAAV genome up to about 5.5 kb or about 6.0 kb. The 20% greater capacity than rAAV is enough to house a strong expression cassette for effective gene expression. A rAAV genome provides advantages of persistent gene expression by the stable circular transduction intermediates and double stranded genome concatemers. Indeed, AAV/HBoV1 vectors featured more persistent transgene expression than the rHBoV1 vector. Furthermore, the rescue and replication of rAAV genomes in HEK293 cells was very efficient, so that the production yield of the AAV/HBoV1 vector was also better than an rHBoV1 vector.

Utilizing the larger packaging capacity of HBoV1, a rAAV2/HBoV1-CFTR vector was previously prepared that harbors a 5.5 kb oversized rAAV genome with a 5.2 kb CFTR expression cassette having a strong chimeric promoter that included the human CMV immediate gene enhancer and the chicken β-actin promoter (CBA promoter). That vector demonstrated about 30% restoration of CFTR-mediate chloride currents in CF HAE following apical infection. Therefore, the vector could efficiently deliver normal CFTR protein expression on the surface of the airway epithelial cells and correct the defective CFTR specific chloride transport in the CF HAE. In addition, the HBoV1 genome can encapsidate the self-complementary double stranded form of a rAAV genome of about 2.7 kb to about 2.8 kb in length, which vector can bypass genome conversion and allow for enhanced or more rapid transgene expression. The AAV/HBoV chimeric vectors could also be expanded to other therapies for other lung diseases such as alpha-antitrypsin deficiency, asthma, and lung cancer, as well as vaccination against wild-type HBoV infections in infants. However, the yields of chimeric virus produced were not suitable for gene therapy applications, in contrast to the vectors and methods described herein.

The capsids and/or genomes of the viruses of the invention may be chimeric, e.g., as a result of directed evolution (see, e.g., U et al., 2009).

II. rAAV Vectors

Besides prophylactic or therapeutic gene products, recombinant AAV vectors and/or viruses can also comprise polynucleotides that do not encode proteins, including, e.g., polynucleotides encoding for antisense mRNA (the complement of mRNA) which can be used to block the translation of normal mRNA by forming a duplex with it, and polynucleotides that encode ribozymes (RNA catalysts). In addition selected pairs of rAAV vectors having portions of open reading frames flanked by appropriately placed splice acceptor sites and/or splice donor sites, or having transcription regulatory sequences such as a heterologous enhancer, a heterologous promoter, or a heterologous enhancer and a promoter, may be employed. See, e.g., U.S. Pat. No. 6,436, 392, the disclosure of which is incorporated by reference herein. For example, a first AAV vector may include a first DNA segment comprising a 5'-inverted terminal repeat of AAV; a second DNA segment comprising a promoter operably linked to a DNA fragment comprising an exon of a gene and a splice donor site, wherein the second DNA segment does not encode a full-length polypeptide; and a third DNA segment comprising a 3'-inverted terminal repeat of AAV; and a second AAV vector comprising linked: a first DNA segment comprising a 5'-inverted terminal repeat of AAV; a second DNA segment comprising a splice acceptor site and a DNA fragment with at least one other exon which together with the DNA segment of the first AAV vector encodes a full-length polypeptide; and a third DNA segment comprising a 3'-inverted terminal repeat of AAV. In one example, a first AAV vector includes the following: a first nucleic acid segment comprising a 5'-inverted terminal repeat of AAV; a second nucleic acid segment comprising a portion of a gene which includes a transcriptional regulatory region; a third nucleic acid segment comprising a splice donor site; and a fourth nucleic acid segment comprising a 3'-inverted terminal repeat of AAV; and a second AAV vector comprising linked: a first nucleic acid segment comprising a 5'-inverted terminal repeat of AAV; a second nucleic acid segment comprising a splice acceptor site; a third nucleic acid segment comprising a portion of a gene which together with the nucleic acid segment of the first AAV vector comprises a gene comprising an open reading frame which encodes a functional polypeptide; and a fourth nucleic acid segment comprising a 3'-inverted terminal repeat of AAV. In a further example, a first AAV vector includes the following: a first nucleic acid segment comprising a 5'-inverted terminal repeat of AAV; a second nucleic acid segment comprising a splice acceptor site; a third nucleic acid segment comprising a portion of a gene; and a fourth nucleic acid segment comprising a 3'-inverted terminal repeat of AAV; and a second composition comprising a second AAV vector comprising: a first nucleic acid segment comprising a 5'-inverted terminal repeat of AAV; a second nucleic acid segment comprising a portion of a gene which together with the nucleic acid segment above having the portion comprises a gene comprising an open reading frame which encodes a functional polypeptide, wherein the portion of the gene includes a transcriptional regulatory region; a third nucleic acid segment comprising a splice donor site; a fourth nucleic acid segment comprising a 3'-inverted terminal repeat of AAV; which vectors in a host cell yield a RNA transcript which comprises sequences from the first AAV vector linked to sequences from the second AAV vector, which sequences are positioned so that the splice donor site is 5' to the splice acceptor site, and which transcript is spliced to a mRNA which encodes the functional protein.

Adeno-associated viruses of any serotype are suitable to prepare rAAV, since the various serotypes are functionally and structurally related, even at the genetic level (see, e.g., Blacklow, 1988; and Rose, 1974). All AAV serotypes apparently exhibit similar replication properties mediated by homologous rep genes; and all generally bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to ITRs. The similar infectivity patterns also suggest that the replication functions in each serotype are under similar regulatory control. Among the various AAV serotypes, AAV2 is most commonly employed.

An AAV vector of the invention typically comprises a polynucleotide that is heterologous to AAV. The polynucleotide is typically of interest because of a capacity to provide a function to a target cell in the context of gene therapy, such as up- or down-regulation of the expression of a certain phenotype. Such a heterologous polynucleotide or "transgene," generally is of sufficient length to provide the desired function or encoding sequence.

Where transcription of the heterologous polynucleotide is desired in the intended target cell, it can be operably linked to its own or to a heterologous promoter, depending for example on the desired level and/or specificity of transcription within the target cell, as is known in the art. Various types of promoters and enhancers are suitable for use in this context. Constitutive promoters provide an ongoing level of gene transcription, and may be preferred when it is desired that the therapeutic or prophylactic polynucleotide be expressed on an ongoing basis. Inducible promoters generally exhibit low activity in the absence of the inducer, and are up-regulated in the presence of the inducer. They may be preferred when expression is desired only at certain times or at certain locations, or when it is desirable to titrate the level of expression using an inducing agent. Promoters and enhancers may also be tissue-specific: that is, they exhibit their activity only in certain cell types, presumably due to gene regulatory elements found uniquely in those cells.

Illustrative examples of promoters are the SV40 late promoter from simian virus 40, the Baculovirus polyhedron enhancer/promoter element, Herpes Simplex Virus thymidine kinase (HSV tk), the immediate early promoter from cytomegalovirus (CMV) and various retroviral promoters including LTR elements. Inducible promoters include heavy metal ion inducible promoters (such as the mouse mammary tumor virus (mMTV) promoter or various growth hormone promoters), and the promoters from T7 phage which are active in the presence of T7 RNA polymerase. By way of illustration, examples of tissue-specific promoters include various surfactin promoters (for expression in the lung), myosin promoters (for expression in muscle), and albumin promoters (for expression in the liver). A large variety of other promoters are known and generally available in the art, and the sequences of many such promoters are available in sequence databases such as the GenBank database.

Where translation is also desired in the intended target cell, the heterologous polynucleotide will preferably also comprise control elements that facilitate translation (such as a ribosome binding site or "RBS" and a polyadenylation signal). Accordingly, the heterologous polynucleotide generally comprises at least one coding region operatively linked to a suitable promoter, and may also comprise, for example, an operatively linked enhancer, ribosome binding site and poly-A signal. The heterologous polynucleotide may comprise one encoding region, or more than one encoding regions under the control of the same or different promoters. The entire unit, containing a combination of control elements and encoding region, is often referred to as an expression cassette.

The heterologous polynucleotide is integrated by recombinant techniques into or in place of the AAV genomic coding region (i.e., in place of the AAV rep and cap genes), but is generally flanked on either side by AAV inverted terminal repeat (ITR) regions. This means that an ITR appears both upstream and downstream from the coding sequence, either in direct juxtaposition, e.g., (although not necessarily) without any intervening sequence of AAV origin in order to reduce the likelihood of recombination that might regenerate a replication-competent AAV genome. However, a single ITR may be sufficient to carry out the functions normally associated with configurations comprising two ITRs (see, for example, WO 94/13788), and vector constructs with only one ITR can thus be employed in conjunction with the packaging and production methods of the present invention.

The native promoters for rep are self-regulating, and can limit the amount of AAV particles produced. The rep gene can also be operably linked to a heterologous promoter, whether rep is provided as part of the vector construct, or separately. Any heterologous promoter that is not strongly down-regulated by rep gene expression is suitable; but inducible promoters may be preferred because constitutive expression of the rep gene can have a negative impact on the host cell. A large variety of inducible promoters are known in the art; including, by way of illustration, heavy metal ion inducible promoters (such as metallothionein promoters); steroid hormone inducible promoters (such as the MMTV promoter or growth hormone promoters); and promoters such as those from T7 phage which are active in the presence of T7 RNA polymerase. One sub-class of inducible promoters are those that are induced by the helper virus that is used to complement the replication and packaging of the rAAV vector. A number of helper-virus-inducible promoters have also been described, including the adenovirus early gene promoter which is inducible by adenovirus E1A protein; the adenovirus major late promoter; the herpesvirus promoter which is inducible by herpesvirus proteins such as VP16 or 1CP4; as well as vaccinia or poxvirus inducible promoters.

Methods for identifying and testing helper-virus-inducible promoters have been described (see, e.g., WO 96/17947). Thus, methods are known in the art to determine whether or not candidate promoters are helper-virus-inducible, and whether or not they will be useful in the generation of high efficiency packaging cells. Briefly, one such method involves replacing the p5 promoter of the AAV rep gene with the putative helper-virus-inducible promoter (either known in the art or identified using well-known techniques such as linkage to promoter-less "reporter" genes). The AAV repcap genes (with p5 replaced), e.g., linked to a positive selectable marker such as an antibiotic resistance gene, are then stably integrated into a suitable host cell (such as the HeLa or A549 cells exemplified below). Cells that are able to grow relatively well under selection conditions (e.g., in the presence of the antibiotic) are then tested for their ability to express the rep and cap genes upon addition of a helper virus. As an initial test for rep and/or cap expression, cells can be readily screened using immunofluorescence to detect Rep and/or Cap proteins. Confirmation of packaging capabilities and efficiencies can then be determined by functional tests for replication and packaging of incoming rAAV vectors. Using this methodology, a helper-virus-inducible promoter derived from the mouse metallothionein gene has been identified as a suitable replacement for the p5 promoter, and used for producing high titers of rAAV particles (as described in WO 96/17947).

Removal of one or more AAV genes is in any case desirable, to reduce the likelihood of generating replication-competent AAV ("RCA"). Accordingly, encoding or promoter sequences for rep, cap, or both, may be removed, since the functions provided by these genes can be provided in trans.

The resultant vector is referred to as being "defective" in these functions. In order to replicate and package the vector, the missing functions are complemented with a packaging gene, or a plurality thereof, which together encode the necessary functions for the various missing rep and/or cap gene products. The packaging genes or gene cassettes are in one embodiment not flanked by AAV ITRs and in one embodiment do not share any substantial homology with the rAAV genome. Thus, in order to minimize homologous recombination during replication between the vector sequence and separately provided packaging genes, it is desirable to avoid overlap of the two polynucleotide sequences. The level of homology and corresponding frequency of recombination increase with increasing length of homologous sequences and with their level of shared identity. The level of homology that will pose a concern in a given system can be determined theoretically and confirmed experimentally, as is known in the art. Typically, however, recombination can be substantially reduced or eliminated if the overlapping sequence is less than about a 25 nucleotide sequence if it is at least 80% identical over its entire length, or less than about a 50 nucleotide sequence if it is at least 70% identical over its entire length. Of course, even lower levels of homology are preferable since they will further reduce the likelihood of recombination. It appears that, even without any overlapping homology, there is some residual frequency of generating RCA. Even further reductions in the frequency of generating RCA (e.g., by nonhomologous recombination) can be obtained by "splitting" the replication and encapsidation functions of AAV, as described by Allen et al., WO 98/27204).

The rAAV vector construct, and the complementary packaging gene constructs can be implemented in this invention in a number of different forms. Viral particles, plasmids, and stably transformed host cells can all be used to introduce such constructs into the packaging cell, either transiently or stably.

In certain embodiments of this invention, the AAV vector and complementary packaging gene(s), if any, are provided in the form of bacterial plasmids, AAV particles, or any combination thereof. In other embodiments, either the AAV vector sequence, the packaging gene(s), or both, are provided in the form of genetically altered (preferably inheritably altered) eukaryotic cells. The development of host cells inheritably altered to express the AAV vector sequence, AAV packaging genes, or both, provides an established source of the material that is expressed at a reliable level.

A variety of different genetically altered cells can thus be used in the context of this invention. By way of illustration, a mammalian host cell may be used with at least one intact copy of a stably integrated rAAV vector. An AAV packaging plasmid comprising at least an AAV rep gene operably linked to a promoter can be used to supply replication functions (as described in U.S. Pat. No. 5,658,776).

Alternatively, a stable mammalian cell line with an AAV rep gene operably linked to a promoter can be used to supply replication functions (see, e.g., Trempe et al., WO 95/13392); Burstein et al. (WO 98/23018); and Johnson et al. (U.S. Pat. No. 5,656,785). The AAV cap gene, providing the encapsidation proteins as described above, can be provided together with an AAV rep gene or separately (see, e.g., the above-referenced applications and patents as well as Allen et al. (WO 98/27204). Other combinations are possible and included within the scope of this invention.

III. Uses of Chimeric Virus

The chimeric virus produced by the methods described herein can be used for administration to an individual for purposes of gene therapy or vaccination. Suitable diseases for therapy include but are not limited to those induced by viral, bacterial, or parasitic infections, various malignancies and hyperproliferative conditions, autoimmune conditions, and congenital deficiencies.

Gene therapy can be conducted to enhance the level of expression of a particular protein either within or secreted by the cell. Vectors of this invention may be used to genetically alter cells either for gene marking, replacement of a missing or defective gene, or insertion of a therapeutic gene. Alternatively, a polynucleotide may be provided to the cell that decreases the level of expression. This may be used for the suppression of an undesirable phenotype, such as the product of a gene amplified or overexpressed during the course of a malignancy, or a gene introduced or overexpressed during the course of a microbial infection. Expression levels may be decreased by supplying a therapeutic or prophylactic polynucleotide comprising a sequence capable, for example, of forming a stable hybrid with either the target gene or RNA transcript (antisense therapy), capable of acting as a ribozyme to cleave the relevant mRNA or capable of acting as a decoy for a product of the target gene.

Vaccination can be conducted to protect cells from infection by infectious pathogens. As the traditional vaccine methods, vectors of this invention may be used to deliver transgenes encoding viral, bacterial, tumor or fungal antigen and their subsequent expression in host cells. The antigens, which expose to the immune system to evoke an immune response, can be in the form of virus-like particle vaccines or subunit vaccines of virus-coding proteins. Alternatively, as the method of passive immunization, vectors of this invention might be used to deliver genes encoding neutralizing antibodies and their subsequent expression in host non-hematopoietic tissues. The vaccine-like protection against pathogen infection can be conducted through direct provision of neutralizing antibody from vector-mediated transgene expression, bypassing the reliance on the natural immune system for mounting desired humoral immune responses.

The introduction of the chimeric vectors by the methods of the present invention may involve use of any number of delivery techniques (both surgical and non-surgical) which are available and well known in the art. Such delivery techniques, for example, include vascular catheterization, cannulization, injection, inhalation, endotracheal, subcutaneous, inunction, topical, oral, percutaneous, intra-arterial, intravenous, and/or intraperitoneal administrations. Vectors can also be introduced by way of bioprostheses, including, by way of illustration, vascular grafts (PTFE and dacron), heart valves, intravascular stents, intravascular paving as well as other non-vascular prostheses. General techniques regarding delivery, frequency, composition and dosage ranges of vector solutions are within the skill of the art.

In particular, for delivery of a vector of the invention to a tissue, any physical or biological method that will introduce the vector to a host animal can be employed. Vector means both a bare recombinant vector and vector DNA packaged into viral coat proteins, as is well known for administration. Simply dissolving a chimeric or rHBoV vector in phosphate buffered saline has been demonstrated to be sufficient to provide a vehicle useful for muscle tissue expression, and there are no known restrictions on the carriers or other components that can be coadministered with the vector (although compositions that degrade DNA should be avoided in the normal manner with vectors). Pharmaceutical compositions can be prepared as injectable formulations or as topical formulations to be delivered to the muscles by transdermal transport. Numerous formulations for both intramuscular injection and transdermal transport have been previously developed and can be used in the practice of the invention. The vectors can be used with any pharmaceutically acceptable carrier for ease of administration and handling.

For purposes of intramuscular injection, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of the chimeric or rHBoV vector as a free acid (DNA contains acidic phosphate groups) or a pharmacologically acceptable salt can be prepared in water suitably mixed with a surfactant such as hydroxypropylcellulose. A dispersion of viral particles can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating the chimeric or rHBoV vector in the required amount in the appropriate solvent with various of the other ingredients enumerated above, as required, followed by filtered sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the methods of preparation include but are not limited to vacuum drying and the freeze drying technique which yield a powder of the active ingredient plus any additional desired ingredient from the previously sterile-filtered solution thereof.

For purposes of topical administration, dilute sterile, aqueous solutions (usually in about 0.1% to 5% concentration), otherwise similar to the above parenteral solutions, are prepared in containers suitable for incorporation into a transdermal patch, and can include known carriers, such as pharmaceutical grade dimethylsulfoxide (DMSO).

Of interest is the correction of the genetic defect of cystic fibrosis, by supplying a properly functioning cystic fibrosis transmembrane conductance regulator (CFTR) to the airway epithelium. Thus, the use of chimeric or rHBoV vectors encoding native CFTR protein, and mutants and fragments thereof, is envisioned.

Compositions of this invention may be used in vivo as well as ex vivo. In vivo gene therapy comprises administering the vectors of this invention directly to a subject. Pharmaceutical compositions can be supplied as liquid solutions or suspensions, as emulsions, or as solid forms suitable for dissolution or suspension in liquid prior to use. For administration into the respiratory tract, one mode of administration is by aerosol, using a composition that provides either a solid or liquid aerosol when used with an appropriate aerosolubilizer device. Another mode of administration into the respiratory tract is using a flexible fiberoptic bronchoscope to instill the vectors. Typically, the viral vectors are in a pharmaceutically suitable pyrogen-free buffer such as Ringer's balanced salt solution (pH 7.4). Although not required, pharmaceutical compositions may optionally be supplied in unit dosage form suitable for administration of a precise amount.

An effective amount of virus is administered, depending on the objectives of treatment. An effective amount may be given in single or divided doses. Where a low percentage of transduction can cure a genetic deficiency, then the objective of treatment is generally to meet or exceed this level of transduction. In some instances, this level of transduction can be achieved by transduction of only about 1 to 5% of the target cells, but is more typically 20% of the cells of the desired tissue type, usually at least about 50%, at least about 80%, at least about 95%, or at least about 99% of the cells of the desired tissue type. As a guide, the number of vector particles present in a single dose given by bronchoscopy will generally be at least about $1\times10^{12}$, e.g., about $1\times10^{13}$, $1\times10^{14}$, $1\times10^{15}$ or $1\times10^{16}$ particles, including both DNAse-resistant and DNAse-susceptible particles. In terms of DNAse-resistant particles (DRPs), the dose will generally be between $1\times10^{12}$ and $1\times10^{16}$ particles, more generally between about $1\times10^{12}$ and $1\times10^{15}$ particles. The treatment can be repeated as often as every two or three weeks, as required, although treatment once in 180 days may be sufficient.

To confirm the presence of the desired DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence of a polypeptide expressed from a gene present in the vector, e.g., by immunological means (immunoprecipitations, immunoaffinity columns, ELISAs and Western blots) or by any other assay useful to identify the presence and/or expression of a particular nucleic acid molecule falling within the scope of the invention.

To detect and quantitate RNA produced from introduced DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the DNA segment in question, they do not provide information as to whether the DNA segment is being expressed. Expression may be evaluated by specifically identifying the polypeptide products of the introduced DNA sequences or evaluating the phenotypic changes brought about by the expression of the introduced DNA segment in the host cell.

Thus, the effectiveness of the genetic alteration can be monitored by several criteria, including analysis of physiological fluid samples, e.g., urine, plasma, serum, blood, cerebrospinal fluid or nasal or lung washes. Samples removed by biopsy or surgical excision may be analyzed by in situ hybridization, PCR amplification using vector-specific probes, RNAse protection, immunohistology, or immunofluorescent cell counting. When the vector is administered by bronchoscopy, lung function tests may be performed, and bronchial lavage may be assessed for the presence of inflammatory cytokines. The treated subject may also be monitored for clinical features, and to determine whether the cells express the function intended to be conveyed by the therapeutic or prophylactic polynucleotide.

The decision of whether to use in vivo or ex vivo therapy, and the selection of a particular composition, dose, and route of administration will depend on a number of different factors, including but not limited to features of the condition and the subject being treated. The assessment of such features and the design of an appropriate therapeutic or prophylactic regimen is ultimately the responsibility of the prescribing physician.

The foregoing description provides, inter alia, methods for generating high titer preparations of recombinant chimeric viruses or rHBoV that are substantially free of helper virus (e.g., adenovirus) and cellular proteins. It is understood that variations may be applied to these methods by those of skill in this art without departing from the spirit of this invention.

IV. Uses and Comparison of Vectors and Methods for AAV/BoV Chimera Production

CF is caused by single gene defect in the cystic fibrosis transmembrane conductance regulator (CFTR), is the most common life-threatening inherent disease with about $450 million spent annually on patient care in the U.S. alone. Gene therapy appears the best cure to permanently treat this disorder, regardless of the gene mutation/genotype, by replacing the defective CFTR gene with a corrected gene. rAAV/BoV vector also can be applied for the gene therapy to treat other airway diseases caused by inherited gene defects such as alpha-antitrypsin (AAT) deficiency and other chronic acquired respiratory disorders such as asthma. Other applications include the treatment lung cancers and prevention of infectious diseases caused by respiratory viruses through vaccination.

Previously, a gene transfer vector, rAAV/HBoV1 for human pulmonary disease gene therapy and vaccines, was constructed (Yan et al., 2013). rAAV/HBoV1 vector is highly efficient at transduction of the human airway and has larger packaging capacity than rAAV vectors that use AAV capsid. This chimeric vector solved the problem of the lack of efficient viral vector to transduce human airway, and is of great interest in the gene therapy application for cystic fibrosis (CF) due to its larger packaging capacity. The system used a non-replicating HBoV nonstructural (NS) and capsid proteins (Cap)-expressing plasmid, pHBoV1NSCap, as the packaging helper to produce rAAV/HBoV1 vector. The production yield of purified vector is $2\times10^{11}$ DRP (DNAse digestion-resistant particles) per 40 (145 mm)-plates transfected HEK 293 cells, that is about 400 to 600 DRP/cell (in crude lysate) or 250 DRP/cell (purified vector), and is about 5 to 10% of the yield of rAAV2 vector production in transfected 293 cells. This production yield is sufficient for routine studies in the laboratory on vector biology and functional assays of transduction. For example, this system an AAV/HBoV vector was produced harboring a 5.5 kb oversized rAAV genome with a 5.2 kb strong CFTR expression cassette. The function and efficacy of this novel CFTR vector has been validated in cystic fibrosis (CF) polarized human airway epithelial cultures grown at an air-liquid interface (HAE-ALI). Following apical infection, the vector can efficiently deliver normal CFTR protein expression on the surface of the airway epithelial cells and correct defective CFTR chloride transport defects in CF HAE-ALI cultures (Yan et al, 2013). However, for preclinical studies in experimental animals and future clinical trial, this production yield is not sufficient.

Thus, prior to this disclosure, where an HBoV nonstructural and capsid proteins-expressing plasmid pHBoV1NSCap was used as helper to cross-genus pseudo-package rAAV genome in HBoV capsid, virus production was not sufficient enough for clinical application. The present disclosure reveals details of HBoV viral protein expression profiles and the involvement of the HBoV non-structural proteins in capsid expression and vector production. These findings are likely relevant to all HBoV serotypes from human as well as other mammalian bocoviruses (not just human HBoV1). Findings on the biological properties of HBoV that are relevant to vector development include: 1) HBoV non-structural protein NP1 plays a role in regulating HBoV capsid expression and rAAV/HBoV vector packaging; 2) knockout of the proximal polyadenylation sites ((pA)p) in Cap coding sequence compensates the NP1 protein for capsid protein expression; and 3) expression of non-structural proteins NS1, NS2, NS3 and NS4 is not essential for vector production. This disclosure also relates to a series of new packaging helpers plasmids that inactivate NS1-4 expression, the exchange of endogenous P5 promoter with the CMV IE enhancer/promoter, as well as codon optimization of the capsid protein-encoding sequence. A 5- to 75-fold increment in rAAV/HBoV production can be achieved using these helpers in HEK293 cell production system, compared to the previous helper pHBoV1NSCap. These capsid expression constructs can also be employed to the baculovirus/insect cells production system for rAAV/HBoV vector production.

The HBoV1 genetic map, which revealed a detail transcriptional profile of the HBoV1 NS and cap genes and the viral proteins expressed from different spliced mRNAs from the pre-RNA transcribed by the native P5 promoter. (See FIGS. 1 and 11). While investigating the involvement of the HBoV non-structural protein on capsid protein expression, it was found that: 1) ectopic expression of the HBoV1 cap ORF is not sufficient to express capsid proteins, due to the poor production of mRNA in the cytoplasm; 2) non-structural protein NP1 is the critical component required for regulating HBoV capsid expression, which facilitates the splicing of capsid protein-encoding mRNA and thereby activates capsid expression; 3) the expression of non-structural proteins NS1, NS2, NS3 and NS4 are not essential for capsid protein expression; 4) internal polyadenylation prevents HBoV1 pre-mRNA transcription through proximal polyadenylation (pA)p sites within the capsid protein coding sequence, knockout of the (pA)p sites compensates for the requirement of NP1 protein in the expression of capsid proteins.

The utility of these findings on HBoV1 biology hinge on whether they can be used to improve the efficiency of chimeric rAAV/HBoV vector production. The ability of a new packaging system to improve chimeric rAAV/HBoV vector production was tested. Two series of HBoV1 capsid expression constructs were generated and tested for their efficiency of pseudopackaging the rAAV genome in HBoV capsid. One set of helpers was NP1 protein expression dependent. They are the revised versions based on the pHBoVNScap helper, but the expression of NS1, NS2, NS3 and NS4 gene is null and the endogenous P5 promoter is replaced with a strong human CMV IE enhancer/promoter. This set of helpers increase vector production by 6- to 12-fold with the yield of 3,000-6,000 DRP/cell (in crude lysate) or 1,500-2,500 DRP/cell (purified vector); the transduction activity of the virus was similar to that produced with the pHBoVNSCap helper. Another set of helpers was NP1 protein expression-independent. Mammalian cell expression vector pcDNA3.1 was used to express HBoV1 capsid proteins from a synthetic HBoV1 cap cDNA (optVP1U or optVP1) without other HBoV1 sequence. optVP1U and optVP1 cDNAs were constructed with a codon optimized capsid coding sequence as well as an alternative start codon to initiate VP1 translation. In addition, the proximal polyadenylation sites (pA)p in the 5' end of capsid protein-encoding region was removed. In optVP1U cDNA, the codon optimization is restricted in the 5' unique region of VP1 and VP2, whereas in optVP1, the codon optimization is through the entire encoding sequence of VP1, VP2 and VP3. The CMV enhancer/promoter sequence was used to express the optVP1 cDNA, and HBoV1 VP1, VP2 and VP3 expression was as efficient as the pHBoVNSCap helper and at a similar ratio of 1:1:10.60- to 80-fold higher chimeric vector production was obtained from this set of NP1 independent helpers. The vector production yields reach 15,000 to 40,000 DRP/cell (in crude lysate) or >10,000 DRP/cell (purified vector). However, compromised transduction activity was observed. The potency of the vector produced from NP1 independent helpers is ⅙ to ⅒ of those produced from the pHBoVNSCap or NP1 dependent helpers.

In summary, an improved rAAV/HBoV1 production system was developed that had at least a 5 to 75-fold higher efficiency than the prototype system. The current production yield is good enough for us to conduct preclinical study of the rAAV/HBoV1 vector in CF ferret model. The rAAV/HBoV1 vector produced from the improved production system using the NP1-dependent helper was a cultured in polarized airway cells and in ferrets in vivo. Although the transduction activity of the vector produced from the NP1-independent helper is compromised, its ability to package rAAV/HBoV1 vector is superiorly high: up to 10-fold more efficient than the NP1-dependent helper.

The invention will be further described by the following non-limiting example.

Example

Materials and Methods
Plasmid Construction

The parent plasmid pHBoV1NSCap has been used to package rAAV2/HBoV1 vector, which contains an incomplete HBoV1 genome (nt 97 to 5,395) without the intact left and right end hairpins (Yan et al., 2013). All other plasmids based on the pHBoV1NSCap were constructed as follows, and they are also diagrammed in the figures.

pHBoV1NSCap-Based Plasmids:
pVP2m1, pVP2m2, pVP2m3 and pVP2m4 were constructed by mutating nt 3,422-3,427 of the HBoV1 sequence, as shown in FIG. 3A, in pHBoV1NSCap.
pCMVNSCap-Based Plasmids:
pCMVNSCap was constructed by replacing the HBoV1 P5 promoter (nt 97-281) with the human cytomegalovirus immediate early enhancer/promoter sequence (CMV) retrieved from the pcDNA3 vector (Invitrogen/Thermo Fisher Scientific Inc. Grand Island, N.Y.) in pHBoV1NSCap. pCMVNSCapbGHpA was constructed by replacing the HBoV1 3' untranslational region (UTR) (nt 5,168-5,395) with the bovine hormone gene polyadenylation signal (bGHpA) of the pcDNA3 in pCMVNSCap. Based on the pCMVNSCap, NS1, NP1, and both NS1 and NP1 encoding sequences were early terminated by introducing a stop codon (Huang et al., 2012), which allowed construction of pCMVNS*Cap, pCMVNS(NP*)Cap and pCMVNS*(NP*)Cap, respectively.

VP cDNA Plasmids:
In pCMVNSCap, nt 282-3,091 of the HBoV1 sequence were deleted to construct pCMVCap1, and moved the VP1 open reading frame (ORF) directly under the CMV promoter to construct pCMVCap2. All D1-A1, D2-A2, and D3-A3 intron sequences were deleted to construct pCMVR6cDNA.

D1-A2 and D3-A3 intron sequences were removed to construct pCMVR7cDNA. D1-A3 intron sequence were removed to construct pCMVR8cDNA. These three cDNA constructs coordinate with three VP-encoding mRNA transcripts that were previously identified, R6, R7, and R8 mRNAs, which are indicated in FIG. 1A.

Intron-Replaced Plasmids:

The erythropoietin gene (Epo) intron 4 (Yan et al., 2000) was inserted between the D1 and A3 sites to construct pCMVCap3. Based on the pCMVNS*Cap plasmid, the D3-A3 intron sequence was deleted to construct pCMVNS*(ln3Δ)Cap. Based on the pCMVNS*(ln3Δ)Cap, the first and second introns were changed to Epo intron 1 and 4, respectively, to construct pCMVEpoln14(ln3Δ)Cap. Additionally, all three introns in pCMVNSCap were changed to Epo introns 1, 2, and 4, respectively, to construct pCMVEpoln124Cap.

(pA)p Knockout [m(pA)p] Constructs:

The potentially used five polyadenylation sites (PASs) and both their upstream and downstream elements [m(pA)p], which span the coding region for the amino acids between methionines of the VP1 and VP3 ORFs, were silently mutated through a Codon Optimization algorithm at IDT (Integrated DNA Technologies, Inc., Coralville, Iowa) (FIG. 2). An optimized Kozak sequence (GTT AAG ACG) was used to express VP1, and remained the GTG codon for VP2, in order to obtain an appropriate ratio of VP1 to VP2 and to VP3. To construct pCMVNS*(NP*)m(pA)pCap and pCMVNS*(ln3Δ)m(pA)pCap, the (pA)p sites in pCMVNS*(NP*)Cap and pCMVNS*(ln3Δ)Cap, respectively were mutated. In the pCMVR6-8cDNA constructs, the (pA)p sites were mutated to make pCMVR6-8cDNAm(pA)p.

Other Plasmids:

pOpt-NP1 was constructed by inserting a codon optimized NP1 ORF, which was synthesized at IDT, into pLenti-CMV-IRES-GFP-WPRE vector (Chen et al., 2011) through XbaI and BamHI sites. pCI-mCherry-HA was constructed by inserting a C-terminal HA-tagged mCherry ORF into pCI vector (Promega, Madison, Wis.) through Xho I and Xba I sites. All nucleotide numbers (nt) of the HBoV1 genome refer to the full-length HBoV1 genome (GenBank accession no.:JQ923422). Constructs were verified for HBoV1 sequence and mutations by Sanger sequencing at MCLAB (South San Francisco, Calif.).

Cell Culture and Transfection

HEK293 cells (CRL-1573) were purchased from American Type Culture Collection (ATCC, Manassas, Va.), and were cultured in Dulbecco's modified Eagle's medium (GE Healthcare Bio-Sciences, Piscataway, N.J.) with 10% fetal calf serum (Sigma-Aldrich, St. Louis, Mo.). Cells grown in 60-mm dishes were transfected with a total of 4 μg of plasmid DNA using LipoD293 reagent (SignaGen Laboratories, Gaithersburg, Md.), following the manufacturer's instructions. The pLenti-CMV-IRES-GFP-WPRE vector (Chen et al., 2011) was cotransfected into HEK293 cells to ensure the same amount of plasmid DNA was transfected for each NP1 complementation experiment. As a control for transfection, 0.4 μg of pCI-mCherry-HA plasmid DNA was cotransfected into HEK293 cells.

Western Blotting

HEK293 cells were transfected with plasmids as indicated in each figure. Cells were harvested and lysed at 2 days post-transfection. Western blotting was performed to analyze the lysates as described In Shen et al. (2015) using the specific antibodies described in each figure. Rat anti-HBoV1 VP, NP1, and NS1 C-terminus (NS1C) were produced previously (Shen et al., 2015). Anti-β-actin and anti-HA monoclonal antibodies were purchased from Sigma-Aldrich.

RNA Isolation and Analyses

RNA Isolation:

Cytoplasmic RNA was purified from transfected cells following the QIAGEN Supplementary Protocol using the RNeasy® Mini Kit (Qiagen, Valencia, Calif.). For the RNA samples used for RNA export examination, the same numbers of cells were extracted for cytoplasmic RNA and total RNA using the RNeasy Mini Kit. Other total RNA samples were prepared using Trizol Regent (Invitrogen), according to the manufacturer's instructions.

Northern Blotting:

Five μg of cytoplasmic or total RNA samples was separated on 1.4% denaturation agarose gel, and was visualized using ethidium bromine (EB) staining. The stained 18S ribosome RNA (rRNA) bands served as loading control. Northern blot analysis was performed as described in Sun et al. (2009), using $^{32}$P-labeled DNA probes as diagrammed in FIG. 1B. In some gels, an RNA ladder (Invitrogen) was used as a size marker (Qiu et al., 2002).

RNAse Protection Assay (RPA):

RPA was performed as described in Chen et al. (2010) and Sun et al. (2009). RPA probes were constructed by cloning the indicated sequence (FIG. 1B) into BamHI/HindIII-digested vector pGEM4Z (Promega). The protected bands by the indicated probe are diagrammed in FIG. 1B.

Quantification:

Images of both Northern blotting and RPA were processed using a GE Typhoon FLA 9000 phosphor imager (GE Healthcare Bio-Sciences, Pittsburgh, Pa.). ImageQuant TL 8.1 software was used to quantify the bands on the images.

TABLE 1

| rAAV2/HBoV Production from HBoV Packaging Helpers | | | | | | | | | | |
|---|---|---|---|---|---|---|---|---|---|---|
| | Left HBoV | | | | NS gene expression | | | | | Relative Production |
| | Sequence | Promoter | pA | (pA)p | NS1 | NS2 | NS3 | NS4 | NP1 | Yield |
| Prototype Helper | | | | | | | | | | |
| pHBoV1NScap | YES | P5 | (pA)d NP1 dependent helper | YES | YES | YES | YES | YES | YES | 1 |
| pCMVNS1(-)Cap | YES | CMV IE | (pA)d | YES | NO | NO | YES | YES | YES | 5.3 +/- 1.0 |
| pCMVHBoVNS1-3(-)cap | YES | CMV IE | (pA)d | YES | NO | NO | NO | YES | YES | 9.3 +/- 0.5 |
| pCMVHBoVNS1-3(-)D'm | YES | CMV IE | (pA)d | YES | NO | NO | NO | NO | YES | 10.7 +/- 3.5 |

TABLE 1-continued rAAV2/HBoV Production from HBoV Packaging Helpers

| Left HBoV Sequence | Promoter | pA | (pA)p | NS1 | NS2 | NS3 | NS4 | NP1 | Relative Production Yield |
|---|---|---|---|---|---|---|---|---|---|
| NP1 independent, VP1 and VP2 5' unique region codon optimized | | | | | | | | | |
| pCMV-R7optVP1U | NO | CMV IE | (pA)d | NO | NO | NO | NO | NO | NO | 1.8 +/− 0.4 |
| pCMV-NS1(−)NP1(−)optVP1U | YES | CMV IE | (pA)d | NO | NO | NO | YES | YES | NO | 11.7 +/− 2.9 |
| pCMV-NS1-3(−)NP1(−)optVP1U | YES | CMV IE | (pA)d | NO | NO | NO | NO | YES | NO | 4.3 +/− 0.8 |
| pcDNAoptVP1hyd | NO | CMV IE | SV40 pA | NO | NO | NO | NO | NO | NO | 9.5 |
| NP1 independent, VP1, VP2 and VP3 codon fully optimized | | | | | | | | | |
| pCDNAoptVP1 | NO | CMV IE | SV40 pA | NO | NO | NO | NO | NO | NO | 63.2 +/− 10.5 |

Left HBoV Sequence: about 2.4 kb HBoV1 genome encodes the non-structural proteins
P5: Endogenous Promoter in HBoV1 genome
(pA)d: 3' distal polyadenylation site in HBoV Genome
(pA)p: proximal polyadenylation sites at center of HBoV genome (within coding sequence of 5' unique sequence of VP1/VP2)
CMV IE: human cytomegalovirus immediate early promoter/enhance
SV40 pA: SV40 virus sequence containing polyadenylation sites
Relative production yield from each helper is normalized to that production of 400-600 DRP (DNAseI digestion resistant particle)/cell in the production system using the prototype helper, pHBoV1, and this yield is set to 1.

Results

Identification of a Non-Canonical Initiation Site that Encodes a Novel Capsid Protein VP2

Previously, a band of capsid protein (VP*) was detected whose size is between VP1 and "VP2" in HBoV1-infected human airway epithelium and HBoV1 plasmid-transfected HEK293 cells (Shen et al., 2015), as well as in the purified rAAV2/HBoV1 vector (Yan et al., 2013). However, it wasn't known whether this VP* band is a cleaved protein of the VP1 or a novel capsid protein translated from a non-canonical initiation site, a GCU codon of the alanine at the amino acid (aa) 92 of the VP1 ORF, which has been previously identified in the expression of VP1 ORF in insect Sf9 cells (Cecchini et al., 2009). Therefore, this initiation site was examined in the expression of HBoV1 capsid proteins in HEK293 cells. Four mutations were made in the GUG and GCU codons in pHBoV1NSCap (FIG. 3A). Two mutants that bear mutations of the GUG codon, which encode the valine of aa 91 of the VP1 ORF, drastically decreased expression of the intermediate band between VP1 and VP3 (FIG. 3B, lanes 1&2). Thus, it was confirmed this intermediate band (VP*) of the HBoV1 capsid proteins is a novel capsid protein of VP2 initiated at the GUG codon at nt 3,422 of the HBoV1 genome.

HBoV1 VP cDNA is Intrinsically Inefficient to Generate VP-Encoding mRNA

Figure 4A:
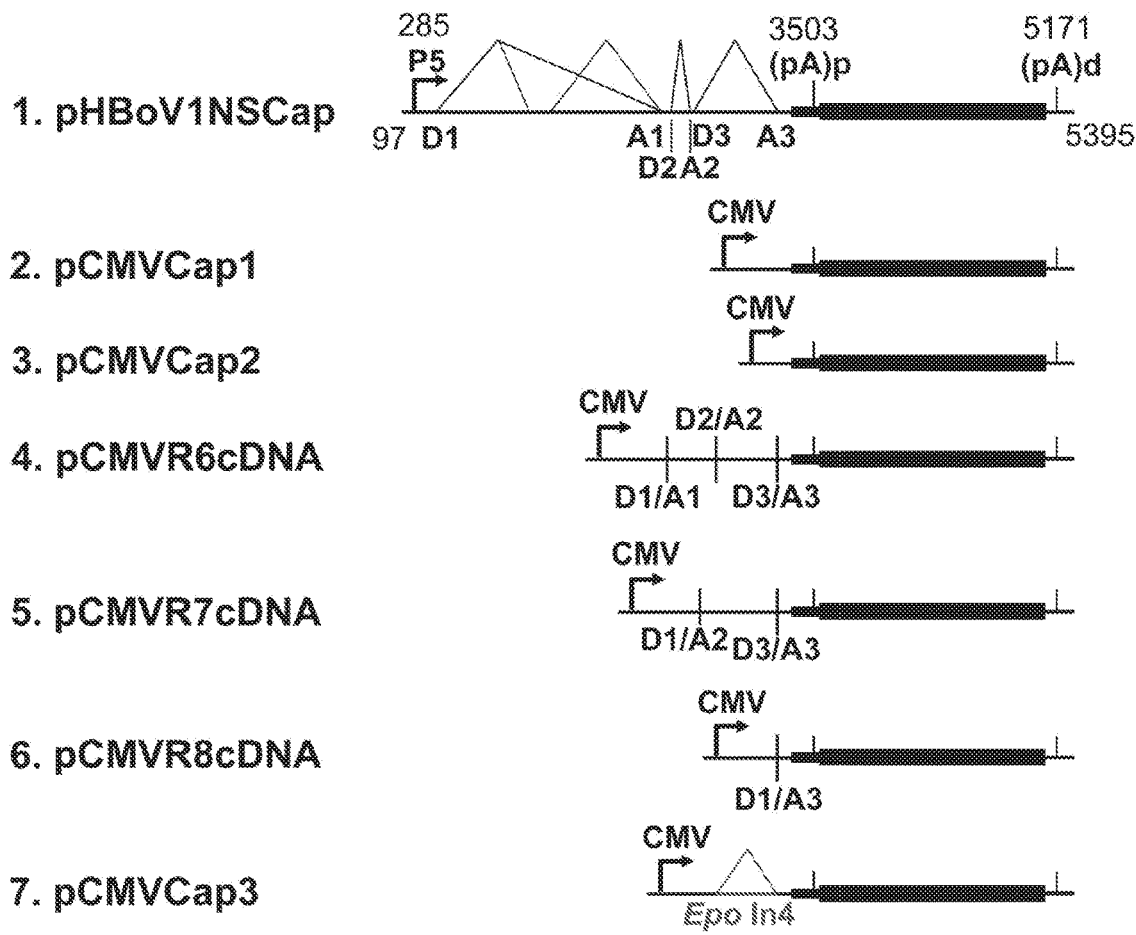
Figure 4B:
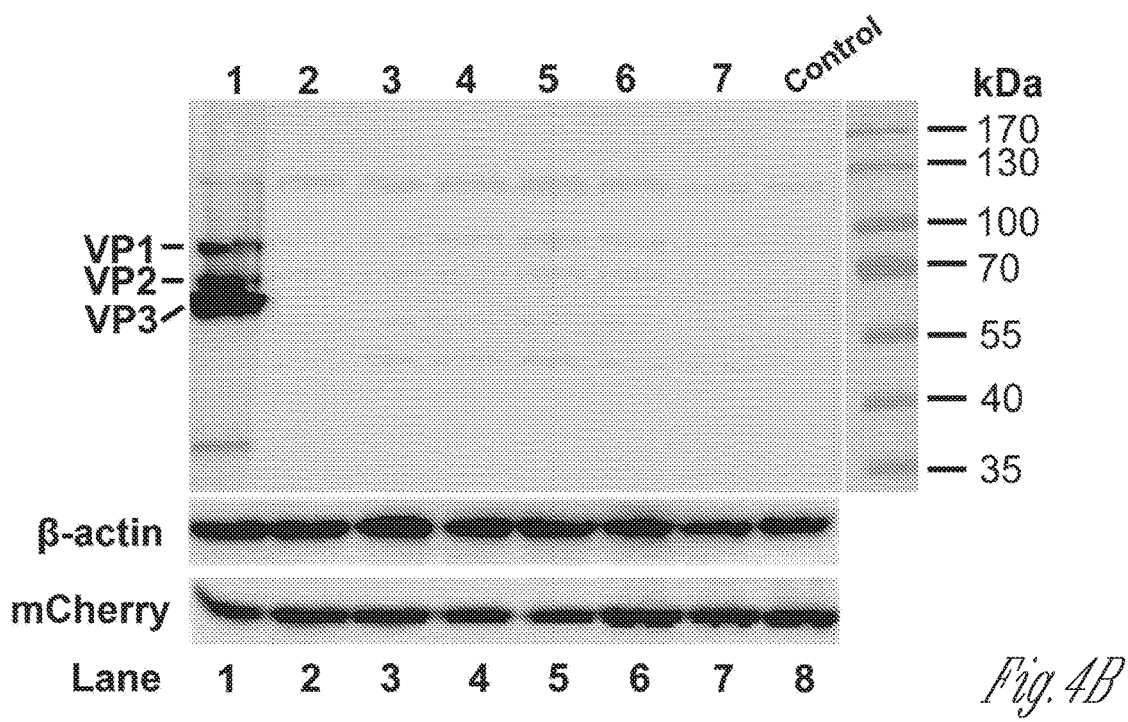
Figure 4C:
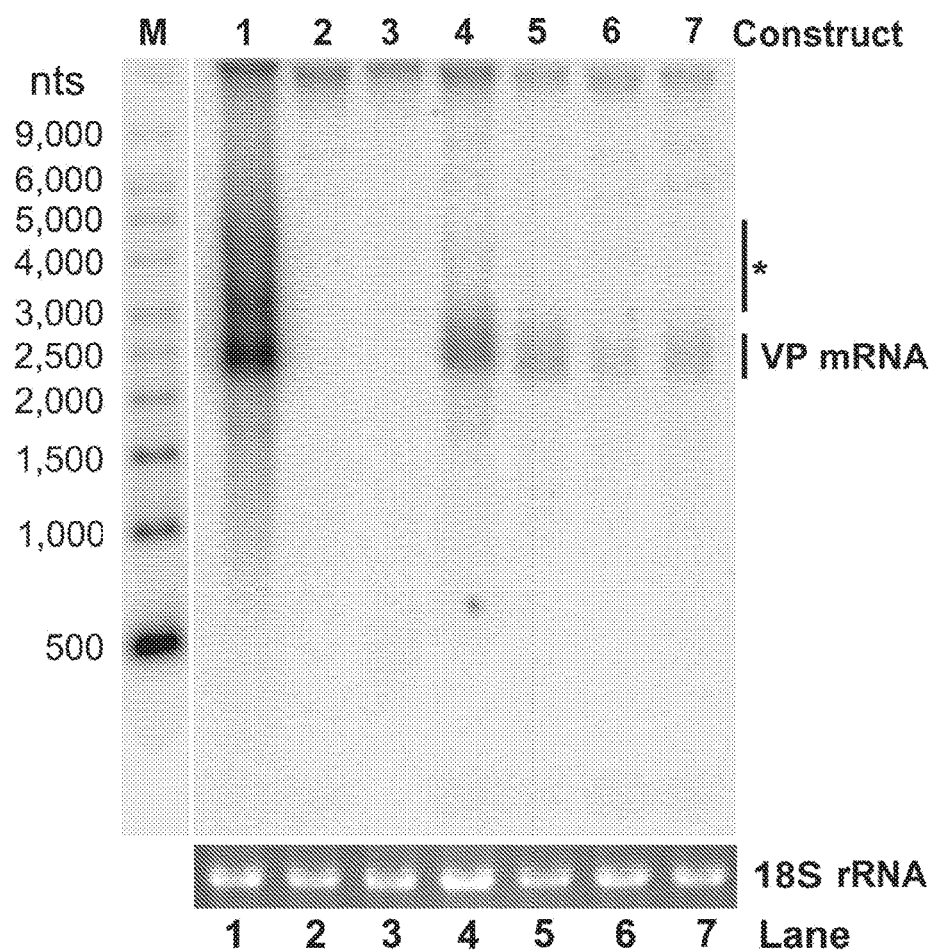
Figure 4D:
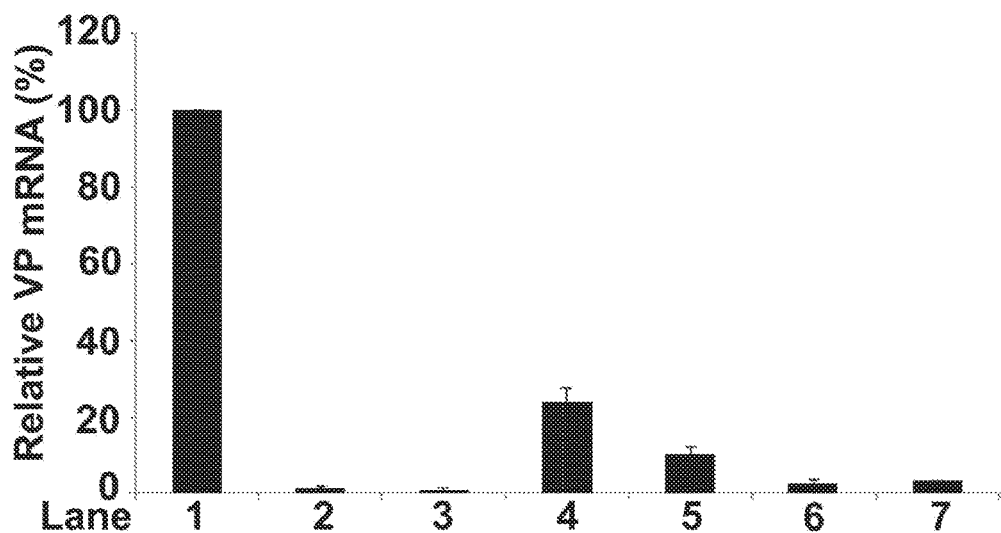

In the rAAV2/HBoV1 vector production system, a non-replicating HBoV1 construct pHBoV1NSCap was used as a packaging plasmid (Yan et al., 2013), which expressed NS1-4 and NP1 (Shen et al., 2015), in addition to capsid proteins. To identify a simple packaging plasmid that expresses only capsid proteins, expressive HBoV1 capsid proteins was attempted ectopically with minimal HBoV1 sequence containing the VP ORFs. To this end, six VP expression plasmids under the control of CMV promoter, as outlined in FIG. 4A, were constructed, including three VP cDNA constructs of R6, R7, and R8 mRNAs (FIG. 1A), and the other three VP ORF constructs that contain various sequences of 5'UTR. Surprisingly, none of them expressed capsid proteins in transfected HEK 293 cells, as detected by Western blotting (FIG. 4B, lanes 2-7). Next, Northern blotting was performed to analyze VP-encoding mRNA in cytoplasm using a VP mRNA-specific Cap probe (FIG. 1B). Only a low abundance of the VP mRNA was detected in the cytoplasmic RNA preparations of the cells transfected with the three cDNA constructs and the pCMVCap3, which was less than about 20% of the VP mRNA generated from the control pHBoV1NSCap (FIGS. 4C&D, lanes 4-7). We detected almost no cytoplasmic VP mRNA from the cells transfected with pCMVCap1/2 (FIGS. 4C&D, lanes 2&3).

Taken together, these results revealed that ectopic expression of the HBoV1 VP ORF is not sufficient to express capsid proteins, due to the poor production of VP mRNA in the cytoplasm.

NP1 Protein Plays an Important Role in the Expression of Capsid Proteins

Figure 5A:
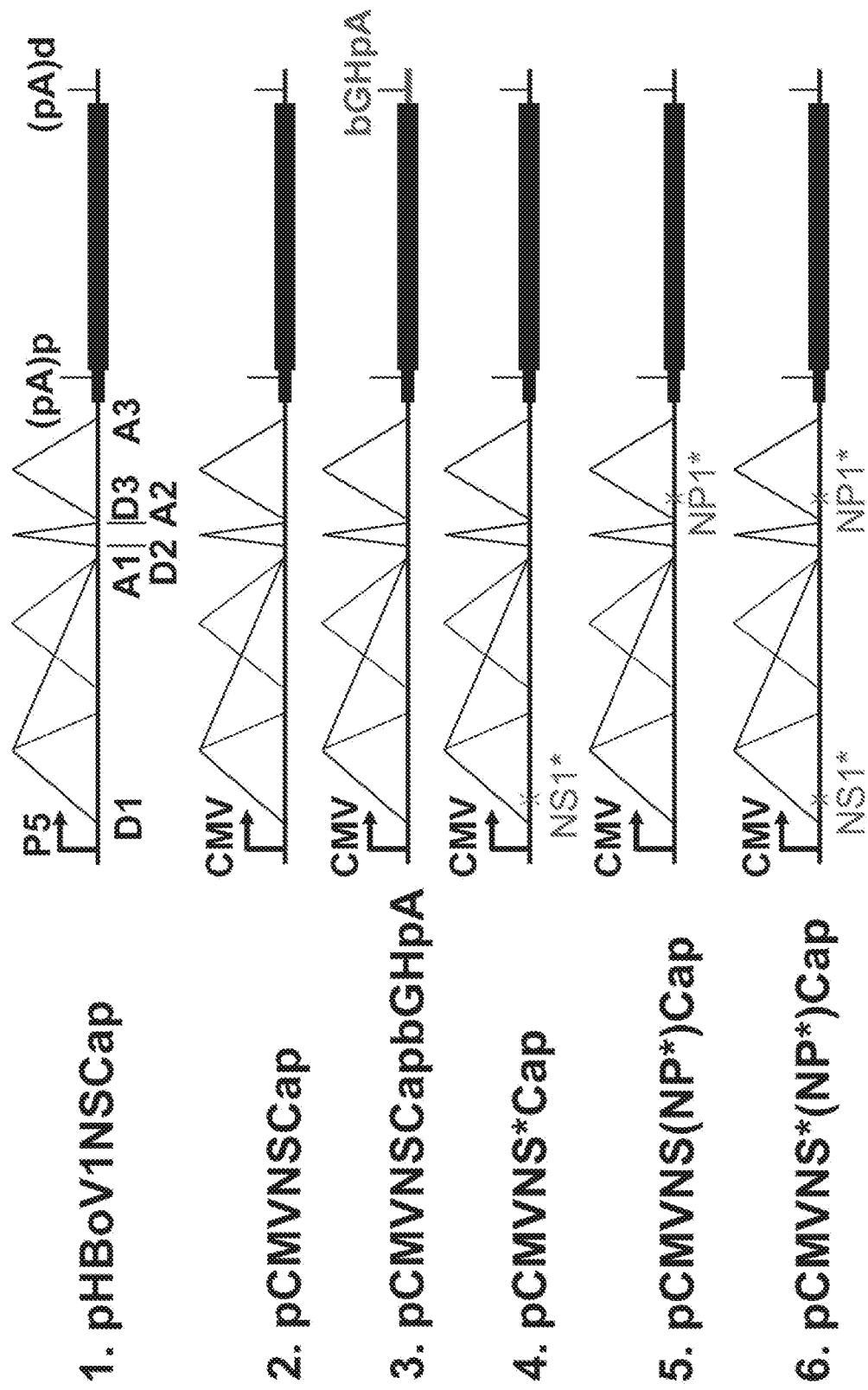
Figure 5B:
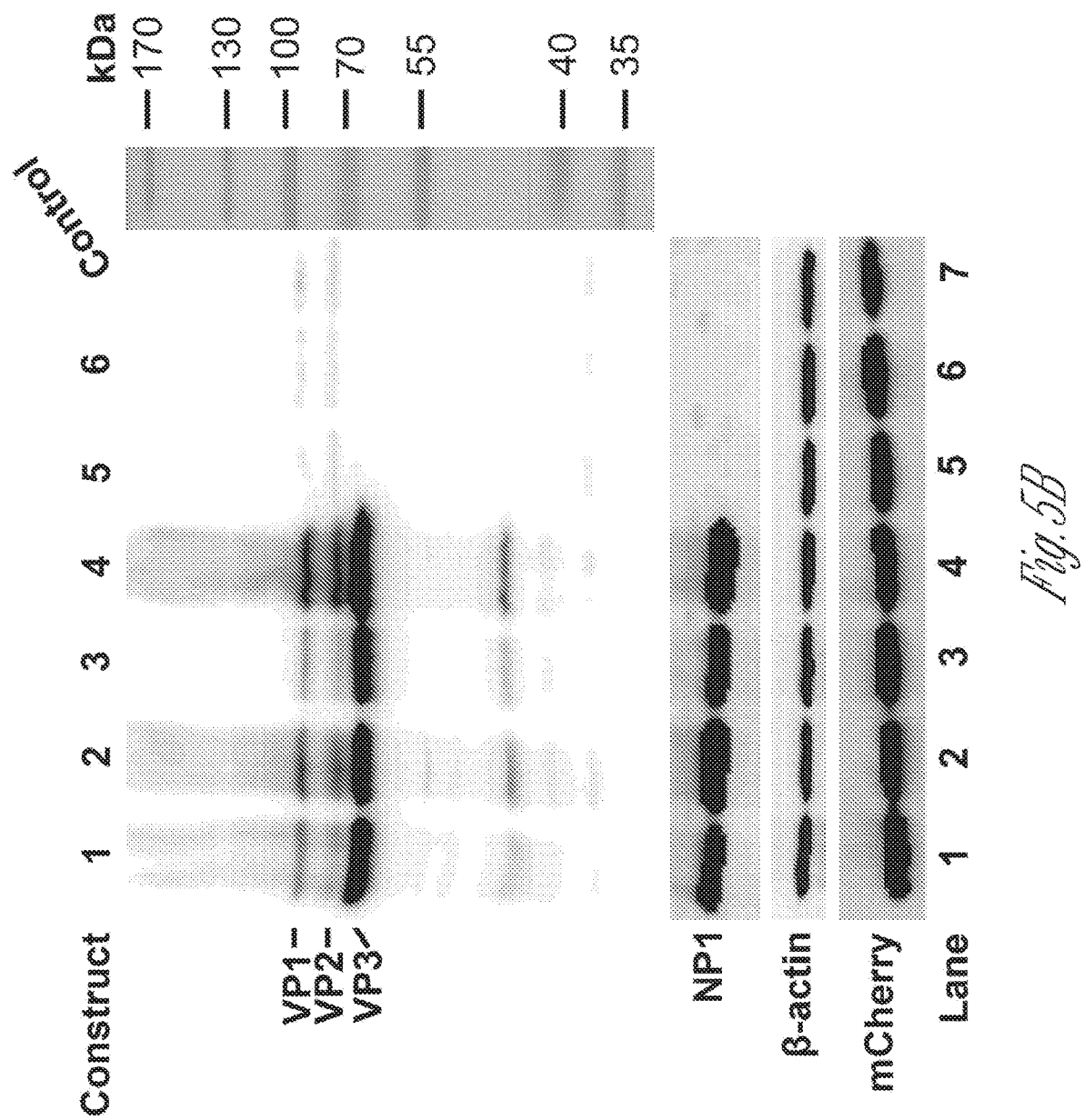
Figure 5C:
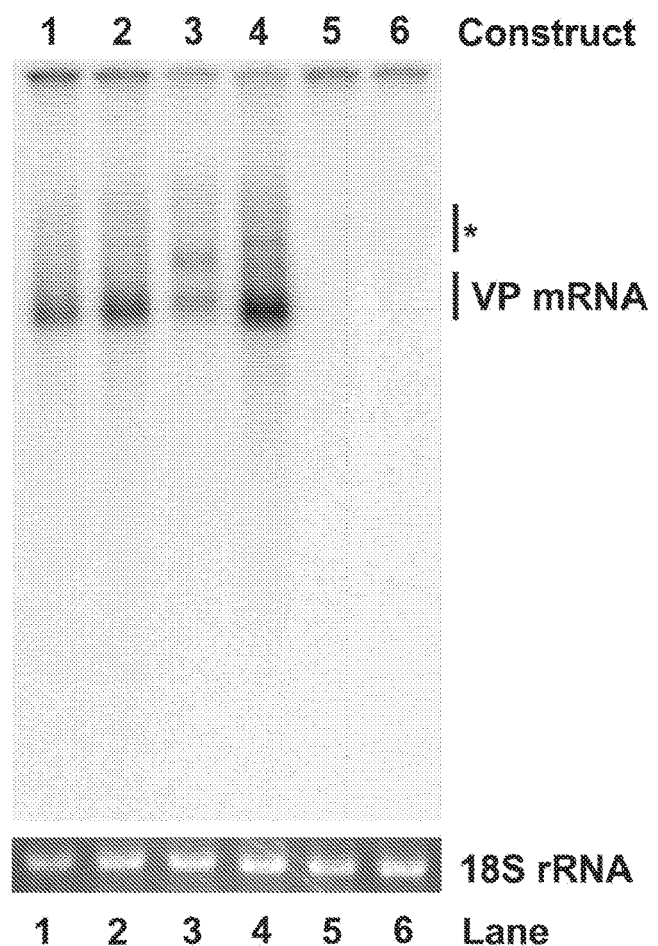
Figure 5D:
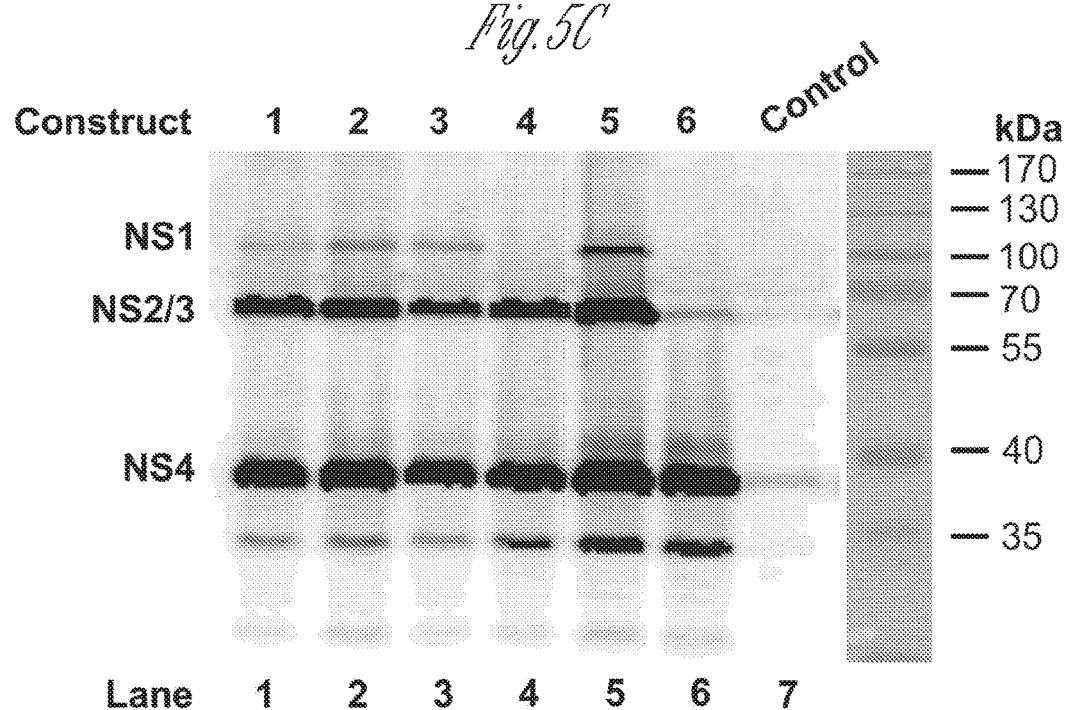

Next, it was investigated how the capsid proteins are expressed from pHBoV1NSCap. To explore systematically the effects of the cis-elements of the viral genome and of the viral proteins in trans on the expression of capsid proteins, five constructs were made, as shown in FIG. 5A. Exchange of either the P5 promoter with the CMV promoter or the 3'UTR to bGHpA did not affect the capsid protein in general (FIG. 5B, lanes 2&3 vs. 1). Knockout of the NS1 and NS2 expression in pCMVNSCap (FIG. 5D, lane 4, NS1) did not diminish the level of capsid proteins (FIG. 5B, lane 4, VP). However, when NP1 expression was knocked out by early termination of the NP1 ORF, both NP1 knockout constructs pCMVNS(NP*)Cap and pCMVNS*(NP*)Cap failed to express appreciable levels of capsid proteins (FIG. 5B, lanes 5&6). Next, the levels of the cytoplasmic VP mRNA in transfected cells were examined. Consistent with the capsid protein expression, NP1 knockout nearly abolished VP mRNA in the cytoplasm (FIG. 5C, lanes 5&6).

Collectively, these results provided evidence that HBoV1 NP1 plays a critical role in the expression of capsid proteins, which is due to the increased level of VP mRNA in cytoplasm, and that NS1 and NS2 proteins in trans and the cis sequences of the P5 promoter and the 3'UTR are not essential to capsid protein expression.

NP1 Protein Facilitates Splicing of VP mRNA at the A3 Splice Acceptor

Figure 6B:
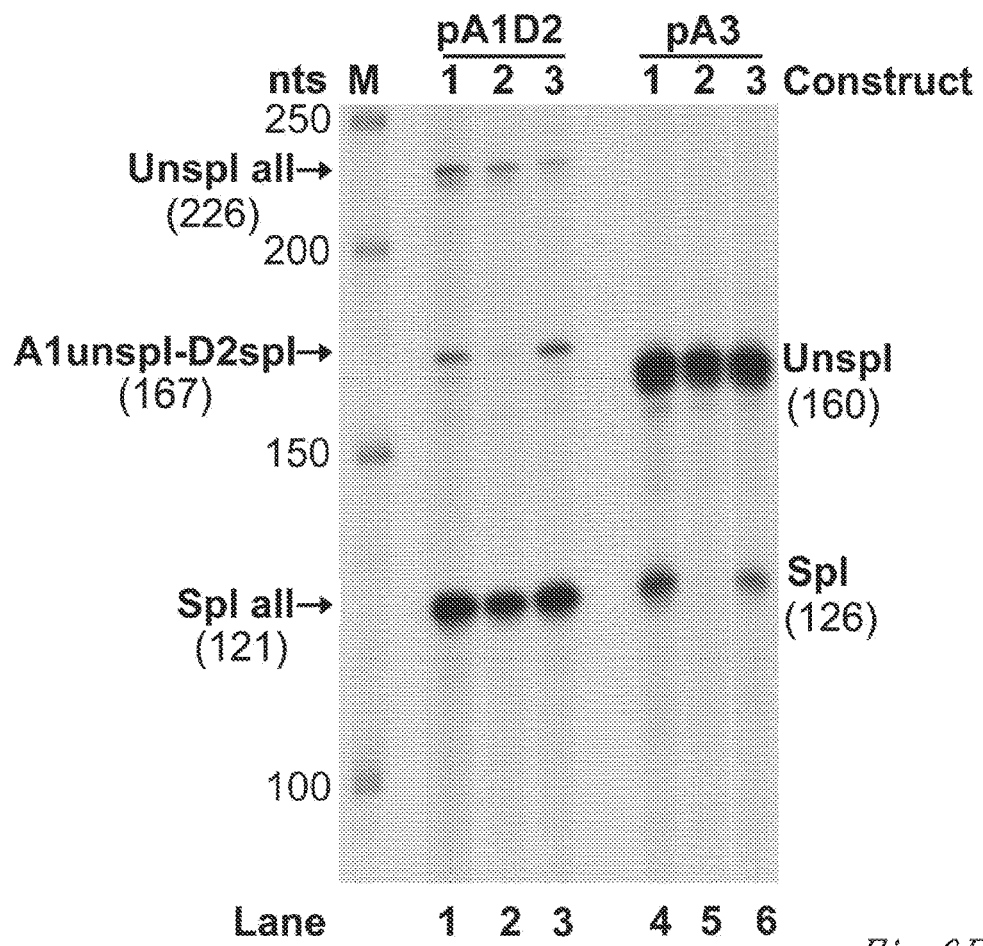
Figure 6E:
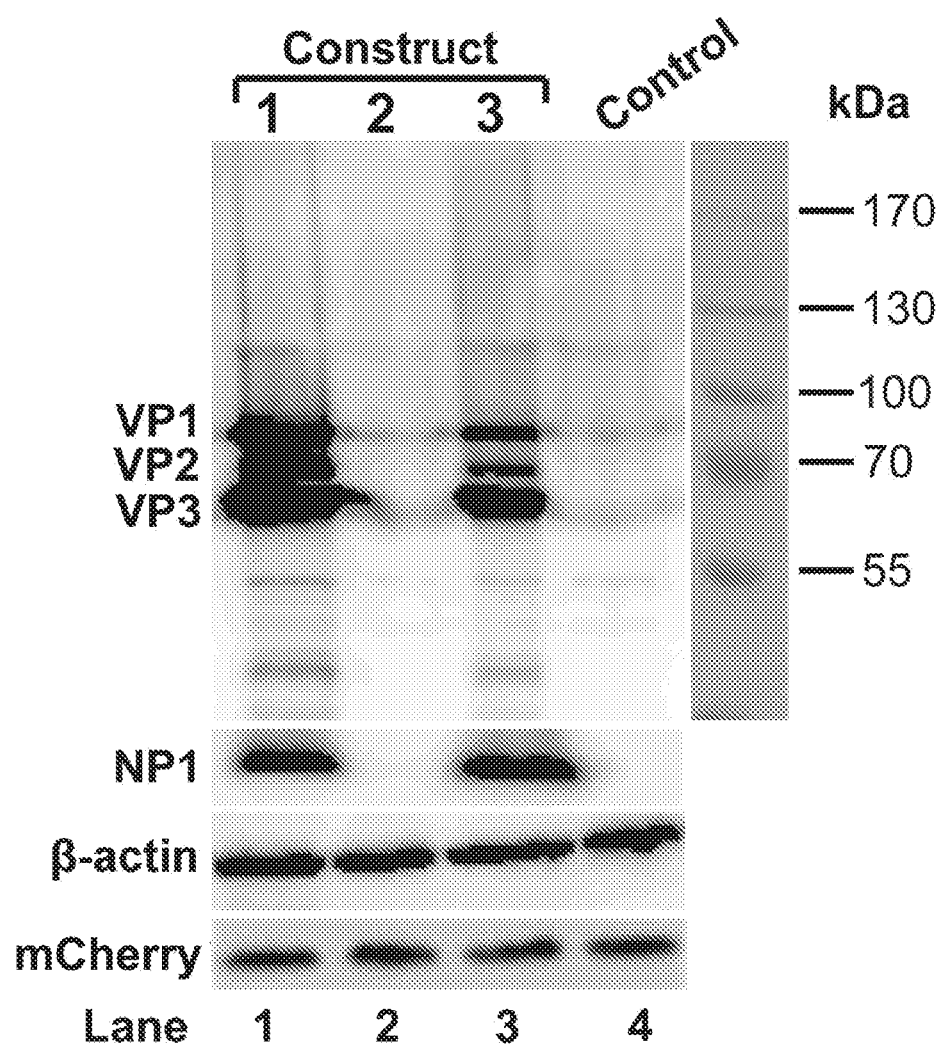

Next, it was investigated how NP1 regulates capsid protein expression. Since splicing at the A3 splice acceptor of the three introns is prerequisite to the production of VP mRNAs (FIG. 1A), we examined the function of NP1 in the splicing at the A3 splice acceptor. When NP1 was knocked out, splicing at the A3 splice acceptor decreased by 78-fold (FIG. 6B, lanes 5 vs. 4), whereas the splicing of the first and second introns did not (FIG. 6B, lanes 2 vs. 1). Complementation of the NP1 In trans restored 67% of the mRNA spliced at the A3 splice acceptor (FIG. 6B, lane 6, and FIG. 6C). In parallel with the inefficient splicing at the A3 splice acceptor, cytoplasmic VP mRNA was not detectable (FIG. 6D, lane 2), and capsid proteins were not expressed from pCMVNS*(NP)Cap (FIG. 6E, lane 2). However, complementation of the NP1 restored both the expressions of VP mRNA and of capsid proteins (FIGS. 6D&E, lane 3).

Figure 6F:
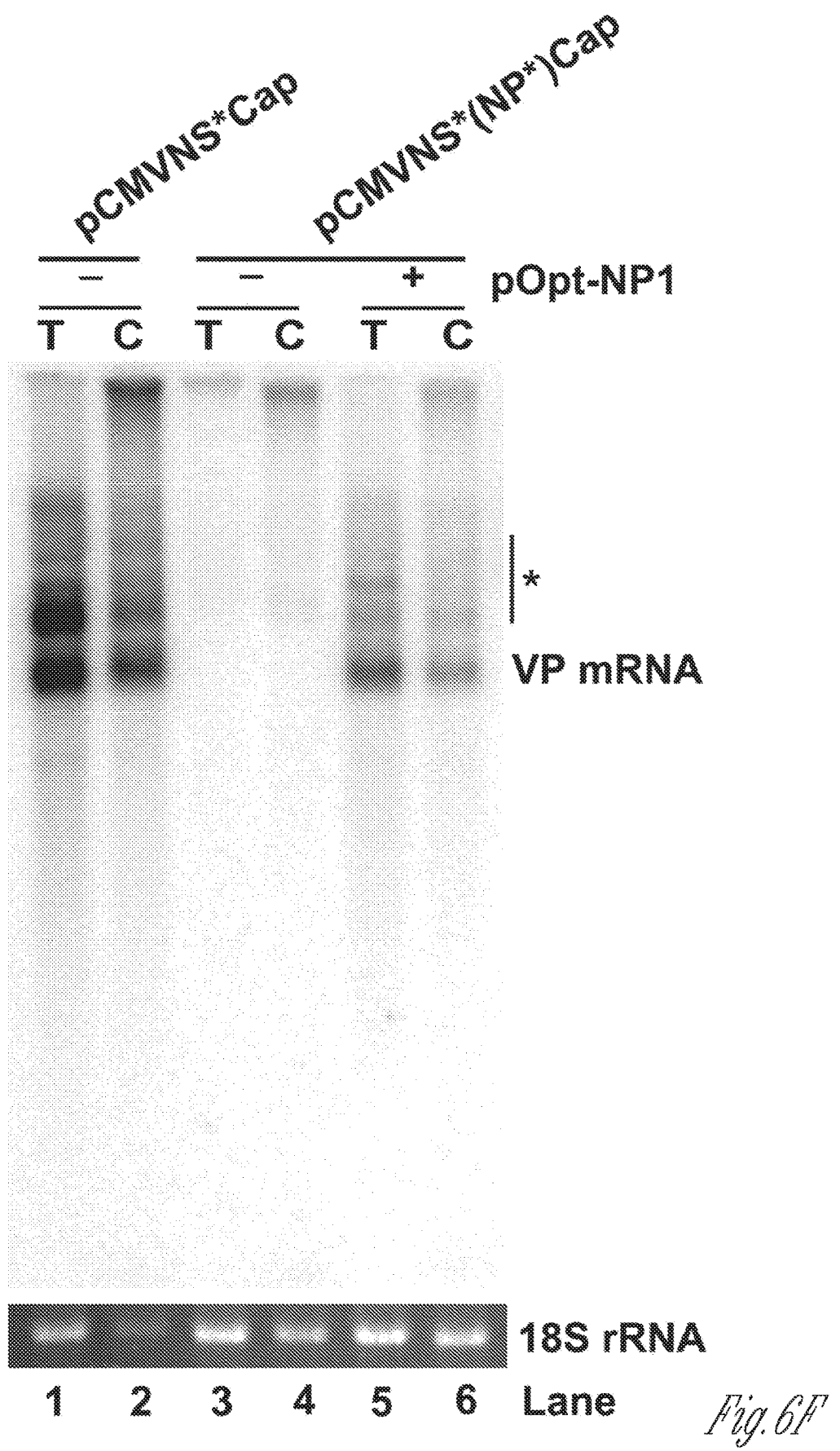
Figure 6G:
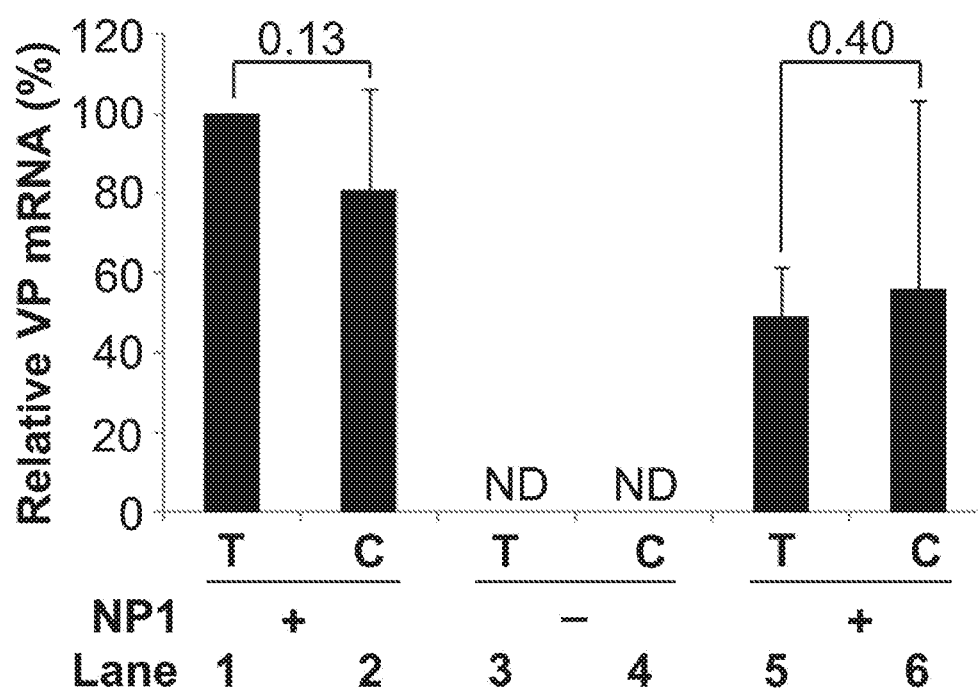
Figure 6H:
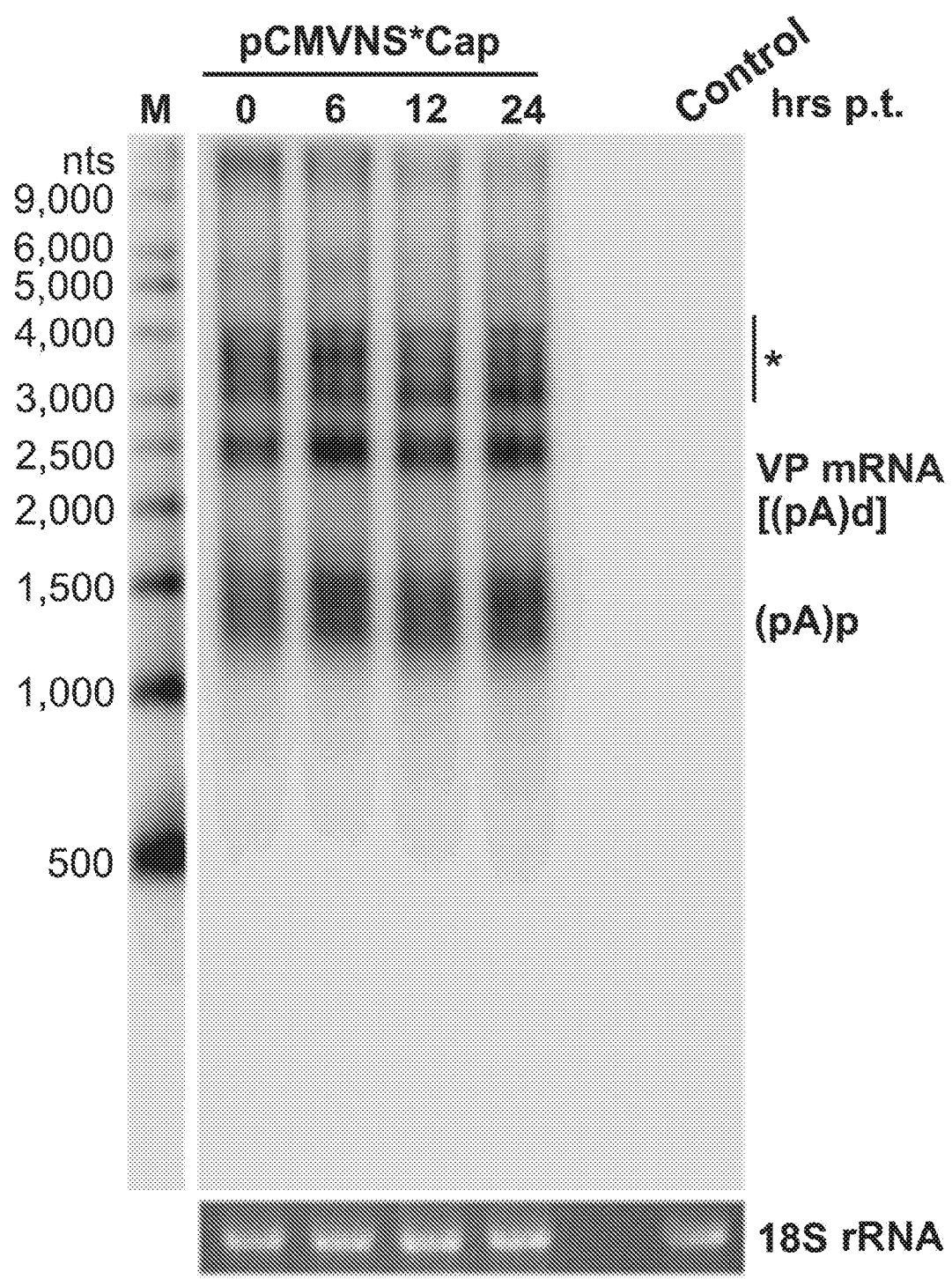

The undetectable level of cytoplasmic mRNA from the NP1 knockout mutant therefore was due to the inhibited production of VP mRNA in the nucleus and not due to the inefficient export of VP mRNA from the nucleus (FIG. 6F, lanes 3&4). VP mRNA was exported from the nucleus to cytoplasm efficiently (FIGS. 6F&G, lanes 1 vs. 2 and 5 vs. 6). In addition, VP mRNA was quite stable in the cells for a period of 24 hours, as determined by the RNA stability assay using actinomycin D (FIG. 6H).

Figures 7A, 7B:
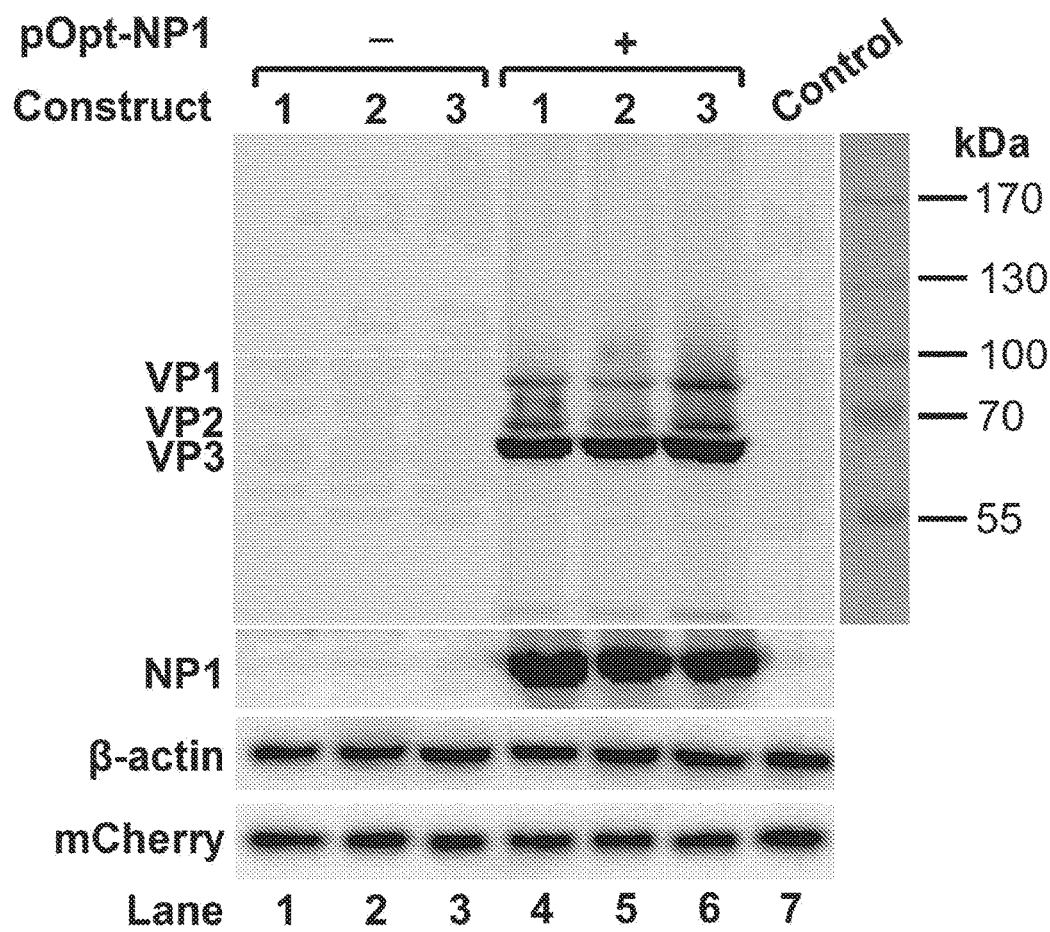
Figure 7C:
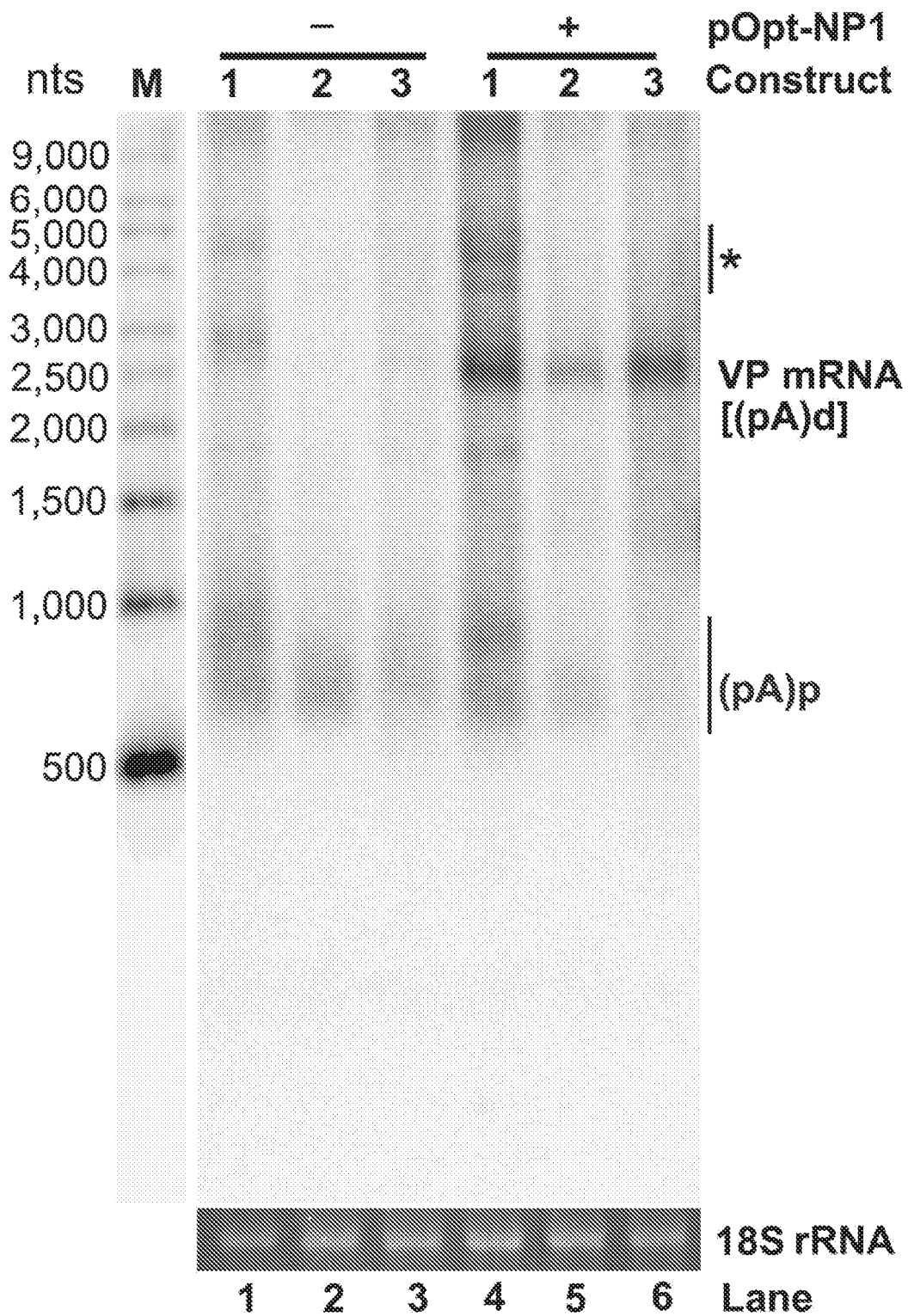

Taken together, these results confirmed that NP1 is required for the splicing of HBoV1 mRNAs at the A3 splice acceptor, which determines the level of VP mRNA in the cytoplasm and, therefore, the production of capsid proteins.
NP1 Protein Activates VP mRNA Expression Independently of Splicing To distinguish the function of NP1 in splicing and internal polyadenylation read-through of VP mRNA, three helper plasmids were constructed: 1) pCMVNS*(ln3Δ)Cap, in which the third intron was removed (FIG. 7A, construct 1); 2) pCMVEpoln14(ln3Δ)Cap, in which the first and second introns were replaced with the Epo introns 1 and 4, respectively, and the third intron was also removed (FIG. 7A, construct 2); and 3) pCMVEpoln124Cap, in which all three introns were replaced with Epo introns (FIG. 7A, construct 3). Since NP1 protein was encoded by the ORF 312 lying in the third intron sequence, all three constructs did not express NP1 (FIG. 7B, lanes 1-3). When NP1 was added back in trans, VP mRNA at approximately (about) 2.5 kb, which is likely the R6 mRNA that reads through the (pA)p site and is polyadenylated at the (pA)d site (FIG. 1A), increased by at least 5-fold (FIGS. 7C&D, VP mRNA), but the (pA)p mRNA at about 0.8 kb, which is spliced of all introns and polyadenylated at the (pA)p site, either remained unchanged or was significantly decreased (FIGS. 7C&D, (pA)p).

Figure 7E:
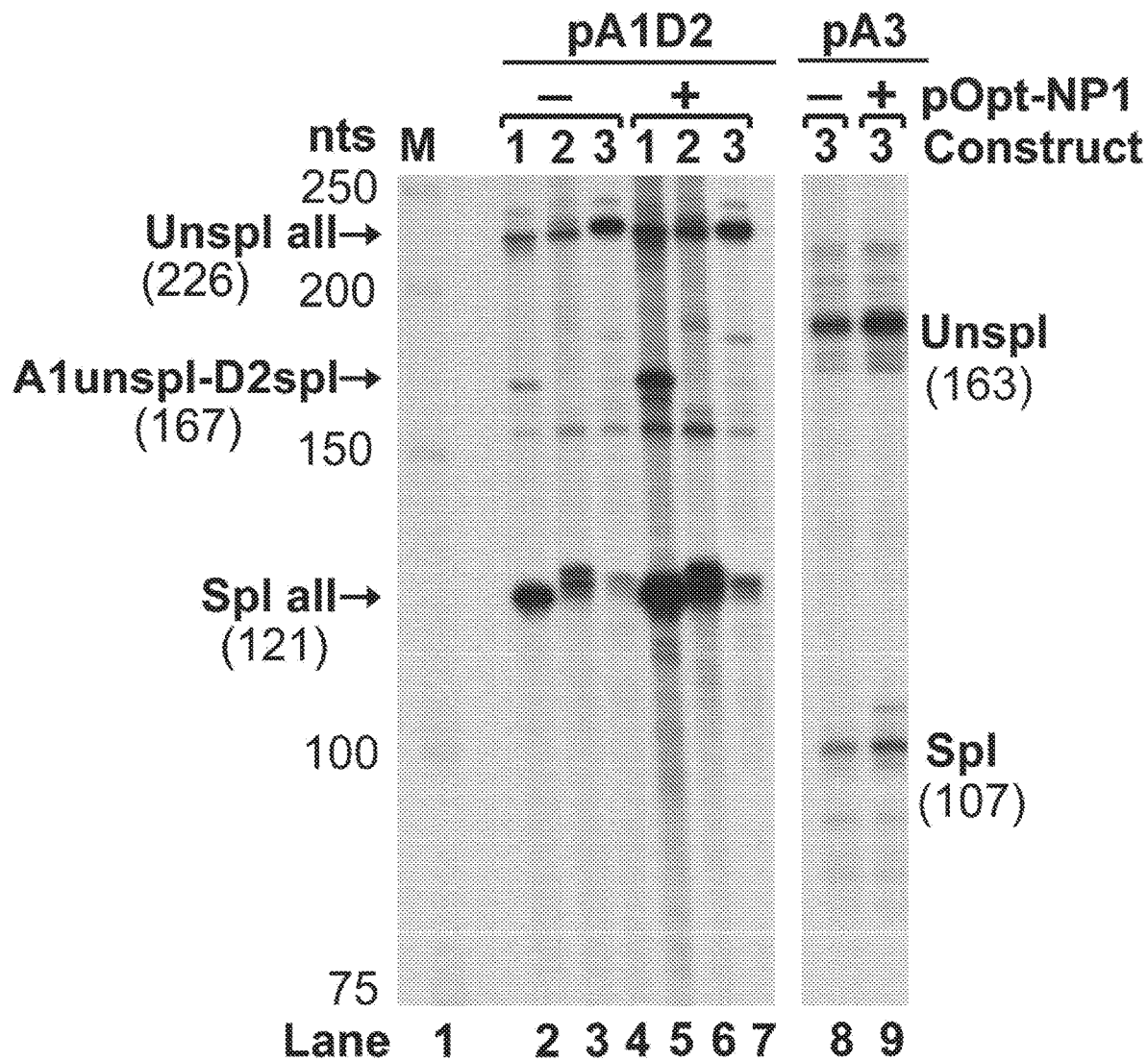

As controls, NP1 did not alter splicing of the introns 1 and 2 of the mRNAs generated from pCMVNS*(ln3Δ)Cap (FIG. 7E, lanes 2&5) or alter splicing of the heterogeneous introns (Epo introns 1 and 4) of the mRNAs generated from pCMVEpoln14*(ln3Δ)Cap (FIG. 7E, lanes 3&6). It also did not alter splicing of the three heterogeneous Epo introns (Epo Introns 1, 2, and 4) of the mRNAs generated from pCMVEpoln124Cap (FIG. 7E, lanes 4 vs. 7, and 8 vs. 9).

Thus, these results strongly suggested that the role of NP1 in increasing the read through of the (pA)p site (the level of VP mRNA) is independent of splicing at the A3 splice acceptor and the intervening intron sequence. Since both the pCMVEpoln14(ln3Δ)Cap and pCMVEpoln124Cap constructs did not contain any NS ORFs, the function of NP1 in facilitating the VP mRNA to read through the (pA)p site is also independent of NS1-4.

Figures 8A, 8B:
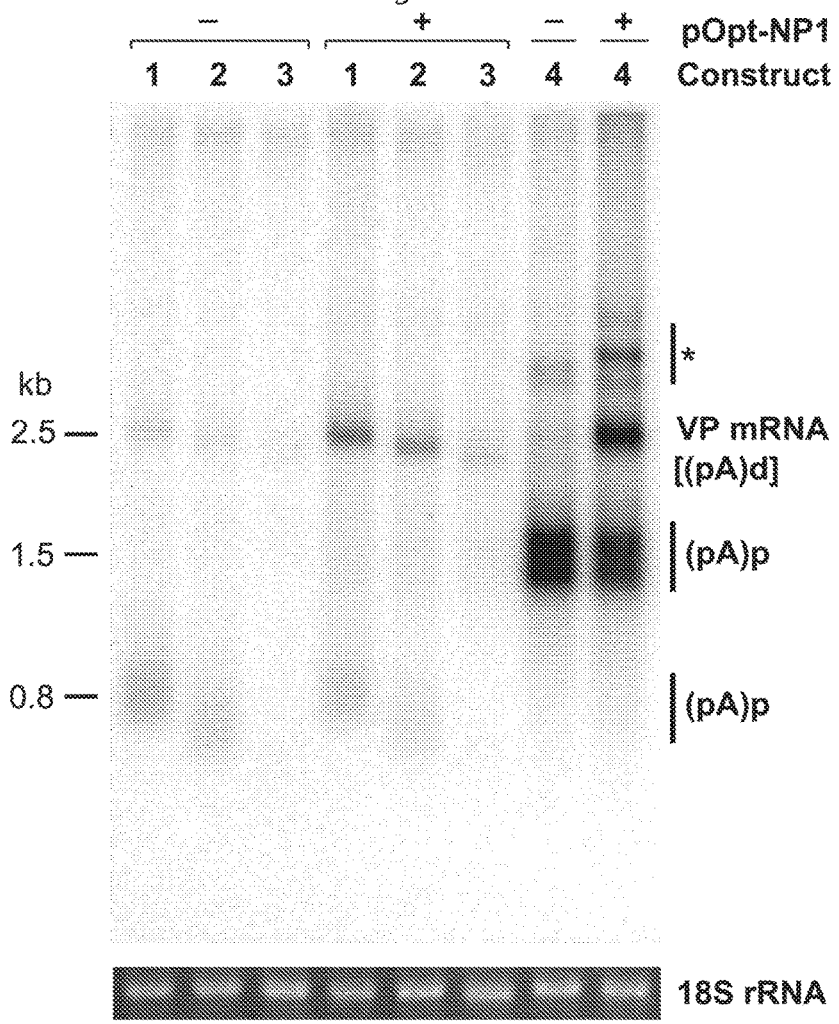
Figure 8C:
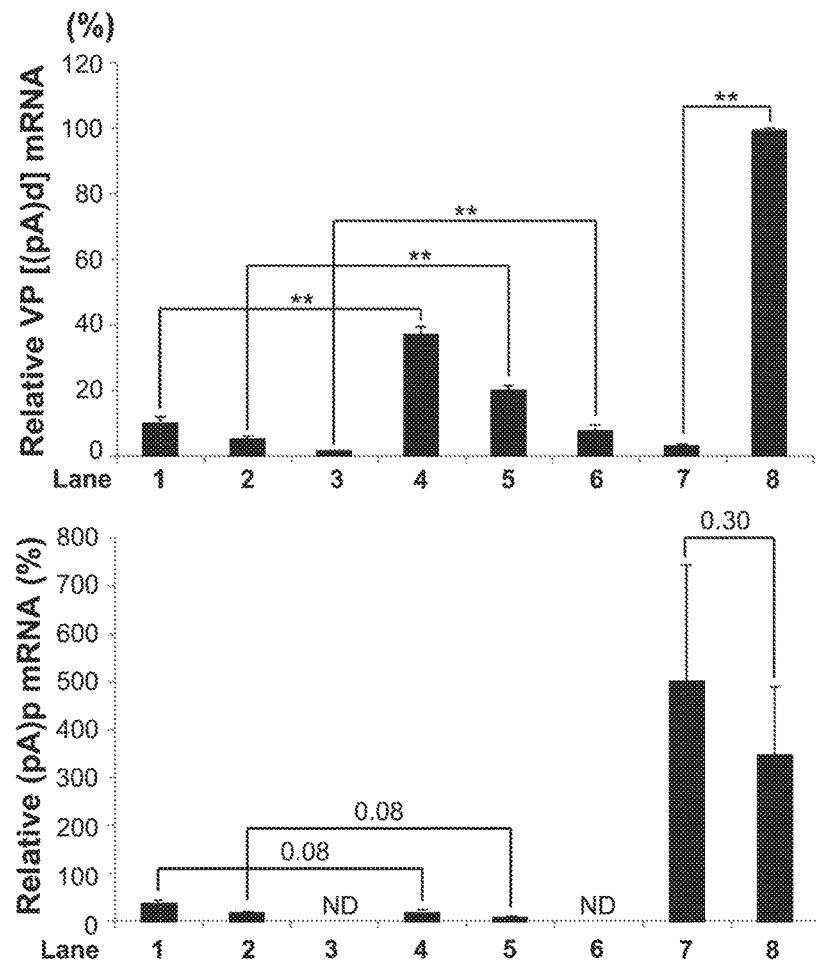
Figure 8D:
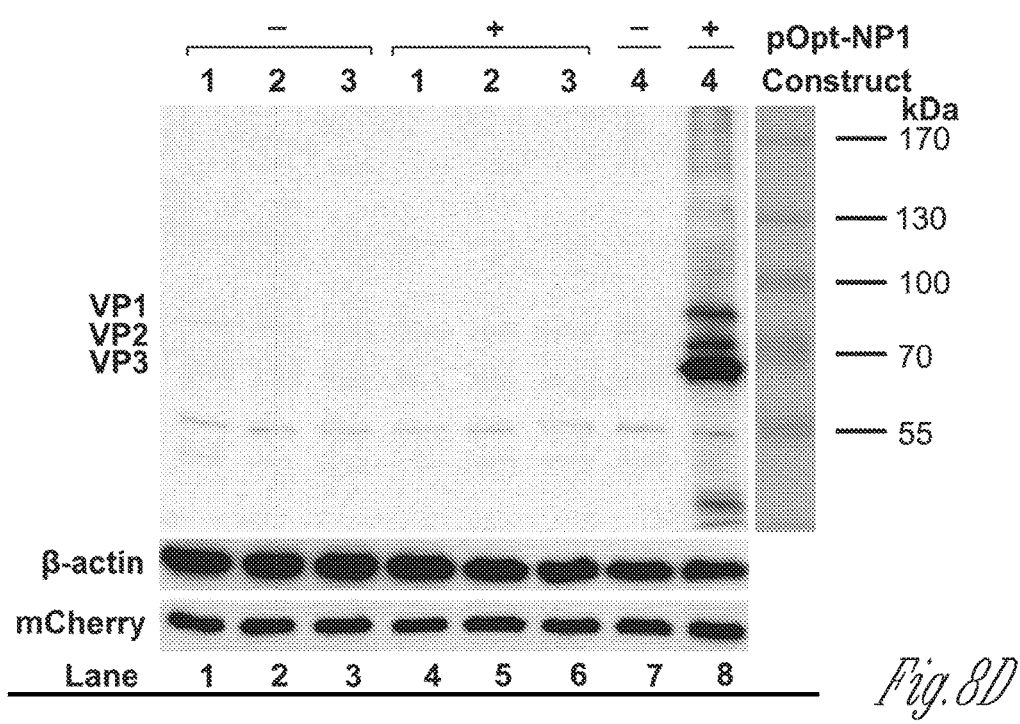

Furthermore, the impact of NP1 on the expression of VP mRNA from various VP cDNA constructs was evaluated. NP1 enhanced VP mRNA expression from the all VP cDNA constructs (FIG. 8B, lanes 4-6 vs. 1-3). With NP1 provided In trans, the level of VP mRNA was increased by 3.7-, 4-, and 6-fold from the expression of R6, R7, and R8 VP cDNAs, respectively (FIGS. 8B&C, lanes 1 vs. 4, 2 vs. 5 and 3 vs. 6). Again, as a control, with NP1 provided in trans, the NS1 and NP1 knockout construct pCMVNS*(NP*)Cap expressed VP mRNA (at about 2.5 kb; R6 In FIG. 1A), at a level of over 30 times more than that without NP1, whereas the level of (pA)p mRNA (at about 1.5 kb; R5s in FIG. 1A) did not significantly change (FIG. 8B, lanes 7 vs. 8, and FIG. 8C). However, the increased VP mRNAs from the cDNA constructs by the NP1 were still not sufficient to express capsid proteins (FIG. 8D, lanes 4-6). Of note, with the NP1 provided in trans, the level of (pA)p mRNA (at about 0.8 kb) generated from the cDNA constructs was not significantly changed (FIG. 8C, (pA)p mRNA). These results suggested that the increased read through VP mRNA is not due to the simple conversion of the (pA)p mRNA to VP mRNA.

Figure 9A:
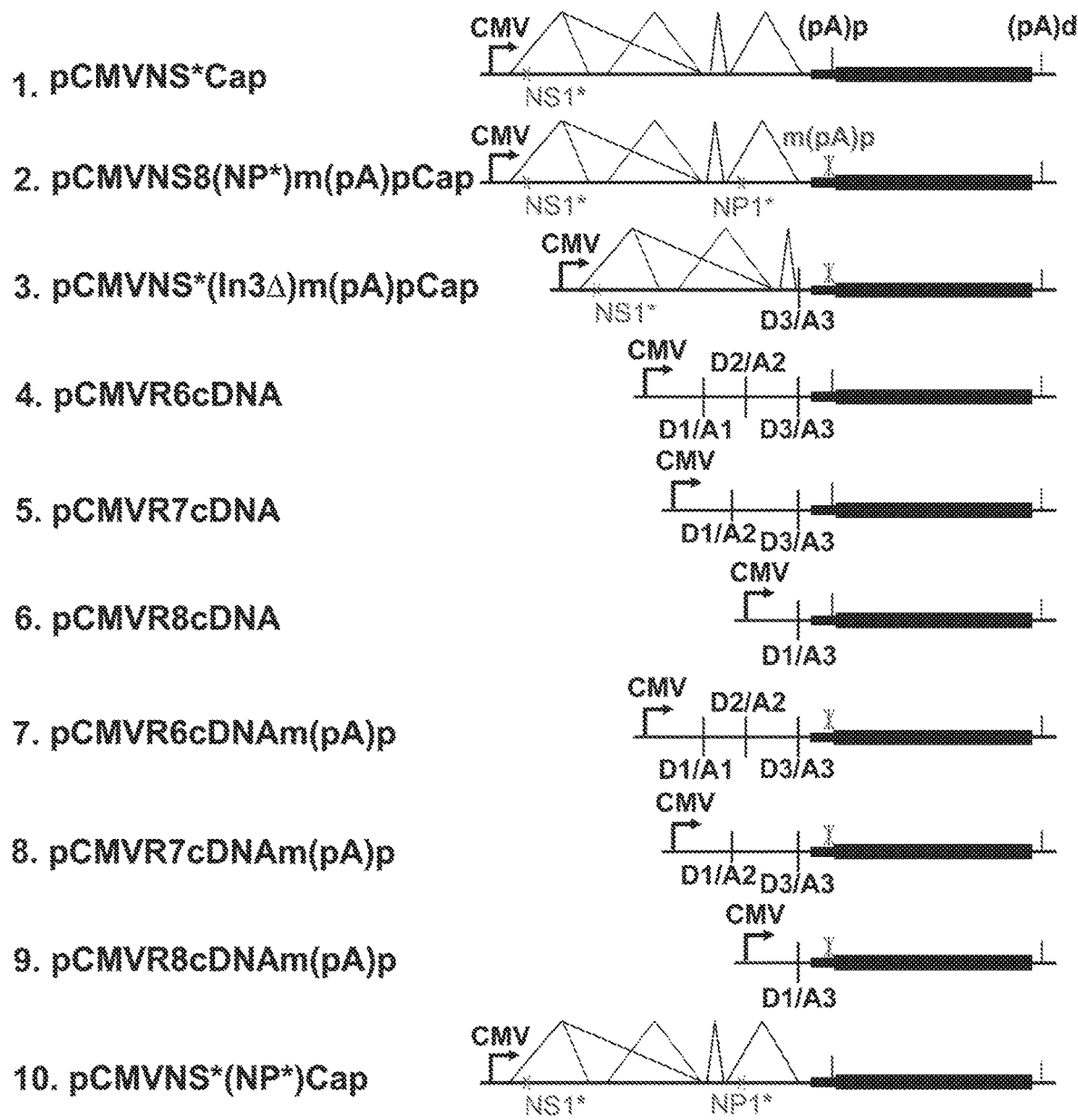
Figure 9B:
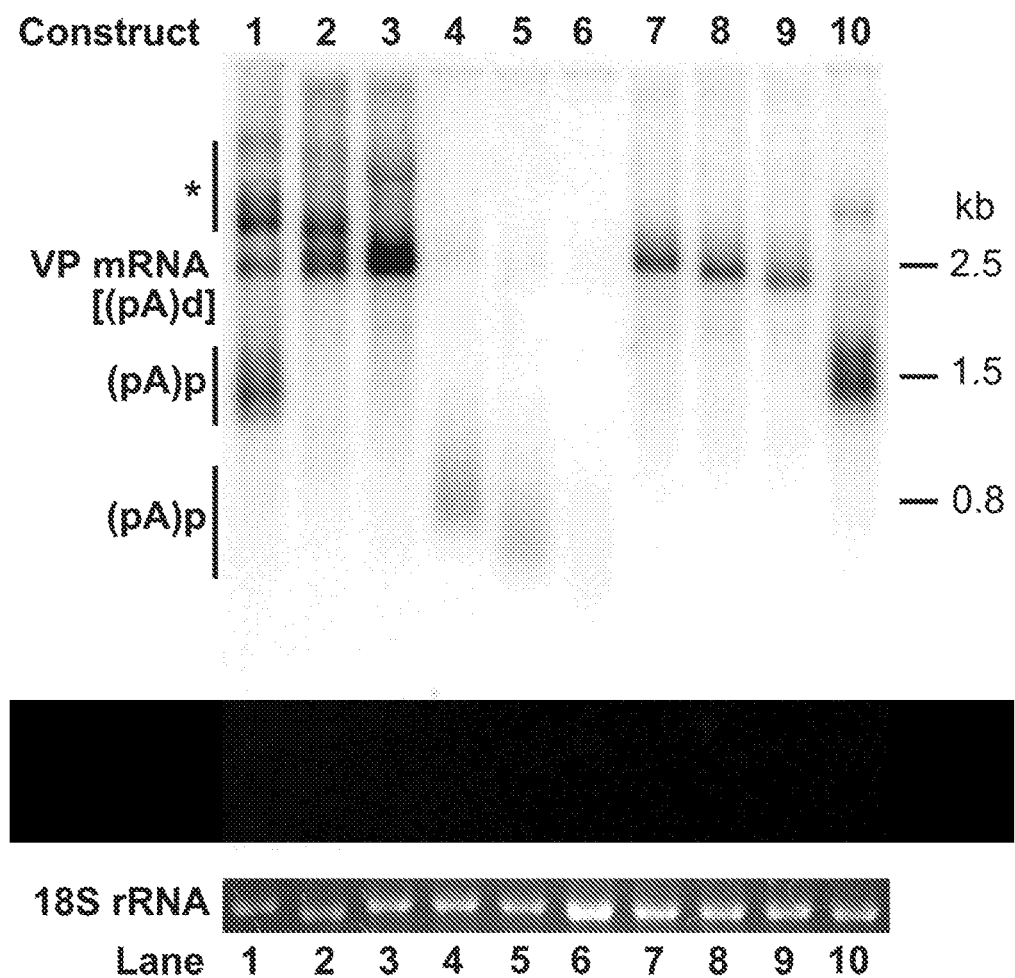
Figure 9C:
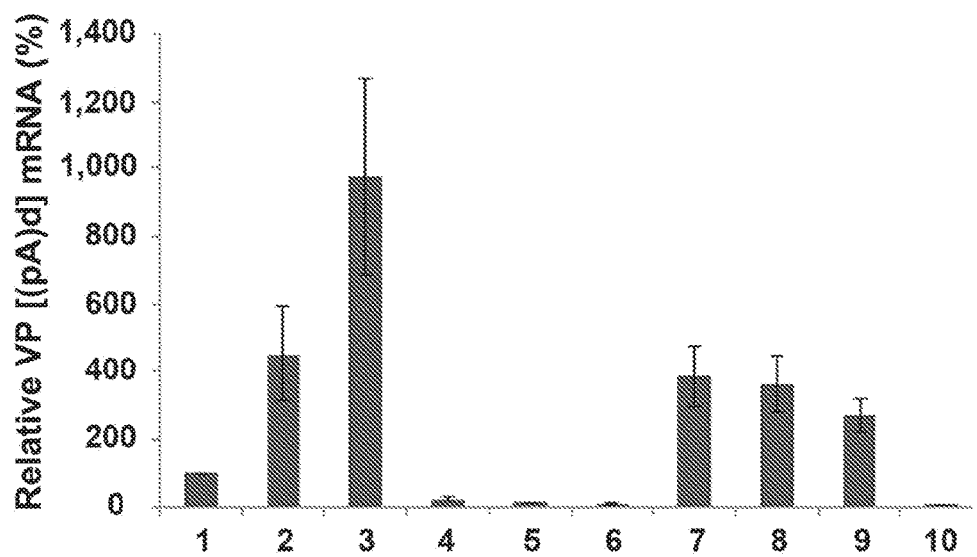
Figure 9D:
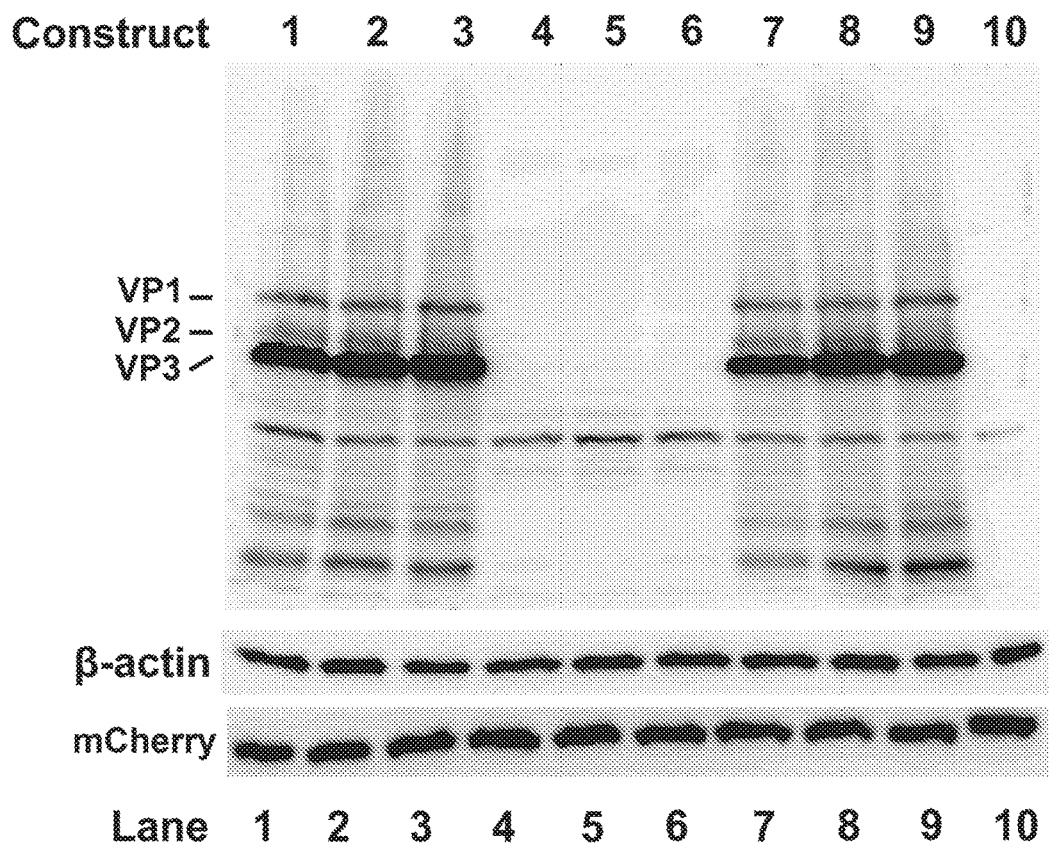

Taken together, these results confirmed that NP1 protein facilitates VP mRNA to read through the (pA)p site, independent of any splicing events.
Knockout of the Polyadenylation Signals in the Center of the Viral Genome Compensates for the Requirement of NP1 Protein in the Expression of Capsid Proteins Next, the role of the (pA)p site in the blockage of the read-through of VP mRNA and capsid protein expression was examined. First, mutations of the polyadenylation signal (PAS) AAUAAA site at nt 3,485 (Chen et al., 2010), as well as mutations of its upstream and downstream regions that often regulate polyadenylation (Zarudnaya et al., 2003; Huang et al., 2012) were made, in pCMVNS*Cap. We failed to decrease the level of (pA)p mRNA or increase the level of VP mRNA (data not shown). Since there are a series of five PASs in the middle of the genome, the VP1 start-VP3 start-encoding region, we made silent mutations of the entire VP1 start-VP3 start-encoding sequence [m(pA)p], which covers al five PASs (FIG. 2). The constructs that bear the m(pA)p mutation were observed to no longer generate (pA)p mRNA (FIG. 9B, (pA)p, lanes 2, 3 and 7-9), but produced much higher levels of VP mRNA (FIGS. 9B&C, VP mRNA, lanes 2, 3, and 7-9). In agreement with this finding, the m(pA)p mutation enabled capsid protein expression in the absence of NP1 from the NSCap gene constructs (FIG. 9D, lanes 2&3 vs. 10), as well as the VP cDNA constructs (FIG. 9D, lanes 7-9 vs. 4-6).

Thus, the present results confirmed that internal polyadenylation prevents HBoV1 pre-mRNA from transcribing through the (pA)p site, which controls the production of VP mRNA, and, therefore, prevents the expression of capsid proteins. Of note, VP mRNA expressed from the NSCap constructs migrated at the same position as the mRNA expressed from the R8cDNA did (FIG. 9B, lanes 1, 2 and 3 vs. 7), suggesting that R6 mRNA is the key VP mRNA.
Discussion The NP1 protein is a unique small non-structural protein expressed only by members of the genus *Bocaparvovirus* among parvoviruses (Chen et al., 2010; Sun et al., 2009; Lederman et al., 1984; Qiu et al., 2007). It is required for efficient replication of *Bocaparvovirus* DNA (Huang et al., 2012; Sun et al., 2009). The NP1 protein shares features among members of *Bocaparvovirus*. Both the BPV1 and HBoV1 NP1 proteins can complement the loss of NP1 during MVC DNA replication to some extents (Sun et al., 2009). HBoV1 NP1 protein could complement some functions of the minute virus of mice (MVM) NS2 during an early phase of infection (Mihaylov et al., 2014).

In a previous study, MVC NP1 was shown to play a role in regulating capsid protein expression by facilitating VP mRNA transcript to read through the internal polyadenylation site (Sukhu et al., 2012). However, in that study, the function of the NP1 in enhancing splicing of VP mRNA at the A3 splice acceptor and in solely facilitating the read-through of the (pA)p site of VP mRNA (Sukhu et al., 2012) was not differentiated, since all VP mRNAs have to be spliced at the A3 splice acceptor (Dijkman et al., 2009; Chen et al., 2010, Sun et al., 2009). In the present study, it was demonstrated that NP1 plays a double role in controlling the production of VP mRNA. First, NP1 is critical to the splicing of the VP mRNA at the A3 splice acceptor, which is essential to generate VP mRNA. Second, NP1 facilitates viral pre-mRNA to read through the internal (pA)p site for the production of VP mRNA, independently of any splicing events. More importantly, the function of NP1 in capsid protein expression is independent of the other four non-structural proteins (NS1-4).

It was observed that when splicing is involved (from the constructs that contain introns), NP1 increased the level of VP mRNA on average to a much greater extent than in the absence of splicing (from these cDNA constructs) (FIGS. 7 vs. 8). This finding suggests that splicing boosts NP1-facilitated read-through of the (pA)p site. Of note, while NP1 increases the read through transcript VP mRNA, (pA)p mRNA does not decrease significantly in most cases, suggesting that the increased read-through of transcripts (VP mRNA) is not merely a conversion of the (pA)p mRNA, but is likely an activation of transcription. Moreover, replacing the D3-A3 Intron with heterogeneous Epo intron 4 destroyed the NP1 protein dependence of the splicing at the A3 splice acceptor (FIG. 7), suggesting that the role of NP1 in enhancing splicing of VP mRNA at the A3 splice site is dependent on the intervening sequence of the third intron. As we know, during cellular mRNA processing, RNA transcription, splicing, and polyadenylation are all coupled (Bentley, 2014). Therefore, it was speculated that NP1 may target the transcription complex, which initiates at the P5 promoter to activate transcription, enhances splicing at the A3 splice site, and prevents internal polyadenylation, since VP mRNA must be spliced at the A3 splice site and read through the (pA)p site. Therefore, the HBoV1 NP1 is the first example for a parvovirus nonstructural protein that has multiple functions in viral pre-mRNA processing.

The level of the VP mRNAs is not proportionally related to the level of capsid proteins (FIGS. 7 & 9). One interpretation could be that there is a minimal level of VP mRNA required for the translation of capsid proteins. However, in the cases of highly expressed VP mRNA from these (pA)p knockout constructs (FIG. 9), the higher level of VP mRNA did not express a higher level of capsid proteins. NP1 may play a role in the translation of VP mRNA. Without NP1 expression from the (pA)p knockout constructs, a higher level of VP1 mRNA is required to efficiently translate capsid proteins.

In this study, expression of the novel VP2 from a non-canonical translation initiation site (GUG) ORF was confirmed. Importantly, simple HBoV1 VP ORF constructs (pCMVR6-cDNAm(pA)p), were identified which do not express any NS proteins (NS1-4 and NP1), express HBoV1 capsid proteins VP1, VP2, and VP3 at a level and at a ratio (VP1:VP2 and VP3) similar to that of the packaging helper plasmid pHBoV1NSCap for rAAV2/HBoV1 vector production (Yan et al., 2013). In fact, pCMVR8cDNA packaged rAAV2/HBoV1 vector at an efficiency higher than that by the pHBoV1NSCap (data not shown). Thus, the cDNAm (pA)p constructs will aid in the optimization of rAAV2/HBoV1 vector production in HEK293 cells without interference from any HBoV1 NS proteins.

In summary, to improve the packaging efficiency of the pHBoV1NSCap in HEK293 cells, the expression of the HBoV1 capsid proteins was studied. Expression of HBoV1 capsid proteins was found to be regulated by NP1, but not by NS1, NS2, NS3, and NS4. Without NP1, HBoV1 capsid protein-encoding transcripts are expressed at a low level that is not sufficient for the expression of capsid proteins.

REFERENCES

Allander et al., *Clin. Infect. Dis.*, 44:904 (2007).
Allander et al., *Proc. Natl. Acad. Sci. U.S.A.* 102:12891 (2005).
Bentley, *Nat. Rev. Genet.*, 15:163 (2014).
Cecchini et al., *Clin. Vaccine Immunol.*, 16:597 (2009).
Chen et al., *PLoS. Pathog.*, 7:e1002088 (2011).
Chen et al., *Virology*, 403:145 (2010).
Christensen et al., *J. Clin. Virol.*, 49:158 (2010).
Cotmore et al., *Arch. Virol.*, 159:1239 (2014).
Deng and Qiu, *J. Virol. Methods*, 195:112 (2014).
Deng et al., *J. Virol.*, 87:4097 (2013).
Deng et al., *PLoS. ONE*, 7:e34353 (2012).
Dijkman et al., *J. Virol.*, 87:7739 (2009).
Don et al., *Pediatr. Pulmonol.*, 45:120 (2010).
Edner et al., *J. Clin. Microbiol.*, 50:531 (2011).
Huang et al., *PLoS. Pathog.*, 8:e1002899 (2012).
Huang et al., *Virology*, 426:167 2012.
Johnson and Qiu, In: C. Tidona and Darai G. (eds.), The Springer Index of Viruses. Second ed. Springer, New York, p. 1209 (2011).
Kantola et al., *Clin. Infect. Dis.*, 46:540 (2008).
Lederman et al., *J. Virol.*, 49:315 (1984).
Martin et al., *J. Infect. Dis.*, 212:516 (2015).
Mihaylov et al., *Virology*, 468-470:226 (2014).
Qiu et al., *J. Virol.*, 76:12435 (2002).
Qiu et al., *J. Virol.*, 81:12080 (2007).
Shen et al., *J. Virol.*, 89:10097 (2015).
Sukhu et al., *J. Virol.*, 87:1098 (2012).
Sun et al., *J. Virol.*, 83:3956 (2009).
Yan et al., *Mol. Ther.*, 21:2181 (2013).
Yan et al., *Proc. Natl. Acad. Sci. U.S.A.*, 97:6716 (2000).
Zarudnaya et al., *Nucleic Adds Res.*, 31:1375 (2003).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method of preparing a chimeric virus comprising bocavirus capsid protein and a recombinant adeno-associated (AAV) viral genome, which method is independent of bocavirus NP1, comprising: a) providing one or more vectors that when introduced to mammalian cells i) do not express bocavirus NS1, NS2, NS3 and NS4, ii) express bocavirus VP1, VP2 and VP3 capsid proteins, iii) do not express a functional bocavirus NP1, wherein the coding region for the one or more bocavirus VP1, VP2 or VP3 is codon optimized; b) expressing the one or more vectors and a rAAV vector having a rAAV genome in mammalian cells that do not express NP1 in trans, thereby producing bocavirus capsid proteins and a rAAV genome; and c) collecting chimeric rAAV/bocavirus.

2. The method of claim 1 wherein the one or more vectors are integrated into the genome of the cell.

3. The method of claim 1 wherein the promoter that expresses bocavirusproteins is not a bocavirus promoter.

4. A method of preparing a chimeric virus comprising bocavirus capsid protein and a recombinant adeno-associated (AAV) viral genome which method is independent of bocavirus NP1, comprising: a) providing a bocavirus genome vector that when introduced to mammalian cells i) expresses bocavirus, NS3 and NS4 but not NS1 and NS2, ii) expresses bocavirus capsid proteins VP1, VP2 and VP3, and iii) does not express a functional bocavirus NP1, wherein the coding region for the one or more of the VP1, VP2 or VP3 in the bocavirus genome vector is codon optimized; b) introducing the bocavirus genome vector and a rAAV vector having an AAV genome into mammalian cells that do not express bocavirus NP1 in trans, thereby producing bocavirus nonstructural proteins NS3 and NS4, bocavirus capsid proteins and a rAAV genome; and c) collecting chimeric rAAV/bocavirus virus.

5. The method of claim 4 wherein the rAAV vector comprises an expression cassette encoding a heterologous gene product.

6. The method of claim 5 wherein the gene product encodes a therapeutic protein.

7. The method of claim 4 wherein the mammalian cells do not provide for expression of any of bocavirus NS1, NS2, NS3 or NS4.

8. The method of claim 4 wherein the rAAV genome is a rAAV-1, rAAV-2, rAAV-3, rAAV-4, rAAV-5, rAAV-6, rAAV-7, rAAV-8 or rAAV-9 genome.

9. The method of claim 4 wherein the gene product is a viral, bacterial, tumor, parasite, or fungal antigen.

10. The method of claim 4 wherein the gene product is cystic fibrosis transmembrane conductance regulator, b-globin, g-globin, tyrosine hydroxylase, glucocerebrosidase, aryl sulfatase A, factor VIII, dystrophin, alpha 1-antitrypsin, surfactant protein SP-D, SP-A or SP-C, C1 inhibitor gene, C1-INH gene, SERPING gene erythropoietin, HBoV protein, influenza virus protein, RSV protein, a neutralizing antibody or an antigen binding fragment thereof, SARS virus protein, or a cytokine.

11. The method of claim 10, wherein the gene product comprises Interferon (IFN)-alpha, IFN-gamma, Tumor Necrosis Factor (TNF), Interleukin (IL)-1, IL-17, or IL-6.

12. The method of claim 4 wherein the bocavirus is a human bocavirus.

* * * * *

UNITED STATES PATENT AND TRADEMARK OFFICE
CERTIFICATE OF CORRECTION

PATENT NO. : 11,702,672 B2
APPLICATION NO. : 16/076219
DATED : July 18, 2023
INVENTOR(S) : Yan et al.

It is certified that error appears in the above-identified patent and that said Letters Patent is hereby corrected as shown below:

On the Title Page

On page 4, in Column 1, under Item (56) "Other Publications", Line 66, delete "Nalronobacterium" and insert --Natronobacterium-- therefor On page 5, in Column 2, under Item (56) "Other Publications", Line 49, delete "Eximaner Interwiew" and insert --Examiner Interview-- therefor On page 7, in Column 2, under Item (56) "Other Publications", Line 65, delete "60/305,204." and insert --60/305,204,-- therefor On page 8, in Column 1, under Item (56) "Other Publications", Line 10, delete "2004227915,," and insert --2004227915,-- therefor On page 8, in Column 1, under Item (56) "Other Publications", Line 56, delete ""Calbichem(r)" and insert --"Calbiochem(r)-- therefor On page 8, in Column 2, under Item (56) "Other Publications", Line 46, delete "2386546,," and insert --2386546,-- therefor On page 8, in Column 2, under Item (56) "Other Publications", Line 67, delete ""Carbiochem(r)" and insert --"Calbiochem(r)-- therefor On page 9, in Column 2, under Item (56) "Other Publications", Line 40, delete "tp" and insert --to-- therefor On page 10, in Column 1, under Item (56) "Other Publications", Line 11, delete "PCT/US 00/15700," and insert --PCT/US00/15700,-- therefor Signed and Sealed this
Twenty-fifth Day of March, 2025

Coke Morgan Stewart
*Acting Director of the United States Patent and Trademark Office*

CERTIFICATE OF CORRECTION (continued)

On page 10, in Column 1, under Item (56) "Other Publications", Line 13, delete "PCT/US 00/15700," and insert --PCT/US00/15700,-- therefor On page 10, in Column 1, under Item (56) "Other Publications", Line 49, delete "Reportt"," and insert --Report",-- therefor On page 11, in Column 1, under Item (56) "Other Publications", Line 13, delete "MX/a/2021Z012681," and insert --MX/a/2021/012681,-- therefor On page 11, in Column 1, under Item (56) "Other Publications", Line 59, delete "Theraputic" and insert --Therapeutic-- therefor On page 11, in Column 2, under Item (56) "Other Publications", Line 37, delete "LPS-lnduced" and insert --LPS-Induced-- therefor On page 12, in Column 1, under Item (56) "Other Publications", Line 18, delete "Wihtin" and insert --Within-- therefor On page 12, in Column 2, under Item (56) "Other Publications", Line 14, delete "Vectiors" and insert --Vectors-- therefor On page 13, in Column 1, under Item (56) "Other Publications", Line 43, delete "Intermolecularcis" and insert --Intermolecular cis-- therefor On page 13, in Column 2, under Item (56) "Other Publications", Line 24, delete "Abudance" and insert --Abundance-- therefor On page 13, in Column 2, under Item (56) "Other Publications", Line 27, delete ""Chapters:" and insert --"Chapter 5:-- therefor On page 13, in Column 2, under Item (56) "Other Publications", Line 60, delete "Methodsd" and insert --Methods-- therefor On page 14, in Column 1, under Item (56) "Other Publications", Line 17, delete ""PMA-lnduced" and insert --"PMA-Induced-- therefor On page 14, in Column 2, under Item (56) "Other Publications", Line 22, delete "fordrug" and insert --for drug-- therefor On page 14, in Column 2, under Item (56) "Other Publications", Line 29, delete "Hyptertension:" and insert --Hypertension:-- therefor On page 15, in Column 2, under Item (56) "Other Publications", Line 69, delete "adenvirus" and insert --adenovirus-- therefor

CERTIFICATE OF CORRECTION (continued)
U.S. Pat. No. 11,702,672 B2

On page 16, in Column 1, under Item (56) "Other Publications", Line 27, delete "fo" and insert --of-- therefor On page 16, in Column 1, under Item (56) "Other Publications", Line 27, delete "fora" and insert --for a-- therefor On page 17, in Column 1, under Item (56) "Other Publications", Line 1, delete ""p53-lndependent" and insert --"p53-Independent-- therefor On page 17, in Column 1, under Item (56) "Other Publications", Line 8, delete ""Adeno-Assodated" and insert --"Adeno-Associated-- therefor On page 17, in Column 1, under Item (56) "Other Publications", Lines 18-19, delete "Ubiquitin-Proteosome" and insert --Ubiquitin-Proteasome-- therefor On page 17, in Column 1, under Item (56) "Other Publications", Line 33, delete "proteaseome-dependent" and insert --proteasome-dependent-- therefor On page 17, in Column 2, under Item (56) "Other Publications", Line 11, delete "theraputic" and insert --therapeutic-- therefor On page 17, in Column 2, under Item (56) "Other Publications", Line 41, delete "AAV-ITR-lndependent" and insert --AAV-ITR-Independent-- therefor On page 18, in Column 1, under Item (56) "Other Publications", Line 11, delete "cytoxicity" and insert --cytotoxicity-- therefor On page 18, in Column 1, under Item (56) "Other Publications", Line 45, delete "Doxorubcin:" and insert --Doxorubicin:-- therefor On page 18, in Column 2, under Item (56) "Other Publications", Line 40, delete ""E2-lnduced" and insert --"E2-Induced-- therefor On page 19, in Column 1, under Item (56) "Other Publications", Line 27, delete "Traffickling" and insert --Trafficking-- therefor On page 19, in Column 1, under Item (56) "Other Publications", Line 31, delete ""Lipopoolysaccharide" and insert --"Lipopolysaccharide-- therefor On page 20, in Column 1, under Item (56) "Other Publications", Line 30, delete "steriodogenesis"," and insert --steroidogenesis",-- therefor On page 21, in Column 1, under Item (56) "Other Publications", Line 51, delete "Parkison" and insert --Parkinson-- therefor CERTIFICATE OF CORRECTION (continued)
U.S. Pat. No. 11,702,672 B2

On page 21, in Column 2, under Item (56) "Other Publications", Line 2, delete "Immunocomponent" and insert --Immunocompetent-- therefor On page 21, in Column 2, under Item (56) "Other Publications", Line 21, delete "resistancce" and insert --resistance-- therefor On page 22, in Column 1, under Item (56) "Other Publications", Line 18, delete "signal-regulatedprotine" and insert --signal-regulated protein-- therefor On page 22, in Column 2, under Item (56) "Other Publications", Line 16, delete "Intravecor" and insert --Intravector-- therefor On page 22, in Column 2, under Item (56) "Other Publications", Line 21, delete "Adeno-Assoviated" and insert --Adeno-Associated-- therefor On page 22, in Column 2, under Item (56) "Other Publications", Line 25, delete "Compouncs" and insert --Compounds-- therefor On page 22, in Column 2, under Item (56) "Other Publications", Line 39, delete "Adeno-Assoviated" and insert --Adeno-Associated-- therefor On page 22, in Column 2, under Item (56) "Other Publications", Line 39, delete "Boca Virus" and insert --Bocavirus-- therefor On page 22, in Column 2, under Item (56) "Other Publications", Line 42, delete "Adeno-Assoviated" and insert --Adeno-Associated-- therefor On page 22, in Column 2, under Item (56) "Other Publications", Line 42, delete "Boca Virus" and insert --Bocavirus-- therefor On page 22, in Column 2, under Item (56) "Other Publications", Line 47, delete "Boca Virus" and insert --Bocavirus-- therefor On page 22, in Column 2, under Item (56) "Other Publications", Line 53, delete "Factoe" and insert --Factor-- therefor On page 22, in Column 2, under Item (56) "Other Publications", Line 55, delete "Oct. 1, 2021, Composition" and insert --Oct. 14, 2021, Compositions-- therefor On page 22, in Column 2, under Item (56) "Other Publications", Line 56, delete "Cyctic" and insert --Cystic-- therefor On page 23, in Column 1, under Item (56) "Other Publications", Line 29, delete "Compositiond" and insert --Compositions-- therefor

CERTIFICATE OF CORRECTION (continued)
U.S. Pat. No. 11,702,672 B2

In the Specification

In Column 4, Line 55, delete "NS 4;" and insert --NS4;-- therefor

In Column 5, Line 5, delete "SERPING" and insert --SERPING1-- therefor

In Column 6, Line 21, delete "IL-8." and insert --IL-6.-- therefor

In Column 6, Line 42, delete "NS 4;" and insert --NS4;-- therefor

In Column 7, Line 17, delete "NS 4;" and insert --NS4;-- therefor

In Column 7, Line 27, delete "NS 4;" and insert --NS4;-- therefor

In Column 7, Line 32, delete "ii)" and insert --iii)-- therefor

In Column 9, Line 43, delete "A1." and insert --A1,-- therefor

In Column 11, Line 54, delete "anti-f-actin" and insert --anti-β-actin-- therefor In Column 12, Line 13, delete "protein:" and insert --protein;-- therefor In Column 19, Line 32, delete "Uke" and insert --Like-- therefor In Column 20, Line 37, delete "U" and insert --Li-- therefor In Column 29, Line 12, delete "bocoviruses" and insert --bocaviruses-- therefor In Column 35, Line 3, delete "In" and insert --in-- therefor In Column 35, Line 51, delete "Introns" and insert --introns-- therefor In Column 35, Line 65, delete "In" and insert --in-- therefor In Column 36, Line 3, delete "In" and insert --in-- therefor In Column 36, Line 33, delete "al" and insert --all-- therefor In Column 36, Line 48, delete "R8cDNA" and insert --R6cDNA-- therefor In Column 37, Line 26, delete "Intron" and insert --intron-- therefor In Column 37, Line 55, delete "(pCMVR6-cDNAm(pA)p)," and insert --(pCMVR6-8cDNAm(pA)p),-- therefor In Column 38, Line 49, delete "Adds" and insert --Acids-- therefor

CERTIFICATE OF CORRECTION (continued)
U.S. Pat. No. 11,702,672 B2

In the Claims

In Column 45, Line 61, in Claim 3, delete "bocavirusproteins" and insert --bocavirus proteins-- therefor In Column 47, Line 1, in Claim 10, delete "b-globin, g-globin," and insert --β-globin, γ-globin,-- therefor

SEQUENCE LISTING

<160> NUMBER OF SEQ ID NOS: 5

<210> SEQ ID NO 1
<211> LENGTH: 657
<212> TYPE: DNA

```
<213> ORGANISM: Artificial Sequence
<220> FEATURE:
<223> OTHER INFORMATION: A synthetic protein

<400> SEQUENCE: 1
atgagctcag ggaatatgaa ggataaacac agatcttaca agagaaaggg gtctcctgaa      60
cgcggagaac ggaaacggca ttggcaaaca acccatcaca gaagcaggag tcggtcaccc     120
atccgccata gcggcgagcg agggtcaggg agctaccacc aggaacaccc catttcacat     180
ctgagcagct gtaccgctag taaaacaagt gaccaggtga tgaagacccg cgaaagcact     240
tctggaaaga aggacaatag aacaaaccct tacaccgtgt tctcccagca ccgagcatcc     300
aatcctgagg ccccagggtg gtgcggattc tattggcata gcacccgcat tgcacgcgac     360
ggtactaaca gtattttcaa tgagatgaag cagcagttcc agcaactgca aatcgacaat     420
aaaatcggat gggataatac acgggagctg ctgtttaatc agaagaagac ccttgaccag     480
aaataccgga atatgttctg gcatttcaga aacaactctg attgcgagag gtgtaattac     540
tgggatgatg tatatcggcg acacctcgct aatgtgagca gtcagactga agccgacgaa     600
atcacagacg aggagatgct gtcagccgct gaatccatgg aggccgatgc cagcaat      657
```

```
<210> SEQ ID NO 2
<211> LENGTH: 2019
<212> TYPE: DNA
<213> ORGANISM: Artificial Sequence
<220> FEATURE:
<223> OTHER INFORMATION: A synthetic protein

<400> SEQUENCE: 2
acggctccac caatcaagag acagccaaga gggtgggtgc tgcccggata cagatacctg      60
ggaccttttca atccactgga caacggcgaa cctgtgaaca cgctgaccg ggccgctcag     120
ctgcacgatc acgcatacag cgagctgatc aagtccggca aaaacccata cctgtacttc     180
aacaaggctg acgaaaaatt catcgacgat ctgaaagacg attggagcat ggcgggatc     240
attgggagct ccttctttaa gatcaagaga gcagtggccc ccgctctggg aaacaaggag     300
agagcacaga aaaggcattt ctactttgca aacagcaata agggcgccaa gaaaacaaag     360
aaatccgaac ccaagcctgg gacttccaaa atgtctgaca ccgatatcca ggaccagcag     420
cccgacactg tggatgcccc tcagaacacc tccggaggag gaacaggctc tatcggagga     480
gggaaggggt ctggagtggg cattagtacc ggaggctggg tcgggggaag tcattttttca     540
gacaagtacg tggtcaccaa aaacacaagg cagttcatca ccacaattca gaatggccac     600
ctgtatataaaa cagaggctat cgaaactacc aaccagagcg ggaagtccca gcggtgcgtg     660
acaactcctt ggacctactt caactttaat cagtactctt gtcactttag tccacaggat     720
tggcagagac tgacaaatga gtacaagcga ttccggccca aagccatgca ggtgaagatc     780
tataaccctgc agatcaagca gattctgtct aatggcgccg acaccacata caacaatgat     840
ctgaccgctg gggtgcacat cttctgcgac ggagagcatg cttaccctaa cgcaagccac     900
ccatgggacg aagatgtcat gcctgatctg ccatataaga catggaaact gttccagtac     960
ggatatatcc ccattgagaa tgaactggca gacctggatg gaaacgcagc aggagggaat    1020
gccactgaga aggctctgct gtaccagatg cctttctttc tgctggaaaa ctctgaccat    1080
caggtgctgc gaaccgggga gagtactgaa ttcacccttta atttcgattg tgagtgggtc    1140
aacaatgaac gcgcctatat cccccctgga ctgatgtttta accccaaagt gcctacccgg    1200
agagtccagt acatcaggca gaatggctca acagctgcaa gcactgggcg cattcagcca    1260
```

-continued

```
tattccaagc ccacctcttg gatgacagga cctggactgc tgagcgcaca gcgagtggga    1320
cctcagtcta gtgacacagc cccattcatg gtctgcacta accccgaggg aactcacatc    1380
aataccggcg ccgctggctt tgggagtgga ttcgatccac cctcaggctg tctggcacct    1440
accaacctgg agtacaaact gcagtggtat cagacaccag aaggcactgg gaacaatggg    1500
aacatcattg ccaatccctc actgagcatg ctgagggacc agctgctgta caagggaaac    1560
cagactacct ataatctggt gggcgacatc tggatgtttc aaaccaggt ctgggatcgc     1620 ttcccaatca cacgagagaa tcccatttgg tgcaagaaac ctcgcgccga caagcatact    1680
atcatggacc cctttgatgg gagcattgcc atggatcacc ctccaggaac tatcttcatt    1740
aagatggcta aaattccagt gcccaccgca gtaacgccg actcatacct gaatatctat     1800
tgcaccggcc aggtctcctg tgagatcgtg tgggaagtca acggtacgc taccaagaac     1860 tggagacccg agaggcgcca tacagcactg gaatgtcac tgggaggcga aagcaattac     1920
acaccaactt atcacgtgga ccccaccggc gcctatattc agcctacttc ttacgatcag    1980
tgtatgccag tcaaaactaa catcaacaag gtcctgtaa                           2019
```

<210> SEQ ID NO 3
<211> LENGTH: 2019
<212> TYPE: DNA
<213> ORGANISM: Artificial Sequence
<220> FEATURE:
<223> OTHER INFORMATION: A synthetic protein

<400> SEQUENCE: 3

```
acggctccac caatcaagag acagccaaga gggtgggtgc tgcccggata cagatacctg     60
ggacctttca atccactgga caacggcgaa cctgtgaaca acgctgaccg ggccgctcag    120
ctgcacgatc acgcatacag cgagctgatc aagtccggca aaaacccata cctgtacttc    180
aacaaggctg acgaaaaatt catcgacgat ctgaaagacg attggagcat ggcgggatc     240 attgggagct ccttctttaa gatcaagaga gcagtggccc ccgctctggg aaacaaggag    300
agagcacaga aaaggcattt ctactttgca acagcaata agggcgccaa gaaaacaaag    360
aaatccgaac ccaagcctgg gacttccaaa atgtctgaca ctgacattca agaccaacaa    420
cctgatactg tggacgcacc acaaaacacc tcaggggag gaacaggaag tattggagga   480
ggaaaaggat ctggtgtggg gatttccact ggagggtggg tcggaggttc tcactttca    540 gacaaatatg tggttactaa aaacacaaga caatttataa ccacaattca gaatggtcac    600
ctctacaaaa cagaggccat tgaaacaaca aaccaaagtg aaaatcaca cgctgcgtc     660 acaactccat ggacatactt taactttaat caatacagct gtcacttctc accacaggat    720
tggcagcgcc ttacaaatga atataagcgc ttcagaccta agcaatgca gtaaagatt    780 tacaacttgc aaataaaaca aatactttca aatggtgctg acacaacata caacaatgac    840
ctcacagctg gcgttcacat cttttgtgat ggagagcatg cttacccaaa tgcatctcat    900
ccatgggatg aggacgtcat gcctgatctt ccatacaaga cctggaaact ttttcaatat    960
ggatatattc ctattgaaaa tgaactcgca gatcttgatg aaatgcagc tggaggcaat   1020 gctacagaaa aagcacttct gtatcagatg ccttttttc tacttgaaaa cagtgaccac   1080
caagtactta gaactggtga gagcactgaa tttactttta cttgactg tgaatgggtt   1140 aacaatgaaa gagcatacat tcctcctgga ctaatgttta tccaaaagt cccaacaaga   1200 agagttcagt acataagaca aaacggaagc acagcagcca gcacaggcag aattcagcca   1260
```

| | |
|---|---|
| tactcaaaac caacaagctg atgacagga cctggcctgc tcagtgcaca aagagtagga | 1320 |
| ccacagtcat cagacactgc tccattcatg gtttgcacta acccagaagg aacacacata | 1380 |
| aacacaggtg ctgcaggatt tggatctggc tttgatcctc caaacggatg tctggcacca | 1440 |
| actaacctag aatacaaact tcagtggtac cagacaccag aaggaacagg aaataatgga | 1500 |
| aacataattg caaacccatc actctcaatg cttagagacc aactcctata caaggaaac | 1560 |
| caaaccacat acaatctagt gggggacata tggatgtttc caaatcaagt ctgggacaga | 1620 |
| tttcctatca ccagagaaaa tccaatctgg tgcaaaaaac caagggctga caaacacaca | 1680 |
| atcatggatc catttgatgg atcaattgca atggatcatc ctccaggcac tatttttata | 1740 |
| aaaatggcaa aaattccagt tccaactgcc tcaaatgcag actcatacct aaacatatac | 1800 |
| tgtactggac aagtcagctg tgaaattgta tgggaggtag aaagatacgc aacaaagaac | 1860 |
| tggcgtccag aaagaagaca tactgcactc gggatgtcac tgggaggaga gagcaactac | 1920 |
| acgcctacat accacgtgga tccaacagga gcatacatcc agcccacgtc atatgatcag | 1980 |
| tgtatgccag taaaaacaaa catcaataaa gtgttgtaa | 2019 |

<210> SEQ ID NO 4
<211> LENGTH: 2016
<212> TYPE: DNA
<213> ORGANISM: Bocavirus

<400> SEQUENCE: 4

| | |
|---|---|
| atgcctccaa ttaagagaca gcctagaggg tgggtgctgc ctggatacag atatcttggg | 60 |
| ccatttaatc cacttgataa cggtgaacct gtaaataacg ctgatcgcgc tgctcaatta | 120 |
| catgatcacg cctactctga actaataaag agtggtaaaa atccataccct gtatttcaat | 180 |
| aaagctgatg aaaaattcat tgatgatcta aaagacgatt ggtcaattgg tggaattatt | 240 |
| ggatccagtt ttttttaaaat aaagcgcgcc gtggctcctg ctctgggaaa taagagaga | 300 |
| gcccaaaaaa gacactttta ctttgctaac tcaaataaag gtgcaaaaaa acaaaaaaa | 360 |
| agtgaaccta accaggaac ctcaaaaatg tctgacactg acattcaaga ccaacaacct | 420 |
| gatactgtgg acgcaccaca aaacacctca gggggaggaa caggaagtat tggaggagga | 480 |
| aaggatctg gtgtggggat ttccactgga gggtgggtcg gaggttctca cttttcagac | 540 |
| aaatatgtgg ttactaaaaa cacaagacaa tttataacca caattcagaa tggtcacctc | 600 |
| tacaaaacag aggccattga acaacaaac caaagtggaa atcacagcg ctgcgtcaca | 660 |
| actccatgga catactttaa cttaatcaa tacagctgtc acttctcacc acaggattgg | 720 |
| cagcgcctta caaatgaata taagcgcttc agacctaaag caatgcaagt aaagatttac | 780 |
| aacttgcaaa taaacaaat actttcaaat ggtgctgaca caacatacaa caatgacctc | 840 |
| acagctggcg ttcacatctt ttgtgatgga gagcatgctt acccaaatgc atctcatcca | 900 |
| tgggatgagg acgtcatgcc tgatcttcca tacaagacct ggaaactttt tcaatatgga | 960 |
| tatattccta ttgaaaatga actcgcagat cttgatggaa atgcagctgg aggcaatgct | 1020 |
| acagaaaag cacttctgta tcagatgcct tttttctac ttgaaaacag tgaccaccaa | 1080 |
| gtacttagaa ctggtgagag cactgaattt actttaact ttgactgtga atgggttaac | 1140 |
| aatgaaagag catacattcc tcctggacta atgtttaatc aaaagtccc aacaagaaga | 1200 |
| gttcagtaca taagacaaaa cggaagcaca gcagccagca caggcagaat tcagccatac | 1260 |
| tcaaaaccaa caagctggat gacaggacct ggcctgctca gtgcacaaag agtaggacca | 1320 |
| cagtcatcag acactgctcc attcatggtt tgcactaacc cagaaggaac acataaac | 1380 |

```
acaggtgctg caggatttgg atctggcttt gatcctccaa acggatgtct ggcaccaact    1440
aacctagaat acaaacttca gtggtaccag acaccagaag gaacaggaaa taatggaaac    1500
ataattgcaa acccatcact ctcaatgctt agagaccaac tcctatacaa aggaaaccaa    1560
accacataca atctagtggg ggacatatgg atgtttccaa atcaagtctg ggacagattt    1620
cctatcacca gagaaaatcc aatctggtgc aaaaaaccaa gggctgacaa acacacaatc    1680
atggatccat ttgatggatc aattgcaatg gatcatcctc caggcactat ttttataaaa    1740
atggcaaaaa ttccagttcc aactgcctca aatgcagact catacctaaa catatactgt    1800
actggacaag tcagctgtga aattgtatgg gaggtagaaa gatacgcaac aaagaactgg    1860
cgtccagaaa gaagacatac tgcactcggg atgtcactgg gaggagagag caactacacg    1920
cctacatacc acgtggatcc aacaggagca tacatccagc ccacgtcata tgatcagtgt    1980
atgccagtaa aaacaaacat caataaagtg ttgtaa                              2016

<210> SEQ ID NO 5
<211> LENGTH: 396
<212> TYPE: DNA
<213> ORGANISM: Artificial Sequence
<220> FEATURE:
<223> OTHER INFORMATION: A synthetic protein

<400> SEQUENCE: 5
gttaagacgc caccaatcaa gagacagcca agagggtggg tgctgcccgg atacagatac      60
ctgggacctt tcaatccact ggacaacggc gaacctgtga acaacgctga ccgggccgct     120
cagctgcacg atcacgcata cagcgagctg atcaagtccg gcaaaaaccc atacctgtac     180
ttcaacaagg ctgacgaaaa attcatcgac gatctgaaag acgattggag cattggcggg     240
atcattggga gctccttctt taagatcaag agagcagtgg cccccgctct gggaaacaag     300
gagagagcac agaaaaggca tttctacttt gcaaacagca ataagggcgc caagaaaaca     360
aagaaatccg aacccaagcc tgggacttcc aaaatg                               396
```